United States Patent
Chen et al.

(10) Patent No.: US 10,829,792 B2
(45) Date of Patent: Nov. 10, 2020

(54) BIOCATALYTIC SYNTHESIS OF STRAINED CARBOCYCLES

(71) Applicant: California Institute of Technology, Pasadena, CA (US)

(72) Inventors: Kai Chen, Pasadena, CA (US); Xiongyi Huang, Pasadena, CA (US); S. B. Jennifer Kan, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 54 days.

(21) Appl. No.: 15/927,971

(22) Filed: Mar. 21, 2018

(65) Prior Publication Data

US 2018/0305721 A1    Oct. 25, 2018

Related U.S. Application Data

(60) Provisional application No. 62/474,435, filed on Mar. 21, 2017, provisional application No. 62/583,073, filed on Nov. 8, 2017.

(51) Int. Cl.
    *C12P 7/62*      (2006.01)
    *C12N 9/02*      (2006.01)

(52) U.S. Cl.
    CPC ............. *C12P 7/62* (2013.01); *C12N 9/0042* (2013.01); *C12N 9/0071* (2013.01); *C12Y 106/02004* (2013.01)

(58) Field of Classification Search
    None
    See application file for complete search history.

(56) References Cited

U.S. PATENT DOCUMENTS

| | | |
|---|---|---|
| 2013/0102780 A1 | 4/2013 | Giguere et al. |
| 2013/0152224 A1 | 6/2013 | Abad et al. |
| 2015/0252061 A1 | 9/2015 | Mazitschek et al. |
| 2016/0032330 A1 | 2/2016 | Renata et al. |
| 2016/0040199 A1 | 2/2016 | Hyster |

FOREIGN PATENT DOCUMENTS

| | | |
|---|---|---|
| WO | 2014058729 A1 | 4/2014 |
| WO | 2014058744 A2 | 4/2014 |
| WO | 2016191612 A2 | 12/2016 |

OTHER PUBLICATIONS

Anding et al., "Olefin Cyclopropanation Catalyzed by Iridium(III) Porphyrin Complexes", Organometallics, Iowa State University Digital Repository, vol. 31, No. 9, Apr. 2012, pp. 3628-3635.
Bajaj et al., "Gram-scale Synthesis of Chiral Cyclopropane-Containing Drugs and Drug Precursors With Engineered Myoglobin Catalysts Featuring Complementary Stereoselectivity", Angew Chem Int Ed Engl., vol. 55, No. 52, Dec. 23, 2016, pp. 16110-16114.
Bordeaux et al., "Highly Diastereoselective and Enantioselective Olefin Cyclopropanation Using Engineered Myoglobin-Based Catalysts", Angewandte Chemie International Edition, vol. 54, No. 6, Feb. 2, 2015, pp. 1744-1748.
Chen et al., "Enzymatic Construction of Highly Strained Carbocycles", Science, vol. 360, No. 6384, Apr. 6, 2018, pp. 71-75.
Coelho et al., "A Serine-Substituted P450 Catalyzes Highly Efficient Carbene Transfer to Olefins in Vivo", Nature Chemical Biology, vol. 9, No. 8, Aug. 2013, pp. 485-487.
Coelho et al., "Olefin Cyclopropanation via Carbene Transfer Catalyzed by Engineered Cytochrome P450 Enzymes", Science, vol. 339, No. 6117, Jan. 18, 2013, pp. 307-310.
Cui et al., "Enantioselective Cyclopropenation of Alkynes With Acceptor/Acceptor-Substituted Diazo Reagents via Co(II)-Based Metalloradical Catalysis", Journal of the American Chemical Society, vol. 133, No. 10, Mar. 16, 2011, pp. 3304-3307.
Hyster et al., "Enzyme-Controlled Nitrogen-Atom Transfer Enables Regiodivergent C—H Amination", Journal of the American Chemical Society, vol. 136, No. 44, Nov. 5, 2014, pp. 15505-15508.
Kan et al., "Directed Evolution of Cytochrome C for Carbon-Silicon Bond Formation: Bringing Silicon to Life", Science, vol. 354, No. 6315, Nov. 25, 2016, pp. 1048-1051.
PCT/US2018/023622 , "International Search Report and Written Opinion", dated Aug. 31, 2018, 14 pages.
Prier et al., "Asymmetric Enzymatic Synthesis of Allylic Amines: A Sigmatropic Rearrangement Strategy", Angew Chem Int Ed Engl., vol. 55, No. 15, Apr. 4, 2016, pp. 4711-4715.
Renata et al., "Expanding the Enzyme Universe: Accessing Non-Natural Reactions by Mechanism-Guided Directed Evolution", Angew. Chem. Int. Ed, vol. 54, No. 11, Mar. 9, 2015, pp. 3351-3367.
Schneider et al., "Enzymatic Synthesis of a Bicyclobutane Fatty Acid by a Hemoprotein-lipoxygenase Fusion Protein From the Cyanobacterium Anabaena PCC 7120", PNAS, vol. 104, No. 48, Nov. 27, 2007, pp. 18941-18945.
Thibodeaux et al., "Enzymatic Chemistry of Cyclopropane, Epoxide, and Aziridine Biosynthesis", American Chemical Society, Chemical Reviews, vol. 112, No. 3, Mar. 14, 2012, pp. 1681-1709.
Uehara et al., "Enantioenriched Synthesis of Cyclopropenes with a Quaternary Stereocenter, Versatile Building Blocks", JACS Communication, vol. 133, No. 2, Jan. 19, 2011, pp. 170-171.
Wang et al., "Improved Cyclopropanation Activity of Histidine-Ligated Cytochrome P450 Enables Enantioselective Formal Synthesis of Levomilnacipran", Angewandte Chemie, vol. 53, No. 26, Jun. 23, 2014, pp. 6810-6813.

*Primary Examiner* — Suzanne M Noakes
*Assistant Examiner* — Jae W Lee
(74) *Attorney, Agent, or Firm* — Kilpatrick Townsend & Stockton LLP

(57) ABSTRACT

Provided herein are methods for producing products containing strained carbocycles, such as cyclopropene moieties and/or bicyclobutane moieties. The methods include combining an alkyne and a carbene precursor in the presence of a heme protein, e.g., a cytochrome P450, under conditions sufficient to form the strained carbocycle. Reaction mixtures for producing strained carbocycles are also described, as well as whole-cell catalysts comprising heme proteins and variants thereof for forming cyclopropenes, bicyclobutanes, and related products.

12 Claims, 15 Drawing Sheets
Specification includes a Sequence Listing.

FIG. 3
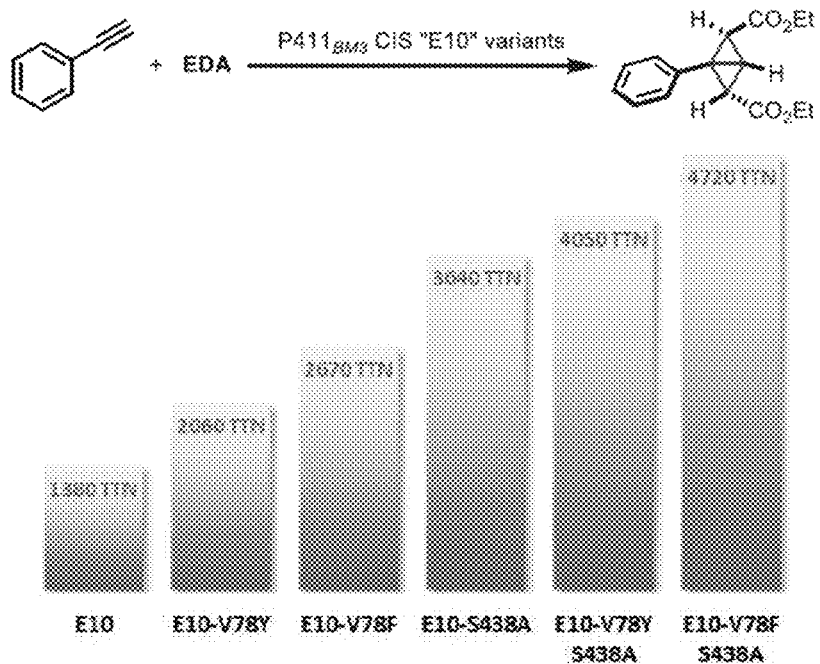
FIG. 4
| Ring Structure | Ring Strain (kcal/mol) | Ring Structure | Ring Strain (kcal/mol) |
|---|---|---|---|
| △ | 27 – 28 | □ | 31 – 34 |
| □ | 26 – 27 | ◇ | ~130 |
| △ (bicyclic) | 56 – 58 | | |
| ◇ | 66 – 69 | △ (tetrahedron) | ~140 |
FIG. 5A
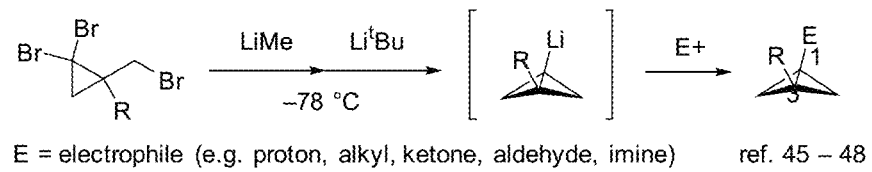
E = electrophile (e.g. proton, alkyl, ketone, aldehyde, imine)    ref. 45 – 48
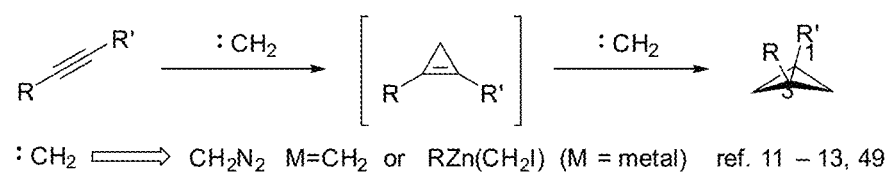
:CH₂ ⟹ CH₂N₂  M=CH₂ or RZn(CH₂I) (M = metal)    ref. 11 – 13, 49

Intramolecular nucleophilic substitution with halocyclobutanes

Intramolecular carbene addition to double bonds

Photo-induced cycloaddition a linolenic acid (highly unstable, ref. 23)
t1/2 » 3 days in DMSO for its methyl ester (ref. 66)

FIG. 7A
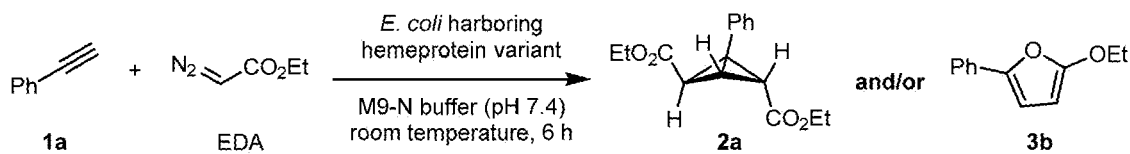
FIG. 7B
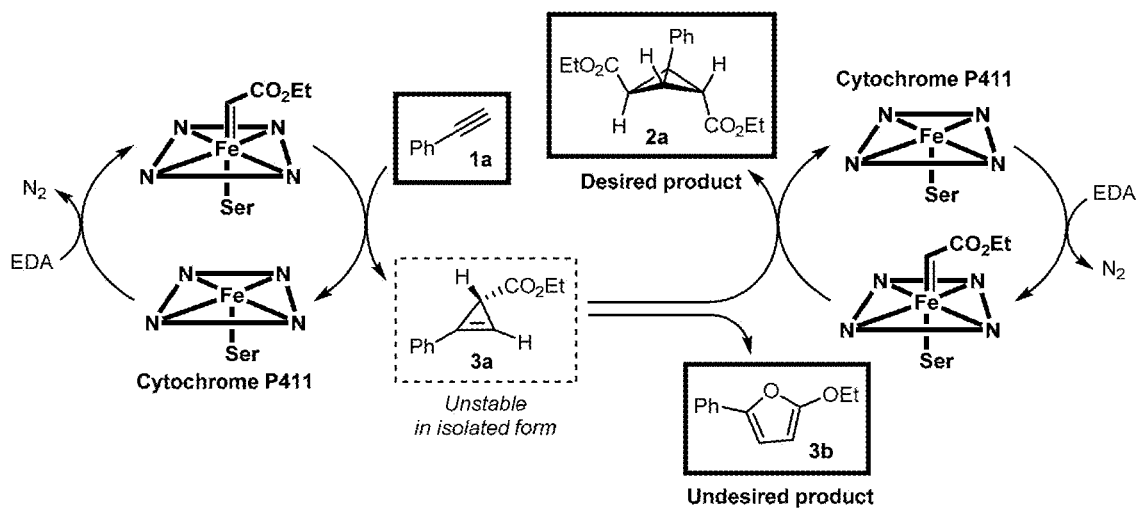
FIG. 7C
Ineffective catalysts (without product 2a or 3b):
Hemin    Hemin + BSA    P450-WT
P450-CIS    P411-CIS    P450-CIS H*
*Rma* cyt *c*    cyt *c* TDE    Myoglobin
Effective catalysts (with products 2a and/or 3b):
P411-S1 I263W:
  210 ± 20 TTN, 3b only
P411-S1 V87A I263F A268G A328V (P4):
  80 ± 10 TTN, 2a: 3b > 50: 1

SEQUENCE LISTING

<160> NUMBER OF SEQ ID NOS: 19

<210> SEQ ID NO 1
<211> LENGTH: 471
<212> TYPE: PRT
<213> ORGANISM: Bacillus megaterium

<400> SEQUENCE: 1

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365
```

-continued

```
Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg
465                 470

<210> SEQ ID NO 2
<211> LENGTH: 471
<212> TYPE: PRT
<213> ORGANISM: Artificial Sequence
<220> FEATURE:
<223> OTHER INFORMATION: synthethic P411-P4 variant of B. megaterium
      P450(BM3) heme domain

<400> SEQUENCE: 2

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255
```

```
Gln Ile Ile Thr Phe Leu Phe Ala Gly His Glu Gly Thr Ser Gly Leu
                260                 265                 270

Leu Ser Phe Ala Leu Tyr Phe Leu Val Lys Asn Pro His Val Leu Gln
            275                 280                 285

Lys Val Ala Glu Ala Ala Arg Val Leu Val Asp Pro Val Pro Ser
        290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Ser Leu Lys Pro Lys Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg
465                 470

<210> SEQ ID NO 3
<211> LENGTH: 471
<212> TYPE: PRT
<213> ORGANISM: Artificial Sequence
<220> FEATURE:
<223> OTHER INFORMATION: synthetic P411-E10 variant of B. megaterium
      P450(BM3) heme domain

<400> SEQUENCE: 3

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140
```

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
            165                 170                 175

Met Val Arg Ala Leu Asp Glu Val Met Asn Lys Leu Gln Arg Ala Asn
        180                 185                 190

Pro Asp Pro Ala Tyr Asp Glu Asn Lys Arg Gln Phe Gln Glu Asp
    195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
            245                 250                 255

Gln Ile Ile Thr Phe Leu Leu Ala Gly His Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Ser
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg
465                 470

<210> SEQ ID NO 4
<211> LENGTH: 1048
<212> TYPE: PRT
<213> ORGANISM: Bacillus megaterium

<400> SEQUENCE: 4

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

```
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
             100                 105                 110

Lys Gly Tyr His Ala Met Met Val Asp Ile Ala Val Gln Leu Val Gln
             115                 120                 125

Lys Trp Glu Arg Leu Asn Ala Asp Glu His Ile Glu Val Pro Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
             180                 185                 190

Pro Asp Asp Pro Ala Tyr Asp Glu Asn Lys Arg Gln Phe Gln Glu Asp
             195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
             260                 265                 270

Leu Ser Phe Ala Leu Tyr Phe Leu Val Lys Asn Pro His Val Leu Gln
             275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
             340                 345                 350

Leu Met Val Leu Ile Pro Gln Leu His Arg Asp Lys Thr Ile Trp Gly
             355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
             420                 425                 430

Ile Lys Glu Thr Leu Thr Leu Lys Pro Glu Gly Phe Val Val Lys Ala
             435                 440                 445

Lys Ser Lys Lys Ile Pro Leu Gly Gly Ile Pro Ser Pro Ser Thr Glu
450                 455                 460
```

```
Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
            850                 855                 860

Ser Asn Tyr Leu Ala Glu Leu Gln Glu Gly Asp Thr Ile Thr Cys Phe
865                 870                 875                 880
```

```
Ile Ser Thr Pro Gln Ser Glu Phe Thr Leu Pro Lys Asp Pro Glu Thr
                885                 890                 895

Pro Leu Ile Met Val Gly Pro Thr Gly Val Ala Pro Phe Arg Gly
        900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 5
<211> LENGTH: 1048
<212> TYPE: PRT
<213> ORGANISM: Artificial Sequence
<220> FEATURE:
<223> OTHER INFORMATION: synthetic full-length P411-P4 variant of B.
      megaterium P450(BM3)

<400> SEQUENCE: 5

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190
```

```
Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Phe Ala Gly His Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Ser
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605
```

```
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
            645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
            675                 680                 685
Pro Lys Glu Ala Ser Tyr Gln Glu Gly Asp His Leu Gly Val Ile Pro
690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Leu Leu Gln Tyr
            740                 745                 750
Val Glu Leu Gln Asp Pro Val Thr Arg Thr Gln Leu Arg Ala Met Ala
    755                 760                 765
Ala Lys Thr Val Cys Pro Pro His Lys Val Glu Leu Glu Ala Leu Leu
    770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
            805                 810                 815
Phe Ile Ala Leu Leu Pro Ser Ile Arg Pro Arg Tyr Tyr Ser Ile Ser
            820                 825                 830
Ser Ser Pro Arg Val Asp Glu Lys Gln Ala Ser Ile Thr Val Ser Val
        835                 840                 845
Val Ser Gly Glu Ala Trp Ser Gly Tyr Gly Glu Tyr Lys Gly Ile Ala
850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
            885                 890                 895
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
    915                 920                 925
Glu Ala His Leu Tyr Phe Gly Cys Arg Ser Pro His Glu Asp Tyr Leu
    930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
            965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
        995                 1000                1005
Val Glu Ala Thr Leu Met Lys Ser Tyr Ala Asp Val His Gln Val
    1010                1015                1020
```

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 6
<211> LENGTH: 1048
<212> TYPE: PRT
<213> ORGANISM: Artificial Sequence
<220> FEATURE:
<223> OTHER INFORMATION: Full-length P411-E10 variant of B. megaterium
      P450BM3

<400> SEQUENCE: 6

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Leu Ala Gly His Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

```
Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Val Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Ser
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750
```

Val Glu Leu Gln Asp Pro Val Thr Arg Thr Gln Leu Arg Ala Met Ala
            755                 760                 765

Ala Lys Thr Val Cys Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
    915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                1000                 1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 7
<211> LENGTH: 414
<212> TYPE: PRT
<213> ORGANISM: Pseudomonas putida

<400> SEQUENCE: 7

Thr Thr Glu Thr Ile Gln Ser Asn Ala Asn Leu Ala Pro Leu Pro Pro
1               5                  10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

```
Phe Ser Ser Glu Cys Pro Phe Ile Pro Arg Glu Ala Gly Glu Ala Tyr
                85                  90                  95

Asp Phe Ile Pro Thr Ser Met Asp Pro Glu Gln Arg Gln Phe Arg
            100                 105                 110

Ala Leu Ala Asn Gln Val Val Gly Met Pro Val Val Asp Lys Leu Glu
            115                 120                 125

Asn Arg Ile Gln Glu Leu Ala Cys Ser Leu Ile Glu Ser Leu Arg Pro
130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
                180                 185                 190

Phe Ala Glu Ala Lys Glu Ala Leu Tyr Asp Tyr Leu Ile Pro Ile Ile
            195                 200                 205

Glu Gln Arg Arg Gln Lys Pro Gly Thr Asp Ala Ile Ser Ile Val Ala
            210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
                260                 265                 270

Glu Leu Ile Glu Arg Pro Glu Arg Ile Pro Ala Ala Cys Glu Glu Leu
            275                 280                 285

Leu Arg Arg Phe Ser Leu Val Ala Asp Gly Arg Ile Leu Thr Ser Asp
290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
                340                 345                 350

Gly Ser His Leu Cys Leu Gly Gln His Leu Ala Arg Arg Glu Ile Ile
            355                 360                 365

Val Thr Leu Lys Glu Trp Leu Thr Arg Ile Pro Asp Phe Ser Ile Ala
            370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 8
<211> LENGTH: 153
<212> TYPE: PRT
<213> ORGANISM: Physeter catodon

<400> SEQUENCE: 8

Val Leu Ser Glu Gly Glu Trp Gln Leu Val Leu His Val Trp Ala Lys
1               5                   10                  15

Val Glu Ala Asp Val Ala Gly His Gly Gln Asp Ile Leu Ile Arg Leu
            20                  25                  30

Phe Lys Ser His Pro Glu Thr Leu Glu Lys Phe Asp Arg Phe Lys His
        35                  40                  45
```

```
Leu Lys Thr Glu Ala Glu Met Lys Ala Ser Glu Asp Leu Lys Lys His
 50                  55                  60

Gly Val Thr Val Leu Thr Ala Leu Gly Ala Ile Leu Lys Lys Lys Gly
 65                  70                  75                  80

His His Glu Ala Glu Leu Lys Pro Leu Ala Gln Ser His Ala Thr Lys
                 85                  90                  95

His Lys Ile Pro Ile Lys Tyr Leu Glu Phe Ile Ser Glu Ala Ile Ile
            100                 105                 110

His Val Leu His Ser Arg His Pro Gly Asp Phe Gly Ala Asp Ala Gln
        115                 120                 125

Gly Ala Met Asn Lys Ala Leu Glu Leu Phe Arg Lys Asp Ile Ala Ala
130                 135                 140

Lys Tyr Lys Glu Leu Gly Tyr Gln Gly
145                 150
```

<210> SEQ ID NO 9
<211> LENGTH: 140
<212> TYPE: PRT
<213> ORGANISM: Campylobacter jejuni

<400> SEQUENCE: 9

```
Met Thr Lys Glu Gln Ile Gln Ile Ile Lys Asp Cys Val Pro Ile Leu
 1               5                  10                  15

Gln Lys Asn Gly Glu Asp Leu Thr Asn Glu Phe Tyr Lys Ile Met Phe
                 20                  25                  30

Asn Asp Tyr Pro Glu Val Lys Pro Met Phe Asn Met Glu Lys Gln Ile
             35                  40                  45

Ser Gly Glu Gln Pro Lys Ala Leu Ala Met Ala Ile Leu Met Ala Ala
 50                  55                  60

Lys Asn Ile Glu Asn Leu Glu Asn Met Arg Ser Phe Val Asp Lys Val
 65                  70                  75                  80

Ala Ile Thr His Val Asn Leu Gly Val Lys Glu Glu His Tyr Pro Ile
                 85                  90                  95

Val Gly Ala Cys Leu Leu Lys Ala Ile Lys Asn Leu Leu Asn Pro Asp
            100                 105                 110

Glu Ala Thr Leu Lys Ala Trp Glu Val Ala Tyr Gly Lys Ile Ala Lys
        115                 120                 125

Phe Tyr Ile Asp Ile Glu Lys Lys Leu Tyr Asp Lys
130                 135                 140
```

<210> SEQ ID NO 10
<211> LENGTH: 146
<212> TYPE: PRT
<213> ORGANISM: Vitreoscilla stercoraria

<400> SEQUENCE: 10

```
Met Leu Asp Gln Gln Thr Ile Asn Ile Ile Lys Ala Thr Val Pro Val
 1               5                  10                  15

Leu Lys Glu His Gly Val Thr Ile Thr Thr Thr Phe Tyr Lys Asn Leu
                 20                  25                  30

Phe Ala Lys His Pro Glu Val Arg Pro Leu Phe Asp Met Gly Arg Gln
             35                  40                  45

Glu Ser Leu Glu Gln Pro Lys Ala Leu Ala Met Thr Val Leu Ala Ala
 50                  55                  60

Ala Gln Asn Ile Glu Asn Leu Pro Ala Ile Leu Pro Ala Val Lys Lys
 65                  70                  75                  80
```

```
Ile Ala Val Lys His Cys Gln Ala Gly Val Ala Ala His Tyr Pro
                85                  90                  95
Ile Val Gly Gln Glu Leu Leu Gly Ala Ile Lys Glu Val Leu Gly Asp
            100                 105                 110
Ala Ala Thr Asp Asp Ile Leu Asp Ala Trp Gly Lys Ala Tyr Gly Val
            115                 120                 125
Ile Ala Asp Val Phe Ile Gln Val Glu Ala Asp Leu Tyr Ala Gln Ala
        130                 135                 140
Val Glu
145

<210> SEQ ID NO 11
<211> LENGTH: 151
<212> TYPE: PRT
<213> ORGANISM: Mus musculus

<400> SEQUENCE: 11

Met Glu Arg Pro Glu Ser Glu Leu Ile Arg Gln Ser Trp Arg Val Val
1               5                   10                  15
Ser Arg Ser Pro Leu Glu His Gly Thr Val Leu Phe Ala Arg Leu Phe
            20                  25                  30
Ala Leu Glu Pro Ser Leu Leu Pro Leu Phe Gln Tyr Asn Gly Arg Gln
        35                  40                  45
Phe Ser Ser Pro Glu Asp Cys Leu Ser Ser Pro Glu Phe Leu Asp His
    50                  55                  60
Ile Arg Lys Val Met Leu Val Ile Asp Ala Ala Val Thr Asn Val Glu
65                  70                  75                  80
Asp Leu Ser Ser Leu Glu Glu Tyr Leu Thr Ser Leu Gly Arg Lys His
                85                  90                  95
Arg Ala Val Gly Val Arg Leu Ser Ser Phe Ser Thr Val Gly Glu Ser
            100                 105                 110
Leu Leu Tyr Met Leu Glu Lys Cys Leu Gly Pro Asp Phe Thr Pro Ala
        115                 120                 125
Thr Arg Thr Ala Trp Ser Arg Leu Tyr Gly Ala Val Val Gln Ala Met
    130                 135                 140
Ser Arg Gly Trp Asp Gly Glu
145                 150

<210> SEQ ID NO 12
<211> LENGTH: 151
<212> TYPE: PRT
<213> ORGANISM: Homo sapiens

<400> SEQUENCE: 12

Met Glu Arg Pro Glu Pro Glu Leu Ile Arg Gln Ser Trp Arg Ala Val
1               5                   10                  15
Ser Arg Ser Pro Leu Glu His Gly Thr Val Leu Phe Ala Arg Leu Phe
            20                  25                  30
Ala Leu Glu Pro Asp Leu Leu Pro Leu Phe Gln Tyr Asn Cys Arg Gln
        35                  40                  45
Phe Ser Ser Pro Glu Asp Cys Leu Ser Ser Pro Glu Phe Leu Asp His
    50                  55                  60
Ile Arg Lys Val Met Leu Val Ile Asp Ala Ala Val Thr Asn Val Glu
65                  70                  75                  80
Asp Leu Ser Ser Leu Glu Glu Tyr Leu Ala Ser Leu Gly Arg Lys His
                85                  90                  95
```

```
Arg Ala Val Gly Val Lys Leu Ser Ser Phe Ser Thr Val Gly Glu Ser
            100                 105                 110

Leu Leu Tyr Met Leu Glu Lys Cys Leu Gly Pro Ala Phe Thr Pro Ala
        115                 120                 125

Thr Arg Ala Ala Trp Ser Gln Leu Tyr Gly Ala Val Val Gln Ala Met
    130                 135                 140

Ser Arg Gly Trp Asp Gly Glu
145                 150

<210> SEQ ID NO 13
<211> LENGTH: 133
<212> TYPE: PRT
<213> ORGANISM: Methylacidiphilum infernorum

<400> SEQUENCE: 13

Met Ile Asp Gln Lys Glu Lys Glu Leu Ile Lys Glu Ser Trp Lys Arg
1               5                   10                  15

Ile Glu Pro Asn Lys Asn Glu Ile Gly Leu Leu Phe Tyr Ala Asn Leu
            20                  25                  30

Phe Lys Glu Glu Pro Thr Val Ser Val Leu Phe Gln Asn Pro Ile Ser
        35                  40                  45

Ser Gln Ser Arg Lys Leu Met Gln Val Leu Gly Ile Leu Val Gln Gly
    50                  55                  60

Ile Asp Asn Leu Glu Gly Leu Ile Pro Thr Leu Gln Asp Leu Gly Arg
65                  70                  75                  80

Arg His Lys Gln Tyr Gly Val Val Asp Ser His Tyr Pro Leu Val Gly
                85                  90                  95

Asp Cys Leu Leu Lys Ser Ile Gln Glu Tyr Leu Gly Gln Gly Phe Thr
            100                 105                 110

Glu Glu Ala Lys Ala Ala Trp Thr Lys Val Tyr Gly Ile Ala Ala Gln
        115                 120                 125

Val Met Thr Ala Glu
        130

<210> SEQ ID NO 14
<211> LENGTH: 190
<212> TYPE: PRT
<213> ORGANISM: Homo sapiens

<400> SEQUENCE: 14

Met Glu Lys Val Pro Gly Glu Met Glu Ile Glu Arg Arg Glu Arg Ser
1               5                   10                  15

Glu Glu Leu Ser Glu Ala Glu Arg Lys Ala Val Gln Ala Met Trp Ala
            20                  25                  30

Arg Leu Tyr Ala Asn Cys Glu Asp Val Gly Val Ala Ile Leu Val Arg
        35                  40                  45

Phe Phe Val Asn Phe Pro Ser Ala Lys Gln Tyr Phe Ser Gln Phe Lys
    50                  55                  60

His Met Glu Asp Pro Leu Glu Met Glu Arg Ser Pro Gln Leu Arg Lys
65                  70                  75                  80

His Ala Cys Arg Val Met Gly Ala Leu Asn Thr Val Val Glu Asn Leu
                85                  90                  95

His Asp Pro Asp Lys Val Ser Ser Val Leu Ala Leu Val Gly Lys Ala
            100                 105                 110

His Ala Leu Lys His Lys Val Glu Pro Val Tyr Phe Lys Ile Leu Ser
        115                 120                 125
```

```
Gly Val Ile Leu Glu Val Val Ala Glu Glu Phe Ala Ser Asp Phe Pro
            130                 135                 140

Pro Glu Thr Gln Arg Ala Trp Ala Lys Leu Arg Gly Leu Ile Tyr Ser
145                 150                 155                 160

His Val Thr Ala Ala Tyr Lys Glu Val Gly Trp Val Gln Gln Val Pro
                165                 170                 175

Asn Ala Thr Thr Pro Pro Ala Thr Leu Pro Ser Ser Gly Pro
                180                 185                 190

<210> SEQ ID NO 15
<211> LENGTH: 338
<212> TYPE: PRT
<213> ORGANISM: Ascaris suum

<400> SEQUENCE: 15

Met Arg Ser Leu Leu Leu Leu Ser Ile Val Phe Phe Val Val Thr Val
1               5                   10                  15

Ser Ala Asn Lys Thr Arg Glu Leu Cys Met Lys Ser Leu Glu His Ala
                20                  25                  30

Lys Val Asp Thr Ser Asn Glu Ala Arg Gln Asp Gly Ile Asp Leu Tyr
            35                  40                  45

Lys His Met Phe Glu Asn Tyr Pro Pro Leu Arg Lys Tyr Phe Lys Asn
        50                  55                  60

Arg Glu Glu Tyr Thr Ala Glu Asp Val Gln Asn Asp Pro Phe Phe Ala
65                  70                  75                  80

Lys Gln Gly Gln Lys Ile Leu Leu Ala Cys His Val Leu Cys Ala Thr
                85                  90                  95

Tyr Asp Asp Arg Glu Thr Phe Asn Ala Tyr Thr Arg Glu Leu Leu Asp
            100                 105                 110

Arg His Ala Arg Asp His Val His Met Pro Pro Glu Val Trp Thr Asp
        115                 120                 125

Phe Trp Lys Leu Phe Glu Glu Tyr Leu Gly Lys Lys Thr Thr Leu Asp
130                 135                 140

Glu Pro Thr Lys Gln Ala Trp His Glu Ile Gly Arg Glu Phe Ala Lys
145                 150                 155                 160

Glu Ile Asn Lys His Gly Arg His Ala Val Arg His Gln Cys Met Arg
                165                 170                 175

Ser Leu Gln His Ile Asp Ile Gly His Ser Glu Thr Ala Lys Gln Asn
            180                 185                 190

Gly Ile Asp Leu Tyr Lys His Met Phe Glu Asn Tyr Pro Ser Met Arg
        195                 200                 205

Glu Ala Phe Lys Asp Arg Glu Asn Tyr Thr Ala Glu Asp Val Gln Lys
210                 215                 220

Asp Pro Phe Phe Val Lys Gln Gly Gln Arg Ile Leu Leu Ala Cys His
225                 230                 235                 240

Leu Leu Cys Ala Ser Tyr Asp Asp Glu Glu Thr Phe His Met Tyr Val
                245                 250                 255

His Glu Leu Met Glu Arg His Glu Arg Leu Gly Val Gln Leu Pro Asp
            260                 265                 270

Gln His Trp Thr Asp Phe Trp Lys Leu Phe Glu Glu Phe Leu Glu Lys
        275                 280                 285

Lys Ser His Leu Cys Glu His Thr Lys His Ala Trp Ala Val Ile Gly
        290                 295                 300

Lys Glu Phe Ala Tyr Glu Ala Thr Arg His Gly Lys Glu His His Glu
305                 310                 315                 320
```

```
His Lys Glu Glu His Lys Glu Glu His Lys Glu Glu His Lys Glu Glu
                325                 330                 335

Gln His

<210> SEQ ID NO 16
<211> LENGTH: 132
<212> TYPE: PRT
<213> ORGANISM: Bacillus subtilis

<400> SEQUENCE: 16

Met Gly Gln Ser Phe Asn Ala Pro Tyr Glu Ala Ile Gly Glu Glu Leu
1               5                   10                  15

Leu Ser Gln Leu Val Asp Thr Phe Tyr Glu Arg Val Ala Ser His Pro
            20                  25                  30

Leu Leu Lys Pro Ile Phe Pro Ser Asp Leu Thr Glu Thr Ala Arg Lys
        35                  40                  45

Gln Lys Gln Phe Leu Thr Gln Tyr Leu Gly Gly Pro Pro Leu Tyr Thr
    50                  55                  60

Glu Glu His Gly His Pro Met Leu Arg Ala Arg His Leu Pro Phe Pro
65                  70                  75                  80

Ile Thr Asn Glu Arg Ala Asp Ala Trp Leu Ser Cys Met Lys Asp Ala
                85                  90                  95

Met Asp His Val Gly Leu Glu Gly Ile Arg Glu Phe Leu Phe Gly
            100                 105                 110

Arg Leu Glu Leu Thr Ala Arg His Met Val Asn Gln Thr Glu Ala Glu
        115                 120                 125

Asp Arg Ser Ser
    130

<210> SEQ ID NO 17
<211> LENGTH: 195
<212> TYPE: PRT
<213> ORGANISM: Methanosarcina acetivorans

<400> SEQUENCE: 17

Met Ser Val Glu Lys Ile Pro Gly Tyr Thr Tyr Gly Glu Thr Glu Asn
1               5                   10                  15

Arg Ala Pro Phe Asn Leu Glu Asp Leu Lys Leu Leu Lys Glu Ala Val
            20                  25                  30

Met Phe Thr Ala Glu Asp Glu Tyr Ile Gln Lys Ala Gly Glu Val
        35                  40                  45

Leu Glu Asp Gln Val Glu Glu Ile Leu Asp Thr Trp Tyr Gly Phe Val
    50                  55                  60

Gly Ser His Pro His Leu Leu Tyr Tyr Phe Thr Ser Pro Asp Gly Thr
65                  70                  75                  80

Pro Asn Glu Lys Tyr Leu Ala Ala Val Arg Lys Arg Phe Ser Arg Trp
                85                  90                  95

Ile Leu Asp Thr Cys Asn Arg Ser Tyr Asp Gln Ala Trp Leu Asp Tyr
            100                 105                 110

Gln Tyr Glu Ile Gly Leu Arg His His Arg Thr Lys Lys Asn Gln Thr
        115                 120                 125

Asp Asn Val Glu Ser Val Pro Asn Ile Gly Tyr Arg Tyr Leu Val Ala
    130                 135                 140

Phe Ile Tyr Pro Ile Thr Ala Thr Met Lys Pro Phe Leu Ala Arg Lys
145                 150                 155                 160
```

Gly His Thr Pro Glu Glu Val Glu Lys Met Tyr Gln Ala Trp Phe Lys
            165                 170                 175

Ala Thr Thr Leu Gln Val Ala Leu Trp Ser Tyr Pro Tyr Val Lys Tyr
            180                 185                 190

Gly Asp Phe
        195

<210> SEQ ID NO 18
<211> LENGTH: 195
<212> TYPE: PRT
<213> ORGANISM: Aeropyrum pernix

<400> SEQUENCE: 18

Met Thr Pro Ser Asp Ile Pro Gly Tyr Asp Tyr Gly Arg Val Glu Lys
1               5                   10                  15

Ser Pro Ile Thr Asp Leu Glu Phe Asp Leu Leu Lys Lys Thr Val Met
            20                  25                  30

Leu Gly Glu Lys Asp Val Met Tyr Leu Lys Lys Ala Cys Asp Val Leu
        35                  40                  45

Lys Asp Gln Val Asp Glu Ile Leu Asp Leu Trp Tyr Gly Trp Val Ala
    50                  55                  60

Ser Asn Glu His Leu Ile Tyr Tyr Phe Ser Asn Pro Asp Thr Gly Glu
65                  70                  75                  80

Pro Ile Lys Glu Tyr Leu Glu Arg Val Arg Ala Arg Phe Gly Ala Trp
                85                  90                  95

Ile Leu Asp Thr Thr Cys Arg Asp Tyr Asn Arg Glu Trp Leu Asp Tyr
            100                 105                 110

Gln Tyr Glu Val Gly Leu Arg His His Arg Ser Lys Lys Gly Val Thr
        115                 120                 125

Asp Gly Val Arg Thr Val Pro His Ile Pro Leu Arg Tyr Leu Ile Ala
    130                 135                 140

Phe Ile Tyr Pro Ile Thr Ala Thr Ile Lys Pro Phe Leu Ala Lys Lys
145                 150                 155                 160

Gly Gly Ser Pro Glu Asp Ile Glu Gly Met Tyr Asn Ala Trp Phe Lys
                165                 170                 175

Ser Val Val Leu Gln Val Ala Ile Trp Ser His Pro Tyr Thr Lys Glu
            180                 185                 190

Asn Asp Trp
        195

<210> SEQ ID NO 19
<211> LENGTH: 192
<212> TYPE: PRT
<213> ORGANISM: Pyrobaculum ferrireducens

<400> SEQUENCE: 19

Met Arg Glu Ile Pro Gly Tyr Glu Phe Gly Lys Val Pro Asp Ala Pro
1               5                   10                  15

Ile Ser Asp Glu Glu Phe Glu Leu Leu Lys Lys Ser Val Met Trp Thr
            20                  25                  30

Glu Glu Asp Glu Lys Tyr Arg Lys Leu Ala Cys Glu Val Leu Lys Gly
        35                  40                  45

Gln Val Glu Gln Ile Leu Asp Leu Trp Tyr Gly Trp Val Gly Ser Asn
    50                  55                  60

Pro His Leu Val Tyr Tyr Phe Gly Asp Arg Ser Gly Arg Pro Ile Pro
65                  70                  75                  80

| | | | | | | | | | | | | | |
|---|---|---|---|---|---|---|---|---|---|---|---|---|---|
| Gln | Tyr | Leu | Glu | Ala 85 | Val | Arg | Lys | Arg 90 | Phe | Gly | Gln | Trp | Ile Leu Asp 95 |
| Thr | Val | Cys | Arg 100 | Ser | Tyr | Asp | Arg | Gln 105 | Trp | Leu | Asn | Tyr | Val Tyr Glu 110 |
| Ile | Gly | Leu | Arg 115 | His | His | Arg | Thr 120 | Lys | Lys | Gly | Lys | Thr 125 | Asp Gly Val |
| Glu | Thr | Val 130 | Glu | His | Ile | Pro 135 | Leu | Arg | Tyr | Met 140 | Val | Ala | Phe Ile Ala |
| Pro 145 | Ile | Gly | Leu | Thr | Ile 150 | Lys | Pro | Phe | Leu | Glu 155 | Lys | Gly | Gly His Pro 160 |
| Pro | Asp | Val | Val | Glu 165 | Lys | Met | Trp | Ala | Ala 170 | Trp | Ile | Lys | Ser Val Val 175 |
| Leu | Gln | Val | Ala | Ile 180 | Trp | Ser | His | Pro 185 | Tyr | Ala | Lys | Pro | Gly Glu Trp 190 |

BIOCATALYTIC SYNTHESIS OF STRAINED CARBOCYCLES

CROSS-REFERENCES TO RELATED APPLICATIONS

The present application claims priority to U.S. Provisional Pat. Appl. No. 62/474,435, filed on Mar. 21, 2017, and U.S. Provisional Pat. Appl. No. 62/583,073, filed on Nov. 8, 2017, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under Grant Nos. CBET1403077 and MCB1513007 awarded by the National Science Foundation. The government has certain rights in the invention.

REFERENCE TO SUBMISSION OF A SEQUENCE LISTING AS A TEXT FILE

The Sequence Listing written in file SEQ_086544-1074284-020920US_ST25.txt created on Apr. 18, 2018, 62,516 bytes, machine format IBM-PC, MS-Windows operating system, is hereby incorporated by reference in its entirety for all purposes.

BACKGROUND OF THE INVENTION

Carbocycles serve as important structural motifs in different fields. (See, e.g., Chen, et al. *Chem. Soc. Rev.* 2012, 41, 4631; Williams, et al. *Bioorg. Med. Chem.* 2012, 20, 3710; Triola, et al. *J. Org. Chem.* 2003, 68, 9924; Ando, et al. *Bioorg. Med. Chem.* 1999, 7, 571.) The higher ring strain energy of cyclopropenes, methylenecyclopropanes and bicyclobutanes, makes these compounds far more reactive than other ring systems. (See, Wiberg. *Angew. Chem. Int. Ed.* 1986, 25, 312; Nakamura, et al. *Chem. Rev.* 2003, 103, 1295; Trost. *Angew. Chem. Int. Ed.* 1986, 25, 1.) In synthetic chemistry, these highly strained rings have been investigated as versatile building blocks with numerous derivatization possibilities; this has led to broad applications of these three-membered carbocycles in pharmaceutical development, chemical biology, material science, etc. (See, e.g., Marek, et al. *Angew. Chem. Int. Ed.* 2007, 46, 7364; Rubin, et al. *Chem. Rev.* 2007, 107, 3117; Fox, et al. *Curr. Org. Chem.* 2005, 9, 719; Parra, et al. *J. Am. Chem. Soc.,* 2014, 136, 15833; Elling, et al. *Chem. Commun.* 2016, 52, 9097.) For instance, difunctionalization of cyclopropenes can introduce various functional groups to the rings, which furnishes practical approaches to highly functionalized three-membered ring structures in pharmaceutical compounds. (See, Tarwade, et al. *J. Am. Chem. Soc.* 2009, 131, 5382; O'Rourke, et al. *Org. Lett.* 2016, 18, 1250; Delaye, et al. *Angew. Chem. Int. Ed.* 2013, 52, 5333; Zhang, et al. *Angew. Chem. Int. Ed.* 2016, 55, 714.) Cyclopropenes can undergo in vivo cycloaddition reactions and function as amenable bioorthogonal fluorescent tags for live cell imaging. (See, Patterson, et al. *J. Am. Chem. Soc.* 2012, 134, 18638; et al. *J. Am. Chem. Soc.* 2013, 135, 13680; et al. *Angew. Chem. Int. Ed.* 2012, 51, 7476.) Besides, bicyclo[1.1.0]butane, is also very useful for constructing a multitude of complicated structural scaffolds in synthetic chemistry. (See, Walczak, et al. *Acc. Chem. Res.* 2015, 48, 1149; Wipf, et al. *Angew. Chem. Int. Ed.* 2006, 45, 4172; Gianatassio, et al. *Science* 2016, 351, 241; Wipf, et al. *Am. Chem. Soc.* 2003, 125, 14694; Panish, et al. *Angew. Chem. Int. Ed.* 2016, 55, 4983.)

To fully realize the broad applicability of cyclopropenes and bicyclobutanes, it is highly desirable to develop practical and efficient methods for synthesizing these molecules with high selectivity. Transition metal-catalyzed carbene transfer to alkynes stands out as the most commonly used strategy to prepare cyclopropenes enantioselectively. (See, e.g., Doyle, et al. *J. Am. Chem. Soc.* 1994, 116, 8492; Lou, et al. *J. Am. Chem. Soc.* 2004, 126, 8916; Briones, et al. *J. Am. Chem. Soc.* 2010, 132, 17211; Uehara, et al. *J. Am. Chem. Soc.* 2011, 133, 170; Goto, et al. *Angew. Chem. int. Ed.* 2011, 50, 6803; Cui, et al. *J. Am. Chem. Soc.* 2011, 133, 3304; Briones, et al. *J. Am. Chem. Soc.* 2012, 134, 11916.) Although synthetic chemists have exploited various transition metal catalysts (e.g., rhodium, iridium, cobalt, copper and gold complexes) to achieve alkyne cyclopropenation, there are still many challenges to be addressed: 1) most existing methods are limited to conjugated carbene precursors with phenyl or cyano groups to stabilize the carbenoid intermediates to achieve good enantio-/chemo-selectivity; 2) complicated chiral ligands or catalytic complexes require multiple-step preparation (4-15 steps); 3) the catalytic efficiency is generally very low with <100 turnovers. For bicyclobutane synthesis, a three-step sequence is commonly involved, which relies on the use of excess organolithium reagents, rendering it less practical for broad substrate scope and industrial production. (See, Dueker, et al. *Tetrahedron Lett.* 1985, 26, 3555; Rehm, et al. *Eur. J. Org. Chem.* 1999, 2079.)

Unlike synthetic catalysts, which require elaborate design, multiple-step preparation and optimization, natural enzymes are genetically encoded and assembled in living cells, making them readily accessible and tunable with molecular biology techniques. (See, e.g., Turner, et al. *Nat. Chem. Biol.* 2013, 9, 285; Kohler, et al. *Chem. Commun.* 2015, 51, 450.) Beyond this, enzymatic reactions commonly operate with high efficiency and selectivity (chemo-, regio- and/or stereo-) under mild conditions, offering significant advantages in terms of reduced environmental impact and greater cost-effectiveness. (See, Wohlgemuth. *Curr. Opin. Biotechnol.* 2010, 21, 713; Steen, et al. *Nature* 2010, 463, 559; Peralta Yahya, et al. *Nature* 2012, 488, 320; Atsumi, et al. *Nature* 2008, 451, 86.) Due to the scarcity of cyclopropenes and bicyclobutanes in nature, no native enzymes have been discovered to catalyze the construction of these highly strained three-membered carbocycles to date. (See, Schneider, et al. *Proc. Natl. Acad. Sci. U.S.A.* 2007, 104, 18941).

Over the last several years, the Arnold lab has been investigating heme-dependent metalloenzymes for non-natural biocatalytic activities, including alkene cyclopropanation, carbenoid N—H insertion, aziridination, sulfimidation, and nitrenoid C—H insertion. See, e.g., Hernandez, Kan, Arnold, et al. *ACS Catalysis* 2016, 6, 7810; Renata, Arnold, et al. *Angew. Chem. Int. Ed.* 2015, 54, 3351; Wang, Arnold, et al. *Chem. Sci.* 2014, 5, 598; Hyster & Arnold. *Isr. J. Chem.* 2015, 55, 14; Coelho, Arnold, et al. *Nat. Chem. Biol.* 2013, 9, 485; Arnold. *Rev. Biophys.* 2015, 48, 404; Coelho, Arnold, et al. *Science* 2013, 339, 307; Kan, Chen, Arnold, et al. *Science* 2016, 354, 1048; Kan, Huang, Chen, Arnold, et al. *Nature* 2017, 552, 13. Now described herein is an efficient and practical protocol for synthesizing these highly strained carbocycles using hemoproteins engineered via directed evolution that catalyze carbene chemistry.

BRIEF SUMMARY OF THE INVENTION

Provided herein are methods for producing products containing cyclopropene moieties and/or bicyclobutane moieties. The methods include combining an alkyne and a carbene precursor in the presence of a heme protein or a variant thereof under conditions sufficient to form the cyclopropene moiety and or the bicyclobutane moiety.

In some embodiments, the heme protein is a cytochrome P450, a globin, a protoglobin, or a variant thereof. In some embodiments, the heme protein is *Bacillus megaterium* cytochrome P450$_{BM3}$ or a variant thereof. In some embodiments, the carbene precursor is a diazo compound such as an α-diazoester.

Also provided are reaction mixtures for producing products containing cyclopropenes and bicyclobutanes, as well as whole-cell catalysts comprising heme proteins and variants thereof for forming such products.

BRIEF DESCRIPTION OF THE DRAWINGS

FIG. 3 shows the P450-catalyzed bicyclobutanation of phenylacetylene.

FIG. 4 shows compounds with ring structures and calculated ring strains. The 4-membered carbocycles, bicyclo[1.1.0]but-1(3)-ene and tricyclo[1.1.0.02,4]butane (tetrahedrane) (with calculated strain energy) have never been isolated, although their derivatives with bulky substituents might be synthesized in stable form under certain conditions.

FIG. 5A shows two major synthetic methods for forming bicyclobutanes.

FIG. 7A shows the reaction of carbene transfer to an alkyne catalyzed by an engineered hemeprotein.

FIG. 7B shows the proposed catalytic cycle of carbene transfer to phenylacetylene to form cyclopropene and bicyclobutane structures.

FIG. 7C shows the screening of hemin and hemeprotein catalysts for bicyclobutane formation (BSA=bovine serum albumin).

DETAILED DESCRIPTION OF THE INVENTION

I. Summary

Figure 1:
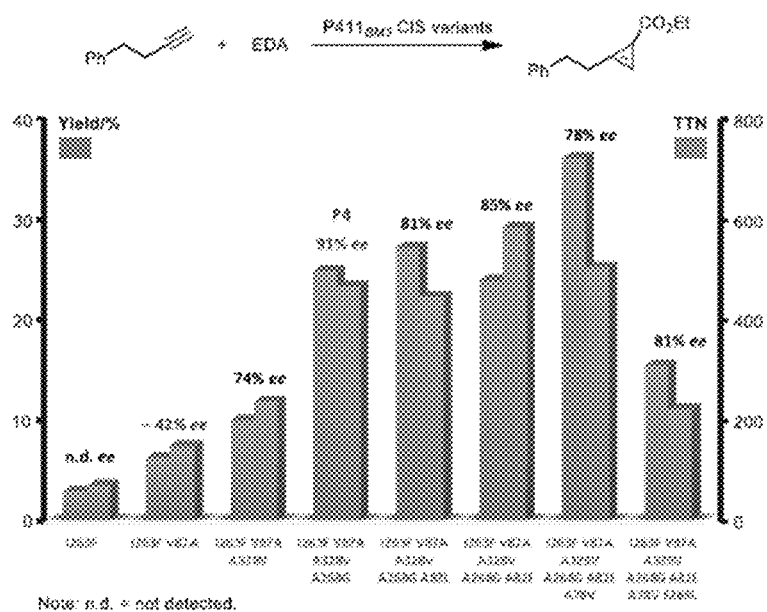
FIG. 1 shows the results of P450-catalyzed alkyne cyclopropenation. Left bars=% yield; right bars=total turnover number (TTN).

Demonstrated herein is a hemoprotein-catalyzed protocol for constructing strained carobcycles such as cyclopropenes and bicyclobutanes. Described herein is the first use of iron-based catalysts for alkyne cyclopropanation and the first example of enantioselective bicyclobutanation through carbene transfer to alkyne. By using directed evolution, it was possible to improve the reactivity of cytochrome P450s for the desired construction of highly strained three-membered carbon rings. With the engineered enzymes, expressed and used in whole bacterial cells, chemoselective and stereodivergent cyclopropenation of aliphatic alkynes was achieved with total turnover numbers (TTNs) up to 3300 and enantiomeric excesses (ee's) up to >99.5%. Also provided herein is a bicyclobutanation transformation sequence starting from aromatic alkynes with TTNs up to 1800. After hydrolysis, the bicyclobutane products can be used to synthesize strained polyesters and other products. The methods described herein can therefore be used to provide a number of useful strained carbocycles. Carbocycles such as cyclopropenes and bicyclobutanes include several classes of compounds including, but not limited to, natural products, pharmaceutical compounds, precursors for industrial products such as polymers, functional materials such as stimuli-responsive materials and self-healing materials, and labeling reagents for biological systems.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "heme protein variant" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The term "whole cell catalyst" includes cells expressing heme-containing enzymes, wherein the whole cell catalyst displays cyclopropene formation activity or bicyclobutane formation activity.

The term "carbene precursor" includes molecules that can be decomposed in the presence of metal (or enzyme) catalysts to form structures that contain at least one divalent carbon with two unshared valence shell electrons (i.e., carbenes) and that can be transferred to a carbon-hydrogen bond, a carbon-carbon bond, a carbon-sulfur bond, a carbon-nitrogen bond, a carbon-boron bond, or a carbon-phosphorus bond to form various carbon ligated products. Examples of carbene precursors include, but are not limited to, diazo reagents, diazirene reagents, and epoxide reagents.

As used herein, the term "anaerobic", when used in reference to a reaction, culture or growth condition, is intended to mean that the concentration of oxygen is less than about 25 µM, preferably less than about 5 µM, and even more preferably less than 1 µM. The term is also intended to include sealed chambers of liquid or solid medium maintained with an atmosphere of less than about 1% oxygen. Preferably, anaerobic conditions are achieved by sparging a reaction mixture with an inert gas such as nitrogen or argon.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. For example, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. For example, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted. For example, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. For example, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. For example, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. For example, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be unsubstituted or substituted. For example, "substituted heteroaryl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. For example, "substituted alkoxy" groups can be substituted with one or more moieties selected from halo, hydroxy, amino, alkylamino, alkoxy, haloalkyl, carboxy, amido, nitro, oxo, and cyano.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. groups can be unsubstituted or substituted. For example, "substituted alkylthio" groups can be substituted with one or more moieties selected from halo, hydroxy, amino, alkylamino, alkoxy, haloalkyl, carboxy, amido, nitro, oxo, and cyano.

As used herein, the term "heteroalkyl" refers to an alkyl group having one or more non-adjacent methylene (i.e., $CH_2$) units that is replaced by O, S, or NH. A carbon atom is the point of attachment for the heteroalkyl group to the remainder of the molecule, but the methylene replacement can occur at any other point along the carbon backbone. In the case of oxygen for example, replacement of $CH_2$ can occur in the middle of an alkyl group (e.g., in the middle of a propyl group, forming methoxymethyl with the formula $CH_3OCH_2$—) or at the end of the alkyl group (e.g., at the end of the propyl group, forming hydroxyethyl with the formula $HOCH_2CH_2$—).

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "alkylsilyl" refers to a moiety —SiR$_3$, wherein at least one R group is alkyl and the other R groups are H or alkyl. The alkyl groups can be substituted with one more halogen atoms.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —NR$_3$, wherein each R group is H or alkyl.

As used herein, the term "amido" refers to a moiety —NRC(O)R or —C(O)NR$_2$, wherein each R group is H or alkyl.

As used herein, the term "phosphine" refers to a moiety —PR$_3$, wherein each R group is H, alkyl, cycloalkyl, aryl, or heterocyclyl.

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98

(1994)). The term nucleic acid is used interchangeably with gene, cDNA, and mRNA encoded by a gene.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes all 64 codons and represents all 20 naturally-occurring amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

III. Description of the Embodiments

Provided herein are methods for the formation of cyclopropenes and bicyclobutanes. In certain aspects, the present invention provides a method for producing a cyclopropene product in the presence of an aliphatic alkyne, a diazo substrate, and a cytochrome P450 enzyme according to Equation 1:

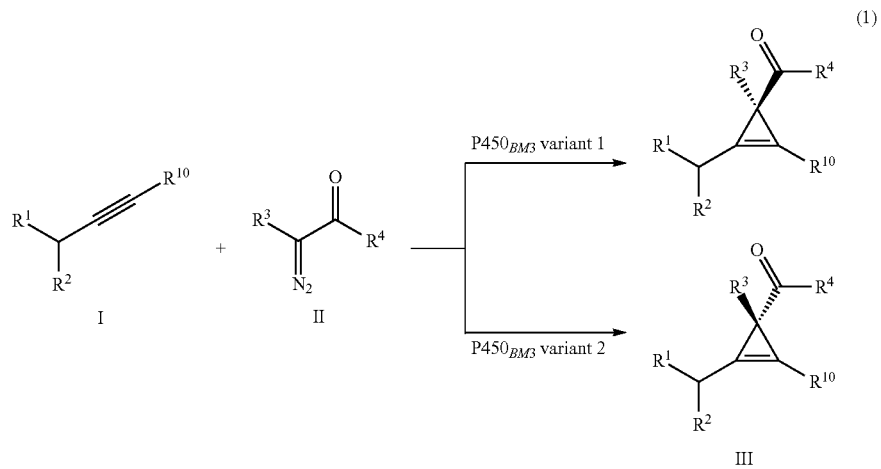

wherein

R¹⁰ is selected from the group consisting of H and CR¹R²;

each R¹⁰ is independently selected from the group consisting of H, $C_{1-18}$ alkyl, $C_{1-18}$ haloalkyl, $C_{2-18}$ alkenyl, $C_{2-18}$ alkynyl, ($C_{3-10}$ cycloalkyl)-$L^1$-, ($C_{6-10}$ aryl)-$L^1$-, (5- to 10-membered heteroaryl)-$L^1$-, (5- to 10-membered heterocyclyl)-$L^1$-, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$C_{1-18}$ alkyl, $C_{3-10}$ cycloalkyl, $C_{6-10}$ aryl, 5- to 10-membered heteroaryl, and 5- to 10-membered heterocyclyl in $R^1$ are optionally and independently substituted with one or more $R^{1a}$;

each $R^{1a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^1$ is selected from the group consisting of a bond and $C_{1-20}$ alkylene;

when $L^1$ is $C_{2-20}$ alkylene, one or more non-adjacent $CH_2$ groups are optionally and independently replaced with O, S, or NH;

when $L^1$ is $C_{3-20}$ alkylene, one or more pairs of adjacent $CH_2$ groups are optionally and independently replaced with C(O)O or C(O)NH;

each $R^2$ is independently selected from the group consisting of H, $C_{1-18}$ alkyl, $C_{1-18}$ haloalkyl, $C_{2-18}$ alkenyl, $C_{2-18}$ alkynyl, ($C_{3-10}$ cycloalkyl)-$L^2$-, ($C_{6-10}$ aryl)-$L^2$-, (5- to 10-membered heteroaryl)-$L^2$-, (5- to 10-membered heterocyclyl)-$L^2$-, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$C_{1-18}$ alkyl, $C_{3-10}$ cycloalkyl, $C_{6-10}$ aryl, 5- to 10-membered heteroaryl, and 5- to 10-membered heterocyclyl in $R^2$ are optionally and independently substituted with one or more $R^{2a}$;

each $R^{2a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^2$ is selected from the group consisting of a bond and $C_{1-20}$ alkylene;

when $L^2$ is $C_{2-20}$ alkylene, one or more non-adjacent $CH_2$ groups are optionally and independently replaced with O, S, or NH;

when $L^2$ is $C_{3-20}$ alkylene, one or more pairs of adjacent $CH_2$ groups are optionally and independently replaced with C(O)O or C(O)NH;

$R^3$ and $R^4$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$; and each $R^7$, $R^8$, and $R^9$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl.

In some embodiments, $R^1$ and $R^2$ are independently selected from the group consisting of H, optionally substituted $C_{1-18}$ alkyl, $C_{1-18}$ polyfluoroalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

In some embodiments, $R^3$ and $R^4$ are independently selected from the group consisting of H, optionally substituted $C_{1-18}$ alkyl, $C_{1-18}$ polyfluoroalkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

In certain aspects, the present invention provides a method for producing a bicyclobutane product in the presence of an alkyne, a diazo substrate, and a hemoprotein according to Equation 2:

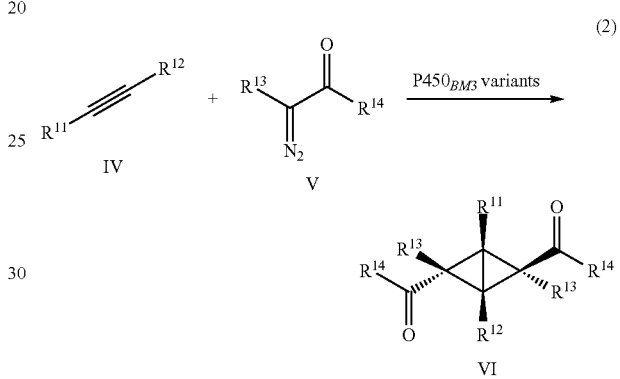

(2)

wherein $R^{11}$ is selected from the group consisting of H, $C_{1-18}$ alkyl, $C_{1-18}$ haloalkyl, $C_{2-18}$ alkenyl, $C_{2-18}$ alkynyl, ($C_{3-10}$ cycloalkyl)-$L^{11}$-, ($C_{6-10}$ aryl)-$L^{11}$-, (5- to 10-membered heteroaryl)-$L^{11}$-, (5- to 10-membered heterocyclyl)-$L^{11}$-, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$, and $P(O)(OR^{17})_2$;

$C_{1-18}$ alkyl, $C_{3-10}$ cycloalkyl, $C_{6-10}$ aryl, 5- to 10-membered heteroaryl, and 5- to 10-membered heterocyclyl in $R^{11}$ are optionally and independently substituted with one or more $R^{11a}$;

each $R^{11a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^{11}$ is selected from the group consisting of a bond and $C_{1-20}$ alkylene;

when $L^{11}$ is $C_{2-20}$ alkylene, one or more non-adjacent $CH_2$ groups are optionally and independently replaced with O, S, or NH;

when $L^{11}$ is $C_{3-20}$ alkylene, one or more pairs of adjacent $CH_2$ groups are optionally and independently replaced with C(O)O or C(O)NH;

$R^{12}$ is selected from the group consisting of H, $C_{1-18}$ alkyl, $C_{1-18}$ haloalkyl, $C_{2-18}$ alkenyl, $C_{2-18}$ alkynyl, ($C_{3-10}$ cycloalkyl)-$L^{12}$-, ($C_{6-10}$ aryl)-$L^{12}$-, (5- to 10-membered heteroaryl)-$L^{12}$-, (5- to 10-membered heterocyclyl)-$L^{12}$-, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$, and $P(O)(OR^{17})_2$;

$C_{1-18}$ alkyl, $C_{3-10}$ cycloalkyl, $C_{6-10}$ aryl, 5- to 10-membered heteroaryl, and 5- to 10-membered heterocyclyl in $R^{12}$ are optionally and independently substituted with one or more $R^{12a}$;

each $R^{12a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^{12}$ is selected from the group consisting of a bond and $C_{1-20}$ alkylene;

when $L^{12}$ is $C_{2-20}$ alkylene, one or more non-adjacent $CH_2$ groups are optionally and independently replaced with O, S, or NH;

when $L^{12}$ is $C_{3-20}$ alkylene, one or more pairs of adjacent $CH_2$ groups are optionally and independently replaced with C(O)O or C(O)NH;

$R^{13}$ and $R^{14}$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$ and $P(O)(OR^{17})_2$; and each $R^{17}$, $R^{18}$, and $R^{19}$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl.

In some embodiments, $R^{11}$ and $R^{12}$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$ and $P(O)(OR^{17})_2$.

In some embodiments, $R^{13}$ and $R^{14}$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$ and $P(O)(OR^{17})_2$.

This method produces products of Formula III and Formula VI, in stereochemically pure form or as a mixture of stereochemically isomeric forms. Exemplary catalysts used in this method include hemoproteins of the sort described in US 2014/0242647 A1.

A. Heme Proteins

The terms "heme protein" and "heme enzyme" are used herein to include any member of a group of proteins containing heme as a prosthetic group. Non-limiting examples of heme proteins include globins, cytochromes, oxidoreductases, any other protein containing a heme as a prosthetic group, and combinations thereof. Heme-containing globins include, but are not limited to, hemoglobin, myoglobin, and combinations thereof. Heme-containing cytochromes include, but are not limited to, cytochrome P450, cytochrome b, cytochrome c1, cytochrome c, and combinations thereof. Heme-containing oxidoreductases include, but are not limited to, catalases, oxidases, oxygenases, haloperoxidases, peroxidases, and combinations thereof. In some instances, the globin protein is from *Methylacidiphilum infernorum*. In some other instances, the cytochrome P450 protein is a cytochrome P450 BM3 (CYP102A1) protein. Exemplary catalysts used in this method include, but are not limited to, heme proteins of the sort described in US 20140242647 A1.

In some embodiments, the heme protein is a member of one of the enzyme classes set forth in Table 1. In other embodiments, the heme protein is a variant or homolog of a member of one of the enzyme classes set forth in Table 1. In yet other embodiments, the heme protein comprises or consists of the heme domain of a member of one of the enzyme classes set forth in Table 1 or a fragment thereof (e.g., a truncated heme domain) that is capable of carrying out the carbene insertion reactions described herein.

TABLE 1

Heme enzymes identified by their enzyme classification number (EC number) and classification name

| EC Number | Name |
| --- | --- |
| 1.1.2.3 | L-lactate dehydrogenase |
| 1.1.2.6 | polyvinyl alcohol dehydrogenase (cytochrome) |
| 1.1.2.7 | methanol dehydrogenase (cytochrome c) |
| 1.1.5.5 | alcohol dehydrogenase (quinone) |
| 1.1.5.6 | formate dehydrogenase-N: |
| 1.1.9.1 | alcohol dehydrogenase (azurin): |
| 1.1.99.3 | gluconate 2-dehydrogenase (acceptor) |
| 1.1.99.11 | fructose 5-dehydrogenase |
| 1.1.99.18 | cellobiose dehydrogenase (acceptor) |
| 1.1.99.20 | alkan-1-ol dehydrogenase (acceptor) |
| 1.2.1.70 | glutamyl-tRNA reductase |
| 1.2.3.7 | indole-3-acetaldehyde oxidase |
| 1.2.99.3 | aldehyde dehydrogenase (pyrroloquinoline-quinone) |
| 1.3.1.6 | fumarate reductase (NADH): |
| 1.3.5.1 | succinate dehydrogenase (ubiquinone) |
| 1.3.5.4 | fumarate reductase (menaquinone) |
| 1.3.99.1 | succinate dehydrogenase |
| 1.4.9.1 | methylamine dehydrogenase (amicyanin) |
| 1.4.9.2. | aralkylamine dehydrogenase (azurin) |
| 1.5.1.20 | methylenetetrahydrofolate reductase [NAD(P)H] |
| 1.5.99.6 | spermidine dehydrogenase |
| 1.6.3.1 | NAD(P)H oxidase |
| 1.7.1.1 | nitrate reductase (NADH) |
| 1.7.1.2 | Nitrate reductase [NAD(P)H] |
| 1.7.1.3 | nitrate reductase (NADPH) |
| 1.7.1.4 | nitrite reductase [NAD(P)H] |
| 1.7.1.14 | nitric oxide reductase [NAD(P), nitrous oxide-forming] |
| 1.7.2.1 | nitrite reductase (NO-forming) |
| 1.7.2.2 | nitrite reductase (cytochrome; ammonia-forming) |
| 1.7.2.3 | trimethylamine-N-oxide reductase (cytochrome c) |
| 1.7.2.5 | nitric oxide reductase (cytochrome c) |
| 1.7.2.6 | hydroxylamine dehydrogenase |
| 1.7.3.6 | hydroxylamine oxidase (cytochrome) |
| 1.7.5.1 | nitrate reductase (quinone) |
| 1.7.5.2 | nitric oxide reductase (menaquinol) |
| 1.7.6.1 | nitrite dismutase |
| 1.7.7.1 | ferredoxin-nitrite reductase |
| 1.7.7.2 | ferredoxin-nitrate reductase |
| 1.7.99.4 | nitrate reductase |
| 1.7.99.8 | hydrazine oxidoreductase |
| 1.8.1.2 | sulfite reductase (NADPH) |
| 1.8.2.1 | sulfite dehydrogenase |
| 1.8.2.2 | thiosulfate dehydrogenase |
| 1.8.2.3 | sulfide-cytochrome-c reductase (flavocytochrome c) |
| 1.8.2.4 | dimethyl sulfide:cytochrome c2 reductase |
| 1.8.3.1 | sulfite oxidase |
| 1.8.7.1 | sulfite reductase (ferredoxin) |
| 1.8.98.1 | CoB-CoM heterodisulfide reductase |
| 1.8.99.1 | sulfite reductase |
| 1.8.99.2 | adenylyl-sulfate reductase |
| 1.8.99.3 | hydrogensulfite reductase |
| 1.9.3.1 | cytochrome-c oxidase |

TABLE 1-continued

Heme enzymes identified by their enzyme classification number (EC number) and classification name

| EC Number | Name |
| --- | --- |
| 1.9.6.1 | nitrate reductase (cytochrome) |
| 1.10.2.2 | ubiquinol-cytochrome-c reductase |
| 1.10.3.1 | catechol oxidase |
| 1.10.3.B1 | caldariellaquinol oxidase (H+-transporting) |
| 1.10.3.3 | L-ascorbate oxidase |
| 1.10.3.9 | photosystem II |
| 1.10.3.10 | ubiquinol oxidase (H+-transporting) |
| 1.10.3.11 | ubiquinol oxidase |
| 1.10.3.12 | menaquinol oxidase (H+-transporting) |
| 1.10.9.1 | plastoquinol-plastocyanin reductase |
| 1.11.1.5 | cytochrome-c peroxidase |
| 1.11.1.6 | Catalase |
| 1.11.1.7 | Peroxidase |
| 1.11.1.B2 | chloride peroxidase (vanadium-containing) |
| 1.11.1.B7 | bromide peroxidase (heme-containing) |
| 1.11.1.8 | iodide peroxidase |
| 1.11.1.10 | chloride peroxidase |
| 1.11.1.11 | L-ascorbate peroxidase |
| 1.11.1.13 | manganese peroxidase |
| 1.11.1.14 | lignin peroxidase |
| 1.11.1.16 | versatile peroxidase |
| 1.11.1.19 | dye decolorizing peroxidase |
| 1.11.1.21 | catalase-peroxidase |
| 1.11.2.1 | unspecific peroxygenase |
| 1.11.2.2 | Myeloperoxidase |
| 1.11.2.3 | plant seed peroxygenase |
| 1.11.2.4 | fatty-acid peroxygenase |
| 1.12.2.1 | cytochrome-c3 hydrogenase |
| 1.12.5.1 | hydrogen:quinone oxidoreductase |
| 1.12.99.6 | hydrogenase (acceptor) |
| 1.13.11.9 | 2,5-dihydroxypyridine 5,6-dioxygenase |
| 1.13.11.11 | tryptophan 2,3-dioxygenase |
| 1.13.11.49 | chlorite O2-lyase |
| 1.13.11.50 | acetylacetone-cleaving enzyme |
| 1.13.11.52 | indoleamine 2,3-dioxygenase |
| 1.13.11.60 | linoleate 8R-lipoxygenase |
| 1.13.99.3 | tryptophan 2'-dioxygenase |
| 1.14.11.9 | flavanone 3-dioxygenase |
| 1.14.12.17 | nitric oxide dioxygenase |
| 1.14.13.39 | nitric-oxide synthase (NADPH dependent) |
| 1.14.13.17 | cholesterol 7alpha-monooxygenase |
| 1.14.13.41 | tyrosine N-monooxygenase |
| 1.14.13.70 | sterol 14alpha-demethylase |
| 1.14.13.71 | N-methylcoclaurine 3'-monooxygenase |
| 1.14.13.81 | magnesium-protoporphyrin IX monomethyl ester (oxidative) cyclase |
| 1.14.13.86 | 2-hydroxyisoflavanone synthase |
| 1.14.13.98 | cholesterol 24-hydroxylase |
| 1.14.13.119 | 5-epiaristolochene 1,3-dihydroxylase |
| 1.14.13.126 | vitamin D3 24-hydroxylase |
| 1.14.13.129 | beta-carotene 3-hydroxylase |
| 1.14.13.141 | cholest-4-en-3-one 26-monooxygenase |
| 1.14.13.142 | 3-ketosteroid 9alpha-monooxygenase |
| 1.14.13.151 | linalool 8-monooxygenase |
| 1.14.13.156 | 1,8-cineole 2-endo-monooxygenase |
| 1.14.13.159 | vitamin D 25-hydroxylase |
| 1.14.14.1 | unspecific monooxygenase |
| 1.14.15.1 | camphor 5-monooxygenase |
| 1.14.15.6 | cholesterol monooxygenase (side-chain-cleaving) |
| 1.14.15.8 | steroid 15beta-monooxygenase |
| 1.14.15.9 | spheroidene monooxygenase |
| 1.14.18.1 | Tyrosinase |
| 1.14.19.1 | stearoyl-CoA 9-desaturase |
| 1.14.19.3 | linoleoyl-CoA desaturase |
| 1.14.21.7 | biflaviolin synthase |
| 1.14.99.1 | prostaglandin-endoperoxide synthase |
| 1.14.99.3 | heme oxygenase |
| 1.14.99.9 | steroid 17alpha-monooxygenase |
| 1.14.99.10 | steroid 21-monooxygenase |
| 1.14.99.15 | 4-methoxybenzoate monooxygenase (O-demethylating) |
| 1.14.99.45 | carotene epsilon-monooxygenase |
| 1.16.5.1 | ascothate ferrireductase (transmembrane) |
| 1.16.9.1 | iron:rusticyanin reductase |
| 1.17.1.4 | xanthine dehydrogenase |
| 1.17.2.2 | lupanine 17-hydroxylase (cytochrome c) |
| 1.17.99.1 | 4-methylphenol dehydrogenase (hydroxylating) |
| 1.17.99.2 | ethylbenzene hydroxylase |
| 1.97.1.1 | chlorate reductase |
| 1.97.1.9 | selenate reductase |
| 2.7.7.65 | diguanylate cyclase |
| 2.7.13.3 | histidine kinase |
| 3.1.4.52 | cyclic-guanylate-specific phosphodiesterase |
| 4.2.1.B9 | colneleic acid/etheroleic acid synthase |
| 4.2.1.22 | Cystathionine beta-synthase |
| 4.2.1.92 | hydroperoxide dehydratase |
| 4.2.1.212 | colneleate synthase |
| 4.3.1.26 | chromopyrrolate synthase |
| 4.6.1.2 | guanylate cyclase |
| 4.99.1.3 | sirohydrochlorin cobaltochelatase |
| 4.99.1.5 | aliphatic aldoxime dehydratase |
| 4.99.1.7 | phenylacetaldoxime dehydratase |
| 5.3.99.3 | prostaglandin-E synthase |
| 5.3.99.4 | prostaglandin-I synthase |
| 5.3.99.5 | Thromboxane-A synthase |
| 5.4.4.5 | 9,12-octadecadienoate 8-hydroperoxide 8R-isomerase |
| 5.4.4.6 | 9,12-octadecadienoate 8-hydroperoxide 8S-isomerase |
| 6.6.1.2 | Cobaltochelatase |

In some embodiments, the heme protein is an engineered variant or a fragment thereof (e.g., a truncated variant containing the heme domain) comprising one or more mutation(s). In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val. In other embodiments, the heme protein variant is a chimeric protein comprising recombined sequences or blocks of amino acids from two, three, or more different heme-containing proteins. As described herein, heme protein catalysts described can be improved through the introduction of mutations which alter the amino acid sequence of the heme protein so as to generate a catalyst that is highly productive and selective for the desired product forming reaction. In particular, there are many examples in the scientific literature that describe processes through which the enantioselectivity and activity of carbene-transfer heme proteins can be optimized to form products that do not contain cyclopropene moieties or bicyclobutane moieties. Specifically, one skilled in the art will know that through a process of random mutagenesis via error-prone PCR, or through a process of site-saturation mutagenesis in which one or more codons are randomized sequentially or simultaneously, or through a process of gene synthesis in which random or directed mutations are introduced, many different mutants of the genes encoding the hemoprotein catalysts described herein can be generated. One skilled in the art will appreciate that heme protein variants can be expressed in a whole cell using an expression vector under the control of an inducible promoter or by means of chromosomal integration under the control of a constitutive promotor. The activity of whole cell catalysts, cell lysates or purified proteins can be screened by GC or HPLC, using parameters including but not limited to turnovers and selectivities as selection criteria to find beneficial mutations.

In some embodiments, the heme enzyme comprises a cytochrome. Cytochromes are a class of heme proteins that are found in bacteria, as well as mitochondria and chloroplasts of eukaryotic organisms, and are typically associated with membranes. Cytochromes typically function in oxidative phosphorylation as components of electron transport chain systems. Cytochromes can be classified by spectroscopy, or by features such as the structure of the heme group, inhibitor sensitivity, or reduction potential. Three of the cytochromes, cytochromes a, b, and d, are classified by their prosthetic group (the prosthetic groups consisting of heme a, heme b, and tetrapyrrolic chelate of iron, respectively). Unlike the aforementioned cytochromes, cytochrome c is not defined in terms of its heme group. Cytochrome f, which performs similar functions to cytochrome $c_1$ but has a different structure, is sometimes regarded as a type of cytochrome c. Cytochrome P450 proteins form a distinct family of cytochromes. In bacteria, mitochondria, and chloroplasts, various cytochromes form different combinations that perform different functions. Cytochromes a and $a_3$ combine to form cytochrome c oxidase (also known as Complex IV), which is the last enzyme in the respiratory chain of bacteria and mitochondria. Cytochromes b and $c_1$ combine to form coenzyme Q—cytochrome c reductase—the third complex in the electron transport chain. Cytochromes $b_6$ and f combine to form plastoquinol-plastocyanin reductase, which is found in the chloroplasts of plants, cyanobacteria and green algae and functions in photosynthesis.

Cytochrome P450 enzymes constitute a large superfamily of heme-thiolate proteins involved in the metabolism of a wide variety of both exogenous and endogenous compounds. Usually, they act as the terminal oxidase in multicomponent electron transfer chains, such as P450-containing monooxygenase systems. Members of the cytochrome P450 enzyme family catalyze myriad oxidative transformations, including, e.g., hydroxylation, epoxidation, oxidative ring coupling, heteroatom release, and heteroatom oxygenation (E. M. Isin et al., *Biochim. Biophys. Acta* 1770, 314 (2007)). P450s typically contain a single polypeptide, ranging from 40 to 55 kDa in molecular weight, and the same general fold has been observed in all P450s with known structures (T. L. Poulous, *Chem Rev.*, 114, 3919 (2014)). The active site of these enzymes contains an $Fe^{III}$-protoporphyrin IX cofactor (heme) ligated proximally by a conserved cysteine thiolate (M. T. Green, *Current Opinion in Chemical Biology* 13, 84 (2009)). The remaining axial iron coordination site is occupied by a water molecule in the resting enzyme, but during native catalysis, this site is capable of binding molecular oxygen. P450 structure is also typically characterized by a long "I helix" (typically around 50 angstroms in length) which runs over the surfaces of the heme and interacts with oxygen and the oxidation substrate. In the presence of an electron source, typically provided by NADH or NADPH from an adjacent fused reductase domain or an accessory cytochrome P450 reductase enzyme, the heme center of cytochrome P450 activates molecular oxygen, generating a high valent iron(IV)-oxo porphyrin cation radical species intermediate and a molecule of water.

Cytochrome P450 BM3 (CYP102A1) proteins are found in the soil bacterium *Bacillus megaterium* and catalyze the NADPH-dependent hydroxylation of long-chain fatty acids at the ω-1 through ω-3 positions. Unlike most other cytochrome P450 proteins, cytochrome P450 BM3 proteins are a natural fusion between the cytochrome P450 domain and an electron donating cofactor. Thus, cytochrome P450 BM3 proteins are useful in a number of biotechnological applications.

In certain embodiments, the hemoprotein is a cytochrome P450 or a variant thereof. In a particular embodiment, the cytochrome P450 is a $P450_{BM3}$ (also known as CYP102A1) or a variant thereof. In some embodiments, the $P450_{BM3}$ hemoprotein is an engineered variant comprising one or more mutation(s). In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val. In other embodiments, the hemoprotein variant is a chimeric protein comprising recombined sequences or blocks of amino acids from two, three, or more different heme-containing proteins.

In some embodiments, the $P450_{BM3}$ protein (CYP102A1) contains mutations of one or more residues selected from V78, F87, P142, T175, A184, S226, H236, E252, I263, T268, A290, A328, L353, I366, C400, T438, and E442 (mature peptide numbering convention) to any other amino acid residues that is among the naturally occurring twenty amino acids. In a further embodiment, the $P450_{BM3}$ protein contains a single mutation of the residue at position A87 to any other amino acid. In a further embodiment, the $P450_{BM3}$ protein contains a single mutation of the residue at position L181 to any other amino acid. In a further embodiment, the $P450_{BM3}$ protein contains a single mutation of the residue at position F261 to any other amino acid. In a further embodiment, the $P450_{BM3}$ protein contains a single mutation of the residue at position T269 to any other amino acid. In a further embodiment, the $P450_{BM3}$ protein contains a single mutation of the residue at position L437 to any other amino acid. In a further embodiment, the $P450_{BM3}$ protein contains a single mutation of the residue at position V328 to any other amino acid. In a further embodiment, the $P450_{BM3}$ protein contains mutations of the residues at positions F261 and T327 to any other amino acid. In a further embodiment, the $P450_{BM3}$ protein contains any combination of mutations of the residues V78, F87, P142, T175, L181, A184, S226, H236, E252, F261, I263, T268, T269, A290, T327, A328, L353, I366, C400, L437, T438, E442 to any other amino acid.

In some embodiments, the heme protein is a cytochrome $P450_{BM3}$ variant including the heme domain amino acid sequence set forth in SEQ ID NO:2 (P411-P4), and wherein the amino acid sequence optionally comprises one or more amino acid mutations. In some embodiments, for example, the cytochrome $P450_{BM3}$ variant comprises an amino acid mutation at position A87 (e.g., an A87F mutation, an A87W mutation, an A87Y mutation, or an A87H mutation). In some embodiments, the A87 mutation is an A87F mutation or an A87W mutation.

In some embodiments, a cytochrome $P450_{BM3}$ variant having the heme domain amino acid sequence set forth in SEQ ID NO:2 will further contain an amino acid mutation at one or both of positions F261 (e.g., F261G) and T327 (e.g., T327P), and optionally an A87F mutation. In some embodiments, the cytochrome $P450_{BM3}$ variant will further contain an amino acid mutation at one to three of positions S72 (e.g., S72W), T269 (e.g., T269L), and L437 (e.g., L437F); the variant may optionally contain an A87F mutation in such cases.

The cytochrome $P450_{BM3}$ variant having the heme domain amino acid sequence set forth in SEQ ID NO:2 can also contain an amino acid mutation at one or both of positions A78 (e.g., A78F) and A330 (e.g., A330V), and optionally an A87F mutation. Such variants may also contain any of the mutations at positions S72, F261, T269, T327, and L437 described above.

In some embodiments, the cytochrome $P450_{BM3}$ variant comprises mutations at one or both of positions L188 (e.g., L188C) and T436 (e.g., T436M), and optionally an A87F mutation. Such variants may also contain any of the mutations at positions S72, A78, F261, T269, T327, A330, and L437 described above.

In some embodiments, a cytochrome $P450_{BM3}$ variant having the heme domain amino acid sequence set forth in SEQ ID NO:2 will further contain an amino acid mutation at position L437 (e.g., L437G), and optionally an A87W mutation. In some embodiments, the cytochrome P450$_{BM3}$ variant will further contain an amino acid mutation at one or both of positions T327 (e.g., T327V) and V328 (e.g., V328Y); the variant may optionally contain an A87W mutation in such cases.

The cytochrome P450$_{BM3}$ variant having the heme domain amino acid sequence set forth in SEQ ID NO:2 can also contain an amino acid mutation at one or both of positions F261 (e.g., F261M) and T436 (e.g., T436H), and optionally an A87W mutation. Such variants may also contain any of the mutations at positions T327, V328, and L437 described above.

P450$_{BM3}$ variants having a heme domain amino acid sequence according to SEQ ID NO:2, including those having the mutations set forth above, can be particularly useful for forming cyclopropene products. Full-length P450$_{BM3}$ variants comprising the amino acid sequence according to SEQ ID NO:5, and any mutations corresponding to those described above, can also be used in the methods provided herein. The heme-domain polypeptide sequences (e.g., a heme domain amino acid sequence according to SEQ ID NO:2) and the full-length polypeptide sequences (e.g., a full-length amino acid sequence according to SEQ ID NO:5) may further contain an N-terminal methionine residue directly proceeding the T1 position in certain instances.

In some embodiments, the heme protein is a cytochrome P450$_{BM3}$ variant comprising the heme domain amino acid sequence set forth in SEQ ID NO:3 (P411-E10), and which optionally comprises one or more amino acid mutations. For example, the variant can contain a mutation a position V78 in SEQ ID NO:3 (e.g., a V78F mutation, a V78Y mutation, a V78H mutation, or a V78W mutation). In some embodiments, the V78 mutation is a V78F mutation or a V78Y mutation. In some embodiments, the cytochrome P450$_{BM3}$ variant comprises an amino acid mutation at position S438 (e.g., an S438 mutation).

P450$_{BM3}$ variants having a heme domain amino acid sequence according to SEQ ID NO:3, including those having the mutations set forth above, can be particularly useful for forming bicyclobutane products. Full-length P450$_{BM3}$ variants comprising the amino acid sequence according to SEQ ID NO:6, and any mutations corresponding to those described above, can also be used in the methods provided herein. The heme-domain polypeptide sequences (e.g., a heme domain amino acid sequence according to SEQ ID NO:3) and the full-length polypeptide sequences (e.g., a full-length amino acid sequence according to SEQ ID NO:6) may further contain an N-terminal methionine residue directly proceeding the T1 position in certain instances.

Other cytochrome P450 enzymes can be used in the methods for forming cyclopropenes and bicyclobutanes. For example, the P450 may be *P. putida* P450cam having the amino acid structure set forth in SEQ ID NO:7 or a variant thereof having one or more mutations. For example, a P450cam may contain one or more mutations at positions P89, Y96, F98, T101, V247, D251, N255, L294, V295, A296, D297, C357, I395, and V396 in SEQ ID NO:7. Cytochrome P450 variants with sequences similar to SEQ ID NOS: 4-7 (e.g., sequences with at least 70%, 75%, 80%, 85%, 90%, or 95% sequence identity to SEQ ID NOS: 4-7), may also contain mutations at the positions corresponding to P89, Y96, F98, T101, V247, D251, N255, L294, V295, A296, D297, C357, I395, and V396 of SEQ ID NO:7.

In some embodiments, the heme enzyme comprises a globin enzyme. Globins are a superfamily of globular heme proteins that are typically involved in the transport and binding of oxygen. A characteristic of globins is a three-dimensional fold consisting of eight alpha helices, often labeled A-H, that can fold into a three-over-three sandwich structure. Some globins also additional terminal helix extensions. So-called "truncated hemoglobins" contain four alpha helices arranged in a two-over-two sandwich. Globins can be divided into three groups: single-domain globins, flavohemoglobins (not observed in archaea), and globin-coupled sensors (not observed in eukaryotes). All three groups are observed in bacteria. Globin proteins include hemoglobin, myoglobin, neuroglobin, cytoglobin, erythrocruorin, leghemoglobin, non-symbiotic hemoglobin, flavohemoglobins (one group of chimeric globins), globin E, globin-coupled sensors (another group of chimeric globins), protoglobin, truncated 2/2 globin, HbN, cyanoglobin, HbO, and Glb3.

In some embodiments, the heme protein used for formation of cyclopropene and/or bicyclobutane products is a globin or a variant thereof. For example, the globin may be sperm whale myoglobin comprising the amino acid sequence set forth in SEQ ID NO:8, or a variant thereof containing one or more mutations. In some embodiments, a sperm whale myoglobin variant may contain a mutation at H64 (e.g., an H64V mutation) or V68 (e.g., a V68A mutation). In some embodiments, the myoglobin variant may further contain mutations at L29 and/or F43. Such mutations may also be made at the corresponding positions of other globins such those containing a three-over-three helix sandwich fold (including but not limited to, *C. jejuni* globin (SEQ ID NO:9), *V. stercoraria* hemoglobin (SEQ ID NO:10), murine neuroglobin (SEQ ID NO:11), human neuroglobin (SEQ ID NO:12), an *M. infernorum* hemoglobin (SEQ ID NO:13), human cytoglobin (SEQ ID NO:14), and *A. suum* hemoglobin (SEQ ID NO:15).

In some embodiments, the globin is a truncated globin such as *B. subtilis* truncated hemoglobin comprising the amino sequence set forth in SEQ ID NO:16 or a variant thereof having one or more mutations. One or more mutations may reside within the distal binding pocket of *B. subtilis* truncated hemoglobin, for example at T45 and/or at Q49 with respect to SEQ ID NO:16, or within the analogous regions of other globins such as those containing a two-over-two helix sandwich fold.

Protoglobins were the first globins identified in Archaea such as *M. acetivorans*, *A. pernix*, and *P. ferrireducens*. Protoglobin tertiary structure frequently includes the canonical globin fold, as well as a pre-A helix (termed "Z" in certain instances) and an N-terminal extension. In some embodiments, the heme protein used for formation of cyclopropene and/or bicyclobutane products is a protoglobin or a variant thereof. For example, the protoglobin may be an *M. acetivorans* protoglobin comprising the amino acid sequence set forth in SEQ ID NO:17, or a variant thereof containing one or more mutations; an *A. pernix* protoglobin comprising the amino acid sequence set forth in SEQ ID NO:18, or a variant thereof containing one or more mutations; or a *P. ferrireducens* protoglobin comprising the amino acid sequence set forth in SEQ ID NO:19, or a variant thereof containing one or more mutations. For example the protoglobin variant may contain one or mutations at positions W59, Y60, F73, F145, or F93 in SEQ ID NO:18, or at analogous positions in other protoglobins (e.g., protoglobins with at least 70%, 75%, 80%, 85%, 90%, or 95% sequence identity to SEQ ID NO:18).

One skilled in the art will appreciate that the P450$_{BM3}$ catalysts and other enzyme catalysts described herein can be improved through the introduction of additional DNA mutations which alter the resulting amino acid sequence of the hemoprotein so as to generate a catalyst that is highly productive and selective for the desired cyclopropenation and bicyclobutanation reactions. In particular, there are many examples in the scientific literature that describe processes through which the enantioselectivity and activity of carbene-transfer hemoproteins can be optimized to produce products that do not include cyclopropenes and bicyclobutanes. Specifically, one skilled in the art will know that through a process of random mutagenesis via error-prone PCR, or through a process of site-directed mutagenesis in which one or more codons are randomized sequentially or simultaneously, or through a process of gene synthesis in which random or directed mutations are introduced, many different mutants of the genes encoding the $P450_{BM3}$ enzymes and other enzymes described herein can be generated. One skilled in the art will appreciate that heme protein variants can be expressed in a whole cell using an expression vector under the control of an inducible promoter or by means of chromosomal integration under the control of a constitutive promoter. The cyclopropenation and bicyclobutanation activities of whole cell catalysts, or purified proteins can be screened by GC or HPLC, using parameters including but not limited to turnovers and selectivities as selection criteria to find beneficial mutations.

One skilled in the art will understand that $P450_{BM3}$ mutants and other enzymes identified as improved in the cyclopropenation and bicyclobutanation can themselves be subjected to additional mutagenesis as described herein, resulting in progressive, cumulative improvements in one or more reaction parameters including but not limited to turnover frequency, total turnover number, yield, chemoselectivity, regioselectivity, diastereoselectivity, enantioselectivity, expression, thermostability, or solvent tolerance.

In some embodiments, the heme protein, homolog, variant, or fragment thereof has a turnover frequency (TOF) between about 1 $min^{-1}$ and 10 $min^{-1}$ (e.g., about 1 $min^{-1}$, 1.5 $min^{-1}$, 2 $min^{-1}$, 2.5 $min^{-1}$, 3 $min^{-1}$, 3.5 $min^{-1}$, 4 $min^{-1}$, 4.5 $min^{-1}$, 5 $min^{-1}$, 5.5 $min^{-1}$, 6 $min^{-1}$, 6.5 $min^{-1}$, 7 $min^{-1}$, 7.5 $min^{-1}$, 8 $min^{-1}$, 8.5 $min^{-1}$, 9 $min^{-1}$, 9.5 $min^{-1}$, or 10 $min^{-1}$). In other embodiments, the TOF is between about 10 $min^{-1}$ and 100 $min^{-1}$ (e.g., about 10 $min^{-1}$, 11 $min^{-1}$, 12 $min^{-1}$, 13 $min^{-1}$, 14 $min^{-1}$, 15 $min^{-1}$, 16 $min^{-1}$, 17 $min^{-1}$, 18 $min^{-1}$, 19 $min^{-1}$, 20 $min^{-1}$, 21 $min^{-1}$, 22 $min^{-1}$, 23 $min^{-1}$, 24 $min^{-1}$, 25 $min^{-1}$, 26 $min^{-1}$, 27 $min^{-1}$, 28 $min^{-1}$, 29 $min^{-1}$, 30 $min^{-1}$, 31 $min^{-1}$, 32 $min^{-1}$, 33 $min^{-1}$, 34 $min^{-1}$, 35 $min^{-1}$, 36 $min^{-1}$, 37 $min^{-1}$, 38 $min^{-1}$, 39 $min^{-1}$, 40 $min^{-1}$, 41 $min^{-1}$, 42 $min^{-1}$, 43 $min^{-1}$, 44 $min^{-1}$, 45 $min^{-1}$, 46 $min^{-1}$, 47 $min^{-1}$, 48 $min^{-1}$, 49 $min^{-1}$, 50 $min^{-1}$, 55 $min^{-1}$, 60 $min^{-1}$, 65 $min^{-1}$, 70 $min^{-1}$, 75 $min^{-1}$, 80 $min^{-1}$, 85 $min^{-1}$, 90 $min^{-1}$, 95 $min^{-1}$, or 100 $min^{-1}$). In other instances, the TOF is greater than about 100 $min^{-1}$ to 1,000 $min^{-1}$ (e.g., greater than about 100 $min^{-1}$, 150 $min^{-1}$, 200 $min^{-1}$, 250 $min^{-1}$, 300 $min^{-1}$, 350 $min^{-1}$, 400 $min^{-1}$, 450 $min^{-1}$, 500 $min^{-1}$, 550 $min^{-1}$, 600 $min^{-1}$, 650 $min^{-1}$, 700 $min^{-1}$, 750 $min^{-1}$, 800 $min^{-1}$, 850 $min^{-1}$, 900 $min^{-1}$, 950 $min^{-1}$, 1,000 $min^{-1}$, or more). In some instances, the TOF is greater than about 10 $min^{-1}$. In other instances, the TOF is greater than about 45 $min^{-1}$.

In other embodiments, the heme protein, homolog, variant, or fragment thereof has a total turnover number (TTN), which refers to the maximum number of molecules of a substrate that the protein can convert before becoming inactivated, of between about 1 and 100 (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100). In some other instances, the TTN is between about 100 and 1,000 (e.g., about 100, 150, 200, 250, 300, 350, 400, 450, 500, 550, 600, 650, 700, 750, 800, 850, 900, 950, or 1,000). In some embodiments, the TTN is between about 1,000 and 2,000 (e.g., about 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 or 2,000). In other embodiments, the TTN is at least about 2,000 (e.g., at least about 2,000, 2,500, 3,000, 3,500, 4,000, 4,500, 5,000, 5,500, 6,000, 6,500, 7,000, 7,500, 8,000, 8,500, 9,000, 9,500, or 10,000). In some instances, the TTN is greater than about 70. In other instances, the TTN is greater than about 1,800.

In some embodiments, the heme protein variant or fragment thereof has enhanced activity of at least about 1.5 to 2,000 fold (e.g., at least about 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, or more) fold compared to the corresponding wild-type heme protein.

In some embodiments, activity is expressed in terms of turnover frequency (TOF). In particular embodiments, the TOF of the heme protein variant or fragment thereof is at least about 1.5, 2, 2.5, 3, 3.5, 4, 4.5, 5, 5.5, 6, 6.5, 7, 7.5, 8, 8.5, 9, 9.5, or 10 fold higher than the corresponding wild-type protein.

In other instances, activity is expressed in terms of total turnover number (TTN). In particular instances, the TTN of the theme protein variant or fragment thereof is about least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or 2,000 fold higher than the corresponding wild-type protein.

In some embodiments, the present invention provides heme proteins, homologs, variants, and fragments thereof that catalyze enantioselective carbene insertion into alkyne carbon-carbon bonds with high enantiomeric excess. In particular embodiments, the heme proteins are variants or fragments thereof that catalyze enantioselective carbene insertion into alkyne bonds with higher enantiomeric excess values than that of the corresponding wild-type protein. In some embodiments, the heme protein, homolog, variants, or fragment thereof catalyzes carbene insertion into alkyne bonds with an enantiomeric excess value of at least about 30% ee (e.g., at least about 30%, 35%, 40%, 45%, 50%, 55%, 60%, 65%, 70%, 75%, 80%, 85%, 90%, 95%, or 100% ee). Preferably, the heme protein, homolog, variant, or fragment thereof catalyzes carbene insertion into alkyne bonds with at least about 80% ee (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100% ee). More preferably, the heme protein, homolog, variant, or fragment thereof catalyzes carbene insertion into alkyne bonds with at least about 95% ee (e.g., at least about 95%, 96%, 97%, 98%, 99%, or 100% ee).

In certain embodiments, a conserved residue in a heme protein of interest that serves as an heme axial ligand can be identified by locating the segment of the DNA sequence in the corresponding gene which encodes the conserved residue. In some instances, this DNA segment is identified through detailed mutagenesis studies in a conserved region of the protein. In other instances, the conserved residue is identified through crystallographic study.

In situations where detailed mutagenesis studies and crystallographic data are not available for a heme protein of interest, the axial ligand may be identified through phylogenetic study. Due to the similarities in amino acid sequence within families of heme proteins (e.g., cytochrome c proteins), standard protein alignment algorithms may show a phylogenetic similarity between a heme protein for which crystallographic or mutagenesis data exist and a new heme protein for which such data do not exist. Thus, the polypeptide sequences of the present invention for which the heme axial ligand is known can be used as a "query sequence" to perform a search against a specific new heme protein of interest or a database comprising heme protein sequences to identify the heme axial ligand. Such analyses can be performed using the BLAST programs (see, e.g., Altschul et al., *J Mol Biol.* 215(3):403-10(1990)). Software for performing BLAST analyses publicly available through the National Center for Biotechnology Information. BLASTP is used for amino acid sequences.

Exemplary parameters for performing amino acid sequence alignments to identify the heme axial ligand in a heme protein of interest using the BLASTP algorithm include E value=10, word size=3, Matrix=Blosum62, Gap opening=11, gap extension=1, and conditional compositional score matrix adjustment. Those skilled in the art will know what modifications can be made to the above parameters, e.g., to either increase or decrease the stringency of the comparison and/or to determine the relatedness of two or more sequences.

In some embodiments, the heme protein comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g., any of the amino acid sequences set forth in SEQ ID NOS:1-6). In other embodiments, the heme protein comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein. In particular embodiments, the heme protein comprises an amino acid sequence that has about 90% or greater (e.g., about 90%, 91%, 92%, 93%, 94%, 95%, 96%, 97%, 98%, 99%, or 100%) identity any of the amino acid sequences described herein. In some instances, the heme protein comprises an amino acid sequence that is about 95%, 96,%, 97%, 98%, 99%, or 100% identical any of the amino acid sequences described herein.

In some embodiments, the heme protein comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NOS:1-19, or variants thereof as described above. The amino acids may be contiguous, or separated by any number of amino acids.

In certain embodiments, mutations can be introduced into the target gene using standard cloning techniques (e.g., site-directed mutagenesis, site-saturated mutagenesis) or by gene synthesis to produce the heme proteins, fragments thereof, variants thereof, or homologs thereof of the present invention.

In some embodiments, the heme protein, fragment thereof, variant thereof, or homolog thereof is recombinantly expressed and optionally isolated and/or purified for carrying out the in vitro carbene insertion reactions of the present invention. In other embodiments, the heme protein, fragment thereof, variant thereof, or homolog thereof is expressed in whole cells such as bacterial cells, archaeal cells, yeast cells, fungal cells, insect cells, plant cells, or mammalian cells, and these cells are used for carrying out the in vivo carbene insertion reactions of the present invention. The wild-type or mutated gene can be expressed in a whole cell using an expression vector under the control of an inducible promoter or by means of chromosomal integration under the control of a constitutive promoter. Carbene insertion activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NSO hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, the present invention provides the heme proteins, fragments thereof, variants thereof, or homologs thereof, such as the cytochrome c variants described herein that are active carbene insertion catalysts, inside living cells. As a non-limiting example, bacterial cells (e.g., *E. coli*) can be used as host whole cell catalysts for the in vivo carbene insertion reactions of the present invention, although any number of host whole cells may be used, including but not limited to the host cells described herein. In some embodiments, host whole cell catalysts containing heme proteins, fragments thereof, variants thereof, or homologs thereof are found to significantly enhance the total turnover number (TTN) compared to the in vitro reactions using isolated heme proteins, fragments thereof, variants thereof, or homologs thereof.

The expression vector comprising a nucleic acid sequence that encodes a heme protein, fragment thereof, variant thereof, or homolog thereof of the invention can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme protein, fragment thereof, variant thereof, or homolog thereof that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes a heme protein that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NOS:1-19. In other embodiments, the nucleic acid sequence encodes a heme protein that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NOS:1-19. In particular embodiments, the nucleic acid sequence encodes a heme protein that comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NOS:1-19. In some instances, the nucleic acid sequence encodes a heme protein that comprises an amino acid sequence that is about 95%, 96,%, 97%, 98%, 99%, or 100% identical to the amino acid sequence set forth in SEQ ID NOS:1-19.

In other embodiments, the nucleic acid sequence encodes a heme protein that comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NOS:1-19. The amino acids may be contiguous, or separated by any number of amino acids.

It is understood that affinity tags may be added to the N- and/or C-terminus of a heme protein, fragment thereof, variant thereof, or homolog thereof expressed using an expression vector to facilitate protein purification. Non-limiting examples of affinity tags include metal binding tags such as His6-tags and other tags such as glutathione S-transferase (GST).

Non-limiting expression vectors for use in bacterial host cells include pCWori, pET vectors such as pET22 (EMD Millipore), pBR322 (ATCC$_{37017}$), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

B. Cyclopropene Products

In some embodiments, methods for producing cyclopropene products comprise combining an alkyne, a carbene precursor, and a heme protein, homolog thereof, variant thereof, or fragment thereof as described herein under conditions sufficient to form the cyclopropene.

In some embodiments, the alkyne is a compound according to Formula I:

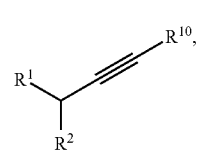

(I)

wherein $R^{10}$ is selected from the group consisting of H and $CR^1R^2$;

each $R^1$ is independently selected from the group consisting of H, $C_{1-18}$ alkyl, $C_{1-18}$ haloalkyl, $C_{2-18}$ alkenyl, $C_{2-18}$ alkynyl, $(C_{3-10}$ cycloalkyl$)$-$L^1$-, $(C_{6-10}$ aryl$)$-$L^1$-, (5- to 10-membered heteroaryl)-$L^1$-, (5- to 10-membered heterocyclyl)-$L^1$-, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$C_{1-18}$ alkyl, $C_{3-10}$ cycloalkyl, $C_{6-10}$ aryl, 5- to 10-membered heteroaryl, and 5- to 10-membered heterocyclyl in $R^1$ are optionally and independently substituted with one or more $R^{1a}$;

each $R^{1a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^1$ is selected from the group consisting of a bond and $C_{1-20}$ alkylene;

when $L^1$ is $C_{2-20}$ alkylene, one or more non-adjacent $CH_2$ groups are optionally and independently replaced with O, S, or NH;

when $L^1$ is $C_{3-20}$ alkylene, one or more pairs of adjacent $CH_2$ groups are optionally and independently replaced with $C(O)O$ or $C(O)NH$;

each $R^2$ is independently selected from the group consisting of H, $C_{1-18}$ alkyl, $C_{1-18}$ haloalkyl, $C_{2-18}$ alkenyl, $C_{2-18}$ alkynyl, $(C_{3-10}$ cycloalkyl$)$-$L^2$-, $(C_{6-10}$ aryl$)$-$L^2$-, (5- to 10-membered heteroaryl) $L^2$-, (5- to 10-membered heterocyclyl)-$L^2$-, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$C_{1-18}$ alkyl, $C_{3-10}$ cycloalkyl, $C_{6-10}$ aryl, 5- to 10-membered heteroaryl, and 5- to 10-membered heterocyclyl in $R^2$ are optionally and independently substituted with one or more $R^{2a}$;

each $R^{2a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

L² is selected from the group consisting of a bond and C$_{1-20}$ alkylene;

when L² is C$_{2-20}$ alkylene, one or more non-adjacent CH$_2$ groups are optionally and independently replaced with O, S, or NH;

when L² is C$_{3-20}$ alkylene, one or more pairs of adjacent CH$_2$ groups are optionally and independently replaced with C(O)O or C(O)NH; and each R⁷, R⁸, and R⁹ is independently selected from the group consisting of H, optionally substituted C$_{1-18}$ alkyl, C$_{2-18}$ alkenyl, C$_{2-18}$ alkynyl, optionally substituted C$_{6-10}$ aryl, optionally substituted 5- to 10-membered heteroaryl, and optionally substituted 5- to 10-membered heterocyclyl.

In some embodiments, the alkyne is a compound according to Formula Ia:

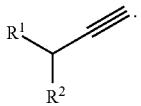

(Ia)

In some embodiments, each R² in alkynes of Formula I is independently selected from H and C$_{1-6}$ alkyl. In some embodiments, R² in alkynes of Formula Ia is selected from H and C$_{1-6}$ alkyl. R² can be, for example, H, methyl, ethyl, n-propyl, isopropyl, n-butyl, isobutyl, sec-butyl, tert-butyl, n-pentyl, isopentyl, or n-hexyl. In some embodiments, R² in alkynes according to Formula I or Formula Ia is H.

In some embodiments, R¹ is selected from the group consisting of C$_{1-18}$ alkyl, C$_{2-18}$ alkynyl, (C$_{3-10}$ cycloalkyl)-L¹-, (C$_{6-10}$ aryl)-L¹-, (5- to 10-membered heteroaryl)-L¹-, and (5- to 10-membered heterocyclyl)-L¹-, each of which is optionally and independently substituted with one or more R$^{1a}$. In some embodiments, R¹ is selected from the group consisting of C$_{1-8}$ alkyl and C$_{2-8}$ alkynyl, each of which is optionally substituted with one or more R$^{1a}$. R¹ can be, for example, optionally substituted methyl, optionally substituted ethyl, optionally substituted n-propyl, optionally substituted isopropyl, optionally substituted n-butyl, optionally substituted isobutyl, optionally substituted sec-butyl, optionally substituted tert-butyl, optionally substituted n-pentyl, optionally substituted isopentyl, optionally substituted n-hexyl, optionally substituted branched hexyl, optionally substituted n-heptyl, optionally substituted branched heptyl, optionally substituted n-octyl, optionally substituted branched octyl, optionally substituted ethynyl, optionally substituted prop-1-yn-1-yl, optionally substituted prop-2-yn-1-yl, optionally substituted but-1-yn-1-yl, optionally substituted but-2-yn-1-yl, optionally substituted but-3-yn-1-yl, optionally substituted pent-1-yn-1-yl, optionally substituted pent-2-yn-1-yl, optionally substituted pent-3-yn-1-yl, optionally substituted pent-4-yn-1-yl, optionally substituted hex-1-yn-1-yl, optionally substituted hex-2-yn-1-yl, optionally substituted hex-3-yn-1-yl, optionally substituted hex-4-yn-1-yl, optionally substituted hex-5-yn-1-yl, optionally substituted hept-1-yn-1-yl, optionally substituted hept-2-yn-1-yl, optionally substituted hept-3-yn-1-yl, optionally substituted hept-4-yn-1-yl, optionally substituted hept-5-yn-1-yl, optionally substituted hept-6-yn-1-yl, optionally substituted oct-1-yn-1-yl, optionally substituted oct-2-yn-1-yl, optionally substituted oct-3-yn-1-yl, optionally substituted oct-4-yn-1-yl, optionally substituted oct-5-yn-1-yl, optionally substituted oct-6-yn-1-yl, or optionally substituted oct-7-yn-1-yl. Alkynes according to Formula I or Formula Ia having alkenyl R¹ groups, cycloalkyl R¹ groups, and the like can also be employed.

In some embodiments, R¹ in alkynes according to Formula I is selected from the group consisting of C$_{1-6}$ alkyl and C$_{2-6}$ alkynyl, each of which is optionally substituted with one or more R$^{1a}$, and R$^{10}$ is H. In some such embodiments, R¹ is C$_{1-6}$ alkyl and R$^{1a}$ is selected from halogen (e.g., Cl or Br), —OH, C$_{1-6}$ alkoxy (e.g., methoxy, ethoxy, n-propoxy, or isopropoxy), and C$_{1-6}$ heteroalkyl (e.g., methoxymethyl or ethoxymethyl).

In some embodiments, R¹ is selected from (C$_{3-10}$ cycloalkyl)-L¹-, (C$_{6-10}$ aryl)-L¹-, (5- to 10-membered heteroaryl)-L¹-, and (5- to 10-membered heterocyclyl)-L¹-, wherein cycloalkyl, aryl, heteroaryl, and heterocyclyl are optionally substituted with one or more R$^{1a}$. In some embodiments, L¹ is a covalent bond. For example, the grouping (C$_{3-10}$ cycloalkyl)-L¹- can be optionally substituted cyclopropyl, optionally substituted cyclobutyl, optionally substituted cyclopentyl, optionally substituted cyclohexyl, or the like. In some embodiments, L¹ is C$_{1-20}$ alkylene (e.g., C$_{1-10}$ alkylene or C$_{1-6}$ alkylene). For example, the grouping (C$_{3-10}$ cycloalkyl)-L¹- can be cyclohexylmethyl, (2-cyclohexyl)eth-1-yl, (3-cyclohexyl)prop-1-yl, or the like. The grouping (C$_{6-10}$ aryl)-L¹- can be, for example, phenethyl. Cycloalkyl groups, aryl groups, and heterocyclyl groups can be further substituted with R$^{1a}$ groups as described above. In some embodiments, R¹ is cyclopropyl, cyclobutyl, cyclohexyl, 1,3-dioxolan-2-yl, or tetrahydropyran-1-yl; and R$^{1a}$ is —OH, C$_{1-6}$ alkoxy (e.g., methoxy, ethoxy, n-propoxy, or isopropoxy), or C$_{1-6}$ heteroalkyl (e.g., methoxymethyl or ethoxymethyl).

In some embodiments, L¹ is C$_{1-20}$ alkylene where one or more non-adjacent CH$_2$ groups are optionally and independently replaced with O, S, or NH. For example, the L¹ moiety may have the formula —(CH$_2$)$_w$(L$^{1a}$)$_x$(CH$_2$)$_y$(L$^{1a}$)$_x$(CH$_2$)$_z$—, where each L$^{1a}$ is independently O, S, or NH; each subscript x is independently 0 or 1; and each of subscripts w, y, and z is a non-zero integer such that the sum of subscript w, subscript x, subscript y, and subscript z is less than or equal to 20. In some such embodiments, each L$^{1a}$ is O. In some embodiments, the L¹ moiety is —CH$_2$O(CH$_2$)$_6$—.

In some embodiments, L¹ is C$_{3-20}$ alkylene wherein one or more pairs of adjacent CH$_2$ groups are optionally and independently replaced with C(O)O or C(O)NH. For example, the L¹ moiety may have the formula —(CH$_2$)$_q$(L$^{1b}$)$_r$(CH$_2$)$_s$(L$^{1b}$)$_t$(CH$_2$)$_u$—, where each L$^{1b}$ is independently C(O)O or C(O)NH; subscript r and subscript t are independently 0 or 1; and each of subscripts q, s, and u is a non-zero integer such that: 1) the sum of subscript q, subscript s, and subscript u is less than or equal to 20 when subscript r and subscript t are 0; 2) the sum of subscript q, subscript s, and subscript u is less than or equal to 18 when the sum of subscript r and subscript t is 1; or 3) the sum of subscript q, subscript s, and subscript u is less than or equal to 16 when the sum of subscript r and subscript t is 2. In some embodiments, the L¹ moiety is —C(O)O(CH$_2$)$_6$—. L¹ groups having both one or more C$^{1a}$ moieties (i.e., O, S, or NH) and one or more L$^{1b}$ moieties (i.e., C(O)O or C(O)NH) can also be employed.

In some embodiments, the alkyne for forming cyclopropene products is selected from:

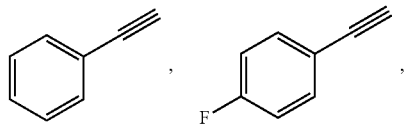

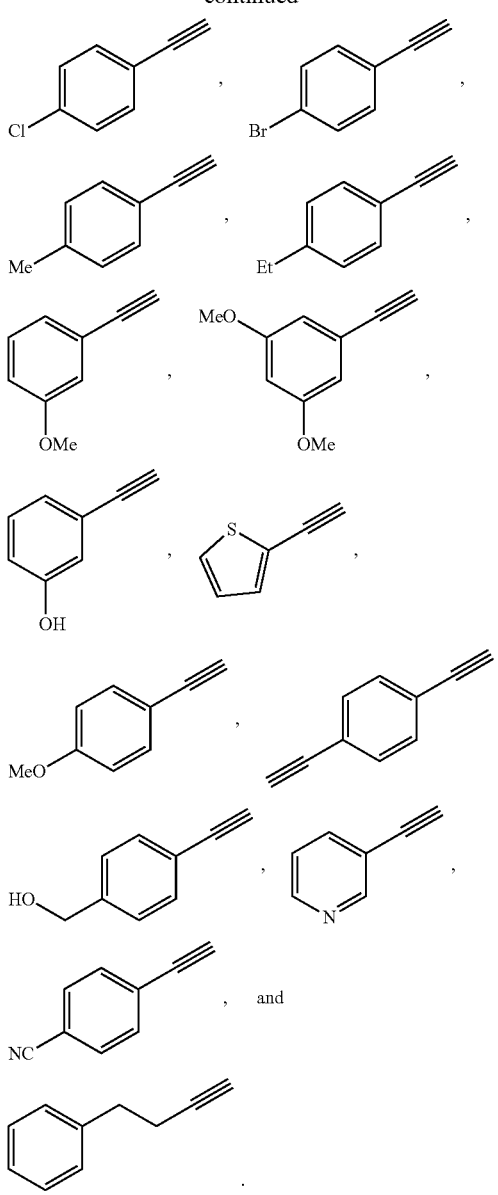

and

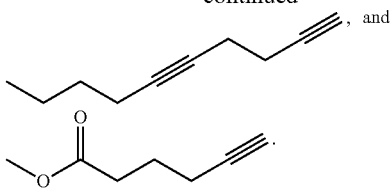

In some embodiments, the alkyne for forming cyclopropene products is selected from:

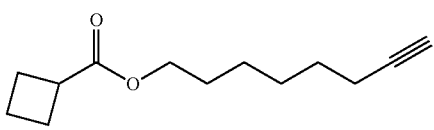

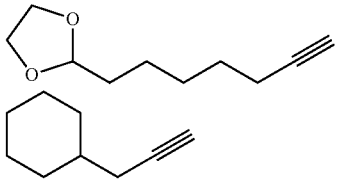

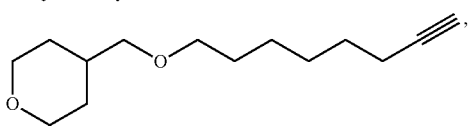

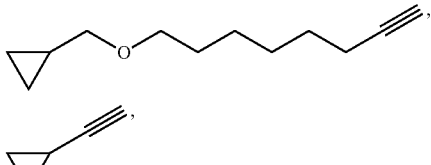

, and

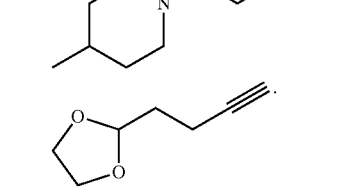

.

A number of carbene precursors can be used in the methods and reaction mixtures of the invention including, but not limited to, amines, azides, hydrazines, hydrazones, epoxides, diazirenes, and diazo reagents. In some embodiments, the carbene precursor is an epoxide (i.e., a compound containing an epoxide moiety). The term "epoxide moiety" refers to a three-membered heterocycle having two carbon atoms and one oxygen atom connected by single bonds. In some embodiments, the carbene precursor is a diazirene (i.e., a compound containing a diazirine moiety). The term "diazirine moiety" refers to a three-membered heterocycle having one carbon atom and two nitrogen atoms, wherein the nitrogen atoms are connected via a double bond. Diazirenes are chemically inert, small hydrophobic carbene pre- In some embodiments, the alkyne for forming cyclopropene products is selected from:

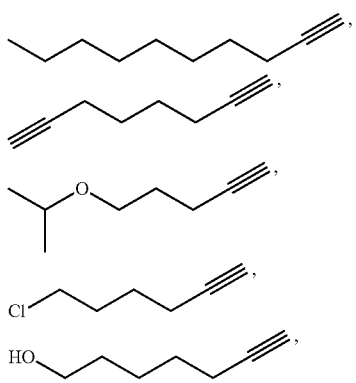

cursors described, for example, in US 2009/0211893, by Turro (*J. Am. Chem. Soc.* 1987, 109, 2101-2107), and by Brunner (*J. Biol. Chem.* 1980, 255, 3313-3318), which are incorporated herein by reference in their entirety.

In some embodiments, the carbene precursor is a diazo reagent, e.g., an α-diazoester, an α-diazoamide, an α-diazonitrile, an α-diazoketone, an α-diazoaldehyde, and an α-diazosilane. Diazo reagents can be formed from a number of starting materials using procedures that are known to those of skill in the art. Ketones (including 1,3-diketones), esters (including (β-ketones), acyl chlorides, and carboxylic acids can be converted to diazo reagents employing diazo transfer conditions with a suitable transfer reagent (e.g., aromatic and aliphatic sulfonyl azides, such as toluenesulfonyl azide, 4-carboxyphenylsulfonyl azide, 2-naphthalenesulfonyl azide, methylsulfonyl azide, and the like) and a suitable base (e.g., triethylamine, triisopropylamine, diazobicyclo[2.2.2]octane, 1,8-diazabicyclo[5.4.0]undec-7-ene, and the like) as described, for example, in U.S. Pat. No. 5,191,069 and by Davies (*J. Am. Chem. Soc.* 1993, 115, 9468-9479), which are incorporated herein by reference in their entirety. The preparation of diazo compounds from azide and hydrazone precursors is described, for example, in U.S. Pat. Nos. 8,350,014 and 8,530,212, which are incorporated herein by reference in their entirety. Alkylnitrite reagents (e.g., (3-methylbutyl)nitrite) can be used to convert α-aminoesters to the corresponding diazo compounds in non-aqueous media as described, for example, by Takamura (*Tetrahedron*, 1975, 31: 227), which is incorporated herein by reference in its entirety. Alternatively, a diazo compound can be formed from an aliphatic amine, an aniline or other arylamine, or a hydrazine using a nitrosating agent (e.g., sodium nitrite) and an acid (e.g., p-toluenesulfonic acid) as described, for example, by Zollinger (*Diazo Chemistry I and II*, VCH Weinheim, 1994) and in US 2005/0266579, which are incorporated herein by reference in their entirety.

In some embodiments, the carbene precursor is a diazo compound such as a compound according to Formula II:

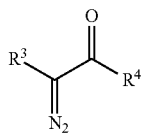

(II)

wherein $R^3$ and $R^4$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$; and each $R^7$, $R^8$, and $R^9$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl.

In some embodiments, $R^3$ and $R^4$ are independently selected from the group consisting of H, $C_{1-6}$ alkoxy, and $C_{1-6}$ alkyl. In some embodiments, $R^4$ is optionally substituted $C_{1-6}$ alkoxy (e.g., the carbene precursor is a diazoester). For example, $R^4$ can be optionally substituted methoxy (e.g., benzyloxy), optionally substituted ethoxy, optionally substituted n-propoxy, optionally substituted isopropoxy, optionally substituted n-butoxy, optionally substituted isobutoxy, or optionally substituted t-butoxy. In some embodiments, $R^4$ is $C_{1-6}$ alkoxy and $R^3$ is H or $C_{1-6}$ alkyl.

In some embodiments, $R^4$ is optionally substituted $C_{1-6}$ alkyl (e.g., the carbene precursor is a diazoketone). $R^4$ can be, for example, methyl, ethyl, n-propyl, isopropyl, n-butyl, isobutyl, sec-butyl, tert-butyl, n-pentyl, isopentyl, n-hexyl, or branched hexyl. In some embodiments, $R^4$ is $C_{1-6}$ alkoxy and $R^3$ is H or $C_{1-6}$ alkyl.

In some embodiments, $R^3$ is H and $R^4$ is $C_{1-6}$ alkoxy in carbene precursors according to Formula II. In some embodiments, the cyclopropene product is a compound according to Formula III as set forth above. In some embodiments, the cyclopropene is selected from:

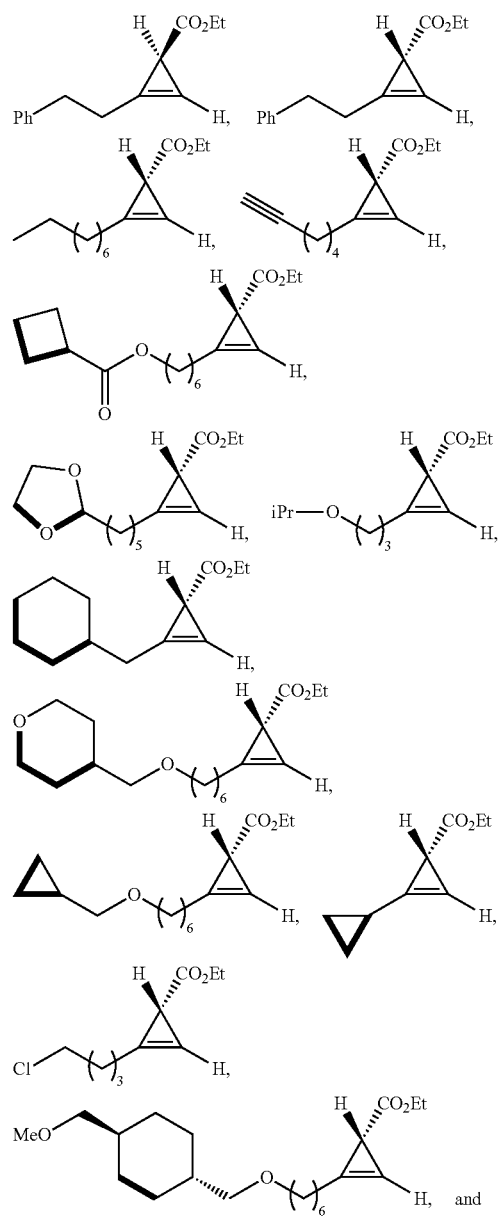

-continued

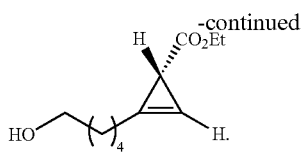

Cyclopropene products prepared according to the methods described herein can themselves be used as intermediate compounds for further elaboration via one more organic transformations. For example, the methods provided herein can further include polymerizing the cyclopropene product. In some embodiments, the present invention provides a method for ring-opening metathesis polymerization (ROMP), as shown in Equation 3. See also, Elling, et al. *J. Am. Chem. Soc.*, 2015, 137, 9922-9926.

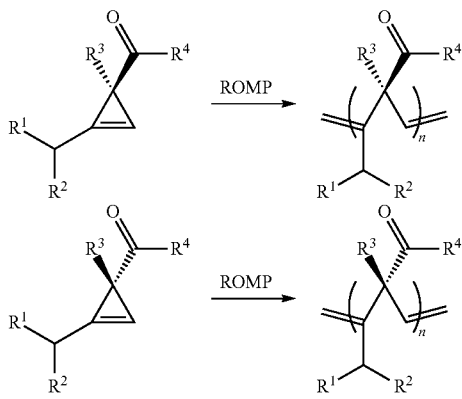

(3)

In Equation 3, $R^1$, $R^2$, $R^3$, and $R^4$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

In some embodiments, the method further comprises converting the cyclopropene product to a cyclopropane. For example, multi-substituted cyclopropanes can be prepared as shown in Equation 4:

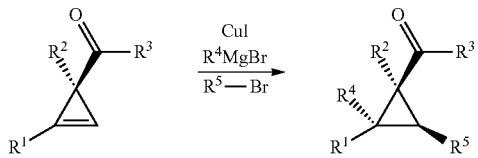

(4)

wherein $R^1$, $R^2$, $R^3$, $R^4$, and $R^5$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

In some embodiments, the method further comprises contacting the cyclopropene product with a diene or a tetrazine under conditions sufficient to form a cycloaddition product. For example, fused ring systems can be built as shown in Equation 5:

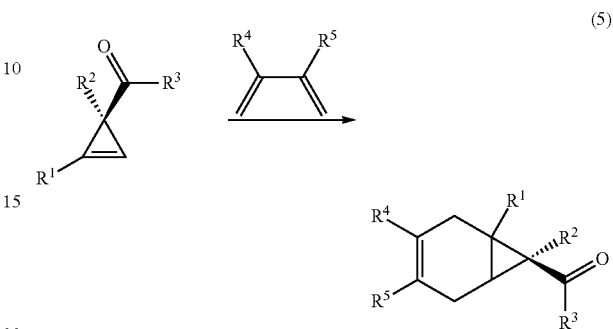

(5)

wherein $R^1$, $R^2$, $R^3$, $R^4$, and $R^5$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

In certain aspects, the present invention provides a method to label molecules via inverse Diels Alder cycloadditions, as shown in Equation 6. See also, Blackman, et al. *J. Am. Chem. Soc.*, 2008, 130, 13518-13519.

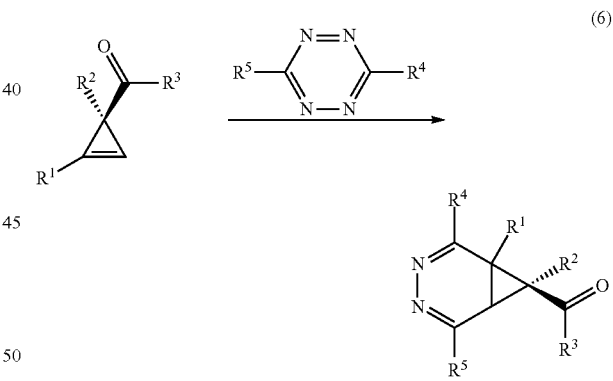

(6)

In Equation 6, $R^1$, $R^2$, $R^3$, $R^4$, and $R^5$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

C. Bicyclobutane Products

In some embodiments, methods for producing bicyclobutane products comprise combining an alkyne, a carbene precursor, and a heme protein, homolog thereof, variant thereof, or fragment thereof as described herein under conditions sufficient to form the bicyclobutane.

In some embodiments, the alkyne is a compound according to Formula IV:

(IV)

wherein $R^{11}$ is selected from the group consisting of H, $C_{1-18}$ alkyl, $C_{1-18}$ haloalkyl, $C_{2-18}$ alkenyl, $C_{2-18}$ alkynyl, $(C_{3-10}$ cycloalkyl)-$L^{11}$-, $(C_{6-10}$ aryl)-$L^{11}$-, (5- to 10-membered heteroaryl)-$L^{11}$-, (5- to 10-membered heterocyclyl)-$L^{11}$-, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$, and $P(O)(OR^{17})_2$;

$C_{1-18}$ alkyl, $C_{3-10}$ cycloalkyl, $C_{6-10}$ aryl, 5- to 10-membered heteroaryl, and 5- to 10-membered heterocyclyl in $R^{11}$ are optionally and independently substituted with one or more $R^{11a}$;

each $R^{11a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^{11}$ is selected from the group consisting of a bond and $C_{1-20}$ alkylene;

when $L^{11}$ is $C_{2-20}$ alkylene, one or more non-adjacent $CH_2$ groups are optionally and independently replaced with O, S, or NH;

when $L^{11}$ is $C_{3-20}$ alkylene, one or more pairs of adjacent $CH_2$ groups are optionally and independently replaced with $C(O)O$ or $C(O)NH$;

$R^{12}$ is selected from the group consisting of H, $C_{1-18}$ alkyl, $C_{1-18}$ haloalkyl, $C_{2-18}$ alkenyl, $C_{2-18}$ alkynyl, $(C_{3-10}$ cycloalkyl)-$L^{12}$-, $(C_{6-10}$ aryl)-$L^{12}$-, (5- to 10-membered heteroaryl)-$L^{12}$-, (5- to 10-membered heterocyclyl)-$L^{12}$-, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$, and $P(O)(OR^{17})_2$;

$C_{1-18}$ alkyl, $C_{3-10}$ cycloalkyl, $C_{6-10}$ aryl, 5- to 10-membered heteroaryl, and 5- to 10-membered heterocyclyl in $R^{12}$ are optionally and independently substituted with one or more $R^{12a}$;

each $R^{12a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^{12}$ is selected from the group consisting of a bond and $C_{1-20}$ alkylene;

when $L^{12}$ is $C_{2-20}$ alkylene, one or more non-adjacent $CH_2$ groups are optionally and independently replaced with O, S, or NH;

when $L^{12}$ is $C_{3-20}$ alkylene, one or more pairs of adjacent $CH_2$ groups are optionally and independently replaced with $C(O)O$ or $C(O)NH$;

each $R^{17}$, $R^{18}$, and $R^{19}$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl.

In some embodiments, and $R^{12}$ in alkynes of Formula IV are independently selected from H and $C_{1-6}$ alkyl. $R^{11}$ and $R^{12}$ can be, for example, H, methyl, ethyl, n-propyl, isopropyl, n-butyl, isobutyl, sec-butyl, tert-butyl, n-pentyl, isopentyl, or n-hexyl. In some embodiments, $R^{12}$ in alkynes according to Formula IV is H.

In some embodiments, $R^{11}$ is selected from the group consisting of $(C_{6-10}$ aryl)-$L^{11}$-, (5- to 10-membered heteroaryl)-$L^{11}$-; $C_{6-10}$ aryl and 5- to 10-membered heteroaryl are optionally substituted with one or more $R^{11a}$; and $L^{11}$ is a bond.

In some embodiments, $R^{11}$ is selected from the group consisting of $C_{1-18}$ alkyl, $C_{2-18}$ alkynyl, $(C_{3-10}$ cycloalkyl)-$L^{11}$-, $(C_{6-10}$ aryl)-$L^{11}$-, (5- to 10-membered heteroaryl)-$L^{11}$-, and (5- to 10-membered heterocyclyl)-$L^{11}$-, each of which is optionally and independently substituted with one or more $R^{11a}$. In some embodiments, $R^{11}$ is selected from the group consisting of $C_{1-8}$ alkyl and $C_{2-8}$ alkynyl, each of which is optionally substituted with one or more $R^{11a}$. $R^{11}$ can be, for example, optionally substituted methyl, optionally substituted ethyl, optionally substituted n-propyl, optionally substituted isopropyl, optionally substituted n-butyl, optionally substituted isobutyl, optionally substituted sec-butyl, optionally substituted tert-butyl, optionally substituted n-pentyl, optionally substituted isopentyl, optionally substituted n-hexyl, optionally substituted branched hexyl, optionally substituted n-heptyl, optionally substituted branched heptyl, optionally substituted n-octyl, optionally substituted branched octyl, optionally substituted ethynyl, optionally substituted prop-1-yn-1-yl, optionally substituted prop-2-yn-1-yl, optionally substituted but-1-yn-1-yl, optionally substituted but-2-yn-1-yl, optionally substituted but-3-yn-1-yl, optionally substituted pent-1-yn-1-yl, optionally substituted pent-2-yn-1-yl, optionally substituted p ent-3-yn-1-yl, optionally substituted pent-4-yn-1-yl, optionally substituted hex-1-yn-1-yl, optionally substituted hex-2-yn-1-yl, optionally substituted hex-3-yn-1-yl, optionally substituted hex-4-yn-1-yl, optionally substituted hex-5-yn-1-yl, optionally substituted hept-1-yn-1-yl, optionally substituted hept-2-yn-1-yl, optionally substituted hept-3-yn-1-yl, optionally substituted hept-4-yn-1-yl, optionally substituted hept-5-yn-1-yl, optionally substituted hept-6-yn-1-yl, optionally substituted oct-1-yn-1-yl, optionally substituted oct-2-yn-1-yl, optionally substituted oct-3-yn-1-yl, optionally substituted oct-4-yn-1-yl, optionally substituted oct-5-yn-1-yl, optionally substituted oct-6-yn-1-yl, or optionally substituted oct-7-yn-1-yl. Alkynes according to Formula IV having alkenyl $R^{11}$ groups, cycloalkyl $R^{11}$ groups, and the like can also be employed.

In some embodiments, $R^{11}$ in alkynes according to Formula IV is selected from the group consisting of $C_{1-6}$ alkyl and $C_{2-6}$ alkynyl, each of which is optionally substituted with one or more $R^{11a}$. In some such embodiments, $R^{11}$ is $C_{1-6}$ alkyl and $R^{11a}$ is selected from halogen (e.g., Cl or Br), —OH, $C_{1-6}$ alkoxy (e.g., methoxy, ethoxy, n-propoxy, or isopropoxy), and $C_{1-6}$ heteroalkyl (e.g., methoxymethyl or ethoxymethyl).

In some embodiments, $R^{11}$ is selected from $(C_{3-10}$ cycloalkyl)-$L^{11}$-, $(C_{6-10}$ aryl)-$L^{11}$-, (5- to 10-membered heteroaryl)-$L^{11}$-, (5- to 10-membered heterocyclyl)-$L^{11}$-, wherein cycloalkyl, aryl, heteroaryl, and heterocyclyl are optionally substituted with one or more $R^{11a}$. In some embodiments, $L^{11}$ is a covalent bond. For example, the grouping $(C_{3-10}$ cycloalkyl)-$L^{11}$- can be optionally substituted cyclopropyl, optionally substituted cyclobutyl, optionally substituted cyclopentyl, optionally substituted cyclohexyl, or the like. In some embodiments, $L^{11}$ is $C_{1-20}$ alkylene (e.g., $C_{1-10}$ alkylene or $C_{1-6}$ alkylene). For example, the grouping $(C_{3-10}$ cycloalkyl)-$L^{11}$- can be cyclohexylmethyl, (2-cyclohexyl)eth-1-yl, (3-cyclohexyl)prop-1-yl, or the like. The grouping $(C_{6-10}$ aryl)-$L^{11}$- can be, for example, phenethyl. Cycloalkyl groups, aryl groups, and heterocyclyl groups can be further substituted with $R^{11a}$ groups as described above. In some embodiments, $R^{11}$ is cyclopropyl, cyclobutyl, cyclohexyl, 1,3-dioxolan-2-yl, or tetrahydropyran-1-yl; and $R^{11a}$ is —OH, $C_{1-6}$ alkoxy (e.g., methoxy, ethoxy, n-propoxy, or isopropoxy), or $C_{1-6}$ heteroalkyl (e.g., methoxymethyl or ethoxymethyl).

In some embodiments, $L^{11}$ is $C_{1-20}$ alkylene where one or more non-adjacent $CH_2$ groups are optionally and independently replaced with O, S, or NH. For example, the $L^{11}$ moiety may have the formula —$(CH_2)_w(L^{11a})_x(CH_2)_y(L^{11a})_x(CH_2)_z$—, where each $L^{11a}$ is independently O, S, or NH; each subscript x is independently 0 or 1; and each of subscripts w, y, and z is a non-zero integer such that the sum of subscript w, subscript x, subscript y, and subscript z is less than or equal to 20. In some such embodiments, each $L^{11a}$ is 0. In some embodiments, the $L^{11}$ moiety is —$CH_2O(CH_2)_6$—.

In some embodiments, $L^{11}$ is $C_{3-20}$ alkylene wherein one or more pairs of adjacent $CH_2$ groups are optionally and independently replaced with C(O)O or C(O)NH. For example, the $L^{11}$ moiety may have the formula —$(CH_2)_q(L^{11b})_r(CH_2)_s(L^{11b})_t(CH_2)_u$—, where each $L^{11b}$ is C(O)O or C(O)NH; subscript r and subscript t are independently 0 or 1; and each of subscripts q, s, and u is a non-zero integer such that: 1) the sum of subscript q, subscript s, and subscript u is less than or equal to 20 when subscript r and subscript t are 0; 2) the sum of subscript q, subscript s, and subscript u is less than or equal to 18 when the sum of subscript r and subscript t is 1; or 3) the sum of subscript q, subscript s, and subscript u is less than or equal to 16 when the sum of subscript r and subscript t is 2. In some embodiments, the $L^{11}$ moiety is —$C(O)O(CH_2)_6$—. $L^{11}$ groups having both one or more $L^{11a}$ moieties (i.e., O, S, or NH) and one or more $L^{11b}$ moieties (i.e., C(O)O or C(O)NH) can also be employed.

In some embodiments, each $R^{11a}$ is independently selected from the group consisting of halogen, —OH, $C_{1-6}$ alkyl, $C_{1-6}$ alkoxy, $C_{1-6}$ heteroalkyl (e.g., hydroxymethyl), and $C_{2-6}$ alkynyl. In some embodiments, the alkyne for forming bicyclobutane products is selected from:

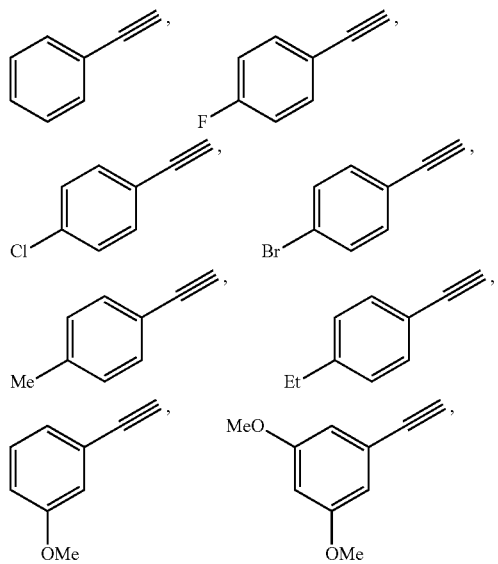

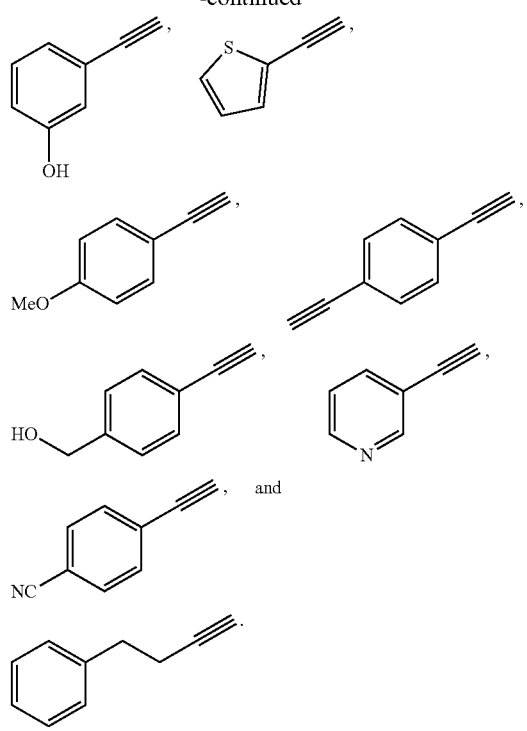

In some embodiments, the alkyne for forming bicyclobutane products is selected from:

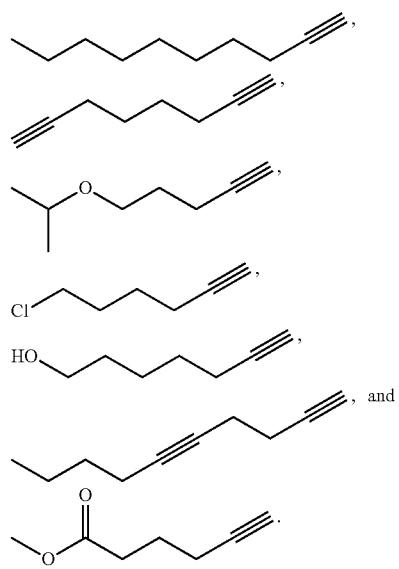

In some embodiments, the alkyne for forming bicyclobutane products is selected from:

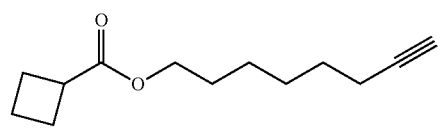

-continued

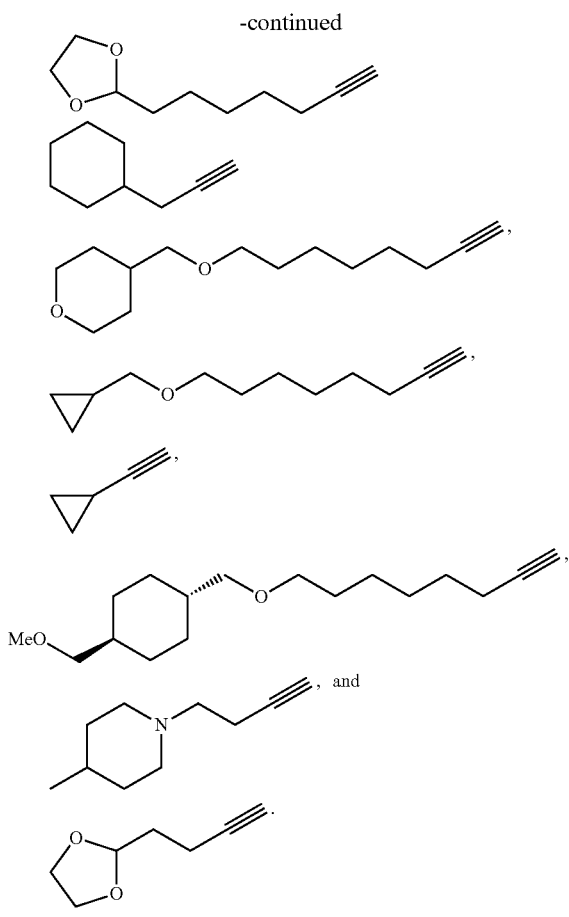

Any suitable carbene precursor (e.g., an amine, an azide, a hydrazine, a hydrazone, an epoxide, a diazirene, or a diazo compound) can be used in the methods. In some embodiments, the carbene precursor is a diazo compound such as a compound according to Formula V:

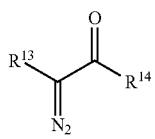

(V)

wherein $R^{13}$ and $R^{14}$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$ and $P(O)(OR^{17})_2$; and each $R^{17}$, $R^{18}$, and $R^{19}$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl.

In some embodiments, $R^{13}$ and $R^{14}$ are independently selected from the group consisting of H, $C_{1-6}$ alkoxy, and $C_{1-6}$ alkyl. In some embodiments, $R^{14}$ is optionally substituted $C_{1-6}$ alkoxy (e.g., the carbene precursor is a diazoester). For example, $R^{14}$ can be optionally substituted methoxy (e.g., benzyloxy), optionally substituted ethoxy, optionally substituted n-propoxy, optionally substituted isopropoxy, optionally substituted n-butoxy, optionally substituted isobutoxy, or optionally substituted t-butoxy. In some embodiments, $R^{14}$ is $C_{1-6}$ alkoxy and $R^{13}$ is H or $C_{1-6}$ alkyl.

In some embodiments, $R^{14}$ is optionally substituted $C_{1-6}$ alkyl (e.g., the carbene precursor is a diazoketone). $R^{14}$ can be, for example, methyl, ethyl, n-propyl, isopropyl, n-butyl, isobutyl, sec-butyl, tert-butyl, n-pentyl, isopentyl, n-hexyl, or branched hexyl. In some embodiments, $R^{14}$ is $C_{1-6}$ alkoxy and $R^{13}$ is H or $C_{1-6}$ alkyl.

In some embodiments, $R^{13}$ is H and $R^{14}$ is $C_{1-6}$ alkoxy in carbene precursors according to Formula V. In some embodiments, the product is a bicyclobutane according to Formula VI as set forth above. In some embodiments, the bicyclobutane is selected from:

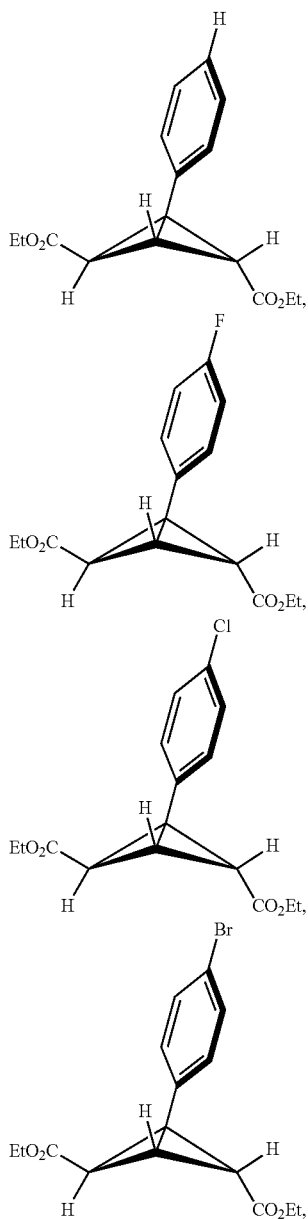

-continued

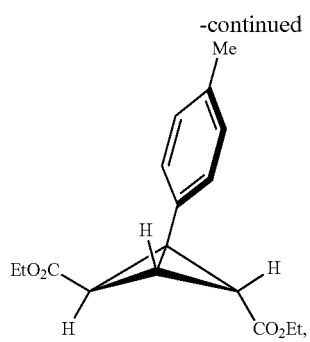
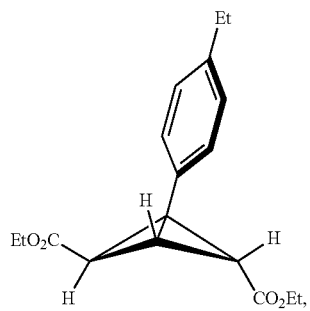
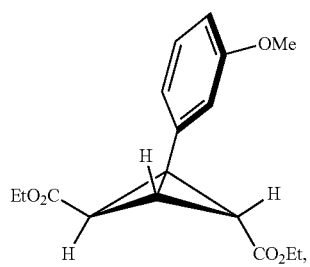
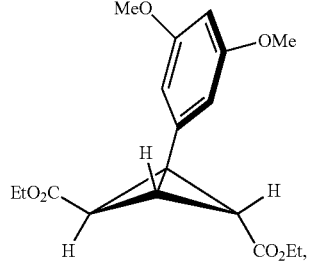
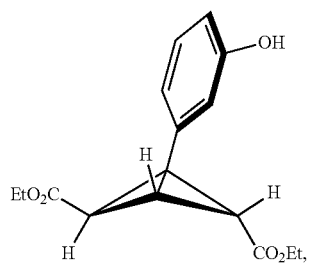
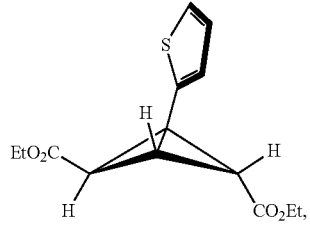

-continued

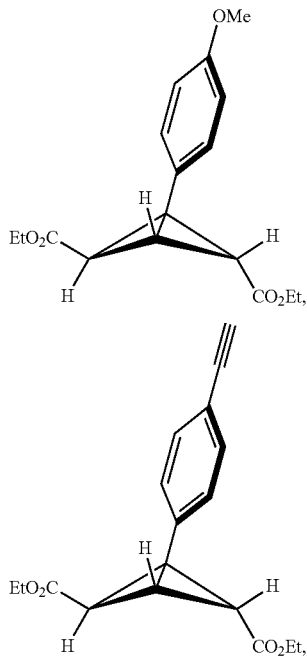
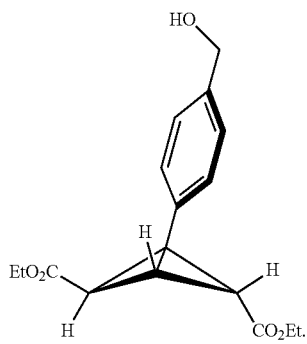
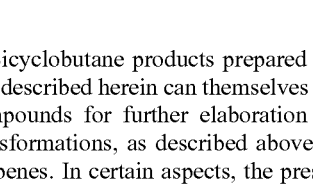

Bicyclobutane products prepared according to the methods described herein can themselves be used as intermediate compounds for further elaboration via one more organic transformations, as described above with respect to cyclopropenes. In certain aspects, the present invention provides a method for producing polyester by using the bicyclobutane product according to Equation 7:

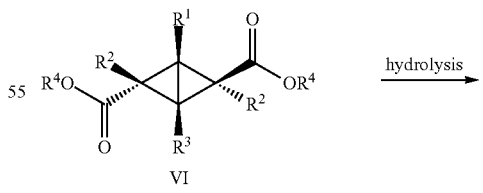
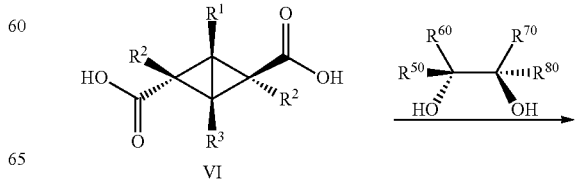

(7)

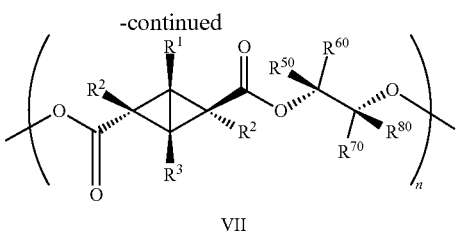

VII wherein $R^1$, $R^2$, $R^3$, $R^4$, $R^{50}$, $R^{60}$, $R^{70}$, and $R^{80}$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

In certain aspects, the present invention provides a method for synthesizing highly functionalized chiral cyclobutane-containing molecules via strain-release amination, as shown in Equation 8. See also, Gianatassio, et al. *Science* 2016, 351, 241-246.

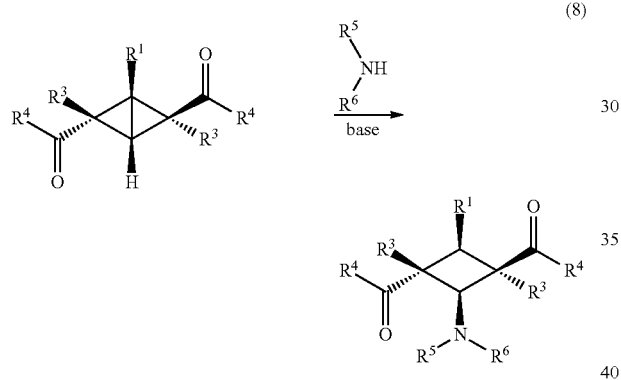

(8)

In Equation 8, $R^1$, $R^2$, $R^3$, $R^4$, $R^5$, and $R^6$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

Accordingly, some of the embodiments disclosed herein provide methods which further include hydrolyzing the bicyclobutane to form a dicarboxylate-substituted bicyclobutane. In some embodiments, the method further comprises contacting the dicarboxylate-substituted bicyclobutane with an amine under conditions sufficient to form a diamido-substituted bicyclobutane. In some embodiments, the method further comprises contacting the dicarboxylate-substituted bicyclobutane with a diol under conditions sufficient to form a polyester.

In certain aspects, the present invention provides a method for producing functionalized polybenzvalenes from bicyclobutane products according to Equation 9. Functionalized polybenzvalenes contains high strain-energies and have potential applications in propulsion technologies. (See, e.g., Agrawal, (2010). *High energy materials: propellants, explosives and pyrotechnics.* John Wiley & Sons.) Non-conjugated polybenzvalene polymers could also isomerize to conjugated conductive polyacetylenes without extrusion of molecular fragments as shown in Equation 10. (See, Swager, et al. *J. Am. Chem. Soc.,* 1988, 110(9), 2973-2974.) This feature makes polybenzvalenes highly desirable for producing conductive polymers with highly ordered morphologies. Furthermore, as this isomerization process can be promoted chemically, photochemically, mechanically, thermally, and by transition metals, polybenzvalene polymers have huge potentials as stimuli-responsive materials. (See, Chen, et al. *Science,* 2017, 357, 475-479.)

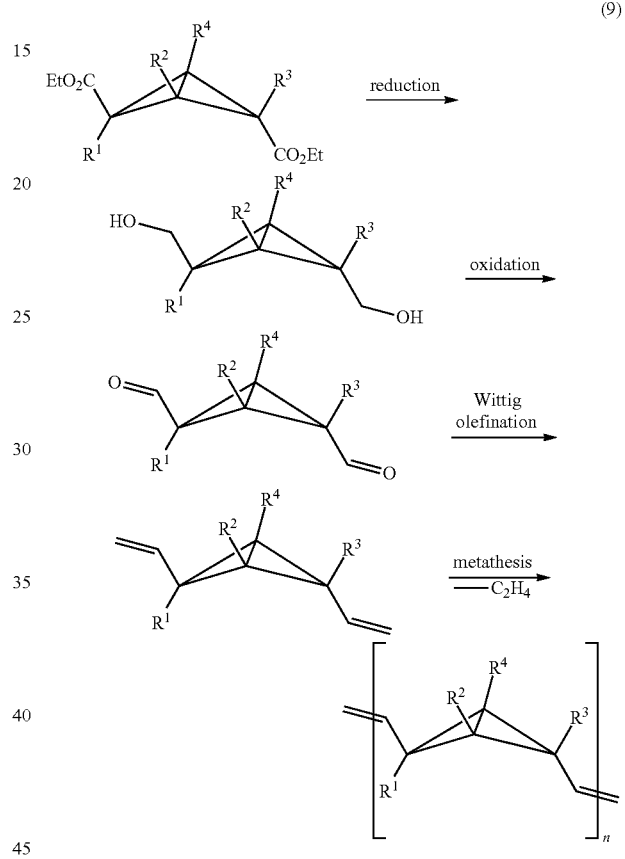

(9)

functionalized polybenzvalene

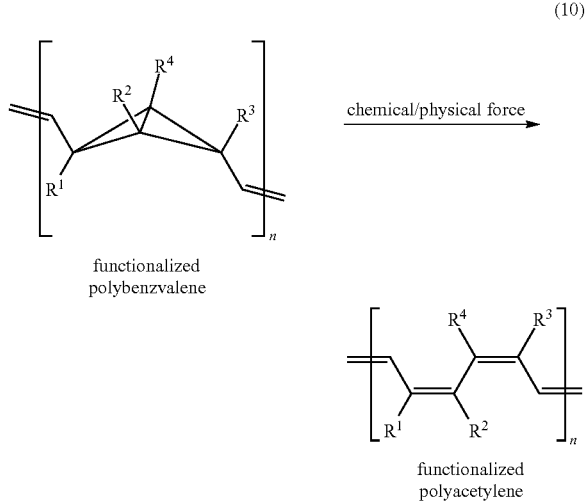

(10)

functionalized polybenzvalene functionalized polyacetylene

In Equation 9 and Equation 10, $R^1$, $R^2$, $R^3$, and $R^4$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$.

Accordingly, some of the embodiments disclosed herein provide methods which further include reducing the bicyclobutane to form a dihydroxy-substituted bicyclobutane. In some embodiments, the methods further include converting the dihydroxy-substituted bicyclobutane to a polybenzvalene or a polyacetylene.

In certain aspects, the present invention provides a method for incorporating bicyclobutane groups into molecules via click chemistry, as shown in Equation 11.

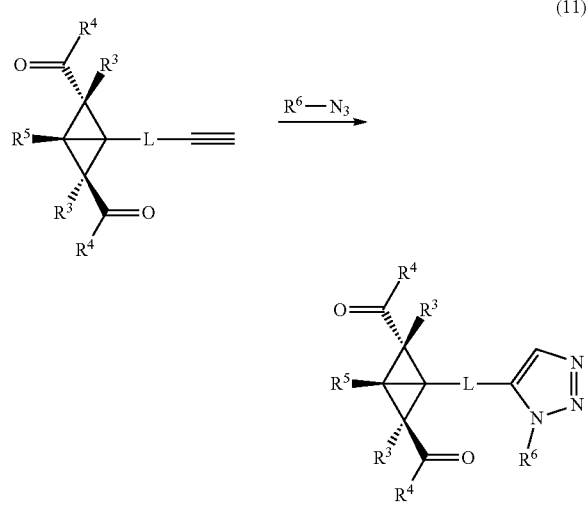

(11)

In Equation 11, $R^1$, $R^2$, $R^3$, $R^4$, $R^5$, and $R^6$ are independently selected from the group consisting of H, optionally substituted $C_{1-18}$ alkyl, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$, and L is a linking moiety (e.g., a linking moiety $L^1$ or $L^{11}$ as described above).

Accordingly, some of the embodiments disclosed herein provide methods wherein the bicyclobutane comprises an alkyne moiety and the method further comprises contacting the alkyne moiety with an azide under conditions sufficient to form a triazole moiety.

The alkyne reagents, carbene precursor reagents, and strained carbocycle products described herein can be further substituted. A compound according to Formula I, Formula Ia, or Formula III may contain, for example, an optionally substituted $R^1$ group or an optionally substituted $R^2$ group, while a compound according to Formula II or Formula III may contain an optionally substituted $R^3$ group, one or more optionally substituted $R^4$ groups. A compound according to Formula IV or Formula VI may contain, for example, an optionally substituted $R^{11}$ group or an optionally substituted $R^{12}$ group, while a compound according to Formula V or Formula VI may contain an optionally substituted $R^{13}$ group, one or more optionally substituted $R^{14}$ groups. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure is substituted with more than one substituent selected from a specified group, the substituent may be either the same or different at every position. Combinations of substituents are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In general, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group.

Suitable monovalent substituents on a substitutable carbon atom of an "optionally substituted" group are independently halogen; $-(CH_2)_{0-4}R^\alpha$; $-(CH_2)_{0-4}OR^\alpha$; $-O(CH_2)_{0-4}R^\alpha$; $-O-(CH_2)_{0-4}C(O)OR^\alpha$; $-(CH_2)_{0-4}CH(OR^\alpha)_2$; $-(CH_2)_{0-4}SR^\alpha$; $-(CH_2)_{0-4}Ph$, wherein Ph is phenyl which may be substituted with $R^\alpha$; $-(CH_2)_{0-4}O(CH_2)_{0-1}$phenyl, which phenyl may be substituted with $R^\alpha$; $-CH=CHPh$, wherein Ph is phenyl which may be substituted with $R^\alpha$; $-(CH_2)_{0-4}O(CH_2)_{0-1}$-Py, wherein Py is pyridyl which may be substituted with $R^\alpha$; $-NO_2$; $-CN$; $-N_3$; $-(CH_2)_{0-4}N(R^\alpha)_2$; $-(CH_2)_{0-4}N(R^\alpha)C(O)R^\alpha$; $-N(R^\alpha)C(S)R^\alpha$; $-(CH_2)_{0-4}N(R^\alpha)C(O)NR^\alpha_2$; $-N(R^\alpha)C(S)NR^\alpha_2$; $-(CH_2)_{0-4}N(R^\alpha)C(O)OR^\alpha$; $-N(R^\alpha)N(R^\alpha)C(O)R^\alpha$; $-N(R^\alpha)N(R^\alpha)C(O)NR^\alpha_2$; $-N(R^\alpha)N(R^\alpha)C(O)OR^\alpha$; $-(CH_2)_{0-4}C(O)R^\alpha$; $-C(S)R^\alpha$; $-(CH_2)_{0-4}C(O)OR^\alpha$; $-(CH_2)_{0-4}C(O)SR^\alpha$; $-(CH_2)_{0-4}C(O)OSiR^\alpha_3$; $-(CH_2)_{0-4}OC(O)R^\alpha$; $-OC(O)(CH_2)_{0-4}SR-SC(S)SR^\alpha$; $-(CH_2)_{0-4}SC(O)R^\alpha$; $-(CH_2)_{0-4}C(O)NR^\alpha_2$; $-C(S)NR^\alpha_2$, $-C(S)SR^\alpha$; $-SC(S)SR^\alpha$, $-(CH_2)_{0-4}OC(O)NR^\alpha_2$; $-C(O)N(OR^\alpha)R^\alpha$; $-C(O)C(O)R^\alpha$; $-C(O)CH_2C(O)R^\alpha$; $-C(NOR^\alpha)R^\alpha$; $-(CH_2)_{0-4}SSR^\alpha$; $-(CH_2)_{0-4}S(O)_2R^\alpha$; $-(CH_2)_{0-4}S(O)_2OR^\alpha$; $-(CH_2)_{0-4}OS(O)_2R^\alpha$; $-S(O)_2NR^\alpha_2$; $-(CH_2)_{0-4}S(O)R^\alpha$; $-N(R^\alpha)S(O)_2NR^\alpha_2$; $-N(R^\alpha)S(O)_2R^\alpha$; $-N(OR^\alpha)R^\alpha$; $-C(NH)NR^\alpha_2$; $-P(O)_2R^\alpha$; $-P(O)R^\alpha_2$; $-OP(O)R^\alpha_2$; $-OP(O)(OR^\alpha)_2$; $SiR^\alpha_3$; $-(C_{1-4}$ straight or branched)alkylene)-O-$N(R^\alpha)_2$; or $-(C_{1-4}$ straight or branched)alkylene)C(O)O-$N(R^\alpha)_2$. Each $R^\alpha$ is independently hydrogen; $C_{1-6}$ alkyl; $-CH_2Ph$, $-O(CH_2)_{0-1}Ph$; $-CH_2$-(5- to 6-membered heteroaryl); $C_{3-8}$ cycloalkyl; $C_{6-10}$ aryl; 4- to 10-membered heterocyclyl; or 6- to 10-membered heteroaryl; and each $R^\alpha$ may be further substituted as described below.

Suitable monovalent substituents on $R^\alpha$ are independently halogen, $-(CH_2)_{0-2}R^\beta$; $-(CH_2)_{0-2}OH$; $-(CH_2)_{0-2}OR^\beta$; $-(CH_2)_{0-2}CH(OR^\beta)_2$; $-CN$; $-N_3$; $-(CH_2)_{0-2}C(O)R^\beta$; $-(CH_2)_{0-2}C(O)OH$; $-(CH_2)_{0-2}C(O)OR^\beta$; $-(CH_2)_{0-2}SR^\beta$; $-(CH_2)_{0-2}SH$; $-(CH_2)_{0-2}NH_2$; $-(CH_2)_{0-2}NHR^\beta$; $-(CH_2)_{0-2}NR^\beta_2$; $-NO_2$; $SiR^\beta_3$; $-OSiR^\beta_3$; $-C(O)SR^\beta$; $-(C_{1-4}$ straight or branched alkylene)-$C(O)OR^\beta$; or $-SSR^\beta_2$; wherein each $R^\beta$ is independently selected from $C_{1-4}$ alkyl; $-CH_2Ph$; $-O(CH_2)_{0-1}Ph$; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^\alpha$ include $=O$ and $=S$.

Suitable divalent substituents on a saturated carbon atom of an "optionally substituted" group include the following: $=O$; $=S$; $=NNR^\gamma{}_2$; $=NNHC(O)R^\gamma$; $=NNHC(O)OR^\gamma$; $=NNHS(O)_2R^\gamma$; $=NR^\gamma$; $=NOR^\gamma$; $-O(C(R^\gamma{}_2))_{2-3}O-$; or $-S(C(R^\gamma{}_2))_{2-3}S-$; wherein each independent occurrence of $R^\gamma$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted" group include: $-O(CR^\beta{}_2)_{2-3}O-$; wherein each independent occurrence of $R^\beta$ is selected from hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\gamma$ include halogen; $-R^\delta$; $-OH$; $-OR^\delta$; $-CN$; $-C(O)OH$; $-C(O)OR^\delta$; $-NH_2$; $-NHR^\delta$; $-NR^\delta{}_2$; or $-NO_2$; wherein each $R^\delta$ is independently $C_{1-4}$ alkyl; $-CH_2Ph$; $-O(CH_2)_{0-1}Ph$; 4- to 10-membered heterocyclyl; or 6- to 10-membered heteroaryl.

Suitable substituents on a substitutable nitrogen of an "optionally substituted" group include $-R^\epsilon$; $-NR^\epsilon{}_2$; $-C(O)R^\epsilon$; $-C(O)OR^\epsilon$; $-C(O)C(O)R^\epsilon$; $-C(O)CH_2C(O)R^\epsilon$; $-S(O)_2R^\epsilon$; $-S(O)_2NR^\epsilon{}_2$; $-C(S)NR^\epsilon{}_2$; $-C(NH)NR^\epsilon{}_2$; or $-N(R^\epsilon)S(O)_2R^\epsilon$; wherein each $R^\epsilon$ is independently hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\epsilon$ are independently halogen; $-R^\delta$; $-OH$; $\delta OR^\delta$; $-CN$; $-C(O)OH$; $-C(O)OR^\delta$; $-NH_2$; $-NHR^\delta$; $-NR^\delta{}_2$; or $-NO_2$; wherein each $R^\delta$ is independently $C_{1-4}$ alkyl; $-CH_2Ph$; $-O(CH_2)_{0-1}Ph$; $C_{6-10}$ aryl; 4- to 10-membered heterocyclyl; or 6- to 10-membered heteroaryl.

D. Reaction Conditions for Enzyme-Catalyzed Carbocycle Formation

The enzymes of the present invention can be used in purified form, partially purified form, or as whole-cell (e.g., bacterial) catalysts, without purification. Many alkyne substrates and carbene precursors can enter *E. coli* cells and interact with the enzymes inside the cells, where the reaction takes place. Thus strained rings can be made in a process wherein intact or partially permeabilized cells expressing the enzyme catalyst are suspended in buffer and combined with alkyne and carbene precursor (dissolved in appropriate solvent or in a form of suspension) and allowed to react. The process can also use purified or partially purified protein in place of whole bacterial cells. Other processes can involve changing contacting conditions (e.g., maintaining the catalyst in a compartment such as behind a filter membrane or bag through which reactants and products can pass or immobilizing the catalyst in some other way). One skilled in the art will be able to identify appropriate processing conditions for a given set of substrates and catalysts.

The methods of the invention include forming reaction mixtures that comprise an alkyne, a carbene precursor, and a heme protein, fragment thereof, homolog thereof, or variant thereof as described above. In some embodiments, the method is carried out in vitro. In other embodiments, the heme protein is localized within a whole cell and the method is carried out in vivo. In some embodiments, the heme protein is expressed in a bacterial, archaeal, yeast or fungal host organism. In some embodiments, the method is carried out under anaerobic conditions. In other embodiments, the process is carried out under aerobic conditions.

The heme proteins, fragments thereof, homologs thereof, or variants thereof can be, for example, purified prior to addition to a reaction mixture or secreted by a cell present in the reaction mixture. The reaction mixture can contain a cell lysate including the heme protein, fragment thereof, homolog thereof, or variant thereof, as well as other proteins and other cellular materials. Alternatively, a heme protein, fragment thereof, homolog thereof, or variant thereof can catalyze the reaction within a cell expressing the heme protein, fragment thereof, homolog thereof, or variant thereof. Any suitable amount of heme protein, fragment thereof, homolog thereof, or variant thereof can be used in the methods of the invention. In general, the reaction mixtures will contain from about 0.01 mol % to about 10 mol % heme protein with respect to the carbene precursor (e.g., diazo reagent) and/or alkyne. The reaction mixtures can contain, for example, from about 0.01 mol % to about 0.1 mol % heme protein, or from about 0.1 mol % to about 1 mol % heme protein, or from about 1 mol % to about 10 mol % heme protein. The reaction mixtures can contain from about 0.05 mol % to about 5 mol % heme protein, or from about 0.05 mol % to about 0.5 mol % heme protein. The reaction mixtures can contain about 0.1, 0.2, 0.3, 0.4, 0.5, 0.6, 0.7, 0.8, 0.9, or about 1 mol % heme protein.

The concentration of the alkyne and the carbene precursor (e.g., a diazo reagent) are typically in the range of from about 100 μM to about 1 M. The concentration can be, for example, from about 100 μM to about 1 mM, or about from 1 mM to about 100 mM, or from about 100 mM to about 500 mM, or from about 500 mM to 1 M. The concentration can be from about 500 μM to about 500 mM, 500 μM to about 50 mM, or from about 1 mM to about 50 mM, or from about 15 mM to about 45 mM, or from about 15 mM to about 30 mM. The concentration of alkyne or carbene precursor can be, for example, about 100, 200, 300, 400, 500, 600, 700, 800, or 900 μM. The concentration of alkyne or carbene precursor can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guanadinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of a cyclopropene product or a bicyclobutane product. The reactions can be conducted at any suitable temperature. In general, the reactions are conducted at a temperature of from about 4° C. to about 40° C. The reactions can be conducted, for example, at about 25° C. or about 37° C. The heme proteins or cells expressing or containing the heme proteins can be heat treated. In some embodiments, heat treatment occurs at a temperature of about 75° C. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the carbene insertion into carbon-carbon bonds occurs in the aqueous phase. In some embodiments, the heme protein, fragment thereof, variant thereof, or homolog thereof, is located in the aqueous layer whereas the substrates and/or products occur in an organic layer. Other reaction conditions may be employed in the methods of the invention, depending on the identity of a particular heme protein, alkyne, or carbene precursor (e.g., diazo reagent).

Reactions can be conducted in vivo with intact cells expressing a heme enzyme of the invention. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Product yields from reactions in vivo can be controlled, in part, by controlling the cell density in the reaction mixtures. Cellular suspensions exhibiting optical densities ranging from about 0.1 to about 50 at 600 nm can be used for the cyclopropene- and bicyclobutane-forming reactions. Other densities can be useful, depending on the cell type, specific heme proteins, or other factors.

The methods of the invention can be assessed in terms of the diastereoselectivity and/or enantioselectivity of carbene insertion into alkyne carbon-carbon bonds—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods of the invention include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments of the invention provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

IV. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1: Enzymatic Cyclopropenation to Yield Compounds of Formula III Using $P450_{BM3}$ Variants In Vivo $P450_{BM3}$ Expression.

45 ml Hyperbroth (100 µg/ml ampicillin) was inoculated with an overnight culture of 5 ml LB (100 µg/ml ampicillin). The overnight culture contained recombinant *E. coli* BL21-DE3 cells harboring a pET22 plasmid, encoding the $P450_{BM3}$ variant under the control of the T7 promoter, and the $P450_{BM3}$ maturation (ccm) operon under the control of a tet promoter, respectively. The cultures were shaken at 220 rpm at 37° C. for approximately 2.5 h. The flask containing the cells was placed on ice for 20 min. The incubator temperature was reduced to 20° C., maintaining the 130 rpm shake rate. Cultures were induced by adding IPTG and aminolevulinic acid to a final concentration of 0.5 mM and 0.5 mM respectively. The cultures were allowed to continue for another 18-22 hours at this temperature and shake rate. Cells were harvested by centrifugation (4° C., 6 min, 4,500× g) to produce a cell pellet.

Preparation of Whole Cell Catalysts.

To prepare whole cells for catalysis, the cell pellet prepared in the previous paragraph was resuspended in M9-N minimal media (M9 media without ammonium chloride) to an optical density ($OD_{600}$) of 60. The cell suspension was used as the catalyst.

Purification of $P450_{BM3}$.

To prepare purified proteins, the cell pellet prepared as described above was stored at −20° C. or below overnight. Frozen cells were resuspended in buffer A (25 mM tris, 20 mM imidazole, 200 mM NaCl, pH 7.5, 4 ml/g of cell wet weight), loaded with 300 μg/ml hemin, and lysed by sonication. To pellet insoluble material, lysates were centrifuged (20,000×g, 15 min, 4° C.). Proteins were expressed in a construct containing a 6x-His tag and purified using a nickel NTA column (1 ml HisTrap HP, GE Healthcare, Piscataway, N.J.) using an AKTAxpress purifier FPLC system (GE Healthcare). P411 enzymes were eluted on a linear gradient from 100% buffer A/0% buffer B (25 mM tris, 300 mM imidazole, 200 mM NaCl, pH 7.5) to 100% buffer B over 10 column volumes. Fractions containing P411 enzymes were pooled, concentrated, and subjected to three exchanges of phosphate buffer (0.1 M KPi, pH 8.0) to remove excess salt and imidazole. Concentrated proteins were aliquotted, flash-frozen on powdered dry ice, and stored at −20° C.

Small-Scale Cyclopropenation Reactions in Whole-Cell Suspension Under Anaerobic Conditions.

Small-scale (400 μL) reactions were carried out in 2 ml glass crimp vials (Agilent Technologies, San Diego, Calif.). Cell suspension ($OD_{600}$=60, 340 μL) was added to an unsealed crimp vial before crimp sealing with a silicone septum. The headspace of the vial was flushed with argon for 10 min (no bubbling). A solution of D-glucose (40 μL, 250 mM) was added, followed by a solution of alkyne of formula I (10 μl, 400 mM in EtOH; for example, 4-phenylbutyne) and a solution of diazo reagent of formula II (10 μl, 400 mM in EtOH; for example, ethyl diazoethanoate or EDA). The reaction vial was left to shake on a plate shaker at 640 rpm for 8 h at room temperature. To quench the reaction, the vial was uncapped and a 1:1 mixture of ethylacetate/cyclohexane (1 ml) was added, followed by 1,2,3-trimethoxybenzene (20 μl, 20 mM in toluene) as an internal standard. The mixture was transferred to a 1.5 ml Eppendorf tube and vortexed and centrifuged (14000×rcf, 5 min). The organic layer was analyzed by gas chromatography (GC), gas chromatography-mass spectrometry (GC-MS), supercritical fluid chromatography (SFC) or normal-phase high performance liquid chromatography (HPLC).

The results of the small scale reactions are shown in FIG. 1 and demonstrate that $P450_{BM3}$ and variants thereof are capable of catalyzing the cyclopropenation to give product of Formula III with high selectivity. Specifically, the best variant P4 found in the initial screen of $P450_{BM3}$ variants encoded the mutations V87A, A328, A268G based on $P411_{BM3}$ "I263F" variant (mutations in P4 relative to wild-type $P450_{BM3}$: V78A, F87P, P142S, T175I, A184V, S226R, H236Q, E252G, I263F, T268G, A290V, A328V, L353V, I366V, C400S, T438S, E442K; mutations in $P411_{BM3}$ "I263F" relative to wild-type $P450_{BM3}$: V78A, F87V, P142S, T175I, A184V, S226R, H236Q, E252G, I263F, T268A, A290V, L353V, I366V, C400S, T438S, E442K), which catalyzed the desired reaction with 450 TTN and 91% ee. This can be improved by further engineering, if desired.

Figure 2:
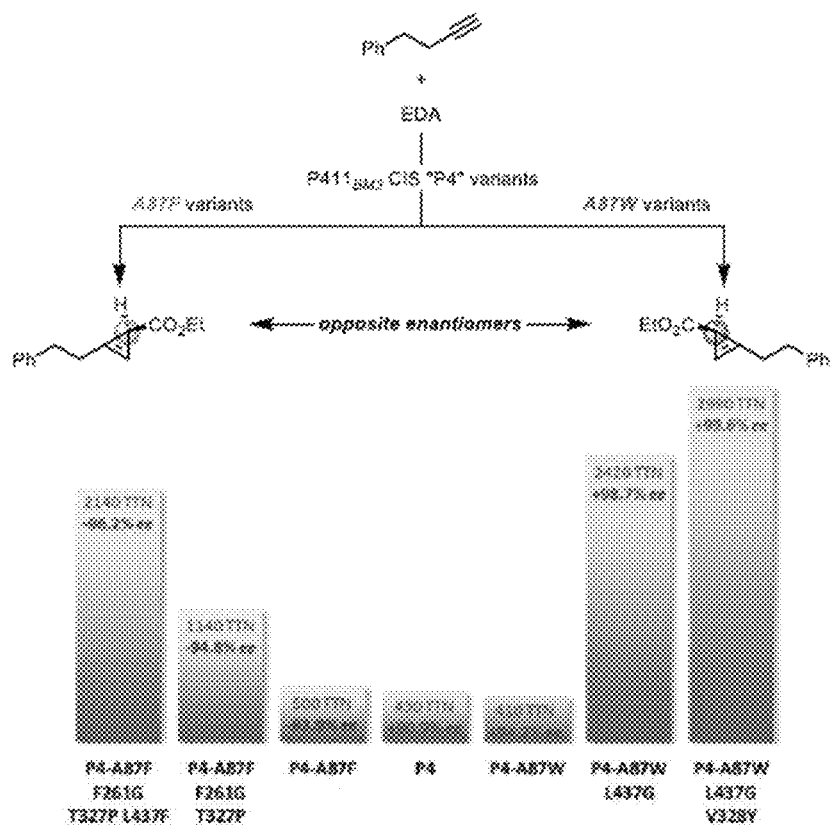
FIG. 2 shows that P450 enzymes can be engineered to provide cyclopropanation products enantioselectively.
Figure 5B:
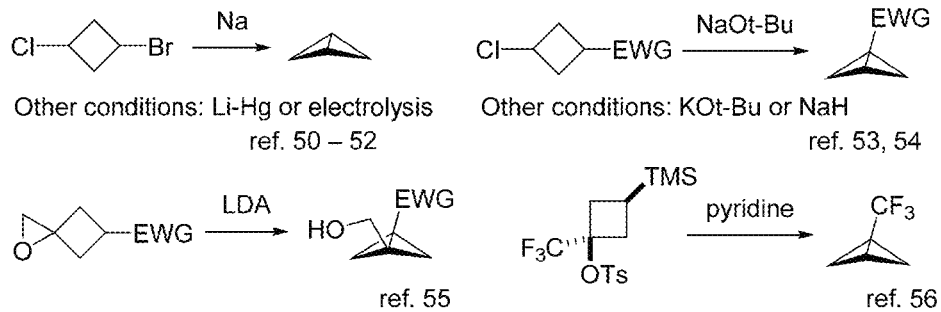
FIG. 5B shows other synthetic methods for forming bicyclobutanes, with selected examples.
Figure 5B:
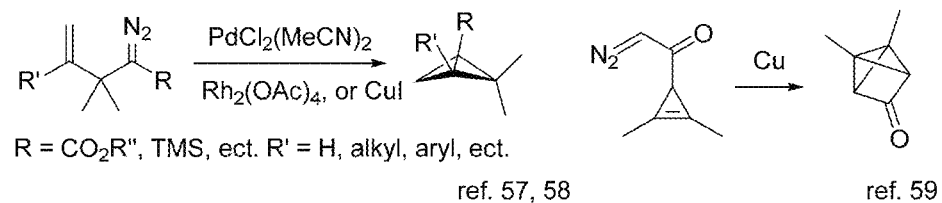
Figure 5B:
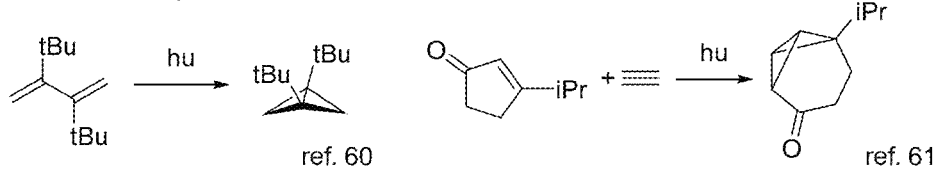
Figure 5C:
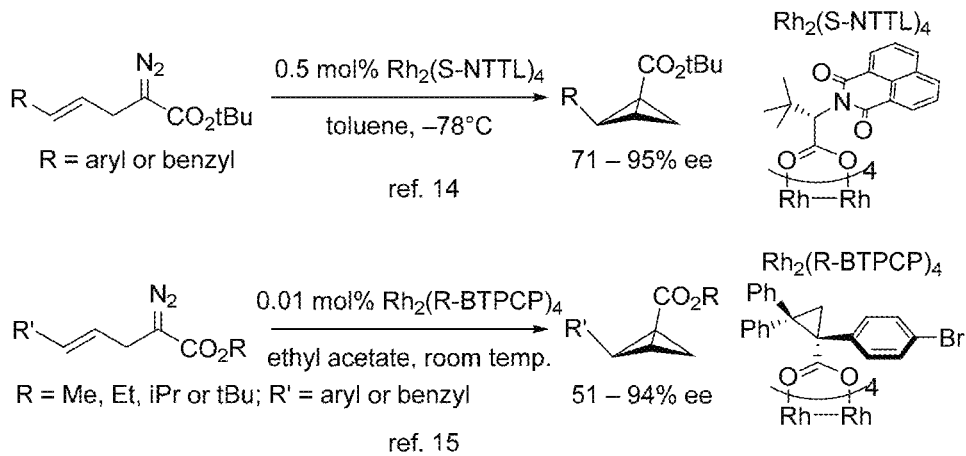
FIG. 5C. shows the only synthetic examples of asymmetric bicyclobutane construction.

The results of the small-scale reactions are shown in FIG. 2 and demonstrate that P4 (mutations in P4 relative to wild-type $P450_{BM3}$: V78A, F87A, P142S, T175I, A184V, S226R, H236Q, E252G, I263F, T268G, A290V, A328V, L353V, I366V, C400S, T438S, E442K) and variants thereof are capable of catalyzing the cyclopropenation to give product of Formula III with high selectivity. Specifically, the best variant for the synthesis of one cyclopropene enantiomer found in the initial screen of P4 variants encoded the mutations A87W, V328Y, L437G based on P4 variant, which catalyzed the desired reaction with 2990 TTN and 99.6% ee. The best variant for the synthesis of the other cyclopropene enantiomer found in the initial screen of P4 variants encoded the mutations S72W, A87F, F261G, T327P, L437F based on P4 variant, which catalyzed the desired reaction with 2140 TTN and −96.2% ee. These two variants can be improved by further engineering, if desired.

Example 2: Enzymatic Bicyclobutanation to Yield Compounds of Formula VI Using $P450_{BM3}$ Variants In Vivo $P450_{BM3}$ Expression.

The procedures for $P450_{BM3}$ expression were identical to those described in Example 1.

Preparation of Whole Cell Catalysts.

The procedures for whole cell catalyst preparation were identical to those described in Example 1, except $OD_{600}$=30.

Small-Scale Bicyclobutanation Reactions in Whole-Cell Suspension Under Anaerobic Conditions.

Small-scale (400 μL) reactions were carried out in 2 ml glass crimp vials (Agilent Technologies, San Diego, Calif.). Cell suspension ($OD_{600}$=30, 340 μL) was added to an unsealed crimp vial before crimp sealing with a silicone septum. The headspace of the vial was flushed with argon for 10 min (no bubbling). A solution of D-glucose (40 μL, 250 mM) was added, followed by a solution of alkyne of Formula IV (10 μl, 400 mM in EtOH; for example, phenylacetylene) and a solution of diazo reagent of Formula V (10 μl, 400 mM in EtOH; for example, ethyl diazoethanoate or EDA). The reaction vial was left to shake on a plate shaker at 640 rpm for 8 h at room temperature. To quench the reaction, the vial was uncapped and a 1:1 mixture of ethylacetate/cyclohexane (1 ml) was added, followed by 1,2,3-trimethoxybenzene (20 μl, 20 mM in toluene) as an internal standard. The mixture was transferred to a 1.5 ml Eppendorf tube and vortexed and centrifuged (14000× ref, 5 min). The organic layer was analyzed by gas chromatography (GC), gas chromatography-mass spectrometry (GC-MS), supercritical fluid chromatography (SFC) or normal-phase high performance liquid chromatography (HPLC).

The results of the small scale reactions are shown in Table 1A and demonstrate that $P450_{BM3}$ and variants thereof are capable of catalyzing the bicyclobutanation to give products of Formula VI with high selectivity. Specifically, the best variant E10) found in the initial screen of $P450_{BM3}$ variants encoded the mutations A78V, F263L based on $P411_{BM3}$ "A82L" variant (mutations in E10 relative to wild-type $P450_{BM3}$: A82L, F87A, P142S, T175I, A184V, S226R, H236Q, E252G, I263L, T268G, A290V, A328V, L353V, I366V, C400S, T438S, E442K; mutations in $P411_{BM3}$ "A82L" relative to wild-type $P450_{BM3}$: V78A, A82L, F87A, P142S, T175I, A184V, S226R, H236Q, E252G, I263F, T268G, A290V, A328V, L353V, I366V, C400S, T438S, E442K), which catalyzed the desired reaction with 1380 TTN. This can be improved by further engineering, if desired.

TABLE 1A

| P411BM3 variant | Result |
| --- | --- |
| "I263F" A328V | 3% yield |
| "I263F" A328V V87A | 7% yield |
| "I263F" A328V V87A A268G | 10% yield |
| "I263F" A328V V87A A268G A82L | 34% yield (280 TTN) |
| "I263F" A328V V87A A268G A82I | 8% yield |
| "A82L" A78V | 34% yield (360 TTN) |
| "A82L" A78V F263L | 43% yield (530 TTN) |
| "A82L" F263Y A78L A74G T327I | 9% yield |

The results of the small scale reactions are shown in FIG. 3 and demonstrate that E10 (mutations in E10 relative to wild-type $P450_{BM3}$: A82L, F87A, P142S, T175I, A184V, S226R, H236Q, E252G, I263L, T268G, A290V, A328V, L353V, I366V, C400S, T438S, E442K) and variants thereof are capable of catalyzing the bicyclobutanation to give product of formula IV with high selectivity. Specifically, the best variant for bicyclobutanation found in the initial screen of E10 variants encoded the mutations V78F, S438A based on E10 variant, which catalyzed the desired reaction with 1880 TTN. This can be improved by further engineering, if desired.

Example 3: Preparation of Bicyclobutane-Dicarboxylic Acids and Polyester Synthesis Using Diacids and Diols Aliphatic polyesters with enhanced hydrophilicity and less toxicity have captured increasing attention due to their good biocompatibility and biodegradability, which allows their broad biologically relevant applications. (See, e.g., Lecomte, et al. *Advances in Polymer Science*, Vol. 245; 2012; pp 173-217; Engels, et al. *Angew. Chem. Int. Ed.* 2013, 52, 9422; Datta, et al. *J. Chem. Technol. Biotechnol.* 2006, 81, 1119; Ikada, Y. et al. *Macromol. Rapid Commun.* 2000, 21, 117.) Especially, in biomedical fields, a myriad of polyesters have been investigated with their potential use as drug delivery vesicles, bone screws and scaffolding or suture wire. (See, Chasin & Langer. *Biodegradable Polymers as Drug Delivery Systems*; Marcel Dekker Inc: New York, 1990.) Employing monomers with (strained) cyclic structures for polyester synthesis would add stiffness to the polymer chain with substantial increase in glass-transition temperature $T_g$. (See, Van Zee et al. *Angew. Chem. Int. Ed.* 2015, 54, 2665; Sanford, et al. *Macromolecules* 2016, 49, 6394; Lavilla, et al. *J. Polym. Sci. A Polym. Chem.* 2012, 50, 1591.) The highly strained bicyclobutane-diester products from enzymatic reactions can be utilized as monomers for polyester synthesis.

Preparation of Monomer Dicarboxylic Acids (e.g., Bicyclo[2.1.1]Hexane-Dicarboxylic Ester).

As described in Equation 12, dicarboxylic ester can be hydrolyzed under basic conditions. Dicarboxylic ester (1.0 equiv.) was treated with sodium hydroxide (5.0 equiv.) in THF/$H_2O$ (1:1 mixture, 0.1 M). The reaction was heated at 50° C. for 12 hours. The reaction mixture was then acidified with HCl (1M), and further purified by column chromatography to afford the corresponding dicarboxylic acid. Analogously, the bicyclobutane-dicarboxylic esters can also be hydrolyzed in a similar manner. See, e.g., Wiberg, et al. *J. Am. Chem. Soc.* 1983, 105, 3638

(12)

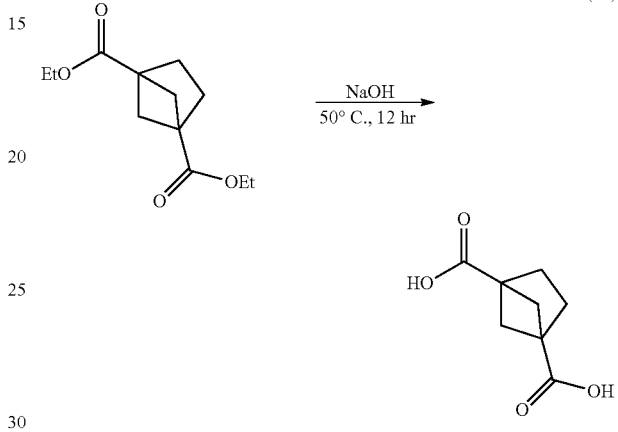

Polyester Synthesis.

Isoidide dicarboxylic acid (IIDCA, 1.0 equiv.) and α,ω-diol (2.0 equiv.) were added into a round-bottom flask inside a Kugelrohr oven. The flask was then charged with nitrogen. The oven was then heated to 130° C. and maintained at this temperature for 5-10 min until the reactants turned into a clear melt. Next, pristine dibutyltin(IV) oxide (DBTO, 1.0 mol %) was added as the catalyst into the flask. The prepolymerization was carried out at 130° C. under a continuous flow of nitrogen for 3 h for the polymerizations based on IIDCA. Subsequently, the polymerization temperatures were adjusted to the desire range of 130-200° C. At the same time vacuum (0.01-0.05 mbar) was applied stepwise to the reaction system to remove the excess diol and condensates. After 3 h, the resulting polymer melt was cooled down and dissolved in chloroform and precipitated into methanol, filtered, and dried in vacuo at 30° C. for 24 h. The bicyclobutanedicarboxylic acid-based polyester could also be synthesized in this manner. (See also, Wu, J et al. *Macromolecules* 2012, 45, 5069)

(13)

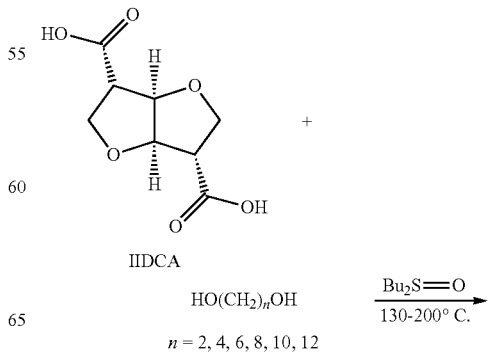

IIDCA $HO(CH_2)_nOH$ $n = 2, 4, 6, 8, 10, 12$ $Bu_2S=O$
130-200° C.

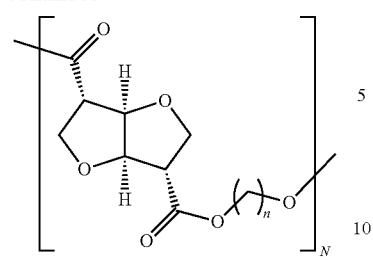

Example 4: Preparation of Bicyclobutane-Diols for Synthesis of Functionalized Polybenzvalene Polymers

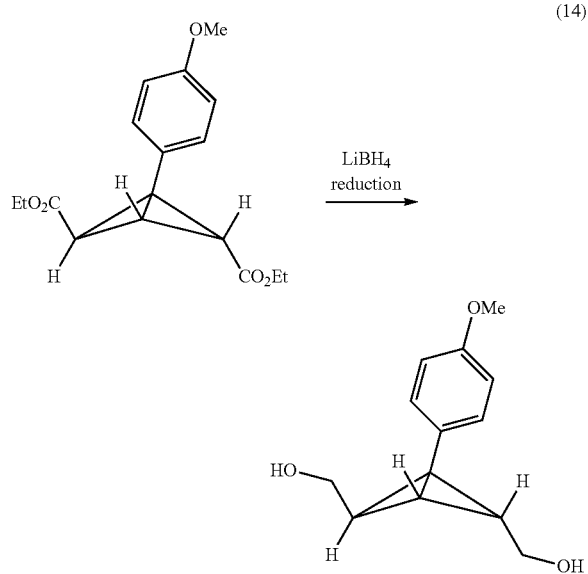

(1R,2R)-1-(4-methoxyphenyl)bicyclo[1.1.0]butane-2,4-diyl)dimethanol was prepared as an illustrative example, as shown in Equation 14. Diethyl (2R,4R)-1-(4-methoxyphenyl)bicyclo[1.1.0]-butane-2,4-dicarboxylate (101.3 mg, 0.33 mmol) was dissolved in anhydrous ether (10 ml) in a 50 ml flask. Dry methanol (67 µl, 1.67 mmol) was added to the solution, followed by the addition of lithium borohydride (LiBH$_4$, 2M in THF, 0.84 ml, 1.67 mmol). The reaction mixture was then heated up to a refluxing temperature, 45° C., for 1 h, before ethyl acetate (0.5 ml) was added and the mixture was stirred at room temperature for 30 min. Then the reaction was quenched with NH$_4$Cl (10 ml, sat. aq.) and diluted with water (10 ml). The product was extracted with ethyl acetate (20 ml×6). The combined organic layer was dried over MgSO$_4$, and then concentrated under reduced pressure. White solid product crashed out during the removal of solvent. Collecting the solid product and recrystallization with acetone/hexane system afforded (1R,2R)-1-(4-methoxyphenyl)bicyclo[1.1.0]butane-2,4-diyl)dimethanol (52.2 mg, 0.237 mmol, 71%).

Example 5: Preparation of Multi-Substituted Cyclopropanes Via Derivatization of Cyclopropenes

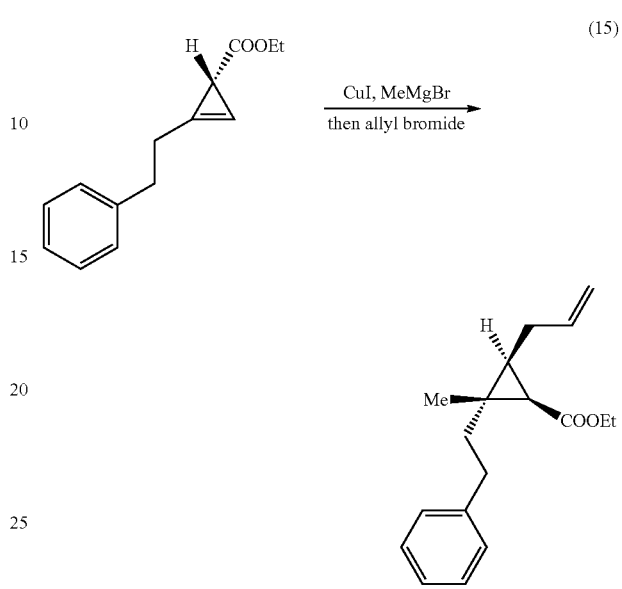

Ethyl (1R,2R,3S)-3-allyl-2-methyl-2-phenethylcyclopropane-1-carboxylate was prepared as an illustrative example. Ethyl (R)-2-phenethylcycloprop-2-ene-1-carboxylate (54.0 mg, 0.25 mmol) and CuI (5.0 mg, 0.026 mmol, 10 mol %) were dissolved in anhydrous ether (3 ml) to form a suspension in a 25 ml flask. Then the flask was charged with argon and cooled to −78° C. Methylmagnesium bromide (0.75 ml, 1 M in ether, diluted from 3M solution in ether) was added dropwise to the reaction mixture over 10 min. The reaction was slowly warmed to −40° C. over 30 min and held at this temperature for another 1 h. A solution of allyl bromide (43 µl, 0.50 mmol) in ether (1 ml) was then added to the reaction dropwise over 5 min. The reaction was stirred at −40° C. for 1 h, before it was quenched with NH$_4$Cl/NH$_3$ (2:1, aq., 5 ml) at −20° C. The aqueous layer was extracted twice with ether. The combined organic layers were washed with water (10 ml), and brine (10 ml), dried over MgSO$_4$, and then concentrated under reduced pressure. The crude product was purified by silica column chromatography with hexane/ethyl acetate (1:0 to 50:1 gradient) to afford ethyl (1R,2R,3S)-3-allyl-2-methyl-2-phenethylcyclopropane-1-carboxylate (48.0 mg, 0.176 mmol, 71%) as a single diastereomer.

Example 6: Preparation of Multi-Substituted Fused Ring Systems Via Derivatization of Cyclopropenes

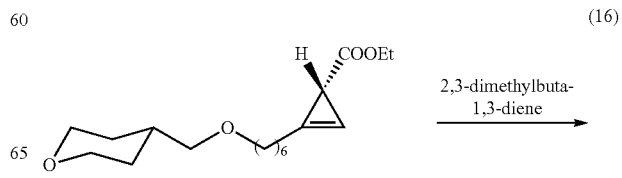

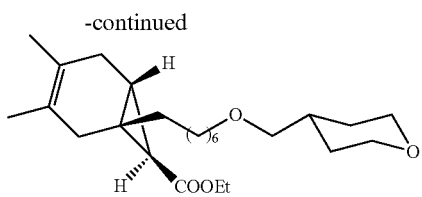

(1R,6R,7R)-3,4-Dimethyl-1-(6-((tetrahydro-2H-pyran-4-yl)methoxy)hexyl)-bicyclo[4.1.0]hept-3-ene-7-carboxylate was prepared as an illustrative example. Ethyl (R)-2-(cyclohexylmethyl)cycloprop-2-ene-1-carboxylate (65.6 mg, 0.211 mmol) was dissolved in 2,3-dimethylbutadiene (0.5 ml). Then the reaction was heated and stirred at 80° C. in a sealed tube for 23 h. After cooling to room temperature, the resulting mixture was concentrated under reduced pressure. The crude product was purified by silica column chromatography with hexane/ethyl acetate (1:0 to 6:1 gradient) to afford ethyl (1R,6R,7R)-3,4-dimethyl-1-(6-((tetrahydro-2H-pyran-4-yl)methoxy)hexyl) bicyclo[4.1.0]hept-3-ene-7-carboxylate (81.1 mg, 0.207 mmol, 98%) as a single diastereomer.

Example 7. Click Reaction Between Terminal Alkyne-Substituted Bicyclobutane and Azide

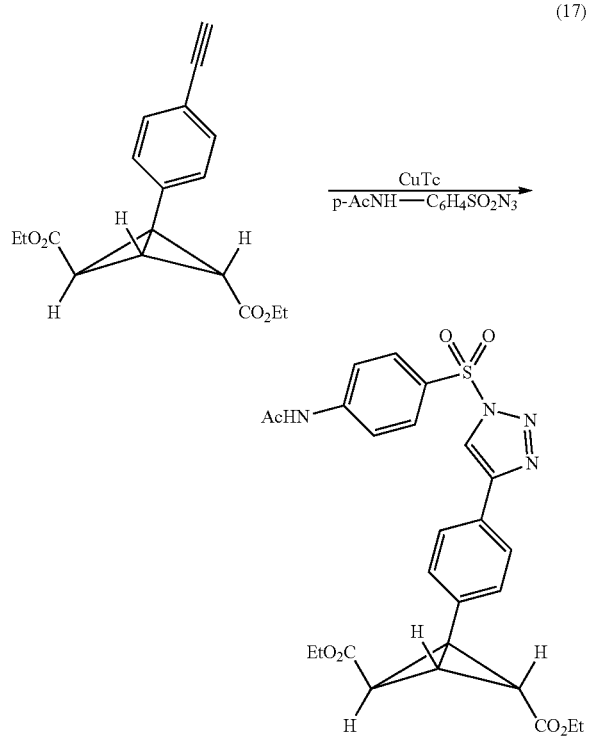

Diethyl (2R,4R)-1-(4-(1-((4-acetamidophenyl)sulfonyl)-1H-1,2,3-triazol-4-yl)phenyl) bicyclo[1.1.0]butane-2,4-dicarboxylate was prepared as an illustrative example). Diethyl (2R,4R)-1-(4-ethynylphenyl)bicyclo[1.1.0]butane-2,4-dicarboxylate (41.6 mg, 0.139 mmol) was dissolved in toluene (3 ml) in a 20 ml vial. Copper(I) thiophene-2-carboxylate (CuTc, 3.2 mg, 12 mol %) was added. The mixture was kept stirring at 0° C. A suspension of 4-acetamidobenzenesulfonyl azide (40.2 mg, 0.167 mmol) in toluene (5 ml) was added dropwise over 1 h. The resulting mixture was then allowed to warm to room temperature and stirred for 15 h. The reaction was diluted with ethyl acetate (15 ml), washed with $NH_4Cl/NH_3$ (2:1, 20 ml, aq.), and brine (50 ml), dried over $MgSO_4$, and then concentrated under reduced pressure. The crude product was purified by silica column chromatography with hexane/ethyl acetate (4:1 to 1:3 gradient) to afford diethyl (2R,4R)-1-(4-(1-((4-acetamidophenyl)sulfonyl)-1H-1,2,3-triazol-4-yl)phenyl) bicyclo[1.1.0]butane-2,4-dicarboxylate (69.2 mg, 0.129 mmol, 93%).

Example 8. Identification of Biocatalysts for Strained Carbocycle Formation

General Materials and Methods.

Unless otherwise noted, all chemicals and reagents were obtained from commercial suppliers (Sigma-Aldrich, VWR, Alfa Aesar) and used without further purification. Silica gel chromatography was carried out using AMD Silica Gel 60, 230-400 mesh. $^1$H and $^{13}$C NMR spectra were taken using a Bruker Prodigy 400 MHz instrument and are internally referenced to the residual solvent peak (chloroform). Data for $^1$H NMR are reported as follows: chemical shift (δ ppm), multiplicity (s=singlet, d=doublet, t=triplet, q=quartet, p=pentet, m=multiplet, dd=doublet of doublets, dt=doublet of triplets, ddd=doublet of doublet of doublets), coupling constant (Hz), integration. Sonication was performed using a Qsonica Q500 sonicator. High-resolution mass spectra were obtained at the California Institute of Technology Mass Spectral Facility. Synthetic reactions were monitored using thin layer chromatography (Merck 60 gel plates) using a UV-lamp for visualization. Substrates were purchased from commercial suppliers.

Chromatography.

Analytical reversed-phase high-performance liquid chromatography (HPLC) was carried out using an Agilent 1200 series instrument and a Kromasil 100 C18 column (4.6×50 mm, 5 μm) with water and acetonitrile as the mobile phase and visualization at 210 nm for library screening. Analytical normal-phase HPLC was carried out using an Agilent 1200 series instrument and chiral columns Chiralpak IC (4.6 mm×25 cm), IA (4.6 mm×25 cm), AS-H (4.6 mm×25 cm) and OJ-H (4.6 mm×25 cm) with n-hexane and isopropanol as the mobile phase and visualization at 210 nm for chiral separation. Gas chromatography (GC) analyses were carried out using an Agilent 7820A or Shimadzu GC-17A gas chromatograph, FID detector, and a J&W HP-5 column (30 m×0.32 mm, 0.25 μm film). Gas chromatography-mass spectrometry (GC-MS) analyses were carried out using a Shimadzu GCMS-QP2010SE system and J&W HP-5m column. Semi-preparative HPLC was performed using an Agilent XDB-C18 column (9.4×250 mm, 5 μm) with water and acetonitrile as the mobile phase.

Cloning and Site-Saturation Mutagenesis.

pET22b(+) containing a C-terminal 6x-His tag was used as a cloning and expression vector for all enzymes described in this study. Site-saturation mutagenesis was performed using a modified QuikChange™ mutagenesis protocol ([1]). The PCR products were digested with DpnI, gel purified, and the gaps were repaired using Gibson Mix™ ([2]). The ligation mixture was used to directly transform *E. coli* strain BL21 E. cloni® (Lucigen). Cells were grown using Luria-Bertani medium (LB) or Hyperbroth (AthenaES) (HB) with 0.1 mg/mL ampicillin ($LB_{amp}$ or $HB_{amp}$). Primer sequences are available upon request. Electrocompetent *E. coli* cells were prepared following the protocol of Sambrook et al. ([3]).

T5 exonuclease, Phusion polymerase, and Taq ligase were purchased from New England Biolabs (NEB, Ipswich, Mass.). M9-N minimal medium (abbreviated as M9-N buffer; pH 7.4) was used as a buffering system for whole cells, lysates, and purified proteins, unless otherwise specified. M9-N buffer was used without a carbon source; it contains 47.7 mM $Na_2HPO_4$, 22.0 mM $KH_2PO_4$, 8.6 mM NaCl, 2.0 mM $MgSO_4$, and 0.1 mM $CaCl_2$.

Determination of Hemeprotein Concentration.

A solution of sodium dithionite (10 mg/mL) was prepared in M9-N buffer. Separately, a solution of 1 M NaOH (0.4 mL) was mixed with pyridine (1 mL), followed by centrifugation (10,000 g, 30 s) to separate the excess aqueous layer gave a pyridine-NaOH solution. To a cuvette containing 700 µL protein solution (purified protein or lysate) in M9-N buffer, 50 µL of dithionite solution (0.1 M in M9-N) and 250 µL pyridine-NaOH solution were added. The cuvette was sealed with Parafilm, and the UV-Vis spectrum of the reduced $Fe^{II}$ state was recorded immediately. To another cuvette containing 700 µL protein solution (purified protein or lysate) in M9-N buffer, 50 µL of potassium ferricyanide (0.1 M in M9-N) and 250 µL pyridine-NaOH solution were added. The cuvette was sealed with Parafilm, and the UV-Vis spectrum of the oxidized $Fe^{III}$ state was recorded immediately. Hemeprotein concentration was determined using $\varepsilon_{557[Re]-540[Ox]}=23.98$ $mM^{-1}$ $cm^{-1}$ ([4]). Cytochrome c concentration is measured using a different procedure, reported previously ([5]).

Expression of P450 and P411 Proteins.

E. coli BL21 E. cloni® cells carrying a plasmid encoding a P450 or P411 variant were grown overnight in 5 mL $LB_{amp}$ (37° C., 250 rpm). The pre-culture was used to inoculate 45 mL of $HB_{amp}$ in a 125 mL Erlenmeyer flask; this culture was incubated at 37° C., 220 rpm for 2 h and 15 min. Cultures were then cooled on ice (20 min), and expression was induced with 0.5 mM IPTG and 1.0 mM 5-aminolevulinic acid (final concentrations). Expression was conducted at room temperature (23° C.), at 130 rpm, for 18-22 h. Cultures were then centrifuged (4,500 g, 5 min, 4° C.), and the pellets were resuspended to an $OD_{600}$ of 30 in M9-N minimal medium (no nitrogen). Aliquots of the cell suspension (4 mL) were used to determine the P450 and P411 expression level after lysis by sonication. The expression level in $OD_{600}$=30 lysates is typically in the range 8-12 µM for P450s, 1-4 µM for P450 H*, and 2-7 µM for P411s.

The same procedure was used for expression of globin proteins, except using 1 mL $LB_{amp}$ pre-culture to inoculate 49 mL of $HB_{amp}$. The expression of cytochrome c variants requires an extra maturation plasmid $pEC_{86}$ in E. coli BL21 E. cloni® cells and follows a procedure described previously ([5]).

Biotransformations.

The cell suspension in M9-N (with a certain $OD_{600}$) was degassed by sparging with argon in sealed vials or flasks for 30 min. Separately, a glucose solution (250 mM in M9-N) was degassed by sparging with argon for 30 minutes. All solutions were uncapped and transferred into an anaerobic chamber. Resuspended cells (340 µL) were added to 2 mL vials, followed by glucose (40 µL, 250 mM in M9-N), alkyne (10 µL of an EtOH stock), and EDA (10 µL of an EtOH stock). Final concentrations were typically 10.0-20.0 mM alkyne, 10.0-20.0 mM EDA (alkyne:EDA=1:1), and 25 mM glucose; final reaction volume was 400 µL. The vials were sealed, removed from the anaerobic chamber, and shaken at room temperature and 560 rpm for 6 h. After the reaction was completed, internal standard 1,3,5-trimethoxybenzene (20 µL of 20 mM stock solution in toluene) was added to the reaction vial followed by mixed solvent (cyclohexane/ethyl acetate=1:1, 1.0 mL). The mixture was transferred to a 1.5 mL microcentrifuge tube, and then subjected to vortex (15 s×3) and centrifugation (14,000 rpm, 5 min) to completely separate the organic and aqueous layers. A sample of the organic layer (0.8 mL) was transferred to a vial for GC analysis. The procedure for preparative-scale enzymatic reactions is outlined in detail (See Section VIII and IX).

Reaction Screening in 96-Well Plate Format.

Single-site-saturation libraries were generated employing the "22c-trick" method ([1]) and screened in one 96-well plate; double-site-saturation libraries were generated using the same method to target two different sites; these were screened in three 96-well plates. E. coli libraries were cultured in $LB_{amp}$ (300 µL/well) at 37° C., 250 rpm and 80% relative humidity overnight. $HB_{amp}$ (950 µL/well) was inoculated with the pre-culture (50 µL/well) and incubated at 37° C., 250 rpm, 80% humidity for 2.5 h. The plates were cooled on ice for 30 minutes, and expression was induced with 0.5 mM IPTG and 1.0 mM 5-aminolevulinic acid (final concentrations). Expression was conducted at 20° C. and 200 rpm for 18-22 h. The cells were pelleted (4,500 g, 5 min, 4° C.) and resuspended with M9-N buffer (340 µL/well) and D-glucose solution (40 µL/well, in M9-N). The 96-well plate was then transferred to an anaerobic chamber. In the anaerobic chamber, alkyne (10 µL/well, 400 mM in EtOH) and EDA (10 µL/well, 400 mM in EtOH). The plate was sealed with an aluminum foil, removed from the anaerobic chamber, and shaken at 560 rpm. See below for reaction workup protocol:

Bicyclobutane Formation Screening.

After 16 h, the seal was removed and mixed solvent (cyclohexane/ethyl acetate=1:1, 600 µL/well) and internal standard 1,3,5-trimethoxybenzene (20 µL/well of a toluene stock) were added. The plate was tightly sealed with a reusable silicone mat, vortexed (15 s×3) and centrifuged (4,500 g, 5 min) to completely separate the organic and aqueous layers. The organic layers (200 µL/well) were transferred to 300 µL vial inserts, which were then placed in 2 mL vials labeled with corresponding wells in the plate for GC or GC-MS analysis (a 2.5-min/run method was used for screening, see Section IV).

Cyclopropene Formation Screening.

After 16 h, the seal was removed and acetonitrile (580 µL/well) and internal standard ethyl phenylacetate (PhEA, 20 mM in acetonitrile, 20 µL/well) were added. The plate was tightly sealed with a reusable silicone mat, vortexed (15 s×3) and centrifuged (4,500 g, 5 min). The supernatant (200 µL/well) was filtered through an AcroPrep 96-well filter plate (0.2 µm) into a shallow-well plate for HPLC analysis (a 1.7-min/run method was used for screening, see Section V).

General Procedure for Testing Transition Metal Catalysts for Designed Carbene Transfer to Alkyne.

To an 8 mL vial were added phenyl acetylene (0.1 mmol), catalyst (Rh—1 mol %; Cu—10 mol %) and DCM or cyclohexane (2 mL). The vial was cooled to −78° C. EDA (0.2 mmol in 0.5 mL corresponding organic solvent) was added through a syringe pump over 1 h. The reaction was stirred at −78° C. for 6 h and then slowly warmed to room temperature over another 6 h. The reaction mixture (0.5 mL) was filtered through a 2 cm-height silica gel and washed with DCM (1 mL). The filtrate was used for GC-MS analysis.

The procedure for testing hemeproteins follows that described above using E. coli expressing corresponding hemeprotein variant as whole-cell catalyst ($OD_{600}$=30). For testing heme (±BSA), 0.5 mM stock of heme (±BSA, 0.75 mg/mL) in M9-N (340 µL) and $Na_2S_2O_4$ (40 µL, 10 mM in M9-N) was used instead of cell suspension and glucose stock. (BSA=bovine serum albumin).

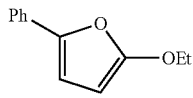

2-Ethoxy-5-phenylfuran (3b)

$^1$H NMR (400 MHz, Benzene-$d_6$) δ 7.58 (dd, J=8.3, 1.3 Hz, 2H), 7.14-7.09 (m, 2H), 6.97 (tt, J=7.4, 1.3 Hz, 1H), 6.37 (d, J=3.3 Hz, 1H), 5.02 (d, J=3.3 Hz, 1H), 3.59 (q, J=7.0 Hz, 2H), 0.98 (t, J=7.0 Hz, 3H). $^{13}$C NMR (101 MHz, $C_6D_6$) δ 161.79, 145.08, 132.15, 129.52, 127.04, 123.49, 107.28, 83.71, 67.27, 15.07. MS (EI) m/z: 188 (M$^+$); calc. for $C_{12}H_{12}O_2$: 188.

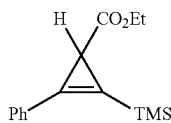

Ethyl 2-phenyl-3-(trimethylsilyl)cycloprop-2-ene-1-carboxylate (3c)

The synthesis of 3c follows a reported procedure ([6]). $^1$H NMR (400 MHz, CDCl$_3$) δ 7.61-7.52 (m, 2H), 7.48-7.36 (m, 3H), 4.25-4.06 (m, 2H), 2.40 (s, 1H), 1.25 (t, J=7.1 Hz, 3H), 0.34 (s, 9H). $^{13}$C NMR (101 MHz, CDCl$_3$) δ 176.13, 129.79, 129.52, 128.65, 127.56, 123.95, 108.00, 60.00, 20.60, 14.37, −1.43. MS (EI) m/z: 260 (M$^+$); calc. for $C_{15}H_{20}O_2Si$: 260.

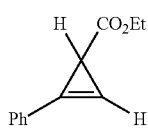

Ethyl 2-phenylcycloprop-2-ene-1-carboxylate (3a)

To a 20 mL vial were added 3c (20.8 mg, 0.08 mmol) and THF (2 mL). And then tetrabutylammonium fluoride (TBAF, 1M in THF, 120 μL) was added to the solution. The reaction was stirred at room temperature for 3 min before it was condensed under reduced pressure (3 min). Quick purification (within 5 min) of the crude product by silica column chromatography with hexane/ethyl acetate (10:1) afforded 3a. 3a was used for qualitative GC-MS analysis. (Note: 3a is highly unstable. It was completely decomposed under deprotection condition after 30 min. Purification step needs to be very quick. After column purification, it is better to leave 3a in the hexane/ethyl acetate eluent rather than concentrate it under reduced pressure. 3a can stay for hours in a solution form, but for less than 30 min in pure form.) MS (EI) m/z: 188 (M$^+$); calc. for $C_{12}H_{12}O_2$: 188.

Protein Purification.

E. coli BL21 E. cloni® cells carrying a plasmid encoding a P411 variant were grown overnight in 105 mL LB$_{amp}$ (37° C., 250 rpm). HB$_{amp}$ (1 L) in a 2.8 L flask was inoculated with 100 mL of the pre-culture and incubated at 37° C. and 240 rpm for 2 h and 15 min. Cultures were then cooled on ice (30 min) and induced with 0.5 mM IPTG and 1.0 mM 5-aminolevulinic acid (final concentrations). Expression was conducted at 20° C., 130 rpm, for 20 h. Cultures were then centrifuged (4,500 g, 8 min, 4° C.) and the cell pellets frozen at 20° C. For purification, frozen cells from two such cultures were resuspended in buffer A (25 mM Tris-HCl buffer, 20 mM imidazole, 100 mM NaCl, pH 7.5, 4 mL/g of cell wet weight), loaded with hemin (1 mg/gram wet cell weight) and powdered DNaseI, and lysed by sonication. To pellet cell debris, lysates were centrifuged (20,000×g, 20 min, 4° C.). Proteins were expressed in a construct containing a 6x-His tag and purified using a nickel NTA column (1 mL HisTrap HP, GE Healthcare, Piscataway, N.J.) using an AKTA or AKTAxpress purifier FPLC system (GE healthcare). P411 enzymes were eluted with a linear gradient from 100% buffer A to 100% buffer B (25 mM tris, 300 mM imidazole, 100 mM NaCl, pH 7.5) over 10 column volumes. Proteins were then pooled, concentrated, and subjected to three exchanges of phosphate buffer (0.1 M KPi, pH 8.0) using centrifugal filters (10 kDa molecular weight cut-off, Amicon Ultra, Merck Millipore) to remove excess salt and imidazole. Concentrated proteins were aliquoted, flash frozen on powdered dry ice, and stored at −80 or −20° C.

Results and Discussion.

In cyclic organic molecules, ring strain arises from distortions of bond angle and bond length, steric clashes of non-bonded substituents, and other effects ([7]). The simplest carbocycles, cyclopropanes and cyclobutanes, possess ring strains of 26-28 kcal/mol ([8]). Introducing carbon-carbon multiple bonds or bridges to these small ring systems induces additional strain as well as structural rigidity. For example, cyclopropenes with an endo-cyclic double bond bear a strain of 54 kcal/mol, whereas bicyclo[1.1.0]butanes, folded into puckered structures, distinguish themselves as one of the most strained four-membered systems, with around 66 kcal/mol strain (FIG. 4) (8). These carbocycles are particularly attractive intermediates in chemical and materials synthesis, since they can undergo strain-release transformations to furnish a myriad of useful scaffolds ([9]-[12]). The structural rigidity imparted by strained rings in supramolecular materials can lead to interesting physical properties, such as mechanical stability ([13]) and high glass-transition temperature ([14]). The intrinsic energy of these strained structures can also be relieved in response to exogenous force, which leads to radical changes in physical properties (e.g., conductivity), a feature highly desirable for stimulus-responsive materials ([15], [16]).

High ring strain, however, greatly increases the difficulty of synthesis. A commonly used method for preparing bicyclobutanes starts from dibromo-2-(bromomethyl)cyclopropane substructures and utilizes organolithium reagents for lithium-halogen exchange followed by nucleophilic substitution under rigorously anhydrous and cryogenic conditions (9). An alternative route relies on the double transfer of a carbene to alkynes, but the few examples in the literature are mostly limited to methylene carbene ([17]-[19]). Asymmetric bicyclobutane construction is particularly challenging, with multiple chiral centers generated at the same time ([20], [21]) (FIG. 5). Cyclopropene synthesis through enantioselective single carbene addition to alkynes also requires chiral transition metal catalysts based on rhodium ([22], [23]) iridium ([24]) and cobalt ([25]). Development of a sustainable catalytic system that performs with high efficiency and selectivity under ambient conditions would be a significant advance for construction of these useful, highly strained carbocycles.

Figure 6A:
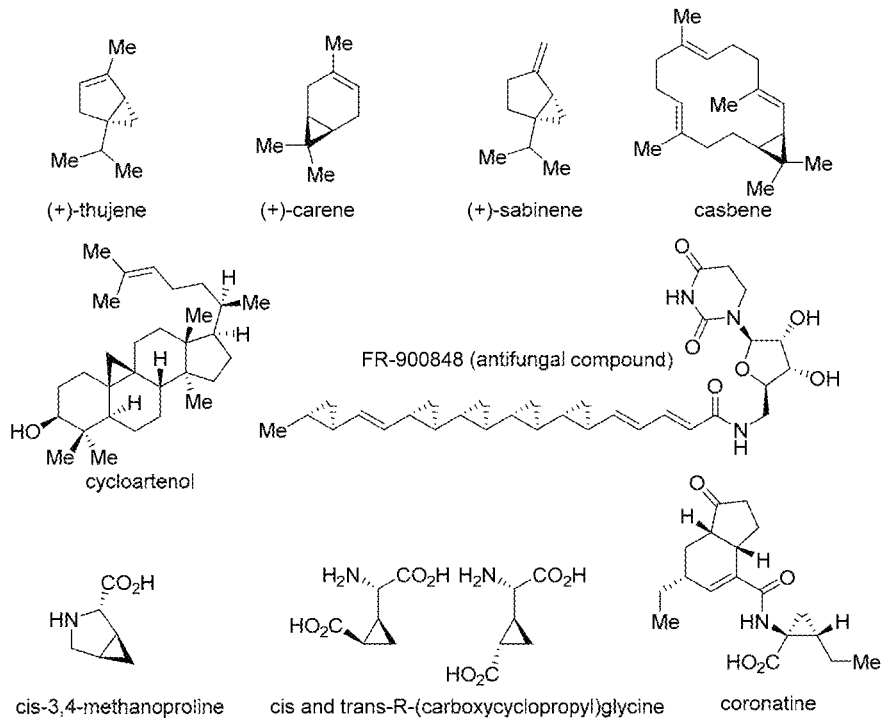
FIG. 6A shows examples of cyclopropane-containing natural products (ref. 21, 62)
Figure 6B:
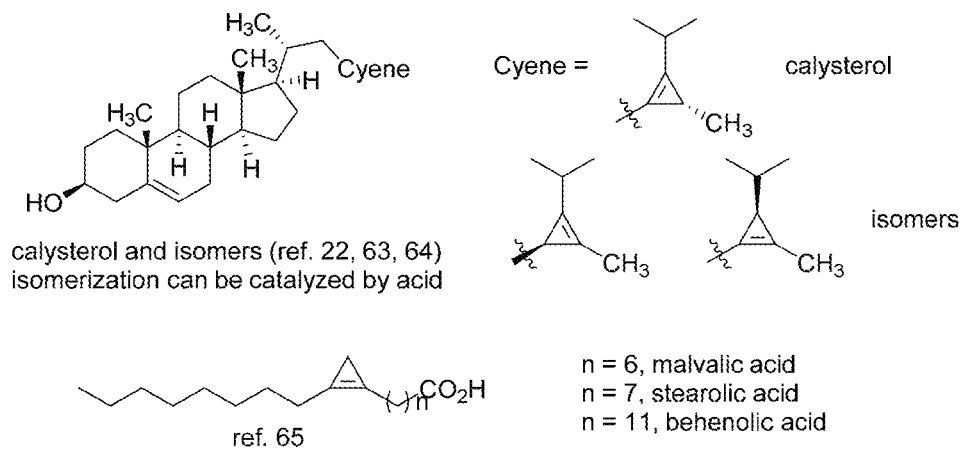
FIG. 6B shows examples of natural products that have been found to contain cyclopropene fragments.
Figure 6C:
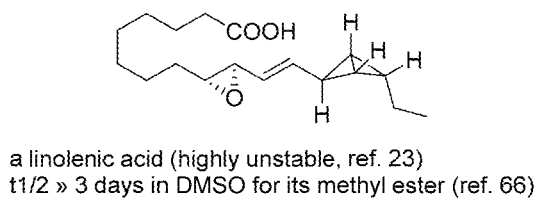
FIG. 6C shows the only natural product that has been found to contain a bicyclobutane fragment.

Enzymes, the catalytic workhorses of biology, are capable of accelerating chemical transformations by orders of magnitude while exhibiting exquisite control over selectivity (26). Although nature synthesizes various cyclopropane-containing products (27), cyclopropene or bicyclobutane fragments are extremely rare (FIG. 6) (28, 29). This may be attributed to the lack of biological machinery for synthesizing these motifs and/or the instability of these structures under biological or natural product isolation/purification conditions. Nevertheless, the studies disclosed herein were conducted upon envisioning that existing enzymes could be repurposed to forge strained carbocycles by taking advantage of their catalytic promiscuity (30, 31) in the presence of non-natural substrates and by using directed evolution to optimize the activity and selectivity of these starting enzymes (32).

In the past several years, the present inventors and others have engineered natural hemeproteins to catalyze reactions not known in nature (33-38). The present studies were begun with the hypothesis that carbene transfer to triple bonds with a heme-dependent enzyme might afford highly strained cyclopropene and bicyclobutane structures and do so enantioselectively. Several challenges were expected at the outset, especially in chiral bicyclobutane formation, as it involves two sequential carbene additions to the alkyne substrate: 1) the enzyme would need to bind the alkyne in a specific conformation in order to transfer the carbene enantioselectively; 2) the high-energy cyclopropene intermediate generated by the first carbene addition would need to be accepted and stabilized by the protein; 3) compared to methylene carbene used previously, a substituted carbene (e.g., with an ester group) might hinder access of the cyclopropene to the iron-carbenoid; and 4) the protein would also need to exert precise stereocontrol over the second carbene transfer step regardless of structural differences between the initial alkyne and the cyclopropene intermediate. Despite these challenges, an investigation was initiated to determine whether a starting enzyme with this unusual and non-natural activity could be identified, and whether its active site could be engineered to create a suitable environment for substrate binding, intermediate stabilization, and selective product formation.

Figure 7D:
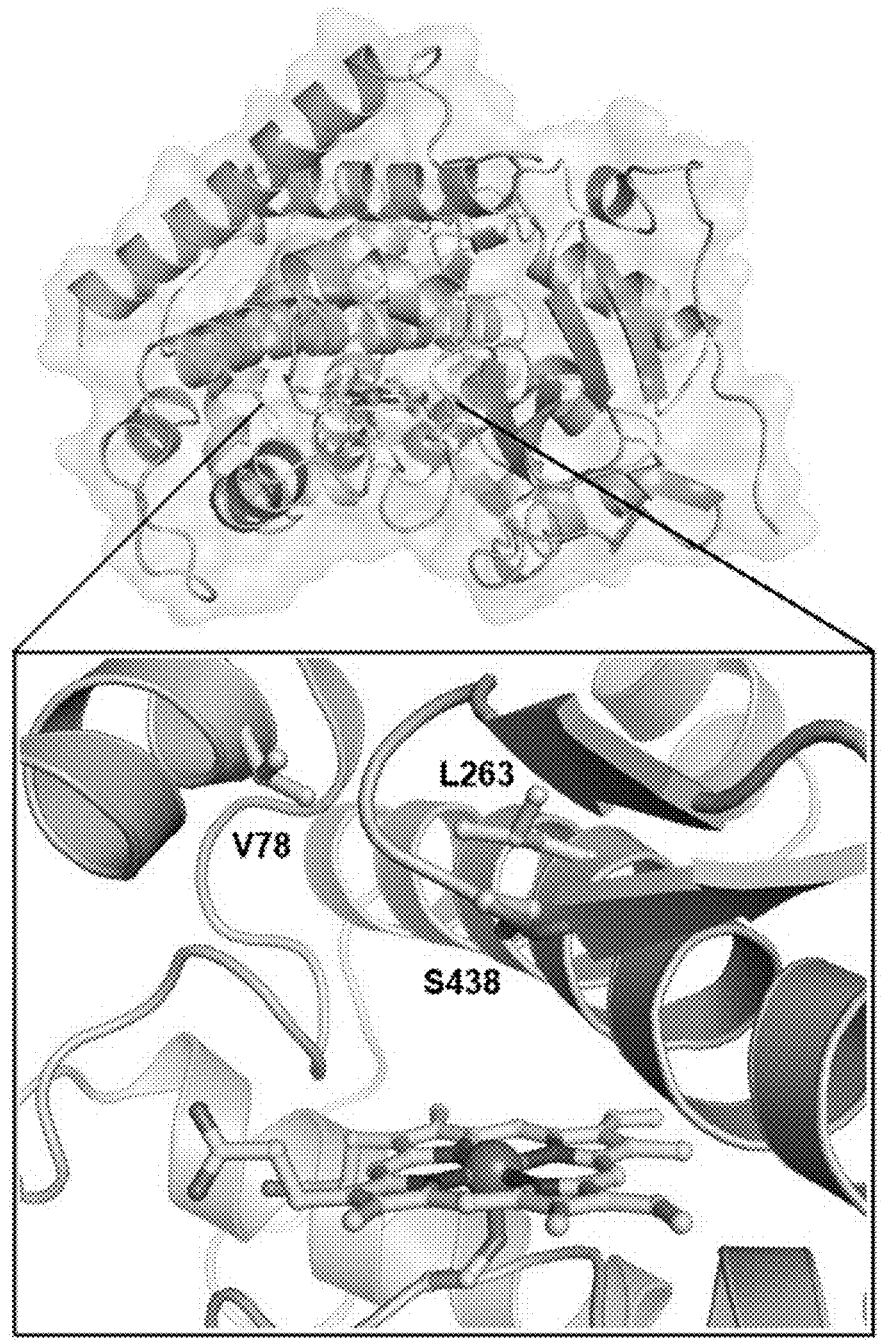
FIG. 7D shows the X-ray crystal structure of P411-E10 (PDB ID: 5UCW) (35) and a view of its distal heme region. The P411 heme axial ligand is S400, and amino acid residues V78, L263 and S438 are shown as gray sticks.

First, free heme (±bovine serum albumin (BSA)), which is known to catalyze styrene cyclopropanation (33), was tested to see if it could transfer carbenes to alkynes. Reactions using ethyl diazoacetate (EDA) and phenylacetylene (1a) as substrates in neutral buffer (M9-N minimal medium, pH 7.4) at room temperature, however, gave no cyclopropene or bicyclobutane product. Next, a panel of hemeproteins including cytochromes P450, cytochromes P411 (P450 with the axial cysteine ligand replaced by serine), cytochromes c and globins in the form of E. coli whole-cell catalysts were tested for the desired transformation under anaerobic conditions (38), but none were fruitful (FIG. 7 and Table 2).

TABLE 2

Screening different catalysts for bicyclobutane formation

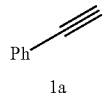

Ineffective transition metal catalysts (with undefined product mixtures):

| Rh$_2$(OAc)$_4$ | Rh$_2$(OPiv)$_4$ | Rh$_2$(S-DOSP)$_4$ | Rh$_2$(esp)$_2$ |
| CuI | CuOTf•PhH | CuCl•NHC | Cu(OTf)$_2$ |

Ineffective heme or hemeprotein catalysts (with no product observed):

| heme | heme + BSA | P450-WT | P450-CIS |
| P411-CIS | P450-CIS H* | Rma cyt c | Rma cyt c TDE |
| myoglobin | myoglobin VA | Rma NOD Q52V | Ape pgb Y60G |

Effective hemeprotein catalysts (with product detected):

P411-Si I263W: 210 ± 20 TTN, 3b only
P411-Si I263F: ~10 UN, 3b; <5 TTN, 2a
P411-Si I263F A328V (P2): 23 ± 8 TTN, 2a: 3b ~10:1
P411-S1 V87A I263F A328V (P3): 60 ± 10 TTN, 2a: 3b >20:1
P411-S1 V87A I263F A268G A328V (P4): 80 ± 10 TTN, 2a: 3b >50:1
P411-P4 A821: 280 ± 30 UN, 2a: 3b >50:1
P411-P4 A78V A82L F263L (E10): 530 ± 20 TTN, 2a: 3b >50:1

(Abbreviations: Piv=pivaloyl, DOSP=N-(p-dodecylphenyl-sulfonyl)prolinato, esp=α,α,α',α'-tetramethyl-1,3-benzene-dipropionic acid, Tf=trifluoromethanesulfonyl, NHC=1,3-bis(2,6-diisopropylphenyl)imidazol-2-ylidene.)

TABLE 3

Information of hemeprotein variants

| Name | Description | Mutations |
|------|-------------|-----------|
| P450-WT | P450$_{BM3}$-wild type (CYP102A1) (39) | — |

TABLE 3-continued

Information of hemeprotein variants

| Name | Description | Mutations |
|---|---|---|
| P450-CIS | P450$_{BM3}$-CIS variant ([33]) | V78A, F87V, P142S, T175I, A184V, S226R, H236Q, E252G, T268A, A290V, L353V, I366V, E442K (relative to P450-WT) |
| P411-CIS | P411$_{BM3}$-CIS variant ([38]) | C400S (relative to P450-CIS) |
| P450-CIS H* | P450$_{BM3}$-CIS H* variant ([40]) | C400H (relative to P450-CIS) |
| P411-S1 | P411$_{BM3}$-CIS S1 variant ([38]) | T438S (relative to P411-CIS) |
| P411-"I263F" | P411$_{BM3}$-CIS "I263F" variant ([41]) | I263F (relative to P411-S1) |
| P411-P2 | P411$_{BM3}$-CIS P2 variant ([34]) | I263F, A328V (relative to P411-S1) |
| P411-P3 | P411$_{BM3}$-CIS P3 variant ([34]) | V87A, I263F, A328V (relative to P411-S1) |
| P411-P4 | P411$_{BM3}$-CIS P4 variant ([34]) | V87A, I263F, A268G, A328V (relative to P411-S1) |
| P411-"A82L" | P411$_{BM3}$-CIS "A82L" variant ([34]) | A82L, V87A, I263F, A268G, A328V (relative to P411-S1) |
| P411-E10 | P411$_{BM3}$-CIS E10) variant ([35]) | A78V, A82L, V87A, I263L, A268G, A328V (relative to P411-S1) |
| Rma cyt c | *Rhodothermus marinus* cytochrome c wild-type ([5]) | — |
| Rma cyt c TDE | *Rhodothermus marinus* cytochrome c TDE variant ([5]) | V75T, M100D, M103E (relative to Rma cyt c) |
| myoglobin | Sperm whale myoglobin-wild type ([42]) | — |
| myoglobin VA | Sperm whale myoglobin-VA variant (Error! Bookmark not defined.) | H64V, V68A (relative to Myoglobin) |
| Rma NOD Q52V | *Rhodothermus marinus* nitric oxide dioxygenase Q52V variant | Q52V (relative to Rma NOD-wild type) |
| Ape pgb Y60G | *Aeropyrum pernix* protoglobin Y60G variant | Y60G (relative to Ape pgb wild-type) |

Figure 8:
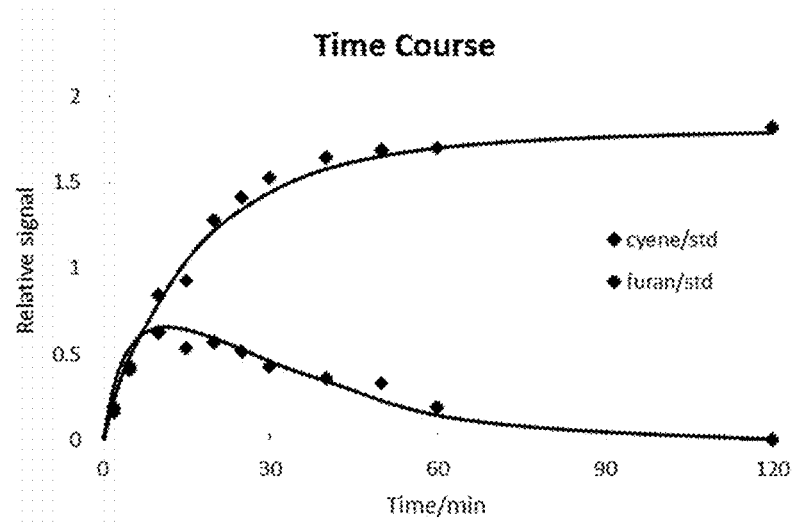
FIG. 8 shows the time course of furan formation with P411-S1 I263W variant.

Interestingly, a P411 variant obtained in a previous cyclopropanation study, P411-S1 I263W (see Supplementary Materials for sources, sequences and mutations), afforded a furan product (3b) with a total turnover number (TTN) of 210. Other furan analogs have been identified as adducts of carbenes and alkynes ([43]), which prompted the consideration of how furan 3b was generated. Preliminary kinetic study of the enzymatic reaction suggested that the enzyme first synthesized an unstable cyclopropene (3a), which subsequently rearranged to the furan either spontaneously or with assistance from the enzyme (FIG. 7B and FIG. 8). For the time-course study, reactions were set up in parallel according to the procedure in biotransformations using whole-cell catalyst (OD$_{600}$=30). The reactions were quenched at certain time points and analyzed by GC-MS. Every data point (average of two reaction) in FIG. 8 is the peak area of cyclopropene 3a or furan 3b divided by that of internal standard on GC-MS. Cyene=cyclopropene. These results provided strong evidence that the P411 hemeprotein is capable of transferring a carbene to an alkyne, which is an activity not previously reported for any protein or even any iron complex.

Example 9. Engineering of Biocatalysts for Bicyclobutane Formation

To divert the enzymatic reaction to bicyclobutane formation, the enzyme would have to transfer a second carbene to cyclopropene intermediate 3a before the cyclopropene rearranges to the undesired furan product (FIG. 7B). Therefore, P411 variants closely related to P411-S1 I263W were tested. It was reasoned that amino acid residue 263, which resides in the distal pocket, above the heme cofactor, might modulate the rate of this step and that the bulky tryptophan (Trp) side chain at this site may be blocking the second carbene transfer. A P411-S1 variant with phenylalanine (Phe) instead of Trp at this position (I263F) in fact catalyzed bicyclobutane formation at a very low level (<5 TTN) (Table 2). Variant 'P4' with 3 additional mutations relative to P411-S1 I263F (V87A, A268G and A328V) ([34]) synthesized the desired bicyclobutane 2a with 80 TTN and with the formation of furan adduct substantially suppressed (2a:3b>50:1, FIG. 7C).

Figure 7E:
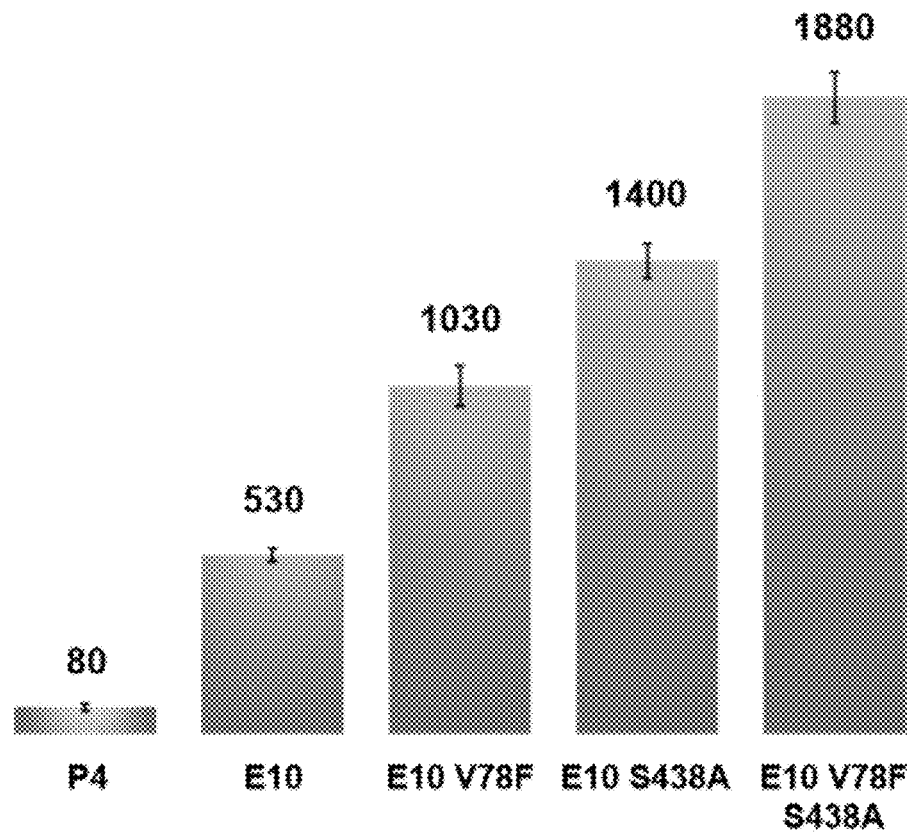
FIG. 7E shows the directed evolution of P411-E10 for bicyclobutane formation (using phenylacetylene and EDA as substrates; numbers refer to total turnovers to product (TTN) measured). Experiments were performed on analytical scale using suspensions of *E. coli* expressing P411-E10 variants (OD$_{600}$=10-30), 10 mM phenylacetylene, 10 mM EDA, 5 vol % EtOH, M9-N buffer (pH 7.4) at room temperature under anaerobic conditions for 6 h. Reactions performed in quadruplicate. TTN refers to the total desired product, as quantified by gas chromatography (GC), divided by total hemeprotein. Because bicyclobutane formation requires two carbene transfers, the number of carbene transfers the hemeprotein catalyzes is 2×TTN in these reactions.

Another related P411 variant, E10 (=P4 A78V A82L F263L), which was engineered from P4 for nitrene transfer reactions ([35]), catalyzed the desired transformation with >6-fold higher activity (530 TTN, FIG. 7E). NMR analysis revealed an exo, endo-configuration of the enzymatically-produced bicyclobutane 2a, which is distinct from the only reported achiral endo, endo-isomer, made using an osmium-porphyrin complex ([44], [45]). This P411-E10 variant was chosen as the starting template for directed evolution of an even more efficient bicyclobutane-constructing enzyme.

Because the side chain of residue 263 influenced formation of the bicyclobutane product, site-saturation mutagenesis (SSM) of variant E10 was performed at position 263 and screened whole *E. coli* cells expressing the mutated proteins for improved production of bicyclobutane 2a. The enzyme having leucine at this position (263L) was the most active; other amino acid residues either lowered the reactivity towards bicyclobutane formation and/or delivered more furan product. In parallel, two additional residues in E10, V78 and S438, were also targeted by SSM. Aromatic residues were found to be activating at 78, with a phenylalanine or tyrosine mutation giving 1.5-2-fold improvement over E10. This beneficial effect may stem from a π-π stacking interaction between the side chain and the alkyne substrate or the cyclopropene intermediate. A single S438A mutation on a loop residing above the heme also significantly increased the activity, giving >2.5-fold increase in turnover. Finally, recombination of V78F/Y and S438A mutations led to the discovery of even more powerful biocatalysts for bicyclobutane formation (e.g., 1880 TTN with E10 V78F S438A, FIG. 7E and FIG. 9).

Figure 9:
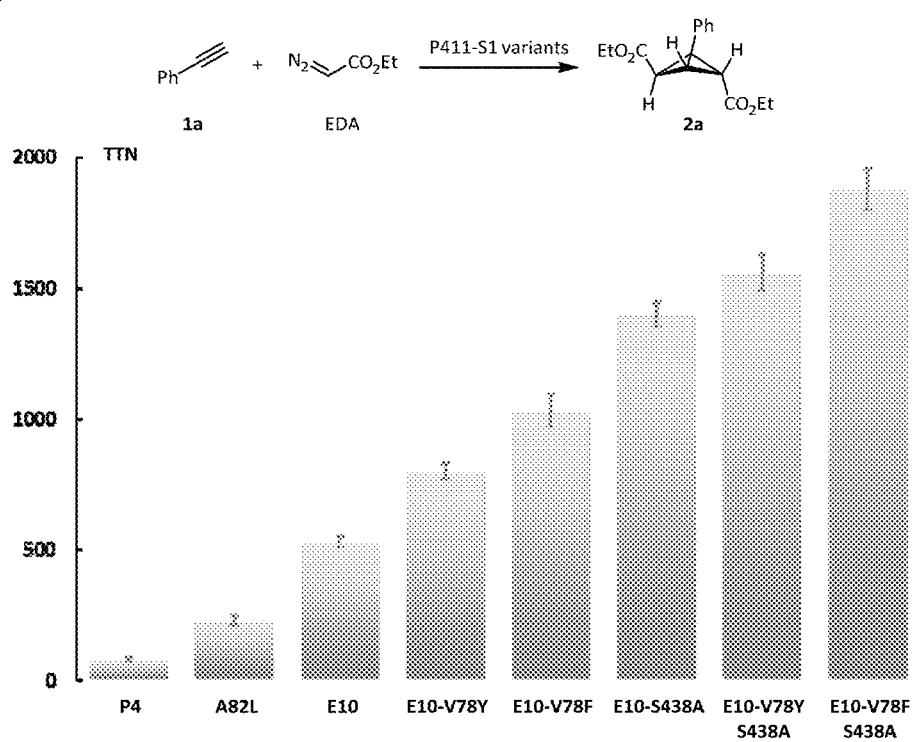
FIG. 9 shows the evolutionary trajectory of P411 variants for bicyclobutane formation.
Figure 10:
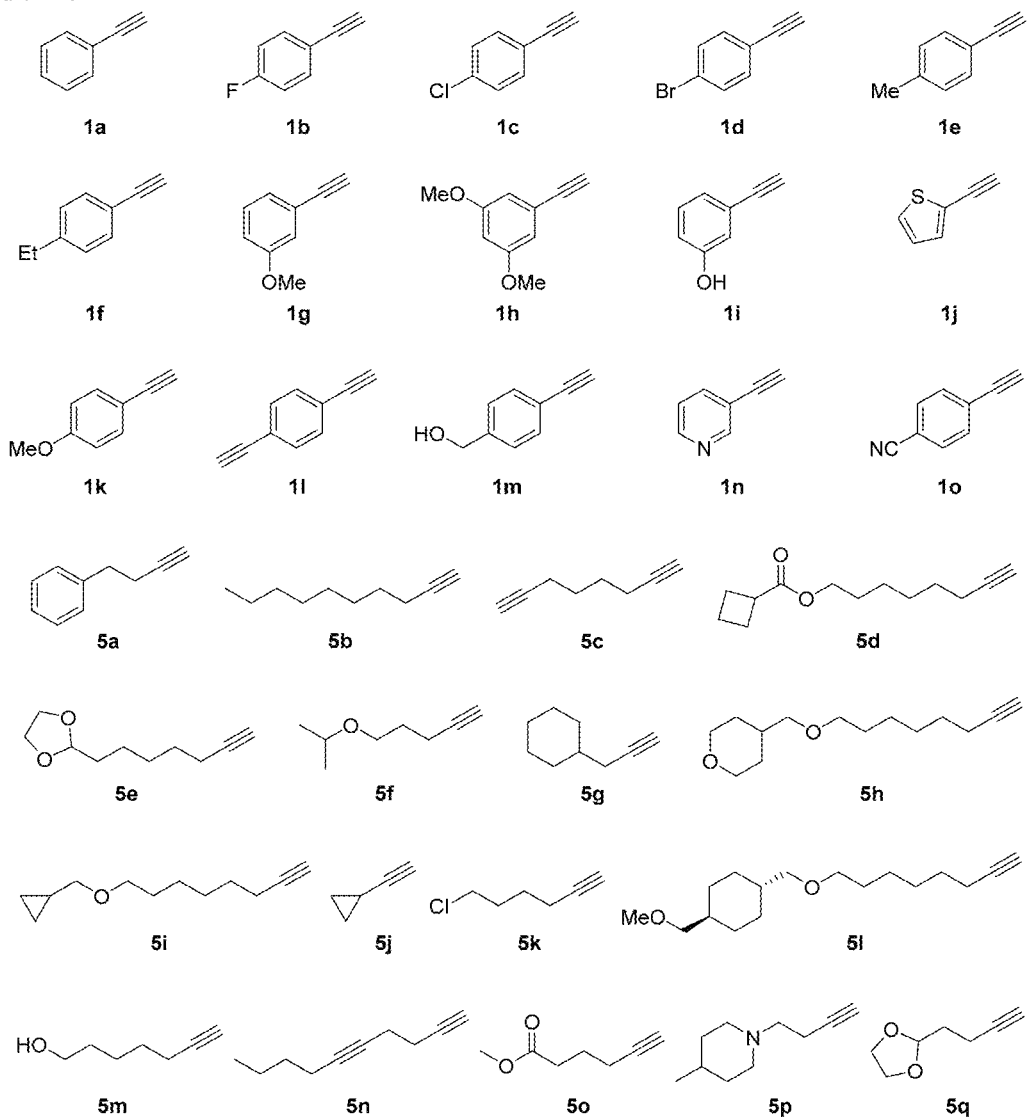
FIG. 10 shows alkyne substrates used in protein evolution studies.

Data in FIG. 9 are also summarized in Table 4. Analytical reactions were set up in quadruplicate according to the procedure for biotransformations described above using whole-cell catalyst and analyzed by GC using the standard calibration curve of 2a. The TTNs were obtained for $OD_{600}$=30 for P4, A82L and E10 variants, $OD_{600}$=15 for E10 V78Y and E10 V78F variants, and $OD_{600}$=10 for E10 S438A, E10 V78Y S438A and E10 V78F S438A variants. TTNs reported are the average of biological duplicates. Each biological set contains four experiments. The errors in all tables are standard deviations.

TABLE 4

P411-S1 variants for bicyclobutane formation

| P411-S1 variants | TTN |
|---|---|
| P4 | 80 ± 10 |
| "A82L" | 280 ± 20 |
| E10 | 530 ± 20 |
| E10 V78Y | 800 ± 30 |
| E10 V78F | 1030 ± 60 |
| E10 S438A | 1400 ± 50 |
| E10 V78Y S438A | 1560 ± 70 |
| E10 V78F S438A | 1880 ± 80 |

TABLE 5

Mutations in related P411-E10 variants

| Name | Description | Mutations relative to P450-WT |
|---|---|---|
| P4 | $P411_{BM3}$-CIS P4 variant ([34]) | V78A, F87A, P142S, T175I, A184V, S226R, H236Q, E252G, I263F, T268G, A290V, A328V, L353V, I366V, C400S, T438S, E442K |
| "A82L" | $P411_{BM3}$-CIS "A82L" variant ([34]) | V78A, A82L, F87A, P142S, T175I, A184V, S226R, H236Q, E252G, I263F, T268G, A290V, A328V, L353V, I366V, C400S, T438S, E442K |
| E10 | $P411_{BM3}$-CIS E10 variant ([35]) | A82L, F87A, P142S, T175I, A184V, S226R, H236Q, E252G, I263L, T268G, A290V, A328V, L353V, I366V, C400S, T438S, E442K |
| E10 V78Y | $P411_{BM3}$-CIS E10 V78Y | V78Y, A82L, F87A, P142S, T175I, A184V, S226R, H236Q, E252G, I263L, T268G, A290V, A328V, L353V, I366V, C400S, T438S, E442K |
| E10 V78F | $P411_{BM3}$-CIS E10 V78F | V78F, A82L, F87A, P142S, T175I, A184V, S226R, H236Q, E252G, I263L, T268G, A290V, A328V, L353V, I366V, C400S, T438S, E442K |
| E10 S438A | $P411_{BM3}$-CIS E10 S438A | A82L, F87A, P142S, T175I, A184V, S226R, H236Q, E252G, I263L, T268G, A290V, A328V, L353V, I366V, C400S, T438A, E442K |
| E10 V78Y S438A | $P411_{BM3}$-CIS E10 V78Y S438A | V78Y, A82L, F87A, P142S, T175I, A184V, S226R, H236Q, E252G, I263L, T268G, A290V, A328V, L353V, I366V, C400S, T438A, E442K |
| E10 V78F S438A | $P411_{BM3}$-CIS E10 V78F S438A | V78F, A82L, F87A, P142S, T175I, A184V, S226R, H236Q, E252G, I263L, T268G, A290V, A328V, L353V, I366V, C400S, T438A, E442K |

Example 10. Analysis of Alkyne Coupling Partners

Figure 11A:
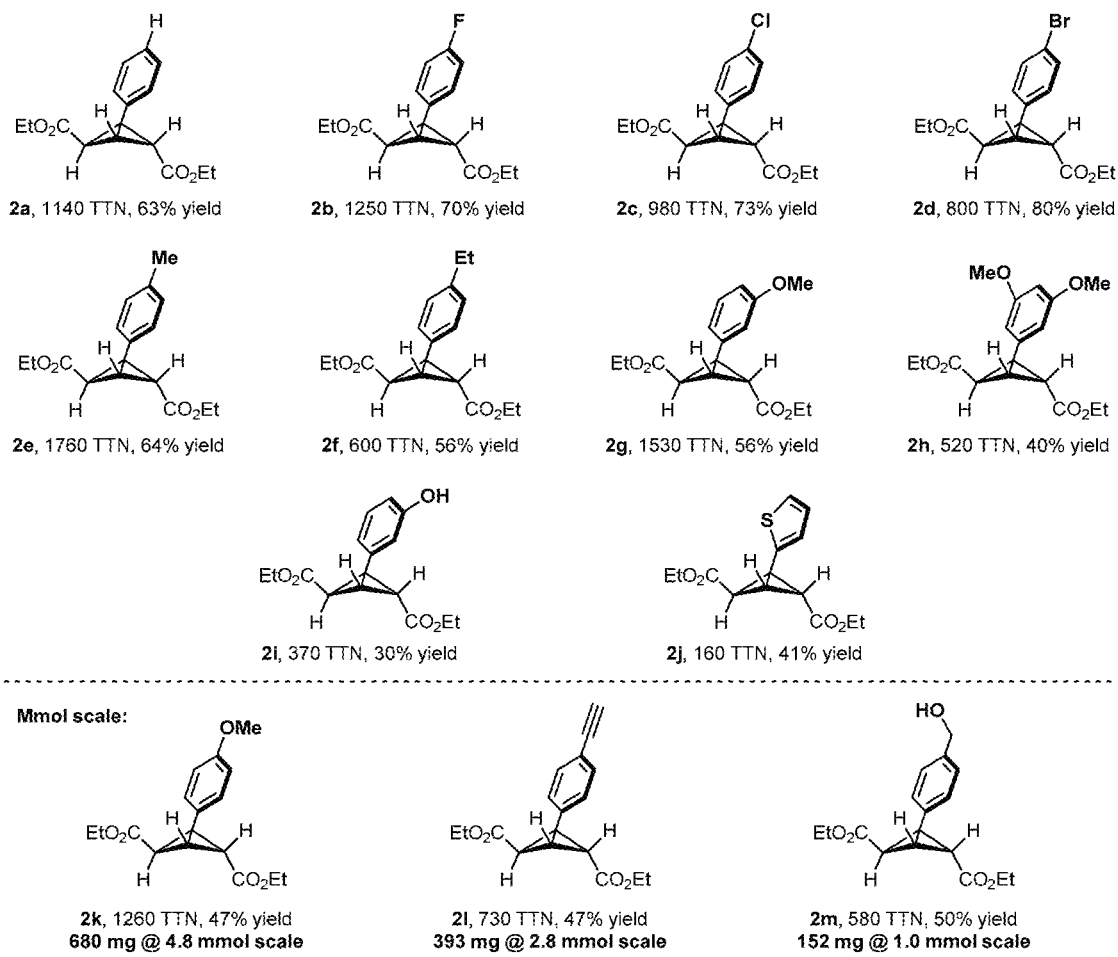
FIG. 11A shows the scope of P411-E10 V78F S438A-catalyzed bicyclobutane formation. Standard conditions of preparative-scale reactions (0.1-0.2 mmol scale, unless otherwise indicated): suspension of *E. coli* (OD$_{600}$=15-20) expressing P411 E10-V78F S438A, 1.0 equiv aromatic alkyne, 2.0-4.0 equiv EDA, 10-15 mM D-glucose, 1-5 vol % EtOH, M9-N buffer (pH 7.4) at room temperature under anaerobic conditions for 12 hours. Isolated yields. TTN determined based on isolated yields.
Figure 11B:
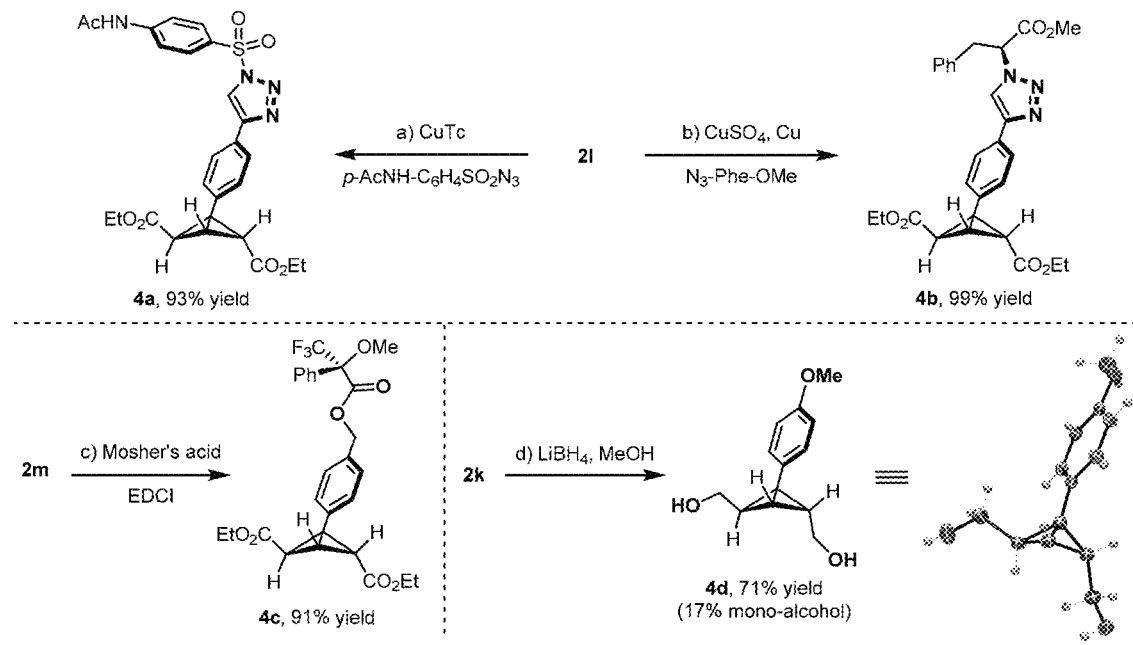
FIG. 11B shows the derivatization of bicyclobutane products. Top panel: copper-catalyzed click cyclization of 2l with azide substrates. Bottom left panel: esterification of 2m with Mosher's acid. Bottom right panel: reduction of 2k to diol with LiBH$_4$.

With the evolved E10 V78F S438A variant in hand, the bacterial catalyst was then assayed against a panel of aromatic alkyne coupling partners. Biotransformations with 10 different substrates were performed on 0.1-0.2 mmol scale. These preparative-scale reactions proceeded smoothly to furnish the corresponding bicyclobutanes with up to 1760 TTN and 80% yield (FIG. 11A). Additionally, three alkynes, 1k, 1l and 1m, were transformed in mmol scale, and bicyclobutanes were isolated in hundred-milligram quantities, demonstrating that the biocatalytic transformation is readily scalable. Among the 13 different substrates, the engineered P411 hemoprotein did not exhibit strong preference toward specific electronic or steric features. Electron-deficient halides (2b-2d), which can be used as pre-functionalities for further transformations as well as electron-rich alkyl or alkoxy groups (2e-2h and 2k) at meta- or para-position of the phenyl group were accepted by the enzyme. Even heterocyclic substrates such as thiophene (2j) served as suitable alkyne partners, albeit with lower reactivity.

Free functionalities, including alcohols (2i and 2m) and a second alkyne (2l), are well-preserved, providing an additional opportunity for derivatization of these products. A terminal alkyne allows copper-catalyzed click chemistry, through which bicyclobutane 2l can be modified with a simple sulfonyl azide (4a) or even decorated with biologically relevant fragments, such as a phenylalanine derivative (4b). An unprotected hydroxyl group could also offer the possibility of linkage to useful structures. Additionally, in order to probe the enantiopurity of bicyclobutane products, 2l and 2m were derivatized with L-azido-phenylalanine and (R)-Mosher's acid, respectively. The diastereomeric excess of these derivatized products would indicate the enantiomeric ratio of the bicyclobutanes. In fact, only single diastereomers of derivatized bicyclobutanes 4b and 4c were observed by NMR. Furthermore, the dicarboxylic esters on the bicyclobutane structure can be reduced easily with a mild reducing reagent, $LiBH_4$, to give diol product 4d with the strained ring structure preserved. The diol product 4d allowed for the unequivocal confirmation of the bicyclobutane structure and determination of the absolute configuration through X-ray crystallography.

Example 11. Analytical-Scale and Preparative-Scale Enzymatic Bicyclobutane Formation All enzymatic reactions for bicyclobutane formation in analytical scale were conducted following the general procedure described below and analyzed with gas chromatography (GC). All TTNs for the different products were approximated using the GC standard curve of bicyclobutane 2a, assuming substituents on the phenyl ring will not significantly affect the GC signals. These estimated TTNs were only used to help determine the reaction scale required to obtain sufficient bicyclobutane products for isolation, purification and characterization.

General Procedure for Analytical-Scale Reactions.

To a 2 mL vial were added degassed suspension of E. coli expressing P411-E10 V78F S438A variant in M9-N buffer ($OD_{600}$=9, 340 µL), alkyne (10 µL of 200 mM stock solution in EtOH, 5 mM final concentration), EDA (10 µL of 400 mM stock solution in EtOH, 10 mM final concentration, 2.0 equiv.), D-glucose (40 µL of 250 mM stock solution in M9-N buffer, 25 mM final concentration) under anaerobic conditions. The vial was capped and shaken at 560 rpm at room temperature for 6 h. After the reaction was completed, internal standard 1,3,5-trimethoxybenzene (20 µL of 20 mM stock solution in toluene) was added to the reaction vial followed by mixed solvent (cyclohexane/ethyl acetate=1:1, 1 mL). The mixture was transferred to a 1.5 mL microcentrifuge tube, and then vortexed (15 s×3) and centrifuged (14,000 rpm, 5 min) to completely separate the organic and aqueous layers. 0.8 mL of organic layer was taken for GC analysis. TTN was calculated based on measured protein concentration. Reactions for every substrate were set up in quadruplicate.

During testing of analytical reactions, electron-withdrawing alkynes 1n and 1o also gave fair amount of products, which were detected by GC-MS. However, problems in isolating these products from preparative-scale reactions were encountered. These results are noteworthy, but they cannot be used for drawing conclusions before further validation.

The results of the analytical reactions are shown in Table 6.

TABLE 6

Analysis data for analytical-scale bicyclobutane formation reactions

| Entry | Pdt[a] | Std[b] | Pdt/Std | [Pdt][c]/ mM | [PC][d]/ µM | TTN | Avg. TTN | Avg. yield |
|---|---|---|---|---|---|---|---|---|
| 2a-(1) | 3012.4 | 593.0 | 5.080 | 3.12 | 1.66 | 1882 | | |
| 2a-(2) | 3010.1 | 580.6 | 5.184 | 3.18 | 1.66 | 1921 | | |
| 2a-(3) | 2851.0 | 585.8 | 4.867 | 2.98 | 1.66 | 1803 | | |
| 2a-(4) | 2921.9 | 565.9 | 5.163 | 3.17 | 1.66 | 1913 | 1880 | 62.2 |
| 2b-(1) | 3204.9 | 554.0 | 5.785 | 3.47 | 1.66 | 2097 | | |
| 2b-(2) | 3278.8 | 558.0 | 5.876 | 3.53 | 1.66 | 2130 | | |
| 2b-(3) | 3274.2 | 565.1 | 5.794 | 3.48 | 1.66 | 2100 | | |
| 2b-(4) | 3154.2 | 559.6 | 5.637 | 3.38 | 1.66 | 2043 | 2092 | 69.3 |
| 2c-(1) | 2479.6 | 549.9 | 4.509 | 2.71 | 1.66 | 1634 | | |
| 2c-(2) | 2406.8 | 577.9 | 4.165 | 2.50 | 1.66 | 1510 | | |
| 2c-(3) | 2317.3 | 577.5 | 4.013 | 2.41 | 1.66 | 1455 | | |
| 2c-(4) | 2185.1 | 587.0 | 3.722 | 2.23 | 1.66 | 1349 | 1438 | 49.2 |
| 2d-(1) | 2007.2 | 576.5 | 3.482 | 2.09 | 1.66 | 1262 | | |
| 2d-(2) | 1673.5 | 564.7 | 2.964 | 1.78 | 1.66 | 1074 | | |
| 2d-(3) | 1436.5 | 570.1 | 2.520 | 1.51 | 1.66 | 913 | | |
| 2d-(4) | 1572.0 | 559.6 | 2.809 | 1.69 | 1.66 | 1018 | 1067 | 35.3 |
| 2e-(1) | 2712.6 | 551.2 | 4.921 | 2.95 | 1.66 | 1784 | | |
| 2e-(2) | 2943.0 | 575.5 | 5.114 | 3.07 | 1.66 | 1854 | | |
| 2e-(3) | 2565.4 | 556.1 | 4.613 | 2.77 | 1.66 | 1672 | | |
| 2e-(4) | 2725.3 | 558.7 | 4.878 | 2.93 | 1.66 | 1768 | 1769 | 58.6 |
| 2f-(1) | 1265.4 | 582.8 | 2.171 | 1.30 | 1.66 | 787 | | |
| 2f-(2) | 1261.3 | 583.0 | 2.163 | 1.30 | 1.66 | 784 | | |
| 2f-(3) | 1247.4 | 574.0 | 2.173 | 1.30 | 1.66 | 788 | | |
| 2f-(4) | 1194.4 | 580.7 | 2.057 | 1.23 | 1.66 | 746 | 773 | 25.7 |
| 2g-(1) | 2899.6 | 605.2 | 4.791 | 2.87 | 1.66 | 1737 | | |
| 2g-(2) | 2881.5 | 587.1 | 4.908 | 2.94 | 1.66 | 1779 | | |
| 2g-(3) | 2797.3 | 586.1 | 4.773 | 2.86 | 1.66 | 1730 | | |
| 2g-(4) | 2657.8 | 571.2 | 4.653 | 2.79 | 1.66 | 1687 | 1733 | 57.4 |

TABLE 6-continued

Analysis data for analytical-scale bicyclobutane formation reactions

| Entry | Pdt[a] | Std[b] | Pdt/Std | [Pdt][c]/ mM | [PC][d]/ µM | TTN | Avg. TTN | Avg. yield |
|---|---|---|---|---|---|---|---|---|
| 2j-(1) | 244.5 | 605.1 | 0.404 | 0.24 | 1.66 | 147 | | |
| 2j-(2) | 255.0 | 625.4 | 0.408 | 0.24 | 1.66 | 148 | | |
| 2j-(3) | 256.9 | 618.4 | 0.415 | 0.25 | 1.66 | 151 | | |
| 2j-(4) | 231.0 | 633.1 | 0.365 | 0.22 | 1.66 | 132 | 145 | 4.8 |
| 2k-(1) | 2837.1 | 565.1 | 5.021 | 3.01 | 1.66 | 1820 | | |
| 2k-(2) | 2818.8 | 591.5 | 4.766 | 2.86 | 1.66 | 1727 | | |
| 2k-(3) | 2792.4 | 572.9 | 4.874 | 2.92 | 1.66 | 1767 | | |
| 2k-(4) | 2824.5 | 581.3 | 4.859 | 2.92 | 1.66 | 1761 | 1769 | 58.6 |
| 2l-(1) | 1921.1 | 566.3 | 3.392 | 2.04 | 1.66 | 1230 | | |
| 2l-(2) | 1703.9 | 549.4 | 3.101 | 1.86 | 1.66 | 1124 | | |
| 2l-(3) | 1797.8 | 565.5 | 3.179 | 1.91 | 1.66 | 1152 | | |
| 2l-(4) | 1656.7 | 565.1 | 2.932 | 1.76 | 1.66 | 1063 | 1113 | 37.8 |

[a]Pdt = product area on GC,

[b]Std = internal standard area on GC,

[c][Pdt] = product concentration in reaction mixture,

[d][PC] = protein concentration in initial reaction mixture,

Avg. = average.

All enzymatic reactions for bicyclobutane formation in preparative scale were conducted following the general procedure described below and the corresponding bicyclobutane products were isolated. Detailed conditions for the preparative-scale reactions of different substrates are indicated separately.

General Procedure for Preparative-Scale Reactions.

To a 40 mL vial or 250 mL flask were added degassed suspension of E. coli expressing P411 E10-V78F S438A variant ($OD_{600}$=10-20), alkyne (0.1-0.2 mmol, larger scales for 1k-1m), EDA (2.0-4.0 equiv.), D-glucose (10-15 mM, 250 mM stock in M9-N), 1-5 vol % EtOH, M9-N buffer (pH 7.4) under anaerobic conditions. The vial or flask was capped and shaken (420 rpm for vials and 220 rpm for flasks) at room temperature for 12 h.

After the reaction was completed, every 30 mL portion of preparative-scale reaction mixture was transferred to a 50 mL Falcon centrifuge tube. The reaction container was washed with water (2 mL×2) followed by mixed organic solvent (cyclohexane/ethyl acetate=1:1, 2 mL×3). The washing solution was combined with the reaction mixture in the centrifuge tubes. Additional 12 mL of cyclohexane/ethyl acetate solvent was added to every tube. After the tube (with ~45 mL mixture in total) was capped, it was vortexed (1 min×3), shaken vigorously, and centrifuged (14,000 g, 5 min). The organic layer was separated and the aqueous layer was subjected to three more rounds of extraction. Then organic layers were combined, dried over $Na_2SO_4$, and concentrated under reduced pressure. Purification by silica column chromatography with hexane/ethyl acetate as eluent afforded the desired bicyclobutanes. TTNs were calculated based on measured protein concentration and the isolated yield of the product.

Diethyl (2R,4R)-1-phenylbicyclo[1.1.0]butane-2,4-dicarboxylate (2a)

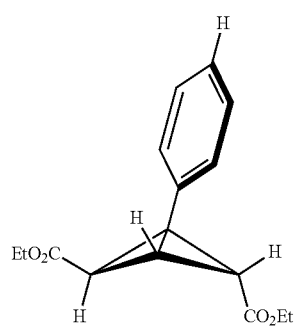

(2a)

| E. coli suspension in M9-N | | | | D-glucose in M9-N | |
|---|---|---|---|---|---|
| OD$_{600}$ | volume/ mL | [PC]/μM | n_pro/ μmol | volume/ mL | [Glu]/ mM |
| 20 | 24.0 | 4.17 | 0.100 | 1.0 | ~10 |

| alkyne (1a) stock in EtOH | | | EDA stock in EtOH | | |
|---|---|---|---|---|---|
| stock/M | volume/μL | n_1/mmol | stock/M | volume/μL | n_2/mmol |
| 1.00 | 180 | 0.18 | 2.00 | 180 | 0.36 |

| | | product | | |
|---|---|---|---|---|
| purification eluent | m[Pdt]/mg | n Pdt]/mmol | yield | TTN |
| Ethyl acetate in hexanes (0% to 10% gradient) | 31.3 | 0.114 | 63% | 1140 |

In the tables for compounds 2a-2m, [PC]=protein concentration in original cell suspension, n_pro=amount of protein in the reaction, [Glu]=D-glucose concentration in reaction mixture, n_1=amount of alkyne in the reaction, n_2=amount of EDA in the reaction, m[Pdt]=mass of product isolated, n[Pdt]=amount of product.

$^1$H NMR (400 MHz, CDCl$_3$) δ 7.34-7.22 (m, 5H), 4.14 (qd, J=7.2, 2.4 Hz, 2H), 4.07 (qd, J=7.2, 3.7 Hz, 2H), 3.26 (s, 1H), 3.13 (d, J=3.0 Hz, 1H), 3.10 (d, J=3.0 Hz, 1H), 1.27 (t, J=7.1 Hz, 3H), 1.13 (t, J=7.1 Hz, 3H). $^{13}$C NMR (101 MHz, CDCl$_3$) δ 170.36, 167.91, 132.68, 128.50, 128.45, 127.56, 60.99, 60.91, 44.64, 42.55, 28.18, 20.47, 14.37, 14.16. HRMS (FAB) m/z: 275.1271 (M+H$^+$); calc. for C$_{16}$H$_{19}$O$_4$: 275.1283. [α]$^{23}_D$=−124.8±1.1° (c 0.1, ethyl acetate).

Diethyl (2R,4R)-1-(4-fluorophenyl)bicyclo[1.1.0]butane-2,4-dicarboxylate (2b)

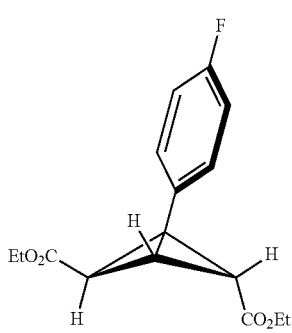

(2b)

| E. coli suspension in M9-N | | | | D-glucose in M9-N | |
|---|---|---|---|---|---|
| OD$_{600}$ | volume/ mL | [PC]/ μM | n_pro/ μmol | volume/ mL | [Glu]/ mM |
| 20 | 24.0 | 4.17 | 0.100 | 1.0 | ~10 |

| alkyne (1b) stock in EtOH | | | EDA stock in EtOH | | |
|---|---|---|---|---|---|
| stock/M | volume/ μL | n_1/ mmol | stock/M | volume/ μL | n_2/ mmol |
| 1.0 | 180 | 0.18 | 2.0 | 180 | 0.36 |

| purification eluent | | product | | |
|---|---|---|---|---|
| Ethyl acetate in hexanes | m[Pdt]/ mg | n[Pdt]/ mmol | yield | TTN |
| (0% to 10% gradient) | 36.6 | 0.125 | 70% | 1250 |

$^1$H NMR (400 MHz, CDCl$_3$) δ 7.32-7.26 (m, 2H), 7.05-6.94 (m, 2H), 4.21-4.11 (m, 2H), 4.11-4.00 (m, 2H), 3.23 (d, J=0.5 Hz, 1H), 3.09 (d, J=3.0 Hz, 1H), 3.04 (dd, J=3.0, 0.6 Hz, 1H), 1.27 (t, J=7.1 Hz, 3H), 1.14 (t, J=7.1 Hz, 3H). $^{13}$C NMR (101 MHz, CDCl$_3$) δ 170.20, 167.80, 163.59 (d, J$_{C-F}$=246.4 Hz), 130.55 (d, J$_{C-F}$=8.2 Hz), 128.31, (d, J$_{C-F}$=3.3 Hz), 115.63, (d, J$_{C-F}$=21.8 Hz), 61.06, 60.98, 44.83, 42.70, 27.50, 19.89, 14.37, 14.20. HRMS (FAB) m/z: 293.1179 (M+H$^+$); calc. for C$_{16}$H$_{18}$FO$_4$: 293.1189. [α]$^{23}_D$=−110.1±2.0° (c 0.1, ethyl acetate).

Diethyl (2R,4R)-1-(4-chlorophenyl)bicyclo[1.1.0]butane-2,4-dicarboxylate (2c)

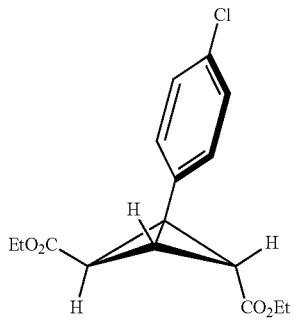

(2c)

| E. coli suspension in M9-N | | | D-glucose in M9-N | |
|---|---|---|---|---|
| OD$_{600}$ | volume/ mL | [PC]/ μM | n_pro/ μmol | volume/ mL | [Glu]/ mM |
| 20 | 36.0 | 4.17 | 0.150 | 1.5 | ~10 |

| alkyne (1c) stock in EtOH | | | EDA stock in EtOH | | |
|---|---|---|---|---|---|
| stock/M | volume/ μL | n_1/ mmol | stock/M | volume/ μL | n_2/ mmol |
| 1.0 | 200 | 0.20 | 2.0 | 400 | 0.80 |

| purification eluent | product | | | |
|---|---|---|---|---|
| Ethyl acetate in hexanes | m[Pdt]/ mg | n[Pdt]/ mmol | yield | TTN |
| (0% to 10% gradient) | 45.2 | 0.146 | 73% | 980 |

$^1$H NMR (400 MHz, CDCl$_3$) δ 7.28 (d, J=8.9 Hz, 2H), 7.23 (d, J=8.6 Hz, 2H), 4.14 (qd, J=7.1, 2.4 Hz, 2H), 4.08 (qd, J=7.1, 2.2 Hz, 2H), 3.24 (d, J=0.6 Hz, 1H), 3.10 (d, J=3.0 Hz, 1H), 3.08 (dd, J=3.0, 0.5 Hz, 1H), 1.27 (t, J=7.1 Hz, 3H), 1.16 (t, J=7.1 Hz, 3H). $^{13}$C NMR (101 MHz, CDCl$_3$) δ 170.06, 167.75, 133.48, 131.27, 129.93, 128.71, 61.10, 61.06, 44.77, 42.65, 27.47, 20.61, 14.36, 14.21. HRMS (FAB) m/z: 309.0902 (M+H$^+$); calc. for C$_{16}$H$_{18}$Cl$_4$: 309.0894. [α]$^{23}_D$=−141.5±2.6° (c 0.1, ethyl acetate).

Diethyl (2R,4R)-1-(4-bromophenyl)bicyclo[1.1.0]butane-2,4-dicarboxylate (2d)

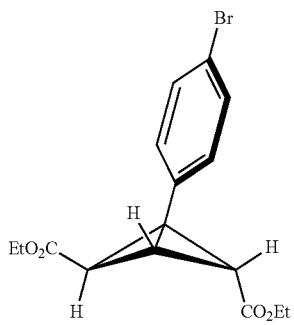

(2d)

| E. coli suspension in M9-N | | | D-glucose in M9-N | |
|---|---|---|---|---|
| OD$_{600}$ | volume/ mL | [PC]/ μM | n_pro/ μmol | volume/ mL | [Glu]/ mM |
| 20 | 36.0 | 4.17 | 0.150 | 1.5 | ~10 |

| alkyne (1d) stock in EtOH | | | EDA stock in EtOH | | |
|---|---|---|---|---|---|
| stock/M | volume/ μL | n_1/ mmol | stock/M | volume/ μL | n_2/ mmol |
| 1.0 | 150 | 0.15 | 2.0 | 300 | 0.60 |

| purification eluent | product | | | |
|---|---|---|---|---|
| Ethyl acetate in hexanes | m[Pdt]/ mg | n[Pdt]/ mmol | yield | TTN |
| (0% to 10% gradient) | 42.5 | 0.120 | 80% | 800 |

$^1$H NMR (400 MHz, CDCl$_3$) δ 7.43 (d, J=8.7 Hz, 2H), 7.17 (d, J=8.7 Hz, 2H), 4.14 (qd, J=7.1, 2.4 Hz, 2H), 4.08 (qd, J=7.1, 1.8 Hz, 2H), 3.24 (d, J=0.6 Hz, 1H), 3.10 (d, J=3.1 Hz, 1H), 3.09 (dd, J=3.1, 0.5 Hz, 1H), 1.27 (t, J=7.1 Hz, 3H), 1.16 (t, J=7.1 Hz, 3H). $^{13}$C NMR (101 MHz, CDCl$_3$) δ 170.02, 167.73, 131.84, 131.64, 130.22, 121.56, 61.11, 61.07, 44.74, 42.62, 27.53, 20.71, 14.36, 14.21. HRMS (FAB) m/z: 353.0399 (M+H$^+$); calc. for C$_{16}$H$_{18}$BrO$_4$: 353.0388 ($^{79}$Br). [α]$^{23}_D$=−128.4±0.8° (c 0.1, ethyl acetate).

Diethyl (2R,4R)-1-(p-tolyl)bicyclo[1.1.0]butane-2,4-dicarboxylate (2e)

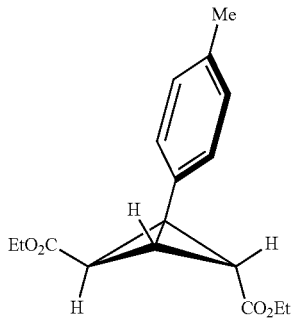

(2e)

| E. coli suspension in M9-N | | | D-glucose in M9-N | |
|---|---|---|---|---|
| OD$_{600}$ | volume/ mL | [PC]/μM | n_pro/ μmol | volume/ mL | [Glu]/ mM |
| 18 | 20.0 | 2.92 | 0.0584 | 1.0 | ~13 |

| alkyne (1e) stock in EtOH | | | EDA stock in EtOH | | |
|---|---|---|---|---|---|
| stock/M | volume/ μL | n_1/ mmol | stock/M | volume/ μL | n_2/ mmol |
| 1.0 | 160 | 0.16 | 2.0 | 160 | 0.32 |

| purification eluent | product | | | |
|---|---|---|---|---|
| Ethyl acetate in hexanes | m[Pdt]/ mg | n[Pdt]/ mmol | yield | TTN |
| (0% to 8% gradient) | 29.6 | 0.103 | 64% | 1760 |

$^1$H NMR (400 MHz, CDCl$_3$) δ 7.19 (d, J=8.2 Hz, 2H), 7.11 (d, J=7.9 Hz, 2H), 4.18-4.03 (m, 4H), 3.23 (d, J=0.6 Hz, 1H), 3.08 (dd, J=3.0, 0.6 Hz, 1H), 3.06 (d, J=3.0 Hz, 1H), 2.32 (s, 3H), 1.26 (t, J=7.1 Hz, 3H), 1.15 (t, J=7.1 Hz, 3H). $^{13}$C NMR (101 MHz, CDCl$_3$) δ 170.48, 168.01, 137.37, 129.42, 129.22, 128.41, 60.94, 60.87, 44.62, 42.50, 28.09, 21.34, 20.07, 14.37, 14.20. HRMS (FAB) m/z: 289.1450 (M+H$^+$); calc. for C$_{17}$H$_{21}$O$_4$: 289.1440. [α]$^{23}_D$=−143.6±1.0° (c 0.1, ethyl acetate).

Diethyl (2R,4R)-1-(4-ethylphenyl)bicyclo[1.1.0]butane-2,4-dicarboxylate (2f)

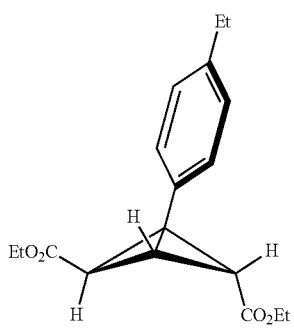

(2f)

| E. coli suspension in M9-N | | | | D-glucose in M9-N | |
|---|---|---|---|---|---|
| OD$_{600}$ | volume/ mL | [PC]/μM | n_pro/ μmol | volume/ mL | [Glu]/ mM |
| 18 | 32.0 | 2.92 | 0.0934 | 1.5 | ~11 |
| alkyne (1f) stock in EtOH | | | EDA stock in EtOH | | |
| stock/M | volume/ μL | n_1/ mmol | stock/M | volume/ μL | n_2/ mmol |
| 1.0 | 100 | 0.10 | 2.0 | 100 | 0.20 |
| purification eluent | | product | | | |
| Ethyl acetate in hexanes | m[Pdt]/ mg | n[Pdt]/ mmol | | yield | TTN |
| (0% to 8% gradient) | 16.8 | 0.0556 | | 56% | 600 |

$^1$H NMR (400 MHz, CDCl$_3$) δ 7.22 (d, J=8.3 Hz, 2H), 7.14 (d, J=8.4 Hz, 2H), 4.20-4.01 (m, 4H), 3.23 (d, J=0.6 Hz, 1H), 3.09 (dd, J=3.0, 0.6 Hz, 1H), 3.07 (d, J=3.0 Hz, 1H), 2.62 (q, J=7.6 Hz, 2H), 1.26 (t, J=7.1 Hz, 3H), 1.21 (t, J=7.6 Hz, 3H), 1.14 (t, J=7.1 Hz, 3H). $^{13}$C NMR (101 MHz, CDCl$_3$) δ 170.49, 168.02, 143.73, 129.69, 128.46, 128.04, 60.93, 60.87, 44.57, 42.50, 28.72, 28.13, 20.14, 15.67, 14.38, 14.19. HRMS (FAB) m/z: 303.1588 (M+H$^+$); calc. for C$_{18}$H$_{23}$O$_4$: 303.1596. [α]$^{23}_D$=−133.7±1.8° (c 0.1, ethyl acetate).

Diethyl (2R,4R)-1-(3-methoxyphenyl)bicyclo[1.1.0]butane-2,4-dicarboxylate (2g)

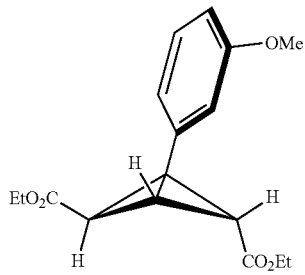

(2g)

| E. coli suspension in M9-N | | | | D-glucose in M9-N | |
|---|---|---|---|---|---|
| OD$_{600}$ | volume/ mL | [PC]/μM | n_pro/ μmol | volume/ mL | [Glu]/ mM |
| 18 | 20.0 | 2.92 | 0.0584 | 1.0 | ~13 |
| alkyne (1g) stock in EtOH | | | EDA stock in EtOH | | |
| stock/M | volume/ μL | n_1/ mmol | stock/M | volume/ μL | n_2/mmol |
| 1.0 | 160 | 0.16 | 2.0 | 160 | 0.32 |
| purification eluent | | product | | | |
| Ethyl acetate in hexanes | m[Pdt]/ mg | n[Pdt]/ mmol | | yield | TTN |
| (0% to 12% gradient) | 27.2 | 0.0894 | | 56% | 1530 |

$^1$H NMR (400 MHz, CDCl$_3$) δ 7.24-7.19 (m, 1H), 6.88 (ddd, J=7.6, 1.6, 1.0 Hz, 1H), 6.85-6.82 (m, 1H), 6.80 (ddd, J=8.2, 2.6, 1.0 Hz, 1H), 4.20-4.01 (m, 4H), 3.78 (s, 3H), 3.25 (d, J=0.6 Hz, 1H), 3.13 (dd, J=3.0, 0.6 Hz, 1H), 3.09 (d, J=3.0 Hz, 1H), 1.26 (t, J=7.1 Hz, 3H), 1.15 (t, J=7.1 Hz, 3H). $^{13}$C NMR (101 MHz, CDCl$_3$) δ 170.31, 167.90, 159.67, 134.22, 129.54, 120.75, 114.01, 113.20, 61.01, 60.95, 55.35, 44.69, 42.58, 28.18, 20.69, 14.37, 14.20. HRMS (FAB) m/z: 305.1383 (M+H$^+$); calc. for C$_{17}$H$_{21}$O$_5$: 305.1389. [α]$^{23}_D$=−122.6±1.5° (c 0.1, ethyl acetate).

Diethyl (2R,4R)-1-(3,5-dimethoxyphenyl)bicyclo[1.1.0]butane-2,4-dicarboxylate (2h)

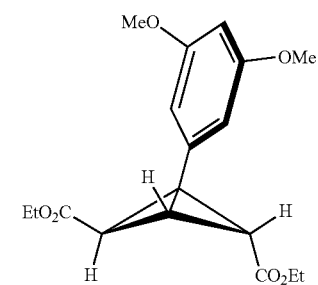

(2h)

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 16 | 45.0 | 2.54 | 0.114 | 3.0 | ~16 |

| alkyne (1h) stock in EtOH | | | EDA stock in EtOH | | |
|---|---|---|---|---|---|
| stock/M | volume/μL | n_1/mmol | stock/M | volume/μL | n_2/mmol |
| 1.0 | 150 | 0.15 | 2.0 | 225 | 0.45 |

| purification eluent | product | | | |
|---|---|---|---|---|
| Ethyl acetate in hexanes | m[Pdt]/mg | n[Pdt]/mmol | yield | TTN |
| (0% to 15% gradient) | 19.8 | 0.0592 | 40% | 520 |

$^1$H NMR (400 MHz, CDCl$_3$) δ 6.44 (d, J=2.2 Hz, 2H), 6.36 (t, J=2.3 Hz, 1H), 4.15 (qd, J=7.1, 2.5 Hz, 2H), 4.09 (qd, J=7.1, 3.9 Hz, 2H), 3.76 (s, 6H), 3.24 (s, 1H), 3.12 (d, J=3.0 Hz, 1H), 3.09 (d, J=3.0 Hz, 1H), 1.26 (t, J=7.1 Hz, 3H), 1.17 (t, J=7.1 Hz, 3H). $^{13}$C NMR (101 MHz, CDCl$_3$) δ 170.14, 167.76, 160.71, 134.80, 106.29, 99.71, 60.88, 60.84, 55.33, 44.56, 42.45, 28.23, 20.67, 14.23, 14.11. HRMS (FAB) m/z: 335.1480 (M+H$^+$); calc. for C$_{18}$H$_{23}$O$_6$: 335.1495. [α]$^{23}_D$=−144.6±3.5° (c 0.1, ethyl acetate).

Diethyl (2R,4R)-1-(3-hydroxyphenyl)bicyclo[1.1.0]butane-2,4-dicarboxylate (2i)

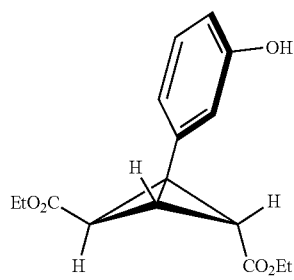

(2i)

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 16 | 45.0 | 2.14 | 0.0963 | 3.0 | ~16 |

| alkyne (1i) stock in EtOH | | | EDA stock in EtOH | | |
|---|---|---|---|---|---|
| stock/M | volume/μL | n_1/mmol | stock/M | volume/μL | n_2/mmol |
| 1.0 | 120 | 0.12 | 2.0 | 180 | 0.36 |

| purification eluent | product | | | |
|---|---|---|---|---|
| Ethyl acetate in hexanes | m[Pdt]/mg | n[Pdt]/mmol | yield | TTN |
| (0% to 20% gradient) | 10.4 | 0.0358 | 30% | 370 |

$^1$H NMR (400 MHz, CDCl$_3$) δ 7.15 (td, J=8.1, 1.7 Hz, 1H), 6.87-6.83 (m, 1H), 6.78-6.74 (m, 1H), 6.73-6.68 (m, 1H), 5.06 (s, 1H), 4.21-4.02 (m, 4H), 3.23 (d, J=0.6 Hz, 1H), 3.11 (dd, J=3.1, 0.6 Hz, 1H), 3.09 (d, J=3.0 Hz, 1H), 1.27 (t, J=7.1 Hz, 3H), 1.15 (t, J=7.1 Hz, 3H). $^{13}$C NMR (101 MHz, CDCl$_3$) δ 170.22, 167.87, 155.59, 134.27, 129.62, 120.76, 115.15, 114.58, 60.94, 60.92, 44.54, 42.43, 27.86, 20.58, 14.23, 14.04. HRMS (FAB) m/z: 291.1237 (M+H$^+$); calc. for C$_{16}$H$_{19}$O$_5$: 291.1232.

Diethyl (2R,4R)-1-(thiophen-2-yl)bicyclo[1.1.0]butane-2,4-dicarboxylate (2j)

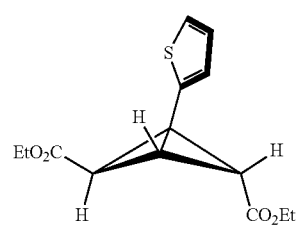

(2j)

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 20 | 54.0 | 4.30 | 0.232 | 3.2 | ~14 |

| alkyne (1j) stock in EtOH | | | EDA stock in EtOH | | |
|---|---|---|---|---|---|
| stock/M | volume/μL | n_1/mmol | stock/M | volume/μL | n_2/mmol |
| 1.0 | 100 | 0.10 | 2.0 | 200 | 0.40 |

| purification eluent | product | | | |
|---|---|---|---|---|
| Ethyl acetate in hexanes | m[Pdt]/mg | n[Pdt]/mmol | yield | TTN |
| (0% to 8% gradient) | 11.4 | 0.0407 | 41% | 160 |

$^1$H NMR (400 MHz, CDCl$_3$) δ 7.20 (dd, J=5.2, 1.2 Hz, 1H), 7.05 (dd, J=3.5, 1.3 Hz, 1H), 6.94 (dd, J=5.2, 3.5 Hz, 1H), 4.19-4.10 (m, 4H), 3.27 (s, 1H), 3.10 (d, J=3.1 Hz, 1H), 3.06 (dd, J=3.1, 0.6 Hz, 1H), 1.28 (t, J=7.1 Hz, 3H), 1.20 (t, J=7.1 Hz, 3H). $^{13}$C NMR (101 MHz, CDCl$_3$) δ 169.92, 167.46, 135.29, 128.55, 126.97, 125.42, 61.14, 61.12, 45.87, 44.10, 23.88, 21.23, 14.37, 14.22. HRMS (FAB) m/z: 281.0839 (M+H$^+$); calc. for C$_{14}$H$_{17}$O$_4$S: 281.0848.

Diethyl (2R,4R)-1-(4-methoxyphenyl)bicyclo[1.1.0]butane-2,4-dicarboxylate (2k)

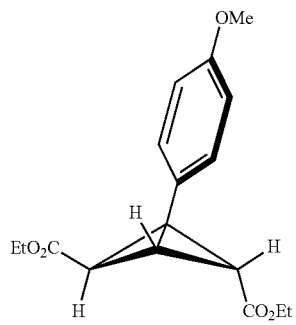

(2k)

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 15 | 24.0 | 2.43 | 0.0583 | 1.0 | ~10 |

| alkyne (1k) stock in EtOH | | | EDA stock in EtOH | | |
|---|---|---|---|---|---|
| stock/M | volume/μL | n_1/mmol | stock/M | volume/μL | n_2/mmol |
| 1.0 | 160 | 0.16 | 2.0 | 160 | 0.32 |

| purification eluent | product | | | |
|---|---|---|---|---|
| Ethyl acetate in hexanes | m[Pdt]/mg | n[Pdt]/mmol | yield | TTN |
| (0% to 8% gradient) | 32.4 | 0.107 | 67% | 1830 |

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 16 | 600 | 2.96 | 1.77 | 30 | ~12 |

| alkyne (1k) stock in EtOH | | | EDA stock in EtOH | | |
|---|---|---|---|---|---|
| stock/M | volume/mL | n_1/mmol | stock/mM | mL | n_2/mmol |
| 2.0 | 2.40 | 4.80 | 2.0 | 7.20 | 14.40 |

| purification eluent | product | | | |
|---|---|---|---|---|
| Ethyl acetate in hexanes | m[Pdt]/mg | n[Pdt]/mmol | yield | TTN |
| (0% to 12% gradient) | 680.4 | 2.34 | 47% | 1260 |

Note:
in 4.8 mmol scale reaction, the EDA stock solution was added in three portions (2.4 mL each portion) every 1 hour.

$^1$H NMR (400 MHz, CDCl$_3$) δ 7.25 (d, J=8.7 Hz, 2H), 6.84 (d, J=8.7 Hz, 2H), 4.20-3.99 (m, 4H), 3.79 (s, 3H), 3.21 (s, 1H), 3.04 (d, J=2.9 Hz, 1H), 3.01 (d, J=2.9 Hz, 1H), 1.27 (t, J=7.1 Hz, 3H), 1.14 (t, J=7.1 Hz, 3H). $^{13}$C NMR (101 MHz, CDCl$_3$) δ 170.53, 168.01, 159.21, 130.03, 124.27, 113.99, 60.93, 60.85, 55.43, 44.68, 42.63, 27.90, 19.35, 14.38, 14.22. HRMS (FAB) m/z: 305.1375 (M+H$^+$); calc. for C$_{17}$H$_{21}$O$_5$: 305.1389. [α]$^{23}_D$=−138.2±1.6° (c 0.1, ethyl acetate).

Diethyl (2R,4R)-1-(4-ethynylxyphenyl)bicyclo[1.1.0]butane-2,4-dicarboxylate (2l)

The title compound was synthesized as summarized below. In the 2.8 mmol scale-reaction, EDA stock solution was added in three portions (1.4 mL each portion) every 1 hour.

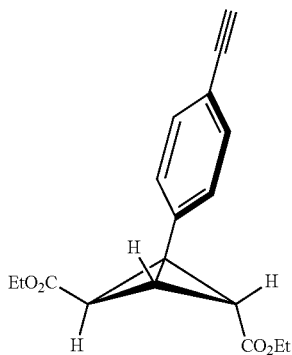

(2l)

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 16 | 36.0 | 3.44 | 0.124 | 2.0 | ~13 |

| alkyne (1l) stock in EtOH | | | EDA stock in EtOH | | |
|---|---|---|---|---|---|
| stock/M | volume/μL | n_1/mmol | stock/M | volume/μL | n_2/mmol |
| 1.0 | 150 | 0.15 | 2.0 | 225 | 0.45 |

| purification eluent | product | | | |
|---|---|---|---|---|
| Ethyl acetate in hexanes | m[Pdt]/mg | n[Pdt]/mmol | yield | TTN |
| (0% to 8% gradient) | 28.7 | 0.0962 | 64% | 780 |

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 18 | 600 | 3.03 | 1.82 | 30 | ~12 |

| alkyne (1l) stock in EtOH | | | EDA stock in EtOH | | |
|---|---|---|---|---|---|
| stock/M | volume/mL | n_1/mmol | stock/M | volume/mL | n_2/mmol |
| 2.0 | 1.40 | 2.80 | 2.0 | 4.20 | 8.40 |

| purification eluent | product | | | |
|---|---|---|---|---|
| Ethyl acetate in hexanes | m[Pdt]/mg | n[Pdt]/mmol | yield | TTN |
| (0% to 10% gradient) | 393.7 | 1.32 | 47% | 730 |

| E. coli suspension in M9-N | | | D-glucose in M9-N | |
|---|---|---|---|---|
| OD$_{600}$ | volume/mL | [PC]/μM | n_pro/μmol | volume/mL | [Glu]/mM |
| 18 | 600 | 3.03 | 1.82 | 30 | ~12 |

| alkyne (1l) stock in EtOH | | | EDA stock in EtOH | | |
|---|---|---|---|---|---|
| stock/M | volume/mL | n_1/mmol | stock/M | volume/mL | n_2/mmol |
| 2.0 | 1.40 | 2.80 | 2.0 | 4.20 | 8.40 |

| purification eluent | product | | | |
|---|---|---|---|---|
| Ethyl acetate in hexanes | m[Pdt]/mg | n[Pdt]/mmol | yield | TTN |
| (0% to 10% gradient) | 393.7 | 1.32 | 47% | 730 |

$^1$H NMR (400 MHz, CDCl$_3$) δ 7.45 (d, J=8.5 Hz, 2H), 7.26 (d, J=8.6 Hz, 2H), 4.17 (qd, J=7.2, 2.9 Hz, 2H), 4.11 (qd, J=7.1, 0.6 Hz, 2H), 3.29 (d, J=0.6 Hz, 1H), 3.18 (dd, J=3.1, 0.6 Hz, 1H), 3.15 (d, J=3.1 Hz, 1H), 3.11 (s, 1H), 1.29 (t, J=7.1 Hz, 3H), 1.17 (t, J=7.1 Hz, 3H). $^{13}$C NMR (101 MHz, CDCl$_3$) δ 170.04, 167.73, 133.79, 132.24, 128.28, 121.22, 83.47, 77.86, 61.12, 61.07, 44.73, 42.67, 27.88, 21.40, 14.36, 14.19. HRMS (FAB) m/z: 299.1282 (M+H$^+$); calc. for C$_{14}$H$_{19}$O$_4$: 299.1283. [α]$^{23}_D$=−152.6±3.1° (c 0.1, ethyl acetate).

Diethyl (2R,4R)-1-(4-(hydroxymethyl)phenyl)bicyclo[1.1.0]butane-2,4-dicarboxylate (2m)

The title compound was prepared as summarized below. In the 1.0 mmol-scale reaction, EDA stock solution was added in four portions (0.5 mL each portion) every 1 hour.

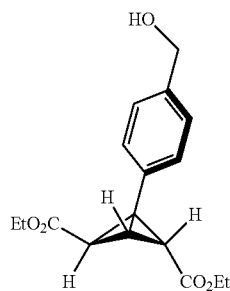

(2m)

| E. coli suspension in M9-N | | | | D-glucose in M9-N | |
|---|---|---|---|---|---|
| OD$_{600}$ | volume/mL | [PC]/μM | n_pro/μmol | volume/mL | [Glu]/mM |
| 20 | 75.0 | 3.72 | 0.279 | 4.0 | ~13 |

| alkyne (1m) stock in EtOH | | | EDA stock in EtOH | | |
|---|---|---|---|---|---|
| stock/M | volume/μL | n_1/mmol | stock/M | volume/μL | n_2/mmol |
| 1.0 | 360 | 0.36 | 2.0 | 540 | 1.08 |

| purification eluent | product | | | |
|---|---|---|---|---|
| Ethyl acetate in hexanes | m[Pdt]/mg | n[Pdt]/mmol | yield | TTN |
| (0% to 25% gradient) | 52.8 | 0.174 | 48% | 630 |

| E. coli suspension in M9-N | | | | D-glucose in M9-N | |
|---|---|---|---|---|---|
| OD$_{600}$ | volume/mL | [PC]/μM | n_pro/μmol | volume/mL | [Glu]/mM |
| 16 | 160 | 2.68 | 0.428 | 10 | ~15 |

| alkyne (1m) stock in EtOH | | | EDA stock in EtOH | | |
|---|---|---|---|---|---|
| stock/M | volume/mL | n_1/mmol | stock/M | volume/mL | n_2/mmol |
| 1.0 | 1.00 | 1.00 | 2.0 | 2.00 | 4.00 |

| purification eluent | product | | | |
|---|---|---|---|---|
| Ethyl acetate in hexanes | m[Pdt]/mg | n[Pdt]/mmol | yield | TTN |
| (0% to 25% gradient) | 152.1 | 0.500 | 50% | 580 |

$^1$H NMR (400 MHz, CDCl$_3$) δ 7.30 (d, J=2.5 Hz, 4H), 4.68 (d, J=5.0 Hz, 2H), 4.14 (qd, J=7.1, 2.3 Hz, 2H), 4.08 (qd, J=7.1, 0.9 Hz, 2H), 3.26 (d, J=0.5 Hz, 1H), 3.13 (dd, J=3.1, 0.6 Hz, 1H), 3.10 (d, J=3.0 Hz, 1H), 1.62 (t, J=5.7 Hz, 1H), 1.27 (t, J=7.1 Hz, 3H), 1.16 (t, J=7.1 Hz, 3H). $^{13}$C NMR (101 MHz, CDCl$_3$) δ 170.30, 167.93, 140.24, 132.11, 128.68, 127.15, 65.20, 61.02, 60.96, 44.72, 42.54, 27.96, 20.58, 14.37, 14.22. HRMS (FAB) m/z: 303.1230 ((M+H$^+$)—H$_2$); calc. for C$_{17}$H$_{19}$O$_5$: 303.1232. [α]$^{23}_D$=−130.8±1.2° (c 0.1, ethyl acetate).

The enantioselectivities of bicyclobutane products are difficult to determine, as there is no method in the literature to prepare the racemic standards. Determination of the enantiopurities of the bicyclobutane products by chiral HPLC was attempted. Purified bicyclobutanes 2a-2c, 2e, 2k and 2l (with >98% purity by $^1$H NMR) were tested under various analytical chiral HPLC separation conditions using with Chiralpak IA, IC, AS-H, and OJ-H columns. In all cases, only one major peak was detected for each product (with >98% peak area at 254 nm). In order to determine whether any of the minor peaks (with 0.5-1% peak area at 254 nm) detected corresponds to an enantiomer of the desired product, those fractions were collected and concentrated for further UV testing (210-280 nm) and GC-MS testing; none turned out to be the enantiomers of the bicyclobutanes. Though there is some possibility that the enantiomers might not be resolved under any of the chiral HPLC condition tested, it is very likely that the bicyclobutanes have high enantiopurity.

Example 12. Engineering of Biocatalysts for Cyclopropene Formation

Figure 12A:
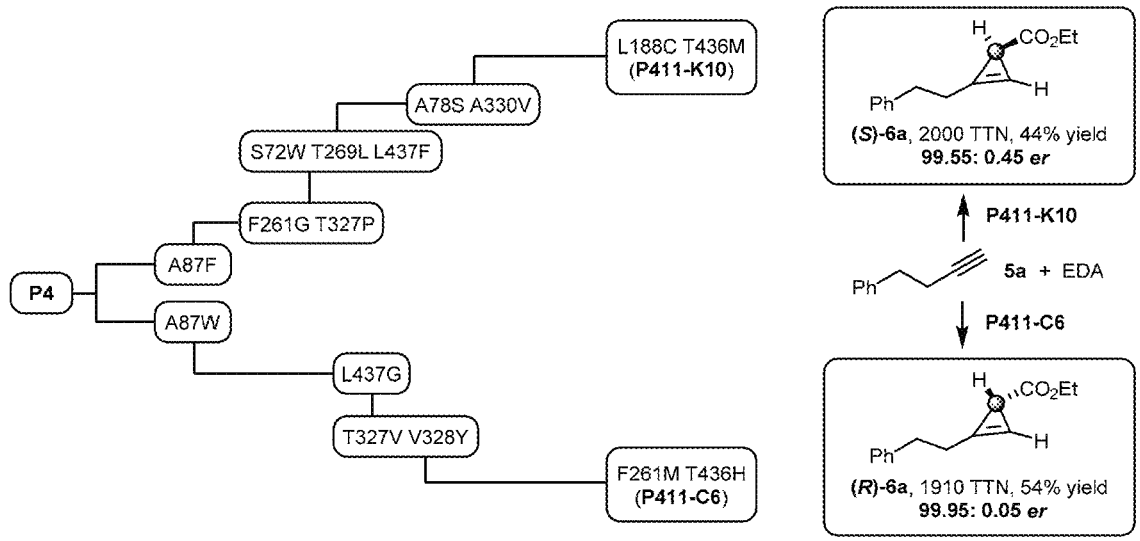
FIG. 12A shows the evolutionary trajectory of P411-P4 variants for stereodivergent cyclopropenation of aliphatic alkynes.
Figure 12B:
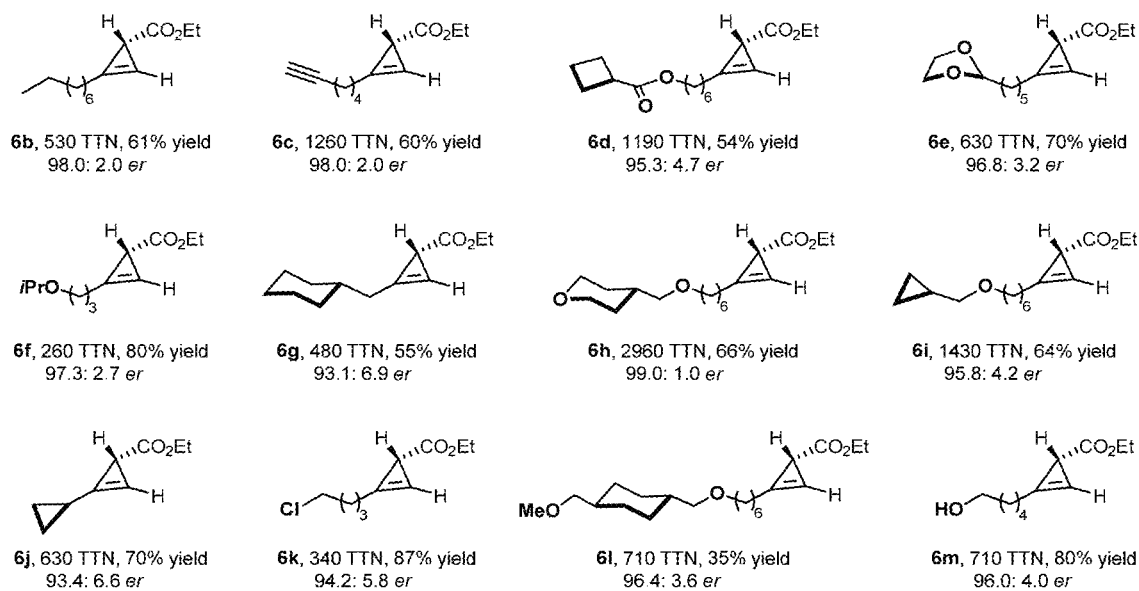
FIG. 12B shows the scope of P411-C6-catalyzed cyclopropene formation. Conditions of preparative-scale reactions (0.08-0.4 mmol scale): suspension of *E. coli* expressing P411-C6 or K10 (OD$_{600}$=10-32), 10-150 mM alkyne, 1.0-4.0 equiv EDA (6.0 equiv for 5m), 10-15 mM D-glucose, 1-5 vol % EtOH, M9-N buffer (pH 7.4) at room temperature under anaerobic conditions for 12 hours. Isolated yields. TTN determined based on isolated yields and enantiomeric ratio (er) determined by chiral HPLC.
Figure 12C:
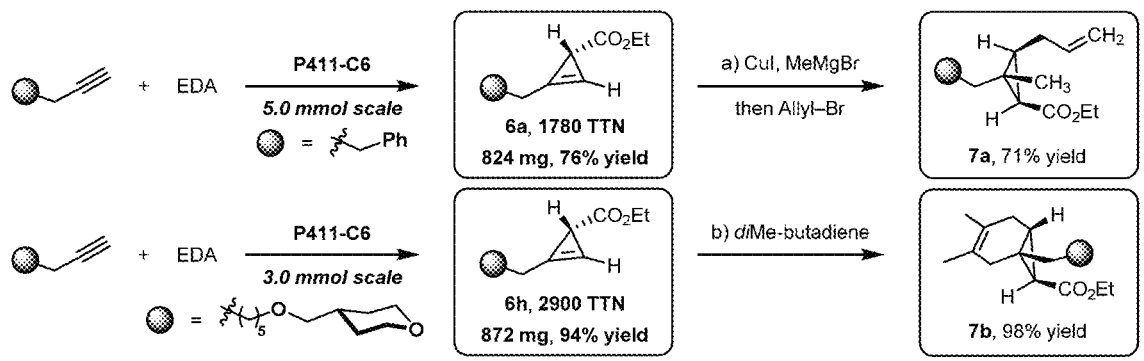
FIG. 12C shows the enzymatic cyclopropenation at mmol scale and derivatization of corresponding products. Top right: copper-catalyzed addition to cyclopropene 6a for synthesizing a multi-substituted cyclopropane. Bottom right: Diels-Alder reaction of cyclopropene 6h with 2,3-diMe-buta-1,3-diene to form a fused ring system.
Figure 13:
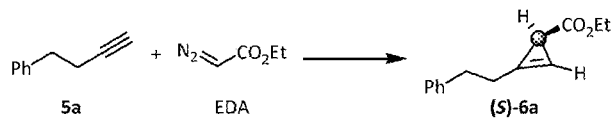
FIG. 13 shows the evolutionary trajectory of P411 variants for the formation of cyclopropene (S)-6a FIG. 14 shows the evolutionary trajectory of P411 variants for the formation of cyclopropene (R)-6a FIG. 15 shows the sites targeted in the evolution of P411-P4 for (S)-cyclopropene formation (PDB: 4WG2, P411-"I263F" (43)).
Figure 13:
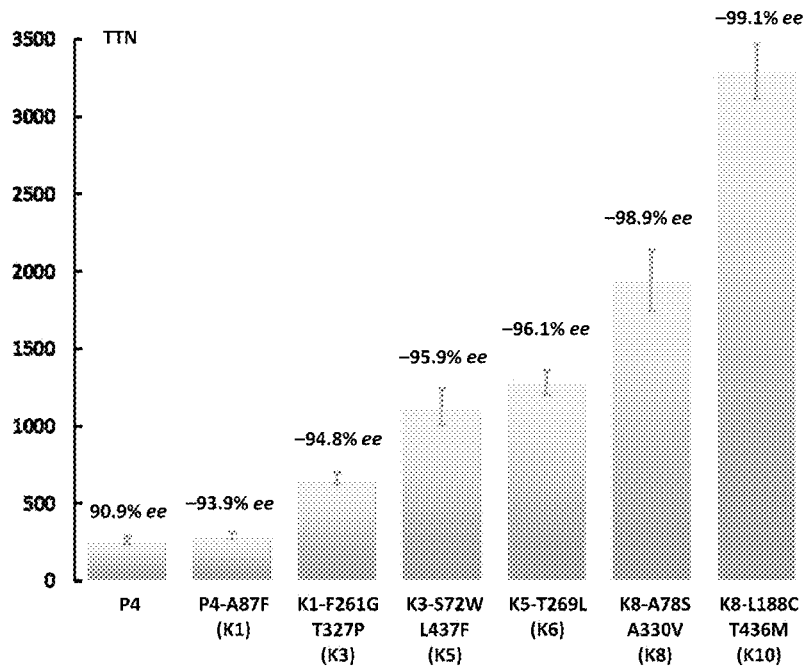
Figure 14:
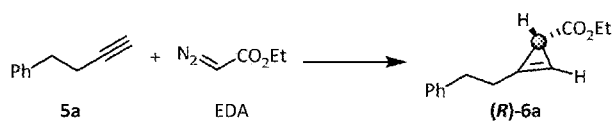
Figure 14:
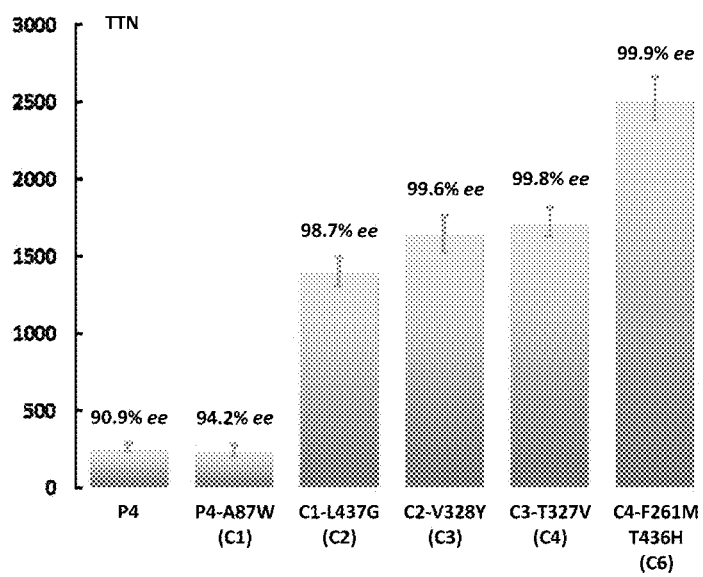

The next investigation focused on whether the enzyme could stop at the cyclopropene product if less reactive aliphatic alkynes are used. To this end, enzyme variants from the P411-S1 lineage were examined for cyclopropene formation, using phenylbutyne (5a) and EDA as starting reagents. It was encouraging to see that P4 catalyzed the desired transformation with 260 TTN and 95.5:4.5 er. Further evolution was performed on P4 to improve its catalytic efficiency. Position 87 was targeted first, known for its importance to substrate recognition in P450-catalyzed oxidations ([46]). A87F (290 TTN, 3.0:97.0 er) and A87W (240 TTN, 97.1:2.9 er) were found to exert the opposite enantiopreference, suggesting that residue 87 also controls substrate orientation for non-native carbene chemistry. Single- and double-site-saturation mutagenesis conducted sequentially on P4 A87F and P4 A87W improved both reactivity and selectivity (FIG. 12A, FIG. 13 and FIG. 14). The final K10 and C6 variants performed with >10-fold higher activity compared to the initial P4 variant and with excellent stereocontrol (99.55:0.45 er and 99.95:0.05 er, respectively).

Figure 15:
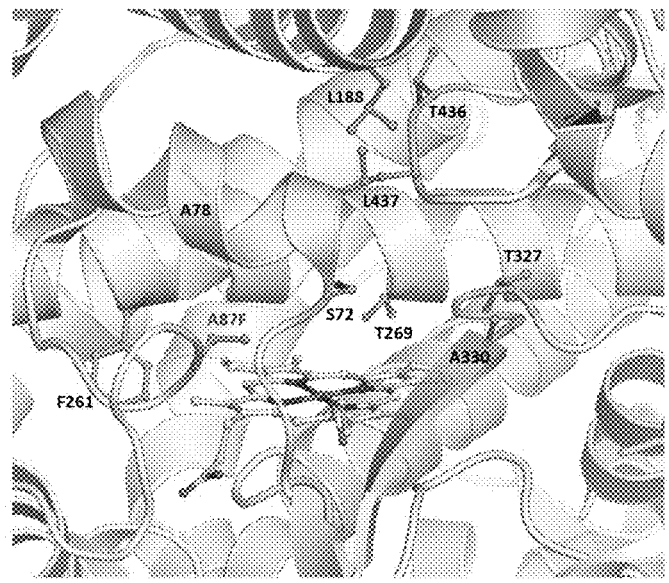
Figure 16:
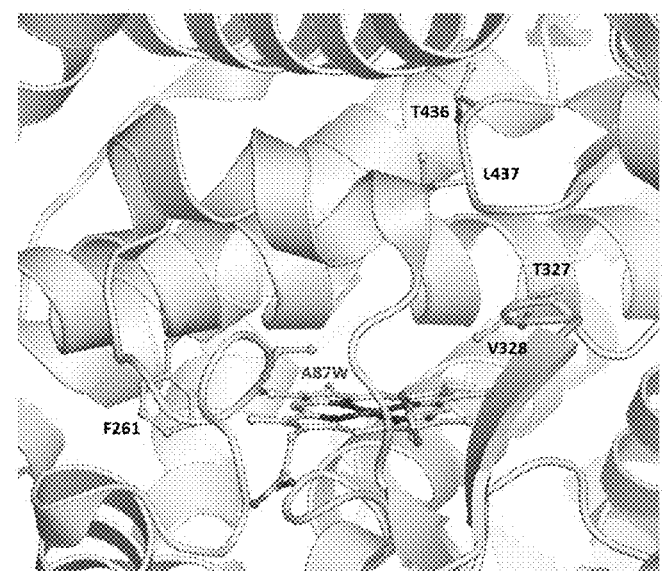
FIG. 16 shows the sites targeted in the directed evolution of P411-P4 for (R)-cyclopropene formation (PDB: 4WG2, P411-"I263F" (43)).
Figure 17:
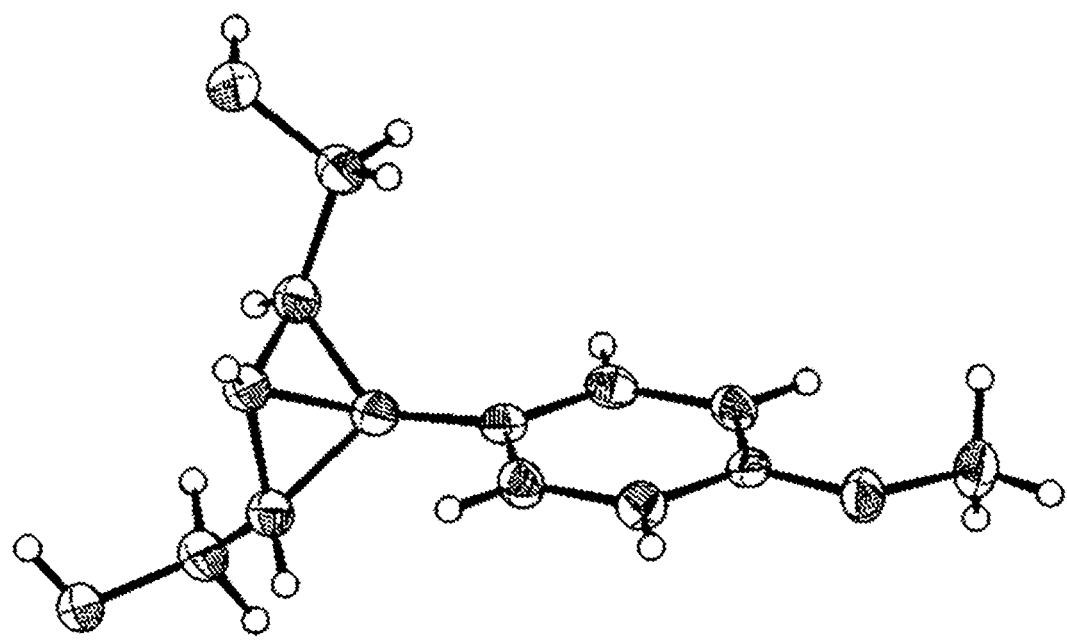
FIG. 17 shows the crystal structure of Compnd 3d.

Data from FIG. 13 and FIG. 14 are summarized in Table 7 and Table 8, and FIG. 15 and FIG. 16 depict the site targeted for mutation. Analytical reactions were set up in quadruplicate according to the procedure in biotransformations described above and using whole-cell catalyst and analyzed by GC using the standard calibration curve of 6a. The TTNs were obtained using $OD_{600}$=60 for P4 and K1 variants, $OD_{600}$=30 for K3, K5 and K6 variants, and $OD_{600}$=15 for K8 and K10 variants. TTNs reported are the average of biological duplicates. The TTNs were obtained using $OD_{600}$=60 for P4 and C1 variants, $OD_{600}$=30 for C2, C3 and C4 variants, and $OD_{600}$=15 for C6 variant. TTNs reported are the average of four experiments. TTNs reported are the average of biological duplicates. Each biological set contains four experiments. The errors in all tables are standard deviations.

TABLE 7

P411-P4 variants for the formation of cyclopropene (S)-6a

| P411-P4 variant | TTN | er |
|---|---|---|
| P4 | 260 ± 30 | 95.5:4.5 |
| P4 A87F (K1) | 290 ± 20 | 3.0:97.0 |
| K1 F261G T327P (K3) | 660 ± 40 | 2.6:97.4 |
| K3 S72W L437F (K5) | 1100 ± 120 | 2.1:97.9 |
| K5 T269L (K6) | 1280 ± 80 | 1.9:98.1 |
| K6 A78S A330V (K8) | 1900 ± 200 | 0.55:99.45 |
| K8 L188C T436M (K10) | 3300 ± 180 | 0.45:99.55 |

TABLE 8

P411-P4 variants for the formation of cyclopropene (R)-6a

| P411-P4 variant | TTN | er |
|---|---|---|
| P4 | 260 ± 30 | 95.5:4.5 |
| P4 A87W (C1) | 240 ± 40 | 97.1:2.9 |
| K1 L437G (C2) | 1400 ± 100 | 99.35:0.65 |
| C2 V328Y (C3) | 1600 ± 120 | 99.80:0.20 |
| C3 T327V (C4) | 1700 ± 100 | 99.90:0.10 |
| C4 F261M T436H (C6) | 2500 ± 140 | 99.95:0.05 |

TABLE 9

Mutations in related P411-P4 variants

| Name | Description | Mutations relative to P450-WT |
|---|---|---|
| P4 | P411$_{BM3}$-CIS P4 variant ([34]) | V78A, F87A, P142S, T175I, A184V, S226R, H236Q, E252G, I263F, T268G, A290V, A328V, L353V, I366V, C400S, T438S, E442K |
| K1 | P411$_{BM3}$-CIS K1 variant | V78A, P142S, T175I, A184V, S226R, H236Q, E252G, I263F, T268G, A290V, A328V, L353V, I366V, C400S, T438S, E442K |
| K3 | P411$_{BM3}$-CIS K3 variant | V78A, P142S, T175I, A184V, S226R, H236Q, E252G, F261G, I263F, T268G, A290V, T327P, A328V, L353V, I366V, C400S, T438S, E442K |

TABLE 9-continued

Mutations in related P411-P4 variants

| Name | Description | Mutations relative to P450-WT |
|---|---|---|
| K5 | P411$_{BM3}$-CIS K5 variant | S72W, V78A, P142S, T175I, A184V, S226R, H236Q, E252G, F261G, I263F, T268G, A290V, T327P, A328V, L353V, I366V, C400S, L437F, T438S, E442K |
| K6 | P411$_{BM3}$-CIS K6 variant | S72W, V78A, P142S, T175I, A184V, S226R, H236Q, E252G, F261G, I263F, T268G, T269L, A290V, T327P, A328V, L353V, I366V, C400S, L437F, T438S, E442K |
| K8 | P411$_{BM3}$-CIS K8 variant | S72W, V78S, P142S, T175I, A184V, S226R, H236Q, E252G, F261G, I263F, T268G, T269L, A290V, T327P, A328V, A330V, L353V, I366V, C400S, L437F, T438S, E442K |
| K10 | P411$_{BM3}$-CIS K10 variant | S72W, V78S, P142S, T175I, A184V, L188C, S226R, H236Q, E252G, F261G, I263F, T268G, T269L, A290V, T327P, A328V, A330V, L353V, I366V, C400S, T436M, L437F, T438S, E442K |

TABLE 10

Mutations in related P411-P4 variants

| Name | Description | Mutations relative to P450-WT |
|---|---|---|
| P4 | P411$_{BM3}$-CIS P4 variant ([34]) | V78A, F87A, P142S, T175I, A184V, S226R, H236Q, E252G, I263F, T268G, A290V, A328V, L353V, I366V, C400S, T438S, E442K |
| C1 | P411$_{BM3}$-CIS C1 variant | V78A, F87W, P142S, T175I, A184V, S226R, H236Q, E252G, I263F, T268G, A290V, A328V, L353V, I366V, C400S, T438S, E442K |
| C2 | P411$_{BM3}$-CIS C2 variant | V78A, F87W, P142S, T175I, A184V, S226R, H236Q, E252G, I263F, T268G, A290V, A328V, L353V, I366V, C400S, L437G, T438S, E442K |
| C3 | P411$_{BM3}$-CIS C3 variant | V78A, F87W, P142S, T175I, A184V, S226R, H236Q, E252G, I263F, T268G, A290V, A328Y, L353V, I366V, C400S, L437G, T438S, E442K |
| C4 | P411$_{BM3}$-CIS C4 variant | V78A, F87W, P142S, T175I, A184V, S226R, H236Q, E252G, I263F, T268G, A290V, T327V, A328Y, L353V, I366V, C400S, L437G, T438S, E442K |
| C6 | P411$_{BM3}$-CIS C6 variant | V78A, F87W, P142S, T175I, A184V, S226R, H236Q, E252G, F261M, I263F, T268G, A290V, T327V, A328Y, L353V, I366V, C400S, T436H, L437G, T438S, E442K |

Example 13. Preparation of Alkyne Substrates

Commercially available substrates were used as received: all aromatic alkynes (1a-1m) (Sigma-Aldrich, Alfa-Aesar and Ark Pharm), aliphatic alkynes (5a-5c, 5g, 5j, 5k, 5m, and 5n) (Sigma-Aldrich, Alfa-Aesar and Ark Pharm), ethyl 2-diazoacetate (Sigma-Aldrich).

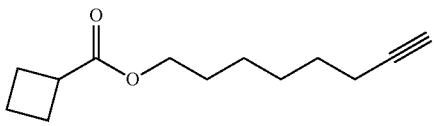

(5d)

Oct-7-yn-1-yl Cyclobutanecarboxylate (5d)

In a 100 mL round-bottom flask, oct-7-yn-1-ol (0.631 g, 5.0 mmol), triethylamine (0.9 mL, 1.3 equiv.) and N,N-dimethylpyridin-4-amine (DMAP, 61 mg, 10 mol %) in dry DCM (20 mL) was cooled to 0° C. A solution of cyclobutanecarbonyl chloride (0.711 g, 6.0 mmol) in dry DCM (5 mL) was added dropwise slowly over 5 min. The reaction was allowed to warm to room temperature and stirred for 8 hours. The reaction mixture was diluted with DCM (20 mL) and washed with water (20 mL) and brine (20 mL), dried over MgSO$_4$, and then concentrated under reduced pressure. The crude product was purified by silica column chromatography with hexane/ethyl acetate (20:1) to afford 5d (1.02 g, 98%). $^1$H NMR (400 MHz, CDCl$_3$) δ 4.06 (t, J=6.7 Hz, 2H), 3.12 (pd, J=8.5, 1.0 Hz, 1H), 2.34-2.13 (m, 6H), 2.04-1.83 (m, 3H), 1.69-1.59 (m, 2H), 1.57-1.48 (m, 2H), 1.47-1.32 (m, 4H). $^{13}$C NMR (101 MHz, CDCl$_3$) δ 175.62, 84.51, 68.25, 64.28, 38.17, 28.54, 28.34, 28.32, 25.45, 25.28, 18.43, 18.33. HRMS (FAB) m/z: 209.1548 (M+H$^+$); calc. for C$_{13}$H$_{21}$O$_2$: 209.1542.

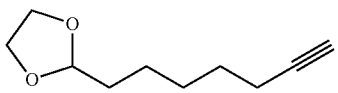

(5e)

2-(Hept-6-yn-1-yl)-1,3-dioxolane (5e)

In a 250 mL round-bottom flask, DMSO (1.95 g, 25.0 mmol) was dissolved in dry DCM (40 mL) and then cooled to −78° C. under argon. A solution of oxalyl dichloride (2.6 mL, 30.0 mmol) in dry DCM (10 mL) was added dropwise slowly over 10 min. After the mixture was stirred at −78° C. for 1 h, a solution of oct-7-yn-1-ol (0.631 g, 5.0 mmol) in dry DCM (10 mL) was added dropwise slowly over 10 min. The resulting mixture was maintained at −78° C. for another 2 h before the dropwise addition of triethylamine (7.0 mL, 50.0 mmol) in dry DCM (10 mL). The reaction was then allowed to warm to room temperature over 1 h and stirred for another 2 h. The reaction mixture was diluted with DCM (30 mL) and washed with HCl (10%, 50 mL), NaHCO$_3$ (50 mL, sat. aq.), and brine (50 mL), dried over MgSO$_4$, and then concentrated under reduced pressure (100 torr). The crude product mixture was used for the next step without further purification. The crude product was dissolved in benzene (50 mL) in a 100 mL round-bottom flask. Ethylene glycol (0.465 g, 7.5 mmol) and TsOH (130 mg, 0.075 mmol) were added. The solution was heated up to a refluxing temperature, 90° C., and maintained for 2 h. After removal of benzene under reduced pressure, the crude product was purified by silica column chromatography with hexane/ether (20:1 to 15:1) to afford 5e (0.675 g, 80%). $^1$H NMR (400 MHz, CDCl$_3$) δ 4.85 (t, J=4.8 Hz, 1H), 4.01-3.91 (m, 2H), 3.90-3.79 (m, 2H), 2.19 (td, J=7.0, 2.6 Hz, 2H), 1.93 (t, J=2.7 Hz, 1H), 1.70-1.61 (m, 2H), 1.59-1.51 (m, 2H), 1.49-1.39 (m, 4H). $^{13}$C NMR (101 MHz, CDCl$_3$) δ 104.66, 84.73, 68.32, 64.99, 33.89, 28.78, 28.53, 23.69, 18.45. HRMS (FAB) m/z: 167.1067 ((M+H$^+$)—H$_2$); calc. for C$_{10}$H$_{15}$O$_2$: 167.1072.

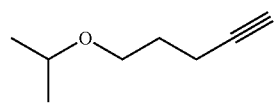

(5f)

5-Isopropoxypent-1-yne (5f)

In a 100 mL round-bottom flask, pent-4-yn-1-ol (0.841 g, 10.0 mmol), triethylamine (1.8 mL, 1.3 equiv.) and DMAP (122 mg, 10 mol %) in dry DCM (50 mL) was cooled to 0° C. 4-Methylbenzenesulfonyl chloride (TsCl, 2.10 g, 11.0 mmol) was added portion-wise. The reaction was allowed to warm to room temperature and stirred for 6 hours. The reaction mixture was diluted with DCM (30 mL) and washed with water (20 mL) and brine (20 mL), dried over MgSO$_4$, and then concentrated under reduced pressure. The crude product was purified by silica column chromatography with hexane: ethyl acetate (4:1) to afford pent-4-yn-1-yl 4-methylbenzenesulfonate (2.35 g, 99%).

Isopropanol (0.361 g, 6.0 mmol) and tetrabutylammonium bromide (161 mg, 0.5 mmol) were dissolved in anhydrous DMF (50 mL) and then cooled to 0° C. NaH (60%, 240 mg, 6.0 mmol) was added portion-wise to the solution. The resulting mixture was stirred at 0° C. for 1 h before the dropwise addition of pent-4-yn-1-yl 4-methylbenzenesulfonate (1.19 g, 5.0 mmol) in anhydrous DMF (10 mL). The reaction was allowed to warm to room temperature and stirred for 4 hours. The reaction mixture was quenched with NH$_4$Cl (20 mL, sat. aq.) and the product was extracted with Et$_2$O (30 mL×3). The combined organic layer was washed with water (20 mL), brine (20 mL), dried over MgSO$_4$, and then concentrated under reduced pressure (200 torr). The crude product was purified by silica column chromatography with pentane/ether (10:1) to afford 5f (0.597 g, 95%).

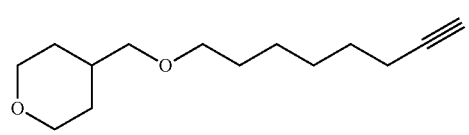

(5h)

4-((Oct-7-yn-1-yloxy)methyl)tetrahydro-2H-pyran (5h)

In a 500 mL round-bottom flask, oct-7-yn-1-ol (6.31 g, 50.0 mmol), triethylamine (9.1 mL, 1.3 equiv.) and DMAP (609 mg, 10 mol %) in dry DCM (200 mL) was cooled to 0° C. TsCl (10.50 g, 55.0 mmol) was added portion-wise. The reaction was allowed to warm to room temperature and stirred for 6 hours. The reaction mixture was diluted with DCM (100 mL) and washed with water (200 mL) and brine (200 mL), dried over MgSO$_4$, and then concentrated under reduced pressure. The crude product was purified by silica column chromatography with hexane: ethyl acetate (10:1) to afford oct-7-yn-1-yl 4-methylbenzenesulfonate (13.29 g, 95%).

In a 100 mL round-bottom flask, (tetrahydro-2H-pyran-4-yl)methanol (0.697 g, 6.0 mmol) and tetrabutylammonium bromide (161 mg, 0.5 mmol) were dissolved in anhydrous DMF (50 mL) and then cooled to 0° C. NaH (60%, 240 mg, 6.0 mmol) was added portion-wise to the solution. The resulting mixture was stirred at 0° C. for 1 h before the dropwise addition of oct-7-yn-1-yl 4-methylbenzenesulfonate (1.40 g, 5.0 mmol) in anhydrous DMF (10 mL). Then reaction was allowed to warm to room temperature and stirred for 4 hours. The reaction mixture was quenched with NH$_4$Cl (20 mL, sat. aq.) and the product was extracted with Et$_2$O (50 mL×3). The combined organic layer was washed with water (20 mL), brine (20 mL), dried over MgSO$_4$, and then concentrated under reduced pressure. The crude product was purified by silica column chromatography with hexane/ethyl acetate (10:1) to afford 5h (1.10 g, 98%). $^1$H NMR (400 MHz, CDCl$_3$) δ 3.96 (ddt, J=11.5, 4.6, 1.1 Hz, 2H), 3.43-3.34 (m, 4H), 3.24 (d, J=6.6 Hz, 2H), 2.18 (td, J=7.0, 2.7 Hz, 2H), 1.93 (t, J=2.7 Hz, 1H), 1.89-1.77 (m, 1H), 1.68-1.61 (m, 2H), 1.60-1.49 (m, 4H), 1.46-1.34 (m, 4H), 1.33-1.25 (m, 2H). $^{13}$C NMR (101 MHz, CDCl$_3$) δ 84.80, 76.11, 71.24, 68.28, 67.90, 35.60, 30.19, 29.70, 28.70, 28.56, 25.83, 18.49. HRMS (FAB) m/z: 225.1855 (M+H$^+$); calc. for C$_{14}$H$_{25}$O$_2$: 225.1855.

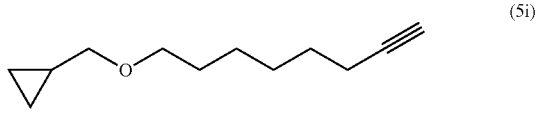

((Oct-7-yn-1-yloxy)methyl)cyclopropane (5i)

In a 100 mL round-bottom flask, cyclopropylmethanol (0.433 g, 6.0 mmol) and tetrabutylammonium bromide (161 mg, 0.5 mmol) were dissolved in anhydrous DMF (50 mL) and then cooled to 0° C. NaH (60%, 240 mg, 6.0 mmol) was added portion-wise to the solution. The resulting mixture was stirred at 0° C. for 1 h before the dropwise addition of oct-7-yn-1-yl 4-methylbenzenesulfonate (1.40 g, 5.0 mmol) in anhydrous DMF (10 mL). The reaction was allowed to warm to room temperature and stirred for 4 hours. The reaction mixture was quenched with NH$_4$Cl (20 mL, sat. aq.) and the product was extracted with Et$_2$O (50 mL×3). The combined organic layer was washed with water (20 mL), brine (20 mL), dried over MgSO$_4$, and then concentrated under reduced pressure. The crude product was purified by silica column chromatography with hexane/ether (50:1) to afford 5i (840 mg, 93%). $^1$H NMR (400 MHz, CDCl$_3$) δ 3.42 (t, J=6.7 Hz, 2H), 3.24 (d, J=6.9 Hz, 2H), 2.18 (td, J=7.0, 2.6 Hz, 2H), 1.93 (t, J=2.6 Hz, 1H), 1.64-1.57 (m, 2H), 1.56-1.49 (m, 2H), 1.47-1.30 (m, 4H), 1.12-0.97 (m, 1H), 0.58-0.45 (m, 2H), 0.19 (dt, J=6.0, 4.5 Hz, 2H). $^{13}$C NMR (101 MHz, CDCl$_3$) δ 84.82, 75.73, 70.77, 68.26, 29.78, 28.72, 28.57, 25.85, 18.49, 10.82, 3.13. HRMS (FAB) m/z: 181.1590 (M+H$^+$); calc. for C$_{12}$H$_{21}$O: 181.1592.

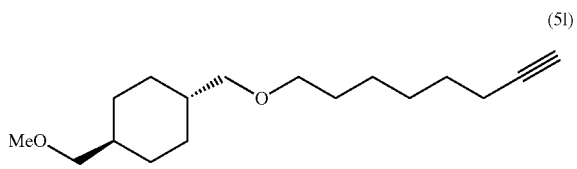 [SMILES: C#CCCCCCCOC[C@H]1CC[C@H](COC)CC1]

Trans-1-(methoxymethyl)-4-((oct-7-yn-1-yloxy)methyl)cyclohexane (5l)

In a 100 mL round-bottom flask, (trans-cyclohexane-1,4-diyl)dimethanol (2.88 g, 20.0 mmol) and tetrabutylammonium bromide (32 mg, 0.1 mmol) were dissolved in anhydrous DMF (50 mL) and then cooled to 0° C. NaH (60%, 960 mg, 24.0 mmol) was added portion-wise to the solution. The resulting mixture was stirred at 0° C. for 1 h before the dropwise addition of methyl iodide (MeI, 1.5 mL, 24.0 mmol) in anhydrous DMF (10 mL). The reaction was allowed to warm to room temperature and stirred for 4 hours. The reaction mixture was quenched with NH$_4$Cl (20 mL, sat. aq.) and the product was extracted with Et$_2$O (50 mL×4). The combined organic layer was washed with water (50 mL), brine (50 mL), dried over MgSO$_4$, and then concentrated under reduced pressure. The crude product was purified by silica column chromatography with hexane/ethyl acetate (1:1) to afford (trans-4-(methoxymethyl)cyclohexyl)methanol (2.02 g, 64%).

In a 100 mL round-bottom flask, (trans-4-(methoxymethyl)cyclohexyl)methanol (0.949 g, 6.0 mmol) and tetrabutylammonium bromide (161 mg, 0.5 mmol) were dissolved in anhydrous DMF (50 mL) and then cooled to 0° C. NaH (60%, 240 mg, 6.0 mmol) was added portion-wise to the solution. The resulting mixture was stirred at 0° C. for 1 h before the dropwise addition of oct-7-yn-1-yl 4-methylbenzenesulfonate (1.40 g, 5.0 mmol) in anhydrous DMF (10 mL). Then reaction was allowed to warm to room temperature and stirred for 4 hours. The reaction mixture was quenched with NH$_4$Cl (20 mL, sat. aq.) and the product was extracted with Et$_2$O (50 mL×3). The combined organic layer was washed with water (20 mL), brine (20 mL), dried over MgSO$_4$, and then concentrated under reduced pressure. The crude product was purified by silica column chromatography with hexane/ethyl acetate (10:1) to afford 5l (743 mg, 56%). $^1$H NMR (400 MHz, CDCl$_3$) δ 3.38 (t, J=6.6 Hz, 2H), 3.32 (s, 3H), 3.20 (d, J=6.5 Hz, 2H), 3.18 (d, J=6.4 Hz, 2H), 2.18 (td, J=7.0, 2.7 Hz, 2H), 1.93 (t, J=2.7 Hz, 1H), 1.86-1.74 (m, 4H), 1.58-1.49 (m, 6H), 1.46-1.30 (m, 4H), 1.01-0.86 (m, 4H). $^{13}$C NMR (101 MHz, CDCl$_3$) δ 84.84, 78.93, 76.90, 71.17, 68.26, 58.98, 38.37 (2 carbons), 29.73, 29.65, 29.55, 28.73, 28.58, 25.85, 18.50. HRMS (FAB) m/z: 267.2325 (M+H$^+$); calc. for C$_{17}$H$_{31}$O$_2$: 267.2324.

Example 14. Analytical-Scale and Preparative-Scale Enzymatic Cyclopropene Formation To evaluate the substrate range of the evolved P411 variants for cyclopropene construction, P411-C6 activity was examined using structurally diverse aliphatic alkynes. Enzymatic reactions with 12 alkynes in preparative scale (up to 5.0 mmol scale) afforded the desired cyclopropenes with TTNs ranging from hundreds to thousands and good to excellent stereoselectivities (FIGS. 3B and 3C). Alkynes with a linear carbon chain (5b) or cyclic fragments (5g, 5h and 5j) all served as good substrates. Different functional groups, including ether (5f, 5i and 5l), ester (5d), acetal (5e), chloride (5k), and free hydroxyl (5m), were well-tolerated. Further optimization of reaction conditions with slow addition of EDA, for example, would likely improve the isolated yields, as was demonstrated for cyclopropene 6h (66% yield, FIG. 3B; and 94% yield, FIG. 3C).

All enzymatic reactions for cyclopropene formation in analytical scale were conducted following the general procedure described below and analyzed with gas chromatography (GC). All TTNs for the different products were determined using the GC standard curve of the corresponding racemic standard product made with $Rh_2(OAc)_4$ (see Section VII). These TTNs were used to guide set-up of preparative-scale reactions.

General Procedure for Analytical-Scale Reactions:

To a 2 mL vial were added degassed suspension of *E. coli* expressing P411-C6 or K10 variant in M9-N buffer ($OD_{600}$=15, 340 μL), alkyne (10 μL of 400 or 800 mM stock solution in EtOH, 10 or 20 mM), EDA (10 μL of 400 or 800 mM stock solution in EtOH, 10 or 20 mM, 1.0 equiv.), D-glucose (40 μL of 250 mM stock solution in M9-N buffer, 25 mM) under anaerobic conditions. The vial was capped and shaken at 560 rpm at room temperature for 6 h. After the reaction was completed, internal standard 1,3,5-trimethoxybenzene (20 μL of 20 mM stock solution in toluene) was added to the reaction vial followed by mixed solvent (cyclohexane/ethyl acetate=1:1, 1 mL). The mixture was transferred to a 1.5 mL microcentrifuge tube, and then vortexed (15 seconds×3) and centrifuged (14,000 rpm, 5 min) to completely separate the organic and aqueous layers. 0.8 mL of organic layer was taken for GC analysis. TTN was calculated based on measured protein concentration. Enantioselectivity was measured by chiral HPLC. Reactions for every substrate were set up in triplicate or quadruplicate.

GC Standard Curve:

All data points represent the average of duplicate runs. The standard curves plot product concentration in mM (y-axis) against the ratio of product area to internal standard area on the GC (x-axis).

All enzymatic reactions for cyclopropene formation in preparative scale were conducted following the general procedure described below and the corresponding cyclopropene products were isolated. Detailed conditions for preparative-scale reactions of different substrates are indicated separately.

General Procedure for Preparative-Scale Reactions.

To a 40 mL vial or 250 mL flask were added degassed suspension of *E. coli* expressing P411-C6 or K10 variant ($OD_{600}$=10-60), alkyne (0.08-0.4 mmol, larger scales for 5a and 5h), EDA (1.0-4.0 equiv.), D-glucose (10-15 mM, 250 mM stock in M9-N), 1-5 vol % EtOH, M9-N buffer (pH 7.4) under anaerobic conditions. The vial or flask was capped and shaken (420 rpm for vials and 220 rpm for flasks) at room temperature for 12 h.

After the reaction was completed, every 30 mL portion of preparative-scale reaction mixture was transferred to a 50 mL Falcon centrifuge tube. The reaction container was washed with water (2 mL×2) followed by mixed organic solvent (cyclohexane/ethyl acetate=1:1, 2 mL×3). The washing solution was combined to reaction mixture in centrifuge tubes. An additional 12 mL of cyclohexane/ethyl acetate solvent was added to every tube. After the tube (with ~45 mL mixture in total) was capped, it was vortex (1 min×3) and shaken vigorously, and centrifuged (14,000 g, 5 min). The organic layer was separated and the aqueous layer was subjected to three more rounds of extraction. The organic layers were combined, dried over $Na_2SO_4$ and concentrated under reduced pressure. Purification by silica column chromatography with hexane/ethyl acetate as eluent afforded the desired cyclopropenes. Enantioselectivity was measured by chiral HPLC. TTNs were calculated based on measured protein concentration and isolated product yield.

Ethyl (S)-2-phenethylcycloprop-2-ene-1-carboxylate (S-6a)

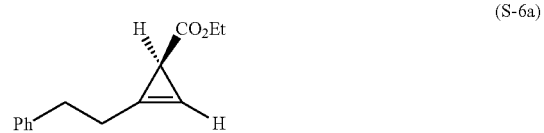 [SMILES: CCOC(=O)[C@H]1C=C1CCc1ccccc1]

Analysis Data (10 mM 5a, P411-K10):

| Pdt-entries | Pdt | Std | Pdt/Std | [Pdt]/mM | [PC]/μM | TTN | Avg. TTN | Avg. yield |
|---|---|---|---|---|---|---|---|---|
| 6a-(1) | 4637.1 | 590.6 | 7.852 | 6.24 | 1.93 | 3242 | | |
| 6a-(2) | 4639.5 | 592.1 | 7.836 | 6.23 | 1.93 | 3236 | | |
| 6a-(3) | 4797.4 | 582.9 | 8.230 | 6.54 | 1.93 | 3399 | | |
| 6a-(4) | 4674.5 | 588.0 | 7.950 | 6.32 | 1.93 | 3283 | 3290 | 63.3% |

Preparative-Scale Reaction:

| E. coli suspension expressing P411-K10 in M9-N | | | | D-glucose in M9-N | |
|---|---|---|---|---|---|
| $OD_{600}$ | volume/mL | [PC]/μM | n_pro/μmol | volume/mL | [Glu]/mM |
| 20 | 28.0 | 3.12 | 0.0874 | 1.5 | ~13 |
| alkyne (5a) stock in EtOH | | | EDA stock in EtOH | | |
| stock/M | volume/μL | n_1/mmol | stock/M | volume/μL | n_2/mmol |
| 0.80 | 500 | 0.40 | 0.80 | 500 | 0.40 |
| purification eluent | | | product | | |
| ethyl acetate in hexanes | m[Pdt]/mg | n[Pdt]/mmol | | yield | TTN |
| (0% to 5% gradient) | 37.8 | 0.175 | | 44% | 2000 |

$^1$H NMR (400 MHz, $CDCl_3$) δ 7.33-7.27 (m, 2H), 7.24-7.18 (m, 3H), 6.36 (dt, J=1.4 Hz, 1H), 4.21-4.05 (m, 2H), 2.96-2.79 (m, 4H), 2.14 (d, J=1.5 Hz, 1H), 1.25 (t, J=7.1 Hz, 3H). $^{13}$C NMR (101 MHz, $CDCl_3$) δ 176.61, 140.81, 128.58, 128.45, 126.36, 115.01, 95.03, 60.39, 33.00, 26.90, 20.00, 14.52. HRMS (FAB) m/z: 217.1221 (M+H$^+$); calc. for $C_{14}H_{17}O_2$: 217.1229. $[α]^{23}_D$=−64.7±3.6° (c 0.1, cyclohexane). HPLC Chiralpak IC column (n-hexane/isopropanol=95:5, 1.0 mL/min), $t_r$=8.89 min (minor), 9.20 min (major), 99.55:0.45 er.

Ethyl (R)-2-phenethylcycloprop-2-ene-1-carboxylate (R-6a)

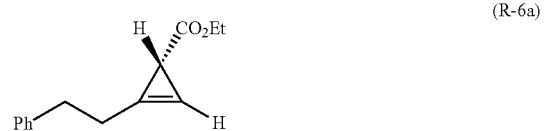 [SMILES: CCOC(=O)[C@@H]1C=C1CCc1ccccc1]

Analysis Data (10 mM 5a, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6a-(1) | 4577.9 | 511.2 | 8.955 | 7.12 | 2.83 | 2518 | | |
| 6a-(2) | 4659.1 | 515.1 | 9.045 | 7.19 | 2.83 | 2543 | | |
| 6a-(3) | 4647.7 | 518.4 | 8.965 | 7.13 | 2.83 | 2521 | | |
| 6a-(4) | 4608.7 | 518.6 | 8.887 | 7.07 | 2.83 | 2499 | 2520 | 71.3% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 20 | 28.0 | 4.04 | 0.113 | 1.5 | ~13 |

| alkyne (5a) stock in EtOH | | | EDA stock in EtOH | | |
|---|---|---|---|---|---|
| stock/M | volume/μL | n_1/mmol | stock/M | volume/μL | n_2/mmol |
| 0.80 | 500 | 0.40 | 0.80 | 500 | 0.40 |

| purification eluent | | | product | |
|---|---|---|---|---|
| Ethyl acetate in hexanes | m[Pdt]/mg | n[Pdt]/mmol | yield | TTN |
| (0% to 5% gradient) | 46.8 | 0.216 | 54% | 1910 |

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 24 | 800 | 5.35 | 4.28 | 50 | ~15 |

| alkyne (5a) stock in EtOH | | | EDA stock in EtOH | | |
|---|---|---|---|---|---|
| stock/M | volume/mL | n_1/mmol | stock/M | volume/mL | n_2/mmol |
| 2.0 | 2.50 | 5.0 | 2.0 | 7.50 | 15.0 |

| purification eluent | | | product | |
|---|---|---|---|---|
| Ethyl acetate in hexanes | m[Pdt]/mg | n[Pdt]/mmol | yield | TTN |
| (0% to 5% gradient) | 824.1 | 3.81 | 76% | 1780 |

In the 5.0-mmol scale reaction, EDA stock solution was added in three portions (2.5 mL each portion) every 1 hour. [α]$^{23}_D$=+62.2±2.5° (c 0.1, cyclohexane). HPLC Chiralpak IC column (n-hexane/isopropanol=95:5, 1.0 mL/min), t$_r$=9.05 min (major), 9.42 min (minor), 99.95:0.05 er.

Ethyl (R)-2-octylcycloprop-2-ene-1-carboxylate (6b)

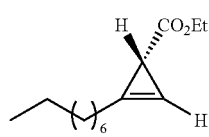

(6b)

Analysis Data (10 mM 5b, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6b-(1) | 1195.2 | 523.7 | 2.282 | 1.49 | 1.82 | 815 | | |
| 6b-(2) | 1128.3 | 528.7 | 2.134 | 1.39 | 1.82 | 763 | | |
| 6b-(3) | 1023.1 | 521.4 | 1.962 | 1.28 | 1.82 | 701 | 760 | 13.9% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 20 | 60.0 | 3.83 | 0.230 | 1.5 | ~12 |

| alkyne (5b) stock in EtOH | | | EDA stock in EtOH | | |
|---|---|---|---|---|---|
| stock/M | volume/μL | n_1/mmol | stock/M | volume/μL | n_2/mmol |
| 0.80 | 250 | 0.20 | 0.80 | 250 | 0.20 |

| purification eluent | | | product | |
|---|---|---|---|---|
| Ethyl acetate in hexanes | m[Pdt]/mg | n[Pdt]/mmol | yield | TTN |
| (0% to 5% gradient) | 27.2 | 0.121 | 61% | 530 |

The cell suspension (OD$_{600}$=20) was added in three portions (20 mL each portion) every 2 hours.
$^1$H NMR (400 MHz, CDCl$_3$) δ 6.31 (dt, J=1.4 Hz, 1H), 4.12 (qd, J=7.1, 5.0 Hz, 2H), 2.48 (td, J=7.3, 1.4 Hz, 2H), 2.12 (d, J=1.6 Hz, 1H), 1.61-1.52 (m, 2H), 1.35-1.22 (m, 13H), 0.91-0.83 (m, 3H). $^{13}$C NMR (101 MHz, CDCl$_3$) δ 176.80, 115.77, 94.01, 60.28, 31.97, 29.39, 29.32, 29.27, 26.80, 25.10, 22.79, 19.86, 14.52, 14.24. HRMS (FAB) m/z: 225.1862 (M+H$^+$); calc. for C$_{14}$H$_{25}$O$_2$: 225.1855. [α]$^{23}_D$=+32.6±1.8° (c 0.1, cyclohexane) [Note: (S)-5b (87% ee) was reported with [α]$^{23}_D$=−30° (c 1.55, CHCl$_3$) ($^{22}$)]. HPLC Chiralpak IC column (n-hexane/isopropanol=95:5, 1.0 mL/min), t$_r$=6.59 min (major), 7.10 min (minor), 98.0:2.0 er.

Ethyl (R)-2-(hex-5-yn-1-yl)cycloprop-2-ene-1-carboxylate (6c)

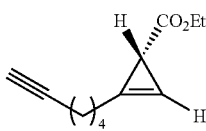

(6c)

Analysis Data (20 mM 5c, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6c-(1) | 1084.2 | 344.6 | 3.146 | 2.39 | 1.67 | 1434 | | |
| 6c-(2) | 1164.4 | 407.1 | 2.860 | 2.17 | 1.67 | 1304 | | |
| 6c-(3) | 1079.9 | 385.7 | 2.800 | 2.13 | 1.67 | 1276 | | |
| 6c-(4) | 985.5 | 350.1 | 2.815 | 2.14 | 1.67 | 1283 | 1324 | 11.1% |

Preparative-Scale Reaction:

| E. coli suspension expressing P411-C6 in M9-N | | | | D-glucose in M9-N | |
|---|---|---|---|---|---|
| OD$_{600}$ | volume/ mL | [PC]/μM | n_pro/ μmol | volume/ mL | [Glu]/ mM |
| 30 | 30.0 | 6.33 | 0.190 | 1.5 | ~12 |

| alkyne (5c) stock in EtOH | | | EDA stock in EtOH | | |
|---|---|---|---|---|---|
| stock/M | volume/ μL | n_1/ mmol | stock/M | volume/ μL | n_2/ mmol |
| 0.80 | 500 | 0.40 | 0.80 | 500 | 0.40 |

| purification eluent | | product | | | |
|---|---|---|---|---|---|
| Ethyl acetate in hexanes | | m[Pdt]/ mg | n[Pdt]/ mmol | yield | TTN |
| (0% to 6% gradient) | | 46.2 | 0.240 | 60% | 1260 |

$^1$H NMR (400 MHz, CDCl$_3$) δ 6.35 (dt, J=1.5 Hz, 1H), 4.20-4.04 (m, 2H), 2.52 (td, J=7.2, 1.4 Hz, 2H), 2.21 (td, J=6.9, 2.6 Hz, 2H), 2.13 (d, J=1.6 Hz, 1H), 1.94 (t, J=2.6 Hz, 1H), 1.71 (dtd, J=8.7, 7.1, 5.4 Hz, 2H), 1.60 (dtd, J=9.1, 6.9, 4.9 Hz, 2H), 1.24 (t, J=7.1 Hz, 3H). $^{13}$C NMR (101 MHz, CDCl$_3$) δ 176.63, 115.25, 94.60, 84.14, 68.69, 60.33, 27.89, 25.84, 24.63, 19.85, 18.23, 14.51. HRMS (FAB) m/z: 193.1220 (M+H$^+$); calc. for C$_{12}$H$_{17}$O$_2$: 193.1229. [α]$^{23}_D$=+52.2±1.8° (c 0.1, cyclohexane). HPLC Chiralpak IC column (n-hexane/isopropanol=95:5, 1.0 mL/min), t$_r$=10.37 min (major), 11.55 min (minor), 98.0:2.0 er.

(R)-6-(3-(Ethoxycarbonyl)cycloprop-1-en-1-yl)hexyl cyclobutanecarboxylate (6d)

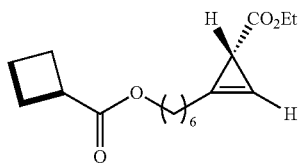

Analysis Data (10 mM 5d, P411-C6):

| Pdt-entries | Pdt | Std | Pdt/Std | [Pdt]/ mM | [PC]/μM | TTN | Avg. TTN | Avg. yield |
|---|---|---|---|---|---|---|---|---|
| 6d-(1) | 24642 | 4192 | 5.878 | 3.88 | 2.01 | 1930 | | |
| 6d-(2) | 22575 | 4190 | 5.388 | 3.56 | 2.01 | 1769 | | |
| 6d-(3) | 22572 | 4242 | 5.321 | 3.51 | 2.01 | 1747 | | |
| 6d-(4) | 24260 | 4249 | 5.710 | 3.77 | 2.01 | 1875 | 1831 | 36.8% |

Preparative-Scale Reaction:

| E. coli suspension expressing P411-C6 in M9-N | | | | D-glucose in M9-N | |
|---|---|---|---|---|---|
| OD$_{600}$ | volume/ mL | [PC]/μM | n_pro/ μmol | volume/ mL | [Glu]/mM |
| 32 | 25.0 | 6.48 | 0.162 | 1.5 | ~11 |

| alkyne (5d) stock in EtOH | | | EDA stock in EtOH | | |
|---|---|---|---|---|---|
| stock/M | volume/ μL | n_1/ mmol | stock/M | volume/ μL | n_2/mmol |
| 1.0 | 360 | 0.36 | 1.0 | 900 | 0.90 |

| purification eluent | | product | | | |
|---|---|---|---|---|---|
| Ethyl acetate in hexanes | | m[Pdt]/ mg | n[Pdt]/ mmol | yield | TTN |
| (0% to 12% gradient) | | 56.7 | 0.193 | 54% | 1190 |

$^1$H NMR (400 MHz, CDCl$_3$) δ 6.33 (dt, J=1.5 Hz, 1H), 4.17-4.08 (m, 2H), 4.05 (t, J=6.7 Hz, 2H), 3.12 (p, J=8.5 Hz, 1H), 2.49 (td, J=7.3, 1.1 Hz, 2H), 2.33-2.13 (m, 4H), 2.12 (d, J=1.6 Hz, 1H), 2.05-1.82 (m, 2H), 1.66-1.55 (m, 4H), 1.43-1.32 (m, 4H), 1.25 (t, J=7.1 Hz, 3H). $^{13}$C NMR (101 MHz, CDCl$_3$) δ 176.74, 175.74, 115.55, 94.26, 64.38, 60.33, 38.29, 28.87, 28.68, 26.68, 25.74, 25.42, 25.03, 19.85, 18.56, 14.54. HRMS (FAB) m/z: 295.1910 (M+H$^+$); calc. for C$_{17}$H$_{27}$O$_4$: 295.1909. [α]$^{23}_D$=+31.7±1.7° (c 0.1, cyclohexane). HPLC Chiralpak IC column (n-hexane/isopropanol=91:9, 1.0 mL/min), t$_r$=17.06 min (major), 19.06 min (minor), 95.3:4.7 er.

Ethyl (R)-2-(5-(1,3-dioxolan-2-yl)pentyl)cycloprop-2-ene-1-carboxylate (6e)

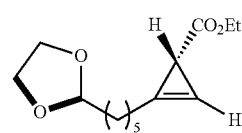

Analysis Data (10 mM 5e, P411-C6):

| Pdt-entries | Pdt | Std | Pdt/Std | [Pdt]/ mM | [PC]/μM | TTN | Avg. TTN | Avg. yield |
|---|---|---|---|---|---|---|---|---|
| 6e-(1) | 7788 | 4377 | 1.779 | 1.48 | 1.77 | 838 | | |
| 6e-(2) | 7579 | 4283 | 1.770 | 1.47 | 1.77 | 834 | | |
| 6e-(3) | 7654 | 4377 | 1.749 | 1.46 | 1.77 | 824 | | |
| 6e-(4) | 7263 | 4296 | 1.691 | 1.41 | 1.77 | 797 | 823 | 14.6% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/ μmol | volume/ mL | [Glu]/ mM |
| 24 | 50.0 | 5.32 | 0.266 | 2.0 | ~10 |

| alkyne (5e) stock in EtOH | | | EDA stock in EtOH | | |
|---|---|---|---|---|---|
| stock/M | volume/μL | n_1/ mmol | stock/M | volume/ μL | n_2/ mmol |
| 1.0 | 240 | 0.24 | 1.0 | 720 | 0.72 |

| purification eluent | product | | | |
|---|---|---|---|---|
| Ethyl acetate in hexanes | m[Pdt]/ mg | n[Pdt]/ mmol | yield | TTN |
| (0% to 15% gradient) | 42.8 | 0.168 | 70% | 630 |

The cell suspension (OD$_{600}$=24) was added in two portions (25 mL each portion) every 2 hours.

$^1$H NMR (400 MHz, Acetone-d$_6$) δ 6.61 (dt, J=1.5 Hz, 1H), 4.81 (t, J=4.8 Hz, 1H), 4.09 (qd, J=7.1, 2.3 Hz, 2H), 3.98-3.88 (m, 2H), 3.87-3.76 (m, 2H), 2.54 (tdd, J=7.1, 2.2, 1.4 Hz, 2H), 2.07 (d, J=1.6 Hz, 1H), 1.67-1.57 (m, 4H), 1.52-1.41 (m, 4H), 1.23 (t, J=7.1 Hz, 3H). $^{13}$C NMR (101 MHz, Acetone-d$_6$) δ 175.78, 115.81, 104.67, 94.74, 65.05, 59.93, 34.29, 27.09, 25.03, 24.19, 19.69, 14.44 (one carbon peak may be overlapping with the solvent peaks). HRMS (FAB) m/z: 255.1593 (M+H$^+$); calc. for C$_{14}$H$_{23}$O$_4$: 255.1596. [α]$^{23}_D$=+29.8±1.3° (c 0.1, cyclohexane). HPLC Chiralpak IC column (n-hexane/isopropanol=95:5, 1.0 mL/min), t$_r$=15.03 min (major), 16.92 min (minor), 96.8:3.2 er.

Ethyl (R)-2-(3-isopropoxypropyl)cycloprop-2-ene-1-carboxylate (6f)

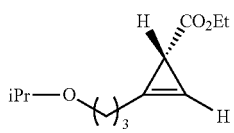

(6f)

Analysis Data (10 mM 5f, P411-C6):

| Pdt-entries | Pdt | Std | Pdt/Std | [Pdt]/ mM | [PC]/μM | TTN | Avg. TTN | Avg. yield |
|---|---|---|---|---|---|---|---|---|
| 6f-(1) | 212.9 | 504.7 | 0.422 | 0.38 | 1.82 | 207 | | |
| 6f-(2) | 289.9 | 514.0 | 0.564 | 0.50 | 1.82 | 276 | | |
| 6f-(3) | 252.4 | 511.2 | 0.494 | 0.44 | 1.82 | 242 | 242 | 4.4% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/ μmol | volume/ mL | [Glu]/ mM |
| 30 | 40.0 | 6.27 | 0.251 | 2.0 | ~12 |

| alkyne (5f) stock in EtOH | | | EDA stock in EtOH | | |
|---|---|---|---|---|---|
| stock/mM | volume/μL | n_1/ mmol | stock/mM | volume/ μL | n_2/ mmol |
| 800 | 100 | 0.08 | 800 | 300 | 0.24 |

| | product | | | |
|---|---|---|---|---|
| purification eluent Ethyl acetate in hexanes | m[Pdt]/ mg | n[Pdt]/ mmol | yield | TTN |
| (0% to 8% gradient) | 13.6 | 0.0641 | 80% | 260 |

$^1$H NMR (400 MHz, CDCl$_3$) δ 6.34 (dt, J=1.4 Hz, 1H), 4.12 (qd, J=7.1, 4.2 Hz, 2H), 3.53 (hept, J=6.2 Hz, 1H), 3.45 (td, J=6.3, 1.9 Hz, 2H), 2.58 (td, J=7.3, 1.4 Hz, 2H), 2.13 (d, J=1.5 Hz, 1H), 1.88-1.78 (m, 2H), 1.24 (t, J=7.1 Hz, 3H), 1.13 (d, J=6.1 Hz, 6H). $^{13}$C NMR (101 MHz, CDCl$_3$) δ 176.69, 115.36, 94.47, 71.61, 66.92, 60.31, 27.43, 22.24, 22.02, 19.89, 14.51. HRMS (FAB) m/z: 213.1485 (M+H$^+$); calc. for C$_{12}$H$_{21}$O$_3$: 213.1491. HPLC Chiralpak IC column (n-hexane/isopropanol=95:5, 1.0 mL/min), t$_r$=9.42 min (major), 10.92 min (minor), 97.3:2.7 er.

Ethyl (R)-2-(cyclohexylmethyl)cycloprop-2-ene-1-carboxylate (6g)

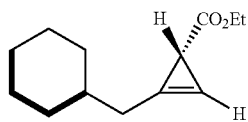

(6g)

Analysis Data (20 mM 5g, P411-C6):

| Pdt-entries | Pdt | Std | Pdt/Std | [Pdt]/ mM | [PC]/μM | TTN | Avg. TTN | Avg. yield |
|---|---|---|---|---|---|---|---|---|
| 6g-(1) | 1044.5 | 704.1 | 1.483 | 0.97 | 1.67 | 585 | | |
| 6g-(2) | 903.7 | 654.8 | 1.380 | 0.91 | 1.67 | 544 | | |
| 6g-(3) | 1102.7 | 701.6 | 1.572 | 1.03 | 1.67 | 620 | | |
| 6g-(4) | 1105.0 | 726.7 | 1.521 | 1.00 | 1.67 | 600 | 587 | 4.9% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/ μmol | volume/ mL | [Glu]/ mM |
| 20 | 60.0 | 3.83 | 0.230 | 1.5 | ~12 |

| alkyne (5g) stock in EtOH | | | EDA stock in EtOH | | |
|---|---|---|---|---|---|
| stock/M | volume/μL | n_1/mmol | stock/M | volume/μL | n_2/mmol |
| 0.80 | 250 | 0.20 | 0.80 | 500 | 0.40 |

| purification eluent | product | | | |
|---|---|---|---|---|
| Ethyl acetate in hexanes | m[Pdt]/ mg | n[Pdt]/ mmol | yield | TTN |
| (0% to 5% gradient) | 23.1 | 0.111 | 55% | 480 |

The cell suspension (OD$_{600}$=20) was added in three portions (20 mL each portion) every 2 hours.

$^1$H NMR (400 MHz, CDCl$_3$) δ 6.33 (d, J=1.4 Hz, 1H), 4.12 (qd, J=7.1, 3.3 Hz, 2H), 2.38 (d, J=7.2 Hz, 2H), 2.10 (d, J=1.6 Hz, 1H), 1.82-1.52 (m, 6H), 1.27-1.07 (m, 6H), 0.98 (qt, J=13.6, 3.7 Hz, 2H). $^{13}$C NMR (101 MHz, CDCl$_3$) δ 176.76, 114.74, 94.58, 60.28, 36.22, 33.18, 33.17, 32.68, 26.41, 26.27, 26.25, 19.93, 14.53. HRMS (FAB) m/z: 209.1537 (M+H$^+$); calc. for C$_{13}$H$_{21}$O$_2$: 209.1542. [α]$^{23}_D$=+53.4±1.5° (c 0.1, cyclohexane). HPLC Chiralpak IC column (n-hexane/isopropanol=95:5, 1.0 mL/min), t$_r$=7.59 min (major), 8.16 min (minor), 93.1:6.1 er.

Ethyl (R)-2-(6-((tetrahydro-2H-pyran-4-yl)methoxy)hexyl)cycloprop-2-ene-1-carboxylate (6h)

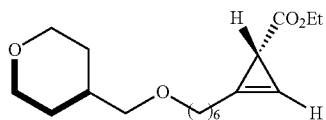

(6h)

Analysis Data (10 mM 5h, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6h-(1) | 40106 | 4085 | 9.818 | 7.31 | 1.77 | 4137 | | |
| 6h-(2) | 40775 | 4175 | 9.766 | 7.28 | 1.77 | 4115 | | |
| 6h-(3) | 39655 | 4125 | 9.613 | 7.16 | 1.77 | 4051 | | |
| 6h-(4) | 38780 | 4188 | 9.260 | 6.90 | 1.77 | 3902 | 4051 | 71.6% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 10 | 70.0 | 1.27 | 0.0886 | 3.0 | ~10 |

| alkyne (5h) stock in EtOH | | | EDA stock in EtOH | | |
|---|---|---|---|---|---|
| stock/M | volume/μL | n_1/mmol | stock/M | volume/mL | n_2/mmol |
| 1.0 | 400 | 0.40 | 1.0 | 1.20 | 1.20 |

| purification eluent | product | | | |
|---|---|---|---|---|
| Ethyl acetate in hexanes | m[Pdt]/mg | n[Pdt]/mmol | yield | TTN |
| (0% to 12% gradient) | 81.3 | 0.262 | 66% | 2960 |

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 20 | 200 | 4.84 | 0.968 | 12.0 | ~11 |

| alkyne (5h) stock in EtOH | | | EDA stock in EtOH | | |
|---|---|---|---|---|---|
| stock/M | volume/mL | n_1/mmol | stock/M | volume/mL | n_2/mmol |
| 2.0 | 1.50 | 3.0 | 2.0 | 4.50 | 9.0 |

| purification eluent | product | | | |
|---|---|---|---|---|
| Ethyl acetate in hexanes | m[Pdt]/mg | n[Pdt]/mmol | yield | TTN |
| (0% to 12% gradient) | 872.4 | 2.81 | 94% | 2900 |

In the 3.0-mmol scale reaction, EDA stock solution was added in three portions (1.5 mL each portion) every 1 hour.

$^1$H NMR (400 MHz, CDCl$_3$) δ 6.32 (dt, J=1.4 Hz, 1H), 4.13 (qd, J=7.1, 5.5 Hz, 2H), 4.00-3.91 (m, 2H), 3.44-3.34 (m, 4H), 3.24 (d, J=6.6 Hz, 2H), 2.49 (td, J=7.3, 1.4 Hz, 2H), 2.12 (d, J=1.5 Hz, 1H), 1.83 (ttt, J=10.5, 6.7, 3.8 Hz, 1H), 1.67-1.62 (m, 2H), 1.60-1.52 (m, 4H), 1.43-1.34 (m, 4H), 1.34-1.28 (m, 2H), 1.25 (t, J=7.1 Hz, 3H). $^{13}$C NMR (101 MHz, CDCl$_3$) δ 176.78, 115.66, 94.15, 76.12, 71.25, 67.90, 60.32, 35.61, 30.19, 29.73, 29.11, 26.77, 26.02, 25.06, 19.86, 14.54. HRMS (FAB) m/z: 311.2210 (M+H$^+$); calc. for C$_{18}$H$_{31}$O$_4$: 311.2222. [α]$^{23}_D$=+74.9±1.8° (c 0.1, cyclohexane). HPLC Chiralpak IC column (n-hexane/isopropanol=88:12, 1.0 mL/min), t$_r$=17.27 min (major), 20.55 min (minor), 99.0:1.0 er.

Ethyl (R)-2-(6-(cyclopropylmethoxy)hexyl)cycloprop-2-ene-1-carboxylate (6i)

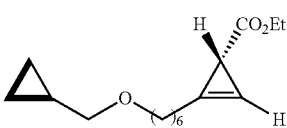

(6i)

Analysis Data (10 mM 5i, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6i-(1) | 26575 | 4144 | 6.413 | 4.44 | 2.01 | 2207 | | |
| 6i-(2) | 26599 | 4150 | 6.409 | 4.43 | 2.01 | 2206 | | |
| 6i-(3) | 26021 | 4086 | 6.368 | 4.40 | 2.01 | 2191 | | |
| 6i-(4) | 26300 | 4154 | 6.331 | 4.38 | 2.01 | 2179 | 2196 | 44.1% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 32 | 25.0 | 6.48 | 0.162 | 1.5 | ~11 |

| alkyne (5i) stock in EtOH | | | EDA stock in EtOH | | |
|---|---|---|---|---|---|
| stock/M | volume/μL | n_1/mmol | stock/M | volume/μL | n_2/mmol |
| 1.0 | 360 | 0.36 | 1.0 | 900 | 0.90 |

| purification eluent | product | | | |
|---|---|---|---|---|
| Ethyl acetate in hexanes | m[Pdt]/mg | n[Pdt]/mmol | yield | TTN |
| (0% to 10% gradient) | 61.8 | 0.232 | 64% | 1430 |

$^1$H NMR (400 MHz, CDCl$_3$) δ 6.32 (dt, J=1.5 Hz, 1H), 4.12 (qd, J=7.1, 5.2 Hz, 2H), 3.42 (t, J=6.7 Hz, 2H), 3.24 (d, J=6.9 Hz, 2H), 2.49 (td, J=7.3, 1.4 Hz, 2H), 2.12 (d, J=1.6 Hz, 1H), 1.62-1.54 (m, 4H), 1.41-1.34 (m, 4H), 1.25 (t, J=7.2 Hz, 3H), 1.12-0.97 (m, 1H), 0.59-0.42 (m, 2H), 0.28-0.09 (m, 2H). $^{13}$C NMR (101 MHz, CDCl$_3$) δ 176.78, 115.68, 94.13, 75.74, 70.78, 60.31, 29.79, 29.11, 26.76, 26.04, 25.05, 19.86, 14.54, 10.82, 3.13. HRMS (FAB) m/z: 267.1955 (M+H$^+$); calc. for C$_{16}$H$_{27}$O$_3$: 267.1960. [α]$^{23}_D$=+43.1±1.5° (c 0.1, cyclohexane). HPLC Chiralpak IC column (n-hexane/isopropanol=95:5, 1.0 mL/min), t$_r$=14.19 min (major), 15.27 min (minor), 95.8:4.2 er.

Ethyl (R or S)-2-([1,1'-bi(cyclopropan)])-2-ene-1-carboxylate (R or S-6j)

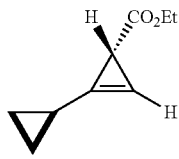

(6j)

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 20 | 25.0 | 4.47 | 0.112 | 1.2 | ~11 |

| alkyne (5j) stock in EtOH | | | EDA stock in EtOH | | |
|---|---|---|---|---|---|
| stock/mM | volume/μL | n_1/mmol | stock/mM | volume/μL | n_2/mmol |
| 400 | 250 | 0.10 | 400 | 375 | 0.15 |

| purification eluent Ether in pentane | m[Pdt]/mg | n[Pdt]/mmol | product | |
|---|---|---|---|---|
| | | | yield | TTN |
| (0% to 20% gradient) | 10.7 | 0.0703 | 70% | 630 |

| E. coli suspension expressing P411-K10 in M9-N | | | | D-glucose in M9-N | |
|---|---|---|---|---|---|
| OD$_{600}$ | volume/mL | [PC]/μM | n_pro/μmol | volume/mL | [Glu]/mM |
| 20 | 25.0 | 3.07 | 0.0767 | 1.2 | ~11 |

| alkyne (5j) stock in EtOH | | | EDA stock in EtOH | | |
|---|---|---|---|---|---|
| stock/mM | volume/μL | n_1/mmol | stock/mM | volume/μL | n_2/mmol |
| 400 | 250 | 0.10 | 400 | 375 | 0.15 |

| purification eluent Ether in pentane | m[Pdt]/mg | n[Pdt]/mmol | product | |
|---|---|---|---|---|
| | | | yield | TTN |
| (0% to 20% gradient) | 11.2 | 0.0736 | 74% | 960 |

$^1$H NMR (600 MHz, Acetone-d$_6$) δ 6.47 (d, J=1.6 Hz, 1H), 4.13-4.03 (m, 2H), 1.99 (d, J=1.5 Hz, 1H), 1.91 (tt, J=7.9, 4.6 Hz, 1H), 1.22 (t, J=7.1 Hz, 3H), 1.01-0.94 (m, 2H), 0.84-0.80 (m, 1H), 0.61-0.58 (m, 1H). $^{13}$C NMR (151 MHz, acetone) δ 175.54, 117.94, 92.45, 59.99, 18.65, 14.46, 6.79, 6.05, 5.78. HRMS (EI) m/z: 152.0865 (M$^+$); calc. for C$_9$H$_{12}$O$_2$: 152.0837. P411-C6: HPLC Chiralpak IC column (n-hexane/isopropanol=95:5, 1.0 mL/min), t$_r$=11.33 min (major), 11.79 min (minor), 93.4:6.6 er. P411-K10: HPLC Chiralpak IC column (n-hexane/isopropanol=95:5, 1.0 mL/min), t$_r$=11.33 min (minor), 11.74 min (major), 66.7:33.3 er.

Ethyl (R)-2-(4-chlorobutyl)cycloprop-2-ene-1-carboxylate (6k)

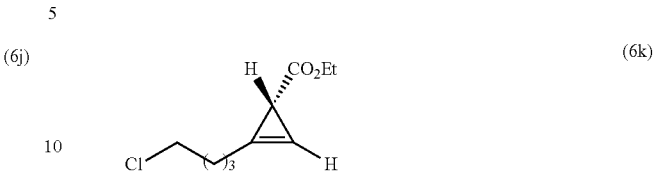

(6k)

Analysis Data (10 mM 5k, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6k-(1) | 322.4 | 517.1 | 0.623 | 0.56 | 1.82 | 308 | | |
| 6k-(2) | 363.5 | 517.4 | 0.703 | 0.63 | 1.82 | 347 | | |
| 6k-(3) | 342.8 | 523.4 | 0.655 | 0.59 | 1.82 | 324 | 326 | 6.0% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 30 | 40.0 | 6.27 | 0.251 | 2.0 | ~12 |

| alkyne (5k) stock in EtOH | | | EDA stock in EtOH | | |
|---|---|---|---|---|---|
| stock/mM | volume/μL | n_1/mmol | stock/mM | volume/μL | n_2/mmol |
| 800 | 125 | 0.10 | 800 | 375 | 0.30 |

| purification eluent Ethyl acetate in hexanes | m[Pdt]/mg | n[Pdt]/mmol | product | |
|---|---|---|---|---|
| | | | yield | TTN |
| (0% to 8% gradient) | 17.6 | 0.0868 | 87% | 340 |

$^1$H NMR (400 MHz, CDCl$_3$) δ 6.37 (s, 1H), 4.12 (dd, J=7.1, 4.2 Hz, 2H), 3.54 (t, J=6.5 Hz, 2H), 2.54 (t, J=7.0 Hz, 2H), 2.13 (s, 1H), 1.91-1.80 (m, 2H), 1.80-1.70 (m, 2H), 1.24 (t, J=7.1 Hz, 3H). $^{13}$C NMR (101 MHz, CDCl$_3$) δ 176.54, 114.98, 94.94, 60.37, 44.67, 31.89, 24.39, 24.12, 19.83, 14.49. HRMS (FAB) m/z: 203.0846 (M+H$^+$); calc. for C$_{10}$H$_{16}$ClO$_2$: 203.0839. [α]$^{23}_D$=+25.7±1.6° (c 0.1, cyclohexane). HPLC Chiralpak IC column (n-hexane/isopropanol=95:5, 1.0 mL/min), t$_r$=11.00 min (major), 12.62 min (minor), 94.2:5.8 er.

Ethyl (R)-2-(6-((trans-4-(methoxymethyl)cyclohexyl)methoxy)hexyl)cycloprop-2-ene-1-carboxylate (6l)

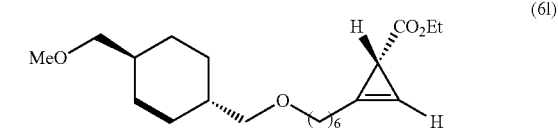

(6l)

Analysis Data (10 mM 51, P411-C6):

| Pdt-entries | Pdt | Std | Pdt/Std | [Pdt]/mM | [PC]/μM | TTN | Avg. TTN | Avg. yield |
|---|---|---|---|---|---|---|---|---|
| 6l-(1) | 14861 | 4259 | 3.489 | 2.41 | 1.93 | 1252 | | |
| 6l-(2) | 13735 | 4274 | 3.214 | 2.22 | 1.93 | 1153 | | |
| 6l-(3) | 16271 | 4222 | 3.854 | 2.66 | 1.93 | 1383 | | |
| 6l-(4) | 13204 | 4323 | 3.054 | 2.11 | 1.93 | 1096 | 1221 | 23.5% |

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 10 | 70.0 | 1.27 | 0.0886 | 3.0 | ~10 |

| alkyne (5l) stock in EtOH | | | EDA stock in EtOH | | |
|---|---|---|---|---|---|
| stock/M | volume/μL | n_1/mmol | stock/M | volume/μL | n_2/mmol |
| 1.0 | 180 | 0.18 | 1.0 | 540 | 0.54 |

| purification eluent | product | | | |
|---|---|---|---|---|
| Ethyl acetate in hexanes | m[Pdt]/mg | n[Pdt]/mmol | yield | TTN |
| (0% to 15% gradient) | 22.1 | 0.0627 | 35% | 710 |

The cell suspension (OD$_{600}$=10) was added in two portions (35 mL each portion) every 2 hours.

$^1$H NMR (400 MHz, CDCl$_3$) δ 6.32 (dt, J=1.4 Hz, 1H), 4.12 (qd, J=7.1, 5.4 Hz, 2H), 3.37 (t, J=6.6 Hz, 2H), 3.32 (s, 3H), 3.21-3.17 (m, 4H), 2.49 (td, J=7.3, 1.4 Hz, 2H), 2.12 (d, J=1.6 Hz, 1H), 1.87-1.74 (m, 4H), 1.63-1.52 (m, 6H), 1.37 (tt, J=6.3, 3.3 Hz, 4H), 1.25 (t, J=7.1 Hz, 3H), 0.99-0.86 (m, 4H). $^{13}$C NMR (101 MHz, CDCl$_3$) δ 176.79, 115.69, 94.12, 78.93, 76.90, 71.17, 60.31, 58.98, 38.37 (two carbons), 29.74, 29.65, 29.55, 29.11, 26.77, 26.03, 25.06, 19.86, 14.54. HRMS (FAB) m/z: 353.2699 (M+H$^+$); calc. for C$_{21}$H$_{37}$O$_4$: 353.2692. [α]$^{23}_D$=+62.6±2.7° (c 0.1, cyclohexane). HPLC Chiralpak IC column (n-hexane/isopropanol=93:7, 1.0 mL/min), t$_r$=10.07 min (major), 11.44 min (minor), 96.4:3.6 er.

Ethyl (R)-2-(6-hydroxyhexyl)cycloprop-2-ene-1-carboxylate (6m)

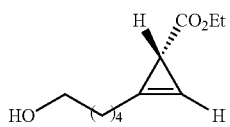

(6m)

Preparative-Scale Reaction:

| E. coli suspension expressing P411-C6 in M9-N | | | | D-glucose in M9-N | |
|---|---|---|---|---|---|
| OD$_{600}$ | volume/mL | [PC]/μM | n_pro/μmol | volume/mL | [Glu]/mM |
| 30 | 40.0 | 6.80 | 0.272 | 1.5 | ~12 |

| alkyne (5m) stock in EtOH | | | EDA stock in EtOH | | |
|---|---|---|---|---|---|
| stock/M | volume/μL | n_1/mmol | stock/M | volume/μL | n_2/mmol |
| 1.0 | 250 | 0.25 | 2.0 | 750 | 1.50 |

| purification eluent | product | | | |
|---|---|---|---|---|
| Ethyl acetate in hexanes | m[Pdt]/mg | n[Pdt]/mmol | yield | TTN |
| (0% to 25% gradient) | 38.2 | 0.193 | 80% | 710 |

$^1$H NMR (400 MHz, Acetone-d$_6$) δ 6.56 (dt, J=1.5 Hz, 1H), 4.05 (qd, J=7.1, 2.5 Hz, 2H), 3.52 (t, J=6.2 Hz, 2H), 2.50 (tt, J=7.1, 1.6 Hz, 2H), 2.03 (d, J=1.6 Hz, 1H), 1.63-1.56 (m, 2H), 1.55-1.49 (m, 2H), 1.48-1.40 (m, 2H), 1.19 (t, J=7.1 Hz, 3H) (O—H proton is not resolved). $^{13}$C NMR (101 MHz, Acetone-d$_6$) δ 176.12, 116.11, 94.99, 62.12, 60.23, 33.34, 27.33, 26.16, 25.47, 19.98, 14.72. HRMS (FAB) m/z: 199.1342 (M+H$^+$); calc. for C$_{11}$H$_{19}$O$_3$: 199.1334. [α]$^{23}_D$=+80.1±3.4° (c 0.1, ethyl acetate). HPLC Chiralpak IC column (n-hexane/isopropanol=88:12, 1.0 mL/min), t$_r$=15.76 min (major), 16.86 min (minor), 96.0:4.0 er.

During the test of analytical reactions, aliphatic alkynes 5n-5q also gave a fair amount of cyclopropene products, which were detected by GC-MS. Making the racemic standards with Rh$_2$(OAc)$_4$ was problematic, resulting in no product formation or products with other impurities.

Example 15. Chemical Elaboration of Cyclopropene Products

Cyclopropenes are used as synthetic building blocks (10,[47]), bio-orthogonal imaging precursors ([48]), and monomers in polymer synthesis ([49]). The ability to construct these motifs using bacteria at scale allows for the further exploration of their potential utility in diverse fields. Two simple transformations of cyclopropenes were carried out to build a multi-substituted cyclopropane 7a and a fused ring system, bicyclo[4.1.0]heptene 7b (FIG. 3C), both of which are substructures common in pharmaceutical candidates and bioactive natural products (27).

Diethyl (2R,4R)-1-(4-(1-((4-acetamidophenyl)sulfonyl)-1H-1,2,3-triazol-4-yl)phenyl) bicyclo[1.1.0]butane-2,4-dicarboxylate (4a)

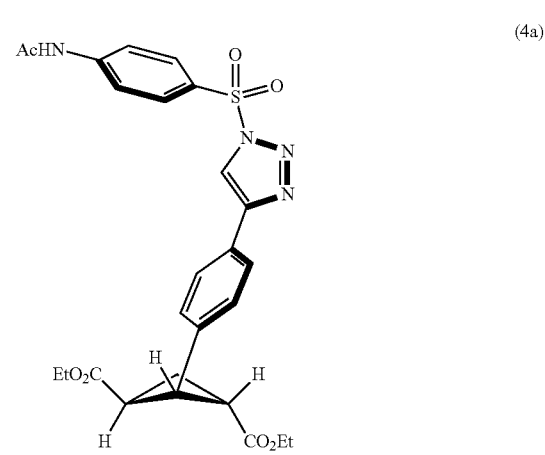

(4a)

Bicyclobutane 2l (41.6 mg, 0.139 mmol) was dissolved in toluene (3 mL) in a 20 mL vial. Copper(I) thiophene-2-carboxylate (CuTc, 3.2 mg, 12 mol %) was added. The mixture was kept stirring at 0° C. A suspension of 4-acetamidobenzenesulfonyl azide (40.2 mg, 0.167 mmol) in toluene (5 mL) was added dropwise over 1 h. The resulting mixture was then allowed to warm to room temperature and stirred for 15 h. The reaction was diluted with ethyl acetate (15 mL), washed with $NH_4Cl/NH_3$ (2:1, 20 mL, aq.), and brine (50 mL), dried over $MgSO_4$, and then concentrated under reduced pressure. The crude product was purified by silica column chromatography with hexane/ethyl acetate (4:1 to 1:3 gradient) to afford 4a (69.2 mg, 0.129 mmol, 93%). $^1$H NMR (400 MHz, $CDCl_3$) δ 8.32 (s, 1H), 8.10 (s, 1H), 8.00 (d, J=9.0 Hz, 2H), 7.74 (dd, J=12.8, 8.7 Hz, 4H), 7.34 (d, J=8.6 Hz, 2H), 4.15 (dq, J=7.1, 3.5 Hz, 2H), 4.08 (q, J=7.1 Hz, 2H), 3.28 (d, J=0.6 Hz, 1H), 3.19 (dd, J=3.1, 0.6 Hz, 1H), 3.14 (d, J=3.1 Hz, 1H), 2.20 (s, 3H), 1.27 (t, J=7.2 Hz, 3H), 1.15 (t, J=7.1 Hz, 3H). $^{13}$C NMR (101 MHz, $CDCl_3$) δ 170.14, 169.15, 167.88, 147.11, 145.13, 134.03, 130.40, 129.53, 128.96, 127.92, 126.19, 119.62, 119.22, 61.17, 61.13, 44.75, 42.63, 27.84, 24.93, 21.39, 14.35, 14.21. HRMS (FAB) m/z: 539.1605 (M+H$^+$); calc. for $C_{26}H_{27}O_7SN_4$: 539.1600. $[α]^{23}_D$=−81.5±2.1° (c 0.1, ethyl acetate).

Diethyl (2R,4R)-1-(4-(1-((S)-1-methoxy-1-oxo-3-phenylpropan-2-yl)-1H-1,2,3-triazol-4-yl)phenyl)bicyclo[1.1.0]butane-2,4-dicarboxylate (4b)

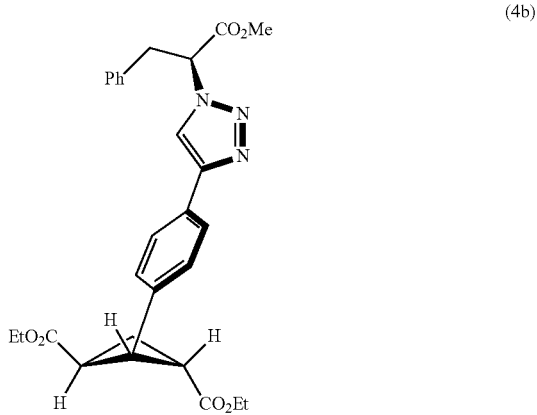

(4b)

Sodium azide (7.02 g, 108 mmol) was dissolved in a mixture of water (30 mL) and DCM (15 mL) at 0° C. Triflic anhydride ($Tf_2O$, 3 mL, 18 mmol) was added dropwise over 10 min. The reaction was then stirred for 2 h. The reaction was diluted with DCM (15 mL), washed by $NaHCO_3$ (50 mL, sat. aq.), and brine (50 mL), and dried over $Na_2SO_4$. A solution of triflic azide ($TfN_3$, ~15 mmol) in DCM was used for the next step.

Methyl L-phenylalaninate hydrochloride (1.73 g, 8.0 mmol), was dissolved in MeOH (16 mL). A aqueous solution of $CuSO_4$ (1.28 mL, 10 g/L, 1 mol %) and N,N-diisopropylethylamine (DIPEA, 2.09 mL, 12.0 mmol) were added. The resulting solution was stirred for 30 min before the dropwise addition of triflic azide ($TfN_3$, ~15 mmol in DCM) over 20 min. The reaction was stirred for 15 h. The reaction mixture was diluted with DCM (40 mL), washed by water (50 mL), HCl (50 mL, 5%, aq.), $NaHCO_3$ (50 mL, sat. aq.), and brine (50 mL), and dried over $Na_2SO_4$. After evaporation of solvent under reduced pressure, the product mixture was purified by silica column chromatography with hexane/ethyl acetate (1:0 to 12:1 gradient) to afford methyl (S)-2-azido-3-phenylpropanoate (1.65 g, 8.0 mmol, quantitative).

Bicyclobutane 2l (49.5 mg, 0.166 mmol) was dissolved in THF/$H_2O$ (1:1, 1.6 mL) in a 20 mL vial. A aqueous solution of $CuSO_4$ (17 μL, 1N, 10 mol %) and Cu powder (10.6 mg, 0.166 mmol) were added. The mixture was kept stirring at 0° C. A solution of methyl (S)-2-azido-3-phenylpropanoate (50.1 mg, 0.249 mmol) in THF (0.5 mL) was added dropwise over 5 min. The resulting mixture was then allowed to warm to room temperature and stirred for 24 h. The reaction was diluted with DCM (15 mL), washed with $NH_4Cl$ (10 mL, aq. sat.), and brine (30 mL), dried over $MgSO_4$, and then concentrated under reduced pressure. The crude product was purified by silica column chromatography with hexane/ethyl acetate (8:1 to 2:1 gradient) to afford 4b (82.5 mg, 0.164 mmol, 99%) as one major diastereomer determined by $^1$H NMR. $^1$H NMR (400 MHz, $CDCl_3$) δ 7.80 (s, 1H), 7.78-7.69 (m, 2H), 7.37-7.30 (m, 2H), 7.28-7.20 (m, 3H), 7.08-7.03 (m, 2H), 5.63 (dd, J=8.1, 6.7 Hz, 1H), 4.15 (qd, J=7.1, 2.6 Hz, 2H), 4.08 (q, J=7.1 Hz, 2H), 3.77 (s, 3H), 3.52 (dd, J=7.4, 3.2 Hz, 2H), 3.28 (d, J=0.5 Hz, 1H), 3.17 (dd, J=3.1, 0.6 Hz, 1H), 3.13 (d, J=3.1 Hz, 1H), 1.27 (t, J=7.1 Hz, 3H), 1.15 (t, J=7.1 Hz, 3H). $^{13}$C NMR (101 MHz, $CDCl_3$) δ 170.24, 168.84, 167.87, 147.40, 134.77, 132.77, 129.67, 129.08, 128.98, 128.84, 127.77, 125.80, 119.75, 64.17, 61.05, 61.01, 53.26, 44.71, 42.64, 39.12, 27.99, 20.89, 14.36, 14.22. HRMS (FAB) m/z: 504.2148 (M+H$^+$); calc. for $C_{28}H_{30}O_6N_3$: 504.2135. $[α]^{23}_D$=−278.7±4.0° (c 0.0625, ethyl acetate).

A diastereomer of 4b was prepared through the same procedure using D-azido-phenylalanine. It was confirmed that the pair of diastereomers can be resolved on $^1$H NMR at the α-C—H position of phenylalanine (splitting peaks: D-phenylalanine: 5.6410, 5.6242, 5.6208, 5.6041; L-phenylalanine: 5.6462, 5.6296, 5.6261, 5.6093; FWHM (full width at half maxima)=0.0030 ppm; Δf1=0.0053 ppm, close to baseline separation).

Diethyl (2R,4R)-1-(4-((((R)-3,3,3-Trifluoro-2-methoxy-2-phenylpropanoyl)oxy) methyl)phenyl)bicyclo[1.1.0]butane-2,4-dicarboxylate (4c)

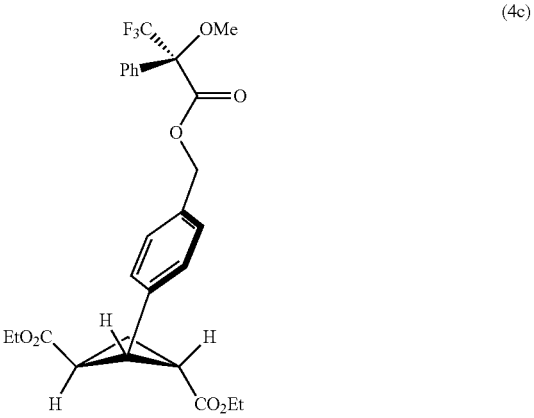

(4c)

Bicyclobutane 2m (16.1 mg, 0.053 mmol) and (R)-3,3,3-trifluoro-2-methoxy-2-phenylpropanoic acid (R-Mosher's acid, 30.4 mg, 0.13 mmol) were dissolved in dry DCM (2 mL) in a 10 mL vial. 1-Ethyl-3-(3-dimethylaminopropyl) carbodiimide hydrochloride (EDCl, 24.9 mg, 0.13 mmol), triethylamine (TEA, 18 µL, 0.13 mmol) and 4-dimethylaminopyridine (DMAP, 2.0 mg, 0.015 mmol) were added to the solution. The reaction mixture was then stirred at room temperature for 16 h. The reaction was diluted with DCM (5 mL), washed with water (10 mL), and brine (10 mL), dried over MgSO$_4$, and then concentrated under reduced pressure. The crude product was purified by silica column chromatography with hexane/ethyl acetate (1:0 to 4:1 gradient) to afford 4c (25.2 mg, 0.048 mmol, 91%) as one major diastereomer determined by $^1$H NMR. $^1$H NMR (400 MHz, CDCl$_3$) δ 7.48-7.41 (m, 2H), 7.41-7.32 (m, 3H), 7.27 (s, 4H), 5.33 (d, J=12.3 Hz, 1H), 5.29 (d, J=12.2 Hz, 1H), 4.15 (qd, J=7.2, 2.6 Hz, 2H), 4.07 (qd, J=7.2, 2.0 Hz, 2H), 3.51 (q, $J_{H-F}$=1.2 Hz, 3H), 3.26 (d, J=0.6 Hz, 1H), 3.14 (dd, J=3.1, 0.6 Hz, 1H), 3.11 (d, J=3.1 Hz, 1H), 1.27 (t, J=7.1 Hz, 3H), 1.13 (t, J=7.1 Hz, 3H). $^{13}$C NMR (101 MHz, CDCl$_3$) δ 170.01, 167.67, 166.43, 133.67, 133.32, 132.11, 129.64, 128.54, 128.53, 128.42, 127.54, 127.28, 127.27, 124.68, 121.81, 118.94, 84.75, 67.60, 60.96, 60.88, 55.54, 44.61, 42.44, 27.66, 20.85, 14.23, 14.03 (CF$_3$, 127.54, 124.68, 121.81, 118.94, $J_{C-F}$=288.8 Hz;). HRMS (FAB) m/z: 519.1651 ((M+H$^+$)—H$_2$); calc. for C$_{27}$H$_{26}$O$_7$F$_3$: 519.1631. $[\alpha]^{23}_D$=−43.2±2.4° (c 0.1, ethyl acetate).

A diastereomer of 4c was prepared through the same procedure using S-Mosher's acid. It was confirmed that the pair of diastereomers can be resolved on $^1$H NMR at one benzylic C—H position and $^{19}$F NMR, albeit not perfectly (splitting peaks on $^1$H NMR: R-Mosher's acid: 5.3027, 5.2721; S-Mosher's acid: 5.3044, 5.2737; FWHM=0.0024-0.0029 ppm; Δf1=0.0017 ppm; chemical shift on $^{19}$F NMR: R-Mosher's acid: −71.665; S-Mosher's acid: −71.654; FWHM=0.015 ppm; Δf1=0.011 ppm).

((1R,2R)-1-(4-methoxyphenyl)bicyclo[1.1.0]butane-2,4-diyl)dimethanol (4d)

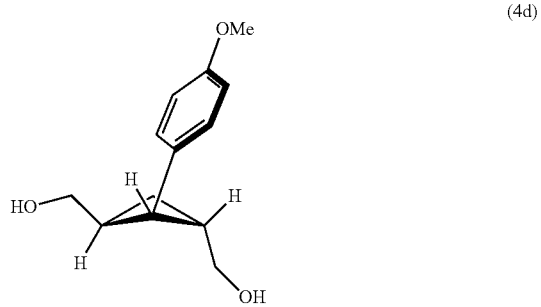

(4d)

Bicyclobutane 2k (101.3 mg, 0.33 mmol) was dissolved in anhydrous ether (10 mL) in a 50 mL flask. Dry methanol (67 µL, 1.67 mmol) was added to the solution, followed by the addition of lithium borohydride (LiBH$_4$, 2M in THF, 0.84 mL, 1.67 mmol). The reaction mixture was then heated up to a refluxing temperature, 45° C., for 1 h, before ethyl acetate (0.5 mL) was added and the mixture was stirred at room temperature for 30 min. Then the reaction was quenched with NH$_4$Cl (10 mL, sat. aq.) and diluted with water (10 mL). The product was extracted with ethyl acetate (20 mL×6). The combined organic layer was dried over MgSO$_4$, and then concentrated under reduced pressure. White solid product crashed out during the removal of solvent. Collecting the solid product and recrystallization with acetone/hexane system afforded the diol 4d (52.2 mg, 0.237 mmol, 71%). $^1$H NMR (400 MHz, Acetone-d$_6$) δ 7.31 (d, J=8.9 Hz, 2H), 6.85 (d, J=8.8 Hz, 2H), 3.78 (s, 3H), 3.71-3.65 (m, 1H), 3.65-3.61 (m, 1H), 3.57-3.51 (m, 1H), 3.49-3.43 (m, 2H), 2.28 (t, J=5.8 Hz, 1H), 1.92 (dd, J=3.6, 1.0 Hz, 1H) (O-H protons are not resolved). $^{13}$C NMR (101 MHz, Acetone) δ 158.07, 129.14, 129.08, 113.58, 60.27, 60.14 (splitting), 55.88, 55.75 (splitting), 54.56, 49.65, 49.61 (splitting), 46.08, 46.04 (splitting), 21.53, 16.55. (Note: the diol product might have two rotating conformations, resulting in splitting of 4 carbon peaks.) HRMS (FAB) m/z: 221.1168 (M+H$^+$); calc. for C$_{13}$H$_{17}$O$_3$: 221.1178. $[\alpha]^{23}_D$=−50.8±1.2° (c 0.1, acetone).

| | |
|---|---|
| Identification code | p17505 |
| Empirical formula | C13 H16 O3 |
| Formula weight | 220.26 |
| Temperature | 175 K |
| Wavelength | 1.54178 Å |
| Crystal system | Monoclinic |
| Space group | P 1 21 1 |
| Unit cell dimensions | a = 5.3738(7) Å α = 90° |
| | b = 7.6719(8) Å β = 98.413(9)° |
| | c = 13.7357(19) Å γ = 90° |
| Volume | 560.19(12) Å$^3$ |
| Z | 2 |
| Density (calculated) | 1.306 Mg/m$^3$ |
| Absorption coefficient | 0.747 mm$^{-1}$ |
| F(000) | 236 |
| Crystal size | 0.22 × 0.18 × 0.06 mm$^3$ |
| Theta range for data collection | 3.252 to 79.483°. |
| Index ranges | −6 <= h <= 6, −9 <= k <= 9, −16 <= l <= 17 |
| Reflections collected | 17841 |
| Independent reflections | 2338 [R(int) = 0.0437] |
| Completeness to theta = 67.679° | 99.9% |
| Absorption correction | Semi-empirical from equivalents |
| Max. and min. transmission | 1.0000 and 0.8812 |
| Refinement method | Full-matrix least-squares on F$^2$ |
| Data/restraints/parameters | 2338/1/148 |
| Goodness-of-fit on F$^2$ | 1.111 |
| Final R indices [I > 2sigma(I)] | R1 = 0.0471, wR2 = 0.1225 |
| R indices (all data) | R1 = 0.0482, wR2 = 0.1232 |
| Absolute structure parameter | 0.15(7) |
| Extinction coefficient | n/a |
| Largest diff. peak and hole | 0.337 and −0.270 e · Å$^{-3}$ |

Ethyl (1R,2R)-4-(hydroxymethyl)-1-(4-methoxyphenyl)bicyclo[1.1.0]butane-2-carboxylate (4e)

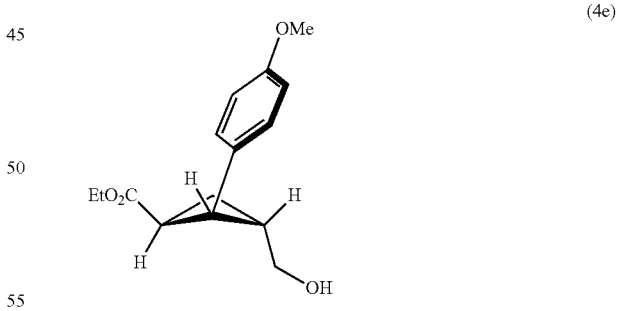

(4e)

Mono-alcohol 4e was obtained from the reduction of bicyclobutane 2k. Collecting the mother liquor after recrystallization, evaporation of organic solvent followed by purification by silica column chromatography with hexane/ethyl acetate (5:1 to 3:1 gradient) afforded 4e (14.6 mg, 0.056 mmol, 17%) with ~7:1 r.r. determined by $^1$H NMR. $^1$H NMR (400 MHz, Acetonitrile-d$_3$) δ 7.20 (d, J=8.8 Hz, 2H), 6.88 (d, J=8.8 Hz, 2H), 4.05 (qd, J=7.1, 0.5 Hz, 2H), 3.78 (s, 3H), 3.43 (t, J=6.3 Hz, 2H), 2.75 (tdd, J=7.0, 3.3, 0.7 Hz, 1H), 2.70 (t, J=5.9 Hz, 1H), 2.68 (s, 1H), 2.64 (d, J=3.3 Hz, 1H), 1.14 (t, J=7.1 Hz, 3H). $^{13}$C NMR (101 MHz, CD$_3$CN) δ

168.54, 159.04, 129.70, 127.38, 114.20, 60.92, 56.42, 55.44, 47.23, 42.52, 24.86, 18.43, 13.99. MS (EI) m/z: 262 (M$^+$); calc. for $C_{15}H_{18}O_4$: 262.

(2-(4-Methoxyphenyl)cyclobut-1-ene-1,3-diyl)dimethanol (4f)

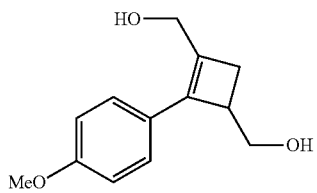

(4f)

Bicyclobutane 2k (54.7 mg, 0.18 mmol) was dissolved in anhydrous ether (5 mL) in a 20 mL vial and then cooled down to −78° C. Lithium aluminum hydride (LAH, 13.7 mg, 0.36 mmol) was slowly added to the solution in portions. The reaction mixture was slowly warmed up to −20° C. over 2 h, before ethyl acetate (0.5 mL) was added and the mixture was stirred at −20° C. for another 30 min. Then the reaction was quenched with NH$_4$Cl (10 mL, sat. aq.) and diluted with water (10 mL). The product was extracted with ethyl acetate (20 mL×3). The combined organic layer was dried over MgSO$_4$, and then concentrated under reduced pressure. The crude product was purified by silica column chromatography with hexane/ethyl acetate (2:1 to 1:2 gradient) to afford 4f (18.1 mg, 0.082 mmol, 46%). $^1$H NMR (400 MHz, Acetonitrile-d$_3$) δ 7.34 (d, J=8.8 Hz, 2H), 6.92 (d, J=8.9 Hz, 2H), 4.30 (d, J=3.1 Hz, 2H), 3.80 (s, 5H), 3.57 (ddd, J=11.2, 7.2, 4.3 Hz, 1H), 3.21-3.12 (m, 1H), 2.95 (t, J=5.7 Hz, 1H), 2.70 (t, J=5.5 Hz, 1H), 2.59 (dd, J=13.7, 4.6 Hz, 1H). $^{13}$C NMR (101 MHz, CD$_3$CN) δ 159.59, 140.27, 140.19, 128.91, 128.55, 114.63, 65.02, 59.23, 55.79, 42.11, 31.40. MS (EI) m/z: 220 (M$^+$); calc. for $C_{13}H_{16}O_3$: 220.

Diethyl (2R,4R)-1-(4-(((4-(4,5,6,7-Tetrachloro-1,3-dioxoisoindolin-2-yl)benzoyl)oxy) methyl)phenyl)bicyclo[1.1.0]butane-2,4-dicarboxylate (4g)

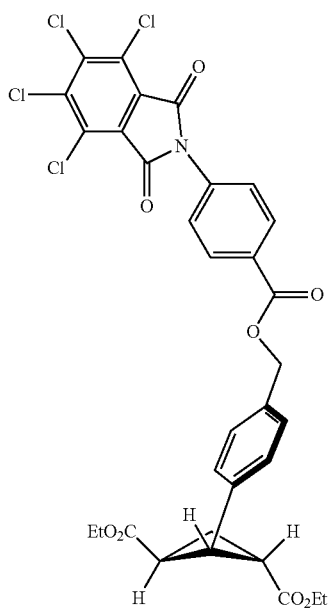

(4g)

Tetrachlorophthalic anhydride (14.30 g, 50.0 mmol) and 4-aminobenzoic acid (6.86 g, 50.0 mmol) were dissolved in PhMe (100 mL) to form a suspension. The mixture was heated up to 110° C. and stirred vigorously, before the addition of TEA (0.35 mL, 5 mol %). The reaction turned clear and then white product started to crash out. The reaction was stirred at the refluxing temperature for 1 h, and then slowly cooled to room temperature. The product 4-(4,5,6,7-tetrachloro-1,3-dioxoisoindolin-2-yl)benzoic acid (20.05 g, 49.5 mmol, 99%) was collected by filtration.

4-(4,5,6,7-Tetrachloro-1,3-dioxoisoindolin-2-yl)benzoic acid (40.5 mg, 0.1 mmol) and DMF (3 drops, cat.) was dissolved in dry DCM (8 mL) and SOCl$_2$ (2 mL). The mixture was heated and stirred at a refluxing temperature, 48° C. for 4 h. After completely removing organic solvent and excess SOCl$_2$ under reduced pressure, the resulting crude product 4-(4,5,6,7-tetrachloro-1,3-dioxoisoindolin-2-yl)benzoyl chloride was dissolved in dry DCM (3 mL) and used directly for next step.

Bicyclobutane 2m (15.2 mg, 0.050 mmol) and TEA (14 μL, 0.10 mmol) were dissolved in dry DCM (2 mL) in a 10 mL vial. The solution of prepared benzoyl chloride in DCM was added to the solution. The reaction mixture was then stirred at room temperature for 12 h. The reaction was diluted with DCM (5 mL), washed with water (10 mL), and brine (10 mL), dried over MgSO$_4$, and then concentrated under reduced pressure. The crude product was purified by silica column chromatography with hexane/ethyl acetate (1:0 to 4:1 gradient) to afford 4g (30.0 mg, 0.0434 mmol, 87%) as a white solid. $^1$H NMR (400 MHz, Acetonitrile-d$_3$) δ 8.21 (d, J=8.6 Hz, 2H), 7.60 (d, J=8.7 Hz, 2H), 7.47 (d, J=8.3 Hz, 2H), 7.34 (d, J=8.2 Hz, 2H), 5.38 (s, 2H), 4.09 (dq, J=14.2, 7.1 Hz, 4H), 3.30 (dd, J=3.1, 0.6 Hz, 1H), 3.16 (d, J=3.1 Hz, 1H), 3.07 (d, J=0.5 Hz, 1H), 1.23 (t, J=7.1 Hz, 3H), 1.15 (t, J=7.1 Hz, 3H). $^{13}$C NMR (101 MHz, CD$_3$CN) δ 170.14, 167.93, 165.82, 163.12 (two carbons), 140.42, 136.05, 135.95, 133.64, 130.76, 130.67, 130.00, 128.81, 128.72, 128.55, 127.57, 66.99, 61.30, 61.25, 45.10, 42.39, 27.43, 21.38, 14.04, 13.92. HRMS (ESI) m/z: 712.0082 (M+H$^+$); calc. for $C_{32}H_{23}Cl_{14}NO_8Na$: 712.0075. $[\alpha]^{23}_D$=−48.5±1.6° (c 0.1, acetone).

Ethyl (1R,2R,3S)-3-allyl-2-methyl-2-phenethylcyclopropane-1-carboxylate (7a)

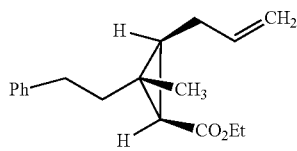

(7a)

Cyclopropene (R)-6a (54.0 mg, 0.25 mmol) and CuI (5.0 mg, 0.026 mmol, 10 mol %) were dissolved in anhydrous ether (3 mL) to form a suspension in a 25 mL flask. Then the flask was charged with argon and cooled to −78° C. Methylmagnesium bromide (0.75 mL, 1M in ether, diluted from 3M solution in ether) was added dropwise to the reaction mixture over 10 min. The reaction was slowly warmed to −40° C. over 30 min and held at this temperature for another 1 h. A solution of allyl bromide (43 μL, 0.50 mmol) in ether (1 mL) was then added to the reaction dropwise over 5 min. The reaction was stirred at −40° C. for 1 h, before it was quenched with NH$_4$Cl/NH$_3$ (2:1, aq., 5 mL) at −20° C. The aqueous layer was extracted twice with ether. The combined organic layers were washed with water (10 mL), and brine (10 mL), dried over MgSO$_4$, and then concentrated under reduced pressure. The crude product was purified by silica column chromatography with hexane/ethyl acetate (1:0 to 50:1 gradient) to afford 7a (48.0 mg, 0.176 mmol, 71%) as a single diastereomer. $^1$H NMR (400 MHz, CDCl$_3$) δ 7.23-7.17 (m, 2H), 7.13-7.07 (m, 3H), 5.73 (ddt, J=17.3, 10.2, 6.2 Hz, 1H), 4.97 (dq, J=17.2, 1.7 Hz, 1H), 4.89 (ddt, J=10.2, 2.0, 1.4 Hz, 1H), 4.07-3.96 (m, 2H), 2.68-2.60 (m, 2H), 2.33 (ddt, J=7.6, 6.2, 1.5 Hz, 2H), 1.57-1.51 (m, 2H), 1.40 (d, J=8.9 Hz, 1H), 1.23 (s, 3H), 1.18 (t, J=7.1 Hz, 3H), 1.09 (dt, J=8.8, 7.4 Hz, 1H). $^{13}$C NMR (101 MHz, CDCl$_3$) δ 171.68, 142.04, 137.72, 128.38, 128.33, 125.81, 114.58, 59.80, 45.06, 32.87, 31.77, 29.13, 27.89, 27.34, 14.39, 11.53. HRMS (FAB) m/z: 273.1849 (M+H$^+$); calc. for C$_{18}$H$_{25}$O$_2$: 273.1855. $[\alpha]^{23}_D$=−61.3±1.7° (c 0.1, ethyl acetate).

Ethyl (1R,6R,7R)-3,4-dimethyl-1-(6-((tetrahydro-2H-pyran-4-yl)methoxy)hexyl) bicyclo[4.1.0]hept-3-ene-7-carboxylate (7b)

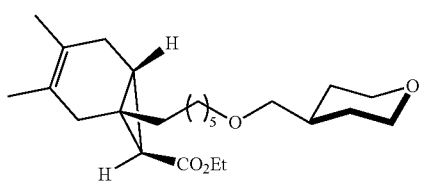

(7b)

Cyclopropene (R)-6g (65.6 mg, 0.211 mmol) was dissolved 2,3-dimethylbutadiene (0.5 mL). Then the reaction was heated and stirred at 80° C. in a sealed tube for 23 h. After cooling to room temperature, the resulting mixture was concentrated under reduced pressure. The crude product was purified by silica column chromatography with hexane/ethyl acetate (1:0 to 6:1 gradient) to afford 7b (81.1 mg, 0.207 mmol, 98%) as a single diastereomer. $^1$H NMR (400 MHz, CDCl$_3$) δ 4.09 (qd, J=7.1, 0.4 Hz, 2H), 4.01-3.90 (m, 2H), 3.45-3.32 (m, 4H), 3.24 (d, J=6.6 Hz, 2H), 2.43-2.29 (m, 1H), 2.30-2.09 (m, 3H), 1.90-1.75 (m, 1H), 1.67-1.60 (m, 4H), 1.58-1.50 (m, 10H), 1.46-1.38 (m, 1H), 1.36-1.26 (m, 5H), 1.26-1.15 (m, 5H). $^{13}$C NMR (101 MHz, CDCl$_3$) δ 173.76, 122.00, 121.77, 76.09, 71.37, 67.91, 60.21, 35.85, 35.60, 32.93, 32.16, 30.85, 30.20, 29.80, 29.69, 27.92, 26.89, 26.86, 26.33, 19.30, 19.09, 14.55. HRMS (FAB) m/z: 393.2992 (M+H$^+$); calc. for C$_{24}$H$_{41}$O$_4$: 393.3005. $[\alpha]^{23}_D$=−48.2±1.1° (c 0.1, ethyl acetate).

A biocatalytic platform has been developed for the construction of highly strained bicyclobutanes and cyclopropenes through directed evolution of a serine-ligated cytochrome P450 (P411) enzyme. That the protein could be quickly adapted to produce these highly strained structures (2-6 mutational steps) highlights the evolvability of the P411 scaffold and its potential to direct the construction of complex motifs. The protein enabled the desired transformations through activation of iron-carbenoid for carbene addition to alkynes, stabilization of the reactive cyclopropene intermediate (in bicyclobutane formation), and precise stereocontrol of the carbene transfer processes. Biotransformations with the evolved enzymes have a surprisingly broad substrate scope with high reactivity and selectivity, providing a route to more than 25 products in preparative scale. This biocatalytic system grants facile access to versatile molecular architectures rarely seen in nature, expanding the set of chemical structures available to biological systems.

V. REFERENCES

1. S. Kille, C. G. Acevedo-Rocha, L. P. Parra, Z.-G. Zhang, D. J. Opperman, M. T. Reetz, J. P. Acevedo, Reducing Codon Redundancy and Screening Effort of Combinatorial Protein Libraries Created by Saturation Mutagenesis. ACS Synth. Biol. 2, 83-92 (2013).
2. D. G. Gibson, L. Young, R.-Y. Chuang, J. C. Venter, C. A. Hutchinson III, H. O. Smith, Enzymatic Assembly of DNA Molecules up to Several Hundred Kilobases. Nat. Methods 6, 343-345 (2009).
3. J. Sambrook, E. Frisch, T. Maniatis, Molecular Cloning: A Laboratory Manual (Cold Spring Harbor Laboratory Press, New York, 1989).
4. E. A. Berry, B. L. Trumpower, Simultaneous Determination of Hemes a, b, and c from Pyridine Hemochrome Spectra. Anal. Biochem. 161, 1-15 (1987).
5. S. B. J. Kan, R. D. Lewis, K. Chen, F. H. Arnold, Directed Evolution of Cytochrome c for Carbon-Silicon Bond Formation: Bringing Silicon to Life. Science 354, 1048-1051 (2016).
6. T. J. Thomas, B. A. Merritt, B. E. Lemma, A. M. McKoy, T. Nguyen, A. K. Swenson, J. L. Mills, M. G. Coleman, Cyclopropenation of Internal Alkynylsilanes and Diazoacetates Catalyzed by Copper(I) N-Heterocyclic Carbene Complexes. Org. Biomol. Chem. 14, 1742-1747 (2016).
7. K. B. Wiberg, The Concept of Strain in Organic Chemistry. Angew. Chem. Int. Ed. 25, 312-322 (1986).
8. E. V. Anslyn, D. A. Dougherty, Modern Physical Organic Chemistry. (University Science, Sausalito, Calif., 2006), Chapter 2: Strain and Stability.
9. M. A. A. Walczak, T. Krainz, P. Wipf, Ring-Strain-Enabled Reaction Discovery: New Heterocycles from Bicyclo[1.1.0]butanes. Acc. Chem. Res. 48, 1149-1158 (2015).
10. I. Marek, S. Simaan, A. Masarwa, Enantiomerically Enriched Cyclopropene Derivatives: Versatile Building Blocks in Asymmetric Synthesis. Angew. Chem. Int. Ed. 46, 7364-7376 (2007).
11. A. de Meijere, S. I. Kozhushkov, H. Schill, Three-Membered-Ring-Based Molecular Architectures. Chem. Rev. 106, 4926-4996 (2006).
12. R. Gianatassio, J. M. Lopchuk, J. Wang, C.-M. Pan, L. R. Malins, L. Prieto, T. A. Brandt, M. R. Collins, G. M. Gallego, N. W. Sach, J. E. Spangler, H. Zhu, J. Zhu, P. S. Baran, Strain-Release Amination. Science 351, 241-246 (2016).
13. A. M. Damn, E. Spuling, A. de Meijere, S. Bräse, Propellanes—From a Chemical Curiosity to "Explosive" Materials and Natural Products. Angew. Chem. Int. Ed. 56, 5684-5718 (2017).
14. J. M. Longo, M. J. Sanford, G. W. Coates, Ring-Opening Copolymerization of Epoxides and Cyclic Anhydrides with Discrete Metal Complexes: Structure-Property Relationships. Chem. Rev. 116, 15167-15197 (2016).
15. T. M. Swager, D. A. Dougherty, R. H. Grubbs, Strained Rings as a Source of Unsaturation: Polybenzvalene, a New Soluble Polyacetylene Precursor. J. Am. Chem. Soc. 110, 2973-2974 (1988).
16. Z. Chen, J. A. M. Mercer, X. Zhu, J. A. H. Romaniuk, R. Pfattner, L. Cegelski, T. J. Martinez, N. Z. Burns, Y.

Xia, Mechanochemical Unzipping of Insulating Polyladderene to Semiconducting Polyacetylene. *Science* 357, 475-479 (2017).

17. W. Mahler, Double Addition of a Carbene to an Acetylene. *J. Am. Chem. Soc.* 84, 4600-4601 (1962).

18. W. von E. Doering, J. F. Coburn Jr, 1,3-Dimethylbicyclo [1.1.0]butane. *Tetrahedron Lett.* 6, 991-995 (1965).

19. P. Wipf, C. R. J. Stephenson, K. Okumura, Transition-Metal-Mediated Cascade Reactions: C,C-Dicyclopropylmethylamines by Way of Double C,C-σ-Bond Insertion into Bicyclobutanes. *J. Am. Chem. Soc.* 125, 14694-14695 (2003).

20. R. Panish, S. R. Chintala, D. T. Boruta, Y. Fang, M. T. Taylor, J. M. Fox, Enantioselective Synthesis of Cyclobutanes via Sequential Rh-Catalyzed Bicyclobutanation/Cu-Catalyzed Homoconjugate Addition. *J. Am. Chem. Soc.* 135, 9283-9286 (2013).

21. C. Qin, H. M. L. Davies, Enantioselective Synthesis of 2-Arylbicyclo[1.1.0]butane Carboxylates. *Org. Lett.* 15, 310-313 (2013).

22. Y. Lou, M. Horikawa, R. A. Kloster, N. A. Hawryluk, E. J. Corey, A New Chiral Rh(II) Catalyst for Enantioselective [2+1]-Cycloaddition. Mechanistic Implications and Applications. *J. Am. Chem. Soc.* 126, 8916-8918 (2004).

23. J. F. Briones, J. Hansen, K. I. Hardcastle, J. Autschbach, H. M. L. Davies, Highly Enantioselective Rh2(S-DOSP)4-Catalyzed Cyclopropenation of Alkynes with Styryldiazoacetates. *J. Am. Chem. Soc.* 132, 17211-17215 (2010).

24. M. Uehara, H. Suematsu, Y. Yasutomi, T. Katsuki, Enantioenriched Synthesis of Cyclopropenes with a Quaternary Stereocenter, Versatile Building Blocks. *J. Am. Chem. Soc.* 133, 170-171 (2011).

25. X. Cui, X. Xu, H. Lu, S. Zhu, L. Wojtas, X. P. Zhang, Enantioselective Cyclopropenation of Alkynes with Acceptor/Acceptor-Substituted Diazo Reagents via Co(II)-Based Metalloradical Catalysis. *J. Am. Chem. Soc.* 133, 3304-3307 (2011).

26. S. J. Benkovic, S. Hammes-Schiffer, A Perspective on Enzyme Catalysis. *Science* 301, 1196-1202 (2003).

27. L. A. Wessjohann, W. Brandt, Biosynthesis and Metabolism of Cyclopropane Rings in Natural Compounds. *Chem. Rev.* 103, 1625-1648 (2003).

28. T. Itoh, C. Djerassi, Acid-Catalyzed and Photochemical Isomerization of Steroidal Cyclopropenes. *J. Am. Chem. Soc.* 105, 4407-4416 (1983).

29. C. Schneider, K. Niisuke, W. E. Boeglin, M. Voehler, D. F. Stec, N. A. Porter, A. R. Brash, Enzymatic Synthesis of a Bicyclobutane Fatty Acid by a HemoproteinLipoxygenase Fusion Protein from the Cyanobacterium *Anabaena* PCC 7120. *Proc. Natl. Acad. Sci. U.S.A.* 104, 18941-18945 (2007).

30. O. Khersonsky, D. S. Tawfik, Enzyme Promiscuity: A Mechanistic and Evolutionary Perspective. *Ann. Rev. Biochem.* 79, 471-505 (2010).

31. U. T. Bornscheuer, R. J. Kazlauskas, Catalytic Promiscuity in Biocatalysis: Using Old Enzymes to Form New Bonds and Follow New Pathways. *Angew. Chem. Int. Ed.* 43, 6032-6040 (2004).

32. H. Renata, Z. J. Wang, F. H. Arnold, Expanding the Enzyme Universe: Accessing Non-Natural Reactions by Mechanism-Guided Directed Evolution. *Angew. Chem. Int. Ed.* 54, 3351-3367 (2015).

33. P. S. Coelho, E. M. Brustad, A. Kannan, F. H. Arnold, Olefin Cyclopropanation via Carbene Transfer Catalyzed by Engineered Cytochrome P450 Enzymes. *Science* 339, 307-310 (2013).

34. C. K. Prier, T. K. Hyster, C. C. Farwell, A. Huang, F. H. Arnold, Asymmetric Enzymatic Synthesis of Allylic Amines: A Sigmatropic Rearrangement Strategy. *Angew. Chem. Int. Ed.* 55, 4711-4715 (2016).

35. C. K. Prier, R. K. Zhang, A. R. Buller, S. Brinkmann-Chen, F. H. Arnold, Enantioselective, Intermolecular Benzylic C—H Amination Catalysed by an Engineered Iron-Haem Enzyme. *Nat. Chem.* 9, 629-634 (2017).

36. P. Bajaj, G. Sreenilayam, V. Tyagi, R. Fasan, Gram-Scale Synthesis of Chiral Cyclopropane-Containing Drugs and Drug Precursors with Engineered Myoglobin Catalysts Featuring Complementary Stereoselectivity. *Angew. Chem. Int. Ed.* 55, 16110-16114 (2016).

37. O. F. Brandenberg, R. Fasan, F. H. Arnold, Exploiting and Engineering Hemoproteins for Abiological Carbene and Nitrene Transfer Reactions. *Curr. Opin. Biotechnol.* 47, 102-111 (2017).

38. P. S. Coelho, Z. J. Wang, M. E. Ener, S. A. Baril, A. Kannan, F. H. Arnold, E. M. Brustad, A Serine-Substituted P450 Catalyzes Highly Efficient Carbene Transfer to Olefins in vivo. *Nat. Chem. Biol.* 9, 485-487 (2013).

39. L. O. Narhi, A. J. Fulco, Characterization of a Catalytically Self-sufficient 119,000-Dalton Cytochrome P-450 Monooxygenase Induced by Barbiturates in *Bacillus megaterium*. *J. Biol. Chem.* 261, 7160-7169 (1986).

40. Z. J. Wang, H. Renata, N. E. Peck, C. C. Farwell, P. S. Coelho, F. H. Arnold, Improved Cyclopropanation Activity of Histidine-Ligated Cytochrome P450 Enables the Enantioselective Formal Synthesis of Levomilnacipran. *Angew. Chem. Int. Ed.* 126, 6810-6813 (2014).

41. T. K. Hyster, C. C. Farwell, A. R. Buller, J. A. McIntosh, F. H. Arnold, Enzyme-Controlled Nitrogen-Atom Transfer Enables Regiodivergent CH Amination. *J. Am. Chem. Soc.* 136, 15505-15508 (2014).

42. M. Bordeaux, V. Tyagi, R. Fasan, Highly Diastereoselective and Enantioselective Olefin Cyclopropanation Using Engineered Myoglobin-Based Catalysts. *Angew. Chem. Int. Ed.* 54, 1744-1748 (2015).

43. H. M. L. Davies, K. R. Romines, Direct Synthesis of Furans by 3+2 Cycloadditions between Rhodium(II) Acetate Stabilized Carbenoids and Acetylenes. *Tetrahedron* 44, 3343-3348 (1988).

44. D. A. Smith, D. N. Reynolds, L. K. Woo, Cyclopropanation Catalyzed by Osmium Porphyrin Complexes. *J. Am. Chem. Soc.* 115, 2511-2513 (1993).

45. C. G. Hamaker, J.-P. Djukic, D. A. Smith, L. K. Woo, Mechanism of Cyclopropanation Reactions Mediated by (5,10,15,20-Tetra-p-tolylporphyrinato)osmium(II) Complexes. *Organometallics* 20, 5189-5199 (2001).

46. J. H. Capdevila, J. Wei, C. Helvig, J. R. Falck, Y. Belosludtsev, G. Truan, S. E. Graham-Lorence, J. A. Peterson, The Highly Stereoselective Oxidation of Polyunsaturated Fatty Acids by Cytochrome P450BM-3. *J. Biol. Chem.* 271, 22663-22671 (1996).

47. P.-O. Delaye, D. Didier, I. Marek, Diastereodivergent Carbometalation/Oxidation/Selective Ring Opening: Formation of All-Carbon Quaternary Stereogenic Centers in Acyclic Systems. *Angew. Chem. Int. Ed.* 52, 5333-5337 (2013).

48. D. M. Patterson, L. A. Nazarova, B. Xie, D. N. Kamber, J. A. Prescher, Functionalized Cyclopropenes as Bioorthogonal Chemical Reporters. *J. Am. Chem. Soc.* 134, 18638-18643 (2012).

49. B. R. Elling, Y. Xia, Living Alternating Ring-Opening Metathesis Polymerization Based on Single Monomer Additions. *J. Am. Chem. Soc.* 137, 9922-9926 (2015).

50. S. Kille, C. G. Acevedo-Rocha, L. P. Parra, Z.-G. Zhang, D. J. Opperman, M. T. Reetz, J. P. Acevedo, Reducing Codon Redundancy and Screening Effort of Combinatorial Protein Libraries Created by Saturation Mutagenesis. *ACS Synth. Biol.* 2, 83-92 (2013).
51. D. G. Gibson, L. Young, R.-Y. Chuang, J. C. Venter, C. A. Hutchinson III, H. O. Smith, Enzymatic Assembly of DNA Molecules up to Several Hundred Kilobases. *Nat. Methods* 6, 343-345 (2009).
52. J. Sambrook, E. F. Frisch, T. Maniatis, *Molecular Cloning: A Laboratory Manual* (Cold Spring Harbor Laboratory Press, New York, 1989).
53. E. A. Berry, B. L. Trumpower, Simultaneous Determination of Hemes a, b, and c from Pyridine Hemochrome Spectra. *Anal. Biochem.* 161, 1-15 (1987).
54. S. B. J. Kan, R. D. Lewis, K. Chen, F. H. Arnold, Directed Evolution of Cytochrome c for Carbon-Silicon Bond Formation: Bringing Silicon to Life. *Science* 354, 1048-1051 (2016).
55. N. O. Nilsen, L. Skattebøl, M. S. Baird, S. R. Buxton, P. D. Slowey, A Simple Route to 1-Bromobicyclo[1.1.0]butanes by Intramolecular Trapping of 1-Bromo-1-lithiocyclopropanes. *Tetrahedron Lett.* 25, 2887-2890 (1984).
56. A. Düker, G. Szeimies, 1-Bromobicyclo[1.1.0]butanes and Strong Bases: Products and Mechanism. *Tetrahedron Lett.* 26, 3555-3558 (1985).
57. M. A. A. Walczak, P. Wipf, Rhodium(I)-Catalyzed Cycloisomerizations of Bicyclobutanes. *J. Am. Chem. Soc.* 130, 6924-6925 (2008).
58. N. M. Abramova, S. V. Zotova, New Method for the Synthesis Bicyclo[1.1.0]butane. *Izv. Akad. Nauk SSSR, Ser. Khim.* 697 (1979).
59. Y. V. Tomilov, A. B. Kostitsyn, E. V. Shuylishov, O. M. Nefedov, Reaction of Diazo Alkanes with Unsaturated Compounds. 9. Catalytic Cyclomethylenation of (Trimethylsilyl)acetylenes with Diazomethane. *Izv. Akad. Nauk SSSR, Ser. Khim.* 1141-1146 (1990).
60. G. M. Lampman, J. C. Aumiller, Bicyclo[1.1.0]butane. *Org. Synth.* 51, 55-59 (1971).
61. R. Jain, M. B. Sponsler, F. D. Corns, D. A. Dougherty, Cyclobutanediyls: A New Class of Localized Biradicals. Synthesis and EPR Spectroscopy. *J. Am. Chem. Soc.* 110, 1356-1366 (1988).
62. M. R. Rifi, Electrochemical Preparation of Bicyclobutanes and Other Strained Cycloalkanes. *J. Am. Chem. Soc.* 89, 4442-4445 (1967).
63. H. K. Hall Jr., E. P. Blanchard Jr., S. C. Cherkofsky, J. B. Sieja, W. A. Sheppard, Synthesis and Polymerization of 1-Bicyclobutanecarbonitriles. *J. Am. Chem. Soc.* 93, 110-120 (1971).
64. J. A. Milligan, C. A. Busacca, C. H. Senanayake, P. Wipf, Hydrophosphination of Bicyclo[1.1.0]butane-1-carbonitriles. *Org. Lett.* 18, 4300-4303 (2016).
65. V. V. Razin, N. V. Ulin, Prototropic Isomerization of 1-Oxaspiro[2.3]hexane-5-carbonitrile and Methyl 1-Oxaspiro[2.3]hexane-5-carboxylate into the Corresponding 3-Hydroxymethylbicyclo[1.1.0]butane-1-carboxylic Acid Derivatives. *Russ. J. Org. Chem.* 39, 33-39 (2003).
66. C. B. Kelly, A. M. Colthart, B. D. Constant, S. R. Corning, L. N. E. Dubois, J. T. Genovese, J. L. Radziewicz, E. M. Sletten, K. R. Whitaker, L. J. Tilley, Enabling the Synthesis of Perfluoroalkyl Bicyclobutanes via 1,3 γ-Silyl Elimination. *Org. Lett.* 13, 1646-1649 (2011).
67. M. S. Baird, H. H. Hussain, The Preparation and Decomposition of Alkyl 2-Diazopent-4-enoates and 1-Trimethylsilyl-1-diazobut-3-enes, *Tetrahedron* 43, 215-224 (1987).
68. Z. Majerski, V. Kostov, M. Hibšer, K. Mlinarić-Majerski, 2,3-Methano-2,4-didehydro-11-homoadamantanone: A [4.1.1]propellanone. *Tetrahedron Lett.* 31, 915-916 (1990).
69. W. von E. Doering, M. Pomerantz, 2,4-Dimethyltricyclo[1.1.1.02,4]pentan-5-one. *Tetrahedron Lett.* 5, 961-966 (1964).
70. H. Hopf, H. Lipka, M. Traetteberg, Photoisomerization of Highly Alkylated Butadienes. *Angew. Chem. Int. Ed.* 33, 204-205 (1994).
71. M. Cavazza, A. Guerriero, F. Pietra, A Photochemical Route to 4-Alkyltropones Including Nezukone. *J. Chem. Soc., Perkin Trans.* 1 0, 2005-2008 (1986).
72. C. J. Thibodeaux, W. Chang, H. Liu, Enzymatic Chemistry of Cyclopropane, Epoxide, and Aziridine Biosynthesis. *Chem. Rev.* 112, 1681-1709 (2012).
73. L. N. Li, H. T. Li, R. W. Lang, T. Itoh, D. Sica, C. Djerassi, Minor and Trace Sterols in Marine Invertebrates. 31. Isolation and Structure Elucidation of 23H-Isocalysterol, a Naturally Occurring Cyclopropene. Some Comparative Observations on the Course of Hydrogenolytic Ring Opening of Steroidal Cyclopropenes and Cyclopropanes. *J. Am. Chem. Soc.* 104, 6726-6732 (1982).
74. C. Margot, C. A. N. Catalan, J. R. Proudfoot, G. Sodano, D. Sica, D. Djerassi, Biosynthesis of Three Cyclopropene-Containing Sterols in the Sponge *Calyx niceaensis*. *J. Chem. Soc., Chem. Commun.* 19, 1441-1442 (1987).
75. F. L. Carter, V. L. Frampton, Review of the Chemistry of Cyclopropene Compounds. *Chem. Rev.* 64, 497-525 (1964).
76. S. M. DeGuire, S. Ma, G. A. Sulikowski, Synthesis of a Bicyclobutane Fatty Acid Identified from the Cyanobacterium *Anabaena* PCC 7120. *Angew. Chem. Int. Ed.* 50, 9940-9942 (2011).
77. L. O. Narhi, A. J. Fulco, Characterization of a Catalytically Self-sufficient 119,000-Dalton Cytochrome P-450 Monooxygenase Induced by Barbiturates in *Bacillus megaterium*. *J. Biol. Chem.* 261, 7160-7169 (1986).
78. Z. J. Wang, H. Renata, N. E. Peck, C. C. Farwell, P. S. Coelho, F. H. Arnold, Improved Cyclopropanation Activity of Histidine-Ligated Cytochrome P450 Enables the Enantioselective Formal Synthesis of Levomilnacipran. *Angew. Chem. Int. Ed.* 126, 6810-6813 (2014).
79. T. K. Hyster, C. C. Farwell, A. R. Buller, J. A. McIntosh, F. H. Arnold, Enzyme-Controlled Nitrogen-Atom Transfer Enables Regiodivergent CH Amination. *J. Am. Chem. Soc.* 136, 15505-15508 (2014).
80. M. Bordeaux, V. Tyagi, R. Fasan, Highly Diastereoselective and Enantioselective Olefin Cyclopropanation Using Engineered Myoglobin-Based Catalysts. *Angew. Chem. Int. Ed.* 54, 1744-1748 (2015).
81. T. J. Thomas, B. A. Merritt, B. E. Lemma, A. M. McKoy, T. Nguyen, A. K. Swenson, J. L. Mills, M. G. Coleman, Cyclopropenation of Internal Alkynylsilanes and Diazoacetates Catalyzed by Copper(I) N-Heterocyclic Carbene Complexes. *Org. Biomol. Chem.* 14, 1742-1747 (2016).

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for preparing a product containing a cyclopropene moiety or a bicyclobutane moiety, the method comprising combining an alkyne and a carbene precursor in the presence of a heme protein under conditions sufficient to form the product containing the cyclopropene moiety or the bicyclobutane moiety,
wherein the heme protein is a cytochrome P450 variant obtained via a process comprising:
generating a site-saturation mutagenesis library of a wild-type cytochrome P450 to provide the cytochrome P450 variant,
contacting the cytochrome P450 variant with the alkyne and the carbene precursor, and
determining that the cytochrome P450 variant catalyzes formation of the product; and
wherein the product is:
[1] a cyclopropene according to Formula III:

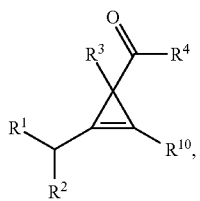

(III)

wherein
$R^{10}$ is selected from the group consisting of H and $CR^1R^2$;
each $R^1$ is independently selected from the group consisting of H, $C_{1-18}$ alkyl, $C_{1-18}$ haloalkyl, $C_{2-18}$ alkenyl, $C_{2-18}$ alkynyl, $(C_{3-10}$ cycloalkyl$)$-$L^1$-, $(C_{6-10}$ aryl$)$-$L^1$-, (5- to 10-membered heteroaryl)-$L^1$-, (5- to 10-membered heterocyclyl)-$L^1$-, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$,
$C_{1-18}$ alkyl, $C_{3-10}$ cycloalkyl, $C_{6-10}$ aryl, 5- to 10-membered heteroaryl, and 5- to 10-membered heterocyclyl in $R^1$ are optionally and independently substituted with one or more $R^{1a}$;
each $R^{1a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;
$L^1$ is selected from the group consisting of a bond and $C_{1-20}$ alkylene;
when $L^1$ is $C_{2-20}$ alkylene, one or more non-adjacent $CH_2$ groups are optionally and independently replaced with O, S, or NH;
when $L^1$ is $C_{3-20}$ alkylene, one or more pairs of adjacent $CH_2$ groups are optionally and independently replaced with $C(O)O$ or $C(O)NH$;
each $R^2$ is independently selected from the group consisting of H, $C_{1-18}$ alkyl, $C_{1-18}$ haloalkyl, $C_{2-18}$ alkenyl, $C_{2-18}$ alkynyl, $(C_{3-10}$ cycloalkyl$)$-$L^2$-, $(C_{6-10}$ aryl$)$-$L^2$-, (5- to 10-membered heteroaryl)-$L^2$-, (5- to 10-membered heterocyclyl)-$L^2$-, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;
$C_{1-18}$ alkyl, $C_{3-10}$ cycloalkyl, $C_{6-10}$ aryl, 5- to 10-membered heteroaryl, and 5- to 10-membered heterocyclyl in $R^2$ are optionally and independently substituted with one or more $R^{2a}$;
each $R^{2a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;
$L^2$ is selected from the group consisting of a bond and $C_{1-20}$ alkylene;
when $L^2$ is $C_{2-20}$ alkylene, one or more non-adjacent $CH_2$ groups are optionally and independently replaced with O, S, or NH;
when $L^2$ is $C_{3-20}$ alkylene, one or more pairs of adjacent $CH_2$ groups are optionally and independently replaced with $C(O)O$ or $C(O)NH$; and
$R^3$ and $R^4$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$; and
each $R^7$, $R^8$, and $R^9$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl; or

[2] a bicyclobutane according to Formula VI:

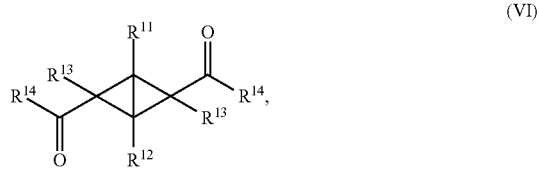

(VI)

wherein $R^{11}$ is selected from the group consisting of H, $C_{1-18}$ alkyl, $C_{1-18}$ haloalkyl, $C_{2-18}$ alkenyl, $C_{2-18}$ alkynyl, ($C_{3-10}$ cycloalkyl)-$L^{11}$-, ($C_{6-10}$ aryl)-$L^{11}$-, (5- to 10-membered heteroaryl)-$L^{11}$-, (5- to 10-membered heterocyclyl)-$L^{11}$-, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$, and $P(O)(OR^{17})_2$;

$C_{1-18}$ alkyl, $C_{3-10}$ cycloalkyl, $C_{6-10}$ aryl, 5- to 10-membered heteroaryl, and 5- to 10-membered heterocyclyl in $R^{11}$ are optionally and independently substituted with one or more $R^{11a}$;

each $R^{11a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^{11}$ is selected from the group consisting of a bond and $C_{1-20}$ alkylene;

when $L^{11}$ is $C_{2-20}$ alkylene, one or more non-adjacent $CH_2$ groups are optionally and independently replaced with O, S, or NH;

when $L^{11}$ is $C_{3-20}$ alkylene, one or more pairs of adjacent $CH_2$ groups are optionally and independently replaced with C(O)O or C(O)NH;

$R^{12}$ is selected from the group consisting of H, $C_{1-18}$ alkyl, $C_{1-18}$ haloalkyl, $C_{2-18}$ alkenyl, $C_{2-18}$ alkynyl, ($C_{3-10}$ cycloalkyl)-$L^{12}$-, ($C_{6-10}$ aryl)-$L^{12}$-, (5- to 10-membered heteroaryl)-$L^{12}$-, (5- to 10-membered heterocyclyl)-$L^{12}$-, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$, and $P(O)(OR^{17})_2$;

$C_{1-18}$ alkyl, $C_{3-10}$ cycloalkyl, $C_{6-10}$ aryl, 5- to 10-membered heteroaryl, and 5- to 10-membered heterocyclyl in $R^{12}$ are optionally and independently substituted with one or more $R^{12a}$;

each $R^{12a}$ is independently selected from the group consisting of halogen, cyano, —OH, $C_{1-6}$ alkyl, $C_{1-6}$ alkoxy, $C_{1-6}$ heteroalkyl, $C_{2-6}$ alkynyl, $C_{3-10}$ cycloalkyl, $C_{6-10}$ aryl, and 5- to 10-membered heterocyclyl;

$L^{12}$ is selected from the group consisting of a bond and $C_{1-20}$ alkylene;

when $L^{12}$ is $C_{2-20}$ alkylene, one or more non-adjacent $CH_2$ groups are optionally and independently replaced with O, S, or NH;

when $L^{12}$ is $C_{3-20}$ alkylene, one or more pairs of adjacent $CH_2$ groups are optionally and independently replaced with C(O)O or C(O)NH;

$R^{13}$ and $R^{14}$ are independently selected from the group consisting of H, optionally substituted $C_{1-18}$ alkyl, optionally substituted $C_{1-18}$ alkoxy, $C_{1-18}$ haloalkyl (e.g., $C_{1-18}$ polyfluoroalkyl), $C_{2-18}$ alkenyl, $C_{2-18}$ alkynyl, optionally substituted $C_{6-10}$ aryl, optionally substituted 5- to 10-membered heteroaryl, optionally substituted 5- to 10-membered heterocyclyl, cyano, halo, nitro, $N(R^{18})_2$, $B(R^{19})_2$, $Si(R^{19})_3$, $C(O)OR^{17}$, $C(O)SR^{17}$, $C(O)N(R^{17})_2$, $C(O)R^{17}$, $C(O)ON(R^{17})_2$, $C(O)NR^{17}OR^{18}$, $C(O)C(O)OR^{17}$ and $P(O)(OR^{17})_2$; and each $R^{17}$, $R^{18}$, and $R^{19}$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 5- to 10-membered heteroaryl, and optionally substituted 5- to 10-membered heterocyclyl.

2. The method of claim 1, wherein the cytochrome P450 variant comprises a mutation at an axial heme coordination residue.

3. The method of claim 1, wherein the cytochrome P450 variant is a *Bacillus megaterium* cytochrome P450$_{BM3}$ variant.

4. The method of claim 3, wherein the cytochrome P450$_{BM3}$ variant comprises one or more amino acid mutations at positions V78, A82, F87, P142, T175, A184, S226, H236, E252, I263, T268, A290, A328, L353, I366, C400, T438, and E442 relative to the amino acid sequence set forth in SEQ ID NO: 1.

5. The method of claim 1, wherein the cytochrome P450$_{BM3}$ variant comprises the amino acid sequence set forth in SEQ ID NO:2, and an amino acid mutation at one or more positions selected from S72, A78, A87, L188, F261, T269, T327, V328, A330, T436, and L437.

6. The method of claim 5, wherein the product comprises the cyclopropene according to Formula III.

7. The method of claim 6, wherein the carbene precursor is a diazo compound.

8. The method of claim 6, wherein the cytochrome P450$_{BM3}$ variant comprises the amino acid sequence set forth in SEQ ID NO:2 and further comprises: i) an A87F mutation and an F261 mutation or a T327 mutation, or ii) an A87W mutation.

9. The method of claim 1, wherein the cytochrome P450$_{BM3}$ variant comprises the amino acid sequence set forth in SEQ ID NO:3, and wherein the amino acid sequence optionally comprises an amino acid mutation at one or both of positions V78 and S438.

10. The method of claim 1, wherein the product comprises the bicyclobutane according to Formula VI.

11. The method of claim 10, wherein the carbene precursor is a diazo compound.

12. The method of claim 10, wherein the cytochrome P450$_{BM3}$ variant comprises the amino acid sequence set forth in SEQ ID NO:3 and further comprises: i) a V78F mutation and an S438 mutation, or ii) a V78Y mutation.

* * * * *